US007666596B2

(12) United States Patent
Halloran

(10) Patent No.: US 7,666,596 B2
(45) Date of Patent: Feb. 23, 2010

(54) TISSUE REJECTION

(75) Inventor: Philip F. Halloran, Edmonton (CA)

(73) Assignee: University of Alberta, Edmonton (CA)

( * ) Notice: Subject to any disclaimer, the term of this patent is extended or adjusted under 35 U.S.C. 154(b) by 260 days.

(21) Appl. No.: 11/434,711

(22) Filed: May 15, 2006

(65) Prior Publication Data

US 2006/0269949 A1 Nov. 30, 2006

Related U.S. Application Data

(60) Provisional application No. 60/683,737, filed on May 23, 2005.

(51) Int. Cl.
*C12Q 1/68* (2006.01)
*C12P 19/34* (2006.01)
(52) U.S. Cl. .......................... 435/6; 435/91.2
(58) Field of Classification Search .................. None
See application file for complete search history.

(56) References Cited

U.S. PATENT DOCUMENTS

| 5,143,854 A | 9/1992 | Pirrung et al. |
| 5,744,305 A | 4/1998 | Fodor et al. |
| 2001/0051344 A1* | 12/2001 | Shalon et al. .................. 435/6 |

OTHER PUBLICATIONS

Sarwal M. et al 'Molecular Heterogeneity in Acute Renal Allograft Rejection Identified by DNA Microarray Profiling' NEJM Jul. 10, 2003, 349;2, pp. 125-138.*
Whitney A.R. et al 'Individuality and variation in gene expression patterns in human blood' PNAS 2003 vol. 100, No. 4 pp. 1896-1901.*
Cheung V.G. et al 'Natural variation in human gene expression assessed in lymphoblastoid cells' nature genetics, vol. 33, Mar. 2003, pp. 422-425.*
Nadeau K.C. et al 'Sequential cytokine dynamics in chronic rejection of rat renal allografts: Roles for cytokines RANTES and MCP-1' Proc. Natl. Acad. Sci. USA vol. 92, pp. 8729-8733, Sep. 1995.*
Chan E. 'Integrating Transcriptomics and Proteomics' Drug Discovery and Development, Apr. 1, 2006, printed pp. 1-6.*
Cobb J.P. et al 'Sepsis gene expression profiling: Murine splenic compared with hepatic responses determined by using complementary DNA microarrays' Crit Care Med 2002 vol. 30, No. 12, pp. 2711-2721.*
Juppner H 'Functional Properties of the PTH/PTHrP Receptor' Bone vol. 17, No. 2, Supplement, Aug. 1995:39S-42S.*
Hoshikawa Y et al 'Hypoxia induces different genes in the lungs of rats compared with mice' Physiol Genomics 12: 209-219, 2003.*
Flechner et al., "Kidney Transplant Rejection and Tissue Injury by Gene Profiling of Biopsies and Peripheral Blood Lymphocytes," *Am. J. Transplant.*, 2004, 4:1475-1489.
Berg et al., "Comparison of Tolerated and Rejected Islet Grafts: A Gene Expression Study," *Cell Transplant.*, 2004, 13:619-629.
Stegall et al., "Gene Expression During Acute Allograft Rejection: Novel Statistical Analysis of Microarray Data," *Am. J. Transplant.*, 2002, 2:913-925.
Woo et al., "A Comparison of cDNA, Oligonucleotide, and Affymetrix GeneChip Gene Expression Microarray Platforms," *J. Biomolecular Techniques*, 2004, 15(4):276-284.
Singh et al., "Microarray-based comparison of three amplification methods for nanogram amounts of total RNA," *Am. J. Physiol. Cell Physiol.*, 2005, 288:C1179-C1189.
Famulski et al., "Changes in the Transcriptome in Allograft Rejection: IFN-γ-Induced Transcripts in Mouse Kidney Allograft," *Am. J. Transplant.*, 2006, 6:1342-1354.
Famulski et al., "IFN-γ inducible transcripts are increased in T cell mediated rejection but some are also increased in tissue injury," *Am. J. Transplant.*, 2005, 5(Suppl 11):448, Abstract.
Famulski et al., "IFN-γ acts on donor tissue to induce a signal that prevents both perforin-granzyme mediated graft destruction and alternative macrophage activation," *Am. J. Transplant.*, 2006, 6(Suppl 2):758, Abstract.
Famulski et al., "Heterogeneity in injury response in renal transplants: distinct patterns reflect acute phase response, cell cycle progression, genes associated with kidney development and fibrogenesis," *Am. J. Transplant.*, 2007, 7(Suppl 2):155, Abstract.
Halloran et al., "Interferon-γ is the principal determinant of the phenotype of T cell mediated kidney allograft rejection," *Am. J. Transplant.*, 2007, 7(Suppl 2):325, Abstract.
Sis et al., "A novel role for donor class I proteins: protection of kidney allografts against early necrosis and alternative macrophage activation," *Am. J. Transplant.*, 2006, 6(Suppl 2):759, Abstract.
Reeve, J., et al., 10 pages Uncorrected Proof accepted for publication as "Diagnosing Rejection in Renal Transplants: A Comparison of Molecular- and Histopathology-Based Approaches," American Journal of Transplantation, 9:1-9 (2009).

* cited by examiner

*Primary Examiner*—Stephen Kapushoc
(74) *Attorney, Agent, or Firm*—Fish & Richardson P.C.

(57) ABSTRACT

This document relates to methods and materials involved in detecting tissue rejection (e.g., organ rejection). For example, this document relates to methods and materials involved in the early detection of kidney tissue rejection.

10 Claims, 18 Drawing Sheets

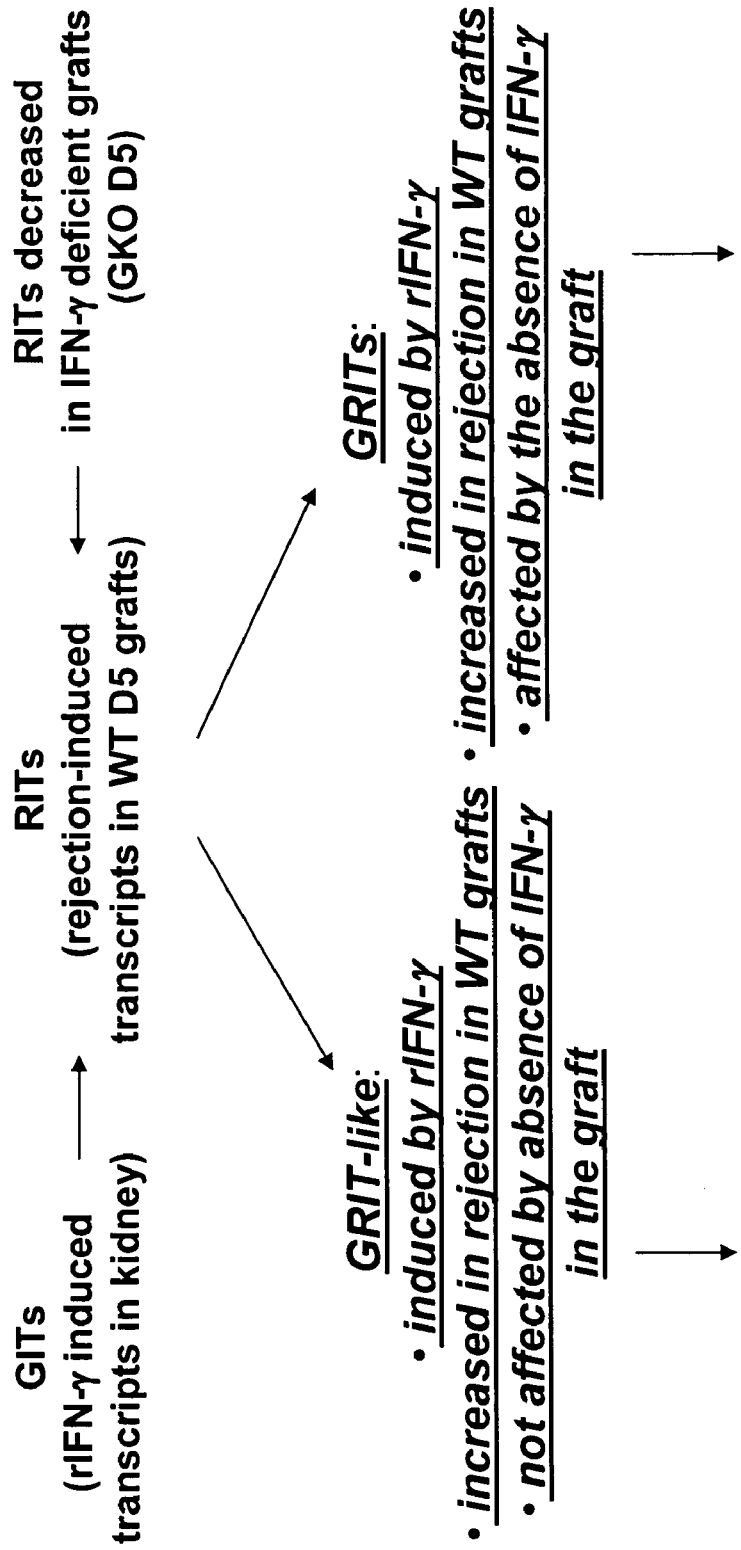

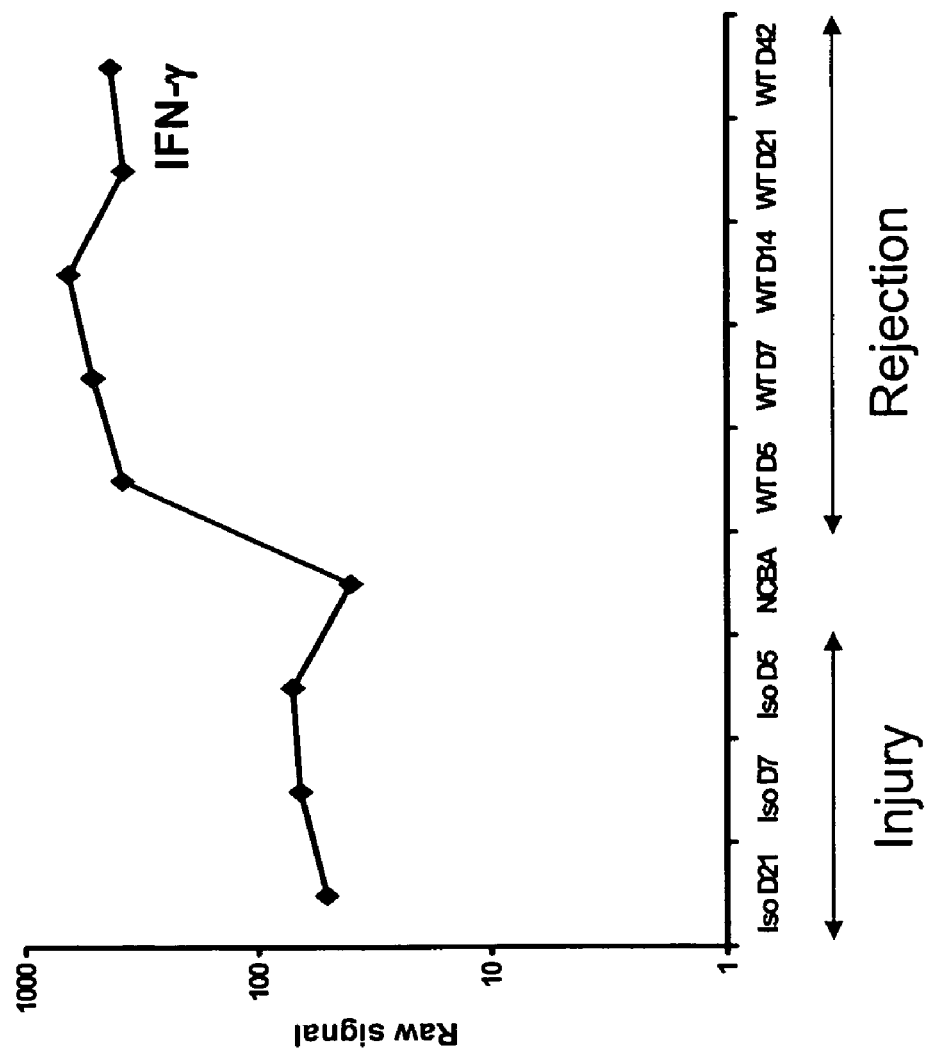

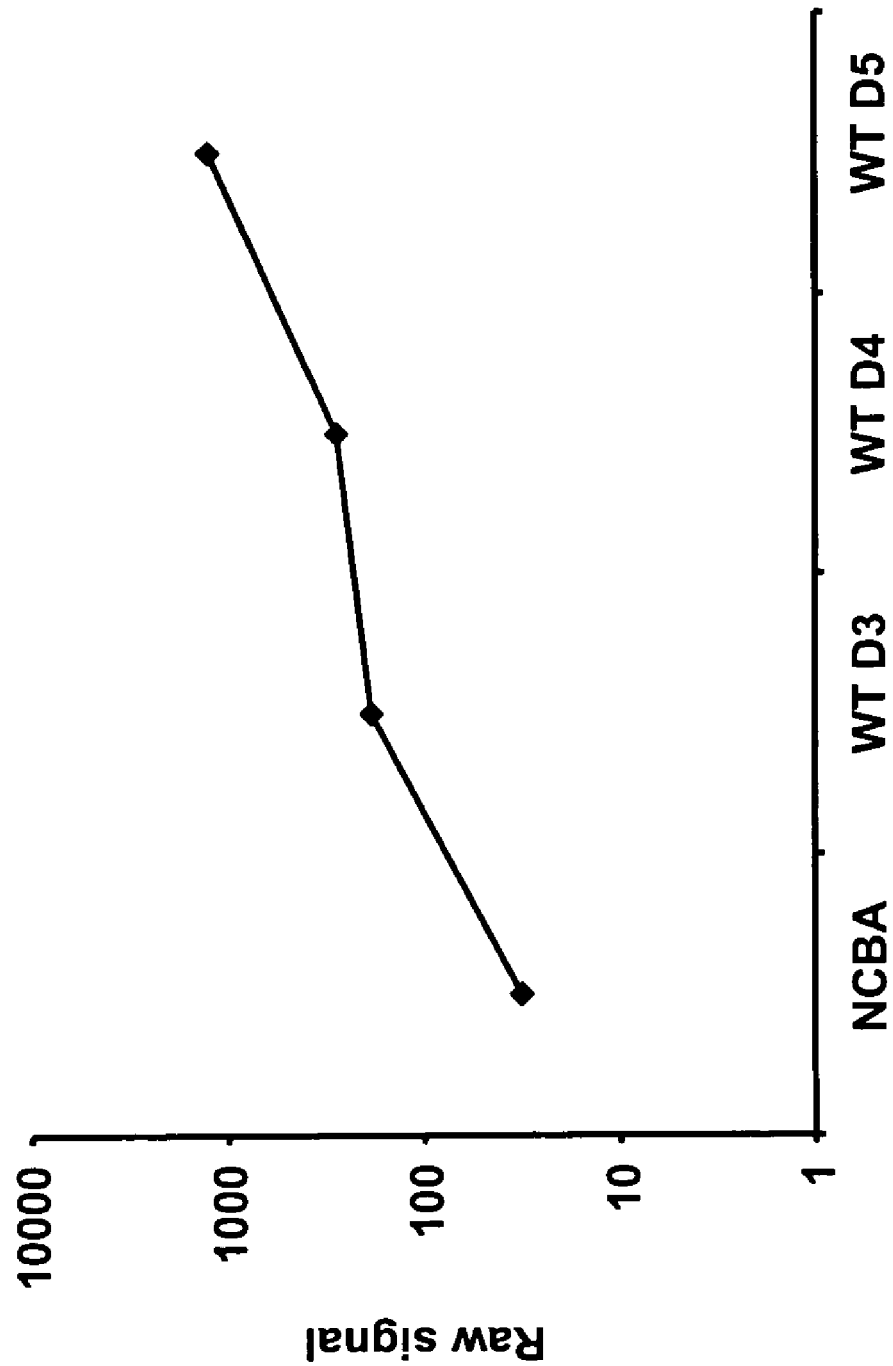

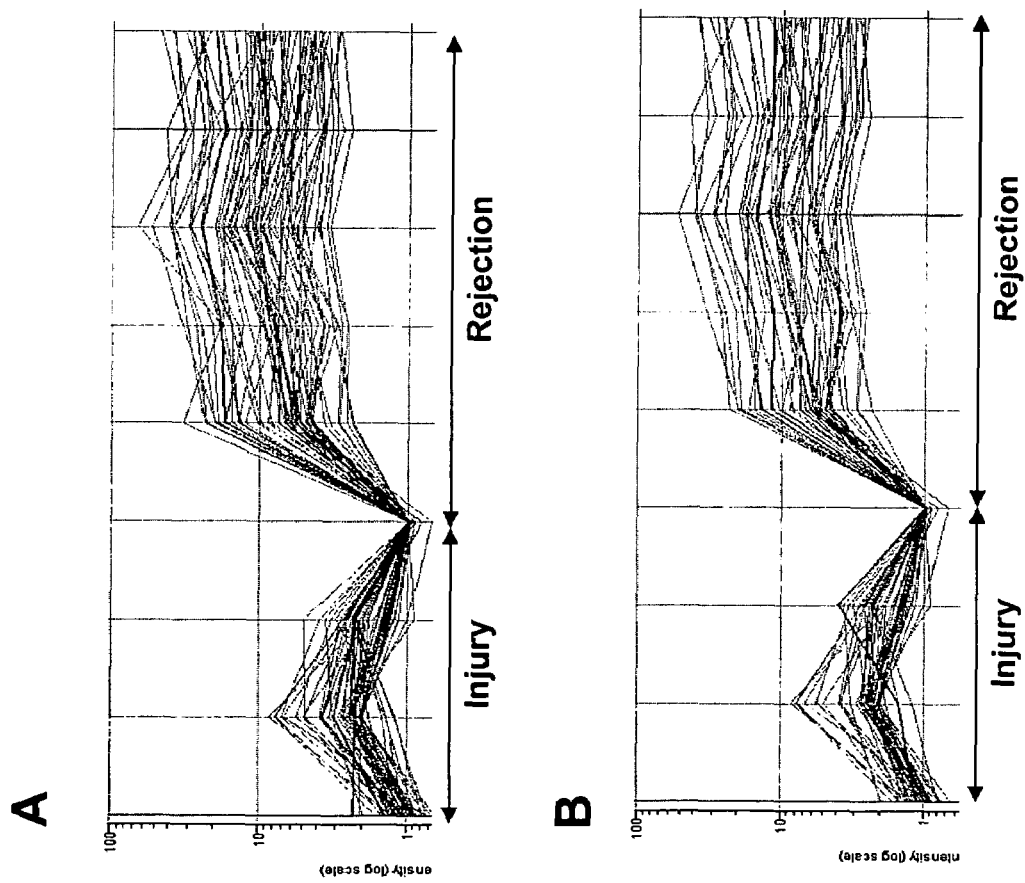

ive Application Ser. No. 60/683,737, filed May 23, 2005.

TISSUE REJECTION

CROSS-REFERENCE TO RELATED APPLICATIONS

This application claims priority from U.S. Provisional Application Ser. No. 60/683,737, filed May 23, 2005.

TECHNICAL FIELD

This document relates to methods and materials involved in tissue rejection (e.g., organ rejection) and detecting tissue rejection.

BACKGROUND

The transplantation of tissue from one mammal to another has been used for years to save lives and to improve the quality of lives. For example, the first successful kidney transplant was performed in the mid-1950s between identical twin brothers. Since then, donors have grown to include not only close relatives but also distant relatives, friends, and total strangers. In some cases, the recipient may reject the transplanted tissue. Thus, tissue rejection is a concern for any recipient of transplanted tissue. If a doctor is able to recognize early signs of tissue rejection, anti-rejection medication often can be used to reverse tissue rejection.

SUMMARY

This document relates to methods and materials involved in detecting tissue rejection (e.g., organ rejection). More particularly, this document relates to methods and materials involved in the early detection of tissue rejection (e.g., kidney rejection) and the assessment of a mammal's probability of rejecting tissue such as a transplanted organ. For example, this document provides nucleic acid arrays that can be used to diagnose tissue rejection in a mammal. Such arrays can allow clinicians to diagnose tissue rejection early based on a determination of the expression levels of nucleic acids that are differentially expressed in tissue being rejected as compared to control tissue not being rejected. The differential expression of such nucleic acids can be detected in tissue being rejected prior to the emergence of visually-observable, histological signs of tissue rejection. Early diagnosis of patients rejecting transplanted tissue (e.g., a kidney) can help clinicians determine appropriate treatments for those patients. For example, a clinician who diagnoses a patient as rejecting transplanted tissue can treat that patient with medication that suppresses tissue rejection (e.g., immunosuppressants).

The description provided herein is based, in part, on the discovery of nucleic acids that are differentially expressed in tissue being rejected as compared to control tissue that is not being rejected. Such nucleic acids can be nucleic acids that are induced by, for example, gamma interferon (IFN-γ). The term "gamma interferon induced transcripts" or "GITs" as used herein refers to transcripts that are expressed in kidneys of mammals treated with IFN-γ at a level at least 2-fold greater than the level of expression in normal kidney tissue. In some embodiments, a "GIT" is identified based expression that is increased at least two-fold in response to IFN-γ in normal kidneys of one or more particular strains (e.g., B6, CBA, and/or BALB/c) as compared to the level of expression in untreated normal kidney. The term "rejection induced transcripts" or "RITs" as used herein refers to transcripts that are elevated at least 2-fold in WT kidney allografts at day 5 post transplant in WT hosts vs. normal kidneys. In some embodiments, a "RIT" is identified based on expression that is increased at least two-fold in WT allografts from one or more particular strains (e.g., B6, CBA, and/or BALB/c) as compared to the level of expression in normal kidney. The term "injury and repair-induced transcripts" or "IRITs" refers to transcripts that are increased at least two-fold in isografts at least once between day 1 and day 21, as compared to normal kidney, and also are increased at least two-fold in CBA allografts at day 5 as compared to normal kidneys.

The term "gamma interferon and rejection induced transcripts" or "GRITs" as used herein refers to IFN-γ and rejection-inducible transcripts. These transcripts are (a) expressed at a level at least 2-fold greater in kidney tissue of mammals treated with IFN-γ than in kidney tissue of untreated mammals, (b) elevated at least 2-fold in tissue from WT kidney allografts at day 5 post transplant in WT hosts as compared to normal kidney tissue, and (c) expressed at levels at least 2-fold lower in kidney tissue from IFN-γ-deficient (GKO) D5 allografts as compared to WT D5 allografts. Thus, the expression of GRITs is affected by the presence or absence of IFN-γ in allografts. The term "GRIT-like" transcripts as used herein refers to transcripts that are (a) expressed at a level at least 2-fold greater in kidney tissue of mammals treated with IFN-γ than in kidney tissue of untreated mammals, (b) elevated at least 2-fold in tissue from WT kidney allografts at day 5 post transplant in WT hosts as compared to normal kidney tissue, and (c) not lower or even increased when IFN-γ is absent in GKO D5 allografts compared to WT D5 allografts. GRIT-like transcripts, despite being inducible by rIFN-γ, are increased in allografts by mechanisms largely independent of IFN-γ.

The term "transcript" as used herein refers to an mRNA identified by one or more numbered Affymetrix probe sets, while a "unique transcript" is an mRNA identified by only one probe set. The term "true interferon gamma dependent and rejection-induced transcripts" or "tGRITs" refers to rejection-induced transcripts that are IFN-γ-dependent in rejection, and also are unique transcripts that are increased at least 2-fold by rIFN-γ. The term "occult interferon gamma dependent and rejection-induced transcripts" or "oGRITs" refers to GRITs that are unique transcripts, but that are not 2-fold induced by rIFN-γ in normal kidneys.

The description provided herein also is based, in part, on the discovery that the expression levels of RITs can be used to distinguish transplanted tissue that is being rejected from transplanted tissue that is not being rejected. For example, the expression levels of nucleic acids listed in Table 2, Table 7, and/or Table 11 can be assessed in transplanted tissue to determine whether or not that transplanted tissue is being rejected. In addition, the description provided herein is based, in part, on the discovery that the expression levels of RITs (e.g., those listed in Table 2, Table 7, and/or Table 11) can be used to distinguish transplanted tissue that is being rejected from transplanted tissue that is not being rejected at a time point prior to the emergence of any visually-observable, histological sign of tissue rejection (e.g., tubulitis for kidney rejection). In some embodiments, expression levels of GRITs or GRIT-like transcripts, including, for example, those listed in Tables 4, 5, and 9 can be assessed to determine whether or not transplanted tissue is being rejected or to distinguish transplanted tissue that is being rejected from transplanted tissue that is not being rejected.

In one aspect, this document features a method for detecting tissue rejection. The method can include determining whether or not tissue transplanted into a mammal contains cells that express at least two of the nucleic acids listed in Table 2 or Table 11 at elevated levels, wherein the presence of the cells indicates that the tissue is being rejected. The mammal can be a human. The tissue can be kidney tissue or a kidney. The method can include determining whether or not the tissue contains cells that express at least five of the nucleic acids, at least ten of the nucleic acids, or at least twenty of the nucleic acids. The determining step can include measuring the level of mRNA expressed from the at least two nucleic acids or measuring the level of polypeptide expressed from the at least two nucleic acids. The method can include determining whether or not the tissue contains cells that express at least two of the nucleic acids at a level greater than the average level of expression exhibited in cells from control tissue that has not been transplanted.

In another aspect, this document features a method for detecting tissue rejection. The method can include determining whether or not a sample contains cells that express at least two of the nucleic acids listed in Table 2 or Table 11 at elevated levels, wherein the sample contains cells, was obtained from tissue that was transplanted into a mammal, and was obtained from the tissue within fifteen days of the tissue being transplanted into the mammal, and wherein the presence of the cells indicates that the tissue is being rejected. The mammal can be a human. The tissue can be kidney tissue or a kidney. The method can include determining whether or not the sample contains cells that express at least five of the nucleic acids, at least ten of the nucleic acids, or at least twenty of the nucleic acids. The determining step can include measuring the level of mRNA expressed from the at least two nucleic acids or measuring the level of polypeptide expressed from the at least two nucleic acids. The sample can be obtained from the tissue within ten days of the tissue being transplanted into the mammal or within five days of the tissue being transplanted into the mammal. The method can include determining whether or not the sample contains cells that express at least two of the nucleic acids at a level greater than the average level of expression exhibited in cells from control tissue that has not been transplanted.

In another aspect, this document features a nucleic acid array containing at least 20 nucleic acid molecules, wherein each of the at least 20 nucleic acid molecules has a different nucleic acid sequence, and wherein at least 50 percent of the nucleic acid molecules of the array contain a sequence from nucleic acid selected from the group consisting of the nucleic acids listed in Table 2 and Table 11. The array can contain at least 50 nucleic acid molecules, wherein each of the at least 50 nucleic acid molecules has a different nucleic acid sequence. The array can contain at least 100 nucleic acid molecules, wherein each of the at least 100 nucleic acid molecules has a different nucleic acid sequence. Each of the nucleic acid molecules that contain a sequence from a nucleic acid selected from the group can contain no more than three mismatches. At least 75 percent of the nucleic acid molecules of the array can contain a sequence from nucleic acid selected from the group. At least 95 percent of the nucleic acid molecules of the array can contain a sequence from nucleic acid selected from the group. The array can include glass. The at least 20 nucleic acid molecules can contain a sequence present in a human.

In another aspect, this document features a computer-readable storage medium having instructions stored thereon for causing a programmable processor to determine whether one or more nucleic acids listed in Table 2 or Table 11 are detected in a sample, wherein the sample is from a transplanted tissue. The computer-readable storage medium can further have instructions stored thereon for causing a programmable processor to determine whether one or more of the nucleic acids listed in Table 2 or Table 11 is expressed at a greater level in the sample than in a control sample of non-transplanted tissue.

This document also features an apparatus for determining whether a transplanted tissue is being rejected. The apparatus can include one or more collectors for obtaining signals representative of the presence of one or more nucleic acids listed in Table 2 or Table 11 in a sample from the transplanted tissue, and a processor for analyzing the signals and determining whether the tissue is being rejected. The one or more collectors can be configured to obtain further signals representative of the presence of the one or more nucleic acids in a control sample from non-transplanted tissue.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a depiction of selection criteria used for identification of GRITs and GRIT-like transcripts. WT D5—wild type allografts, GKO D5—IFN-γ-deficient allografts.

FIG. 2C is a graph showing the signal strength of IFN-γ over the time course of in injury and rejection. Clustering was based on distance as the similarity measure. ISO—isografts, WT—allografts, NCBA—control kidneys.

FIGS. 4A, 4B, and 4C are graphs showing expression profiles of IFN-γ, GRITs, and GRIT-like transcripts, respectively, early after transplantation. ISO—isografts, WT—allografts, GKO D5—IFN-γ deficient grafts, NCBA—control kidneys.

FIG. 7A is a graph showing an expression profile of Tgfbi superimposed on that for injury-induced RIT. FIG. 7B is a graph showing an expression profile of STAT-1 superimposed on that for injury-induced RIT.

DETAILED DESCRIPTION

Figure 2A:
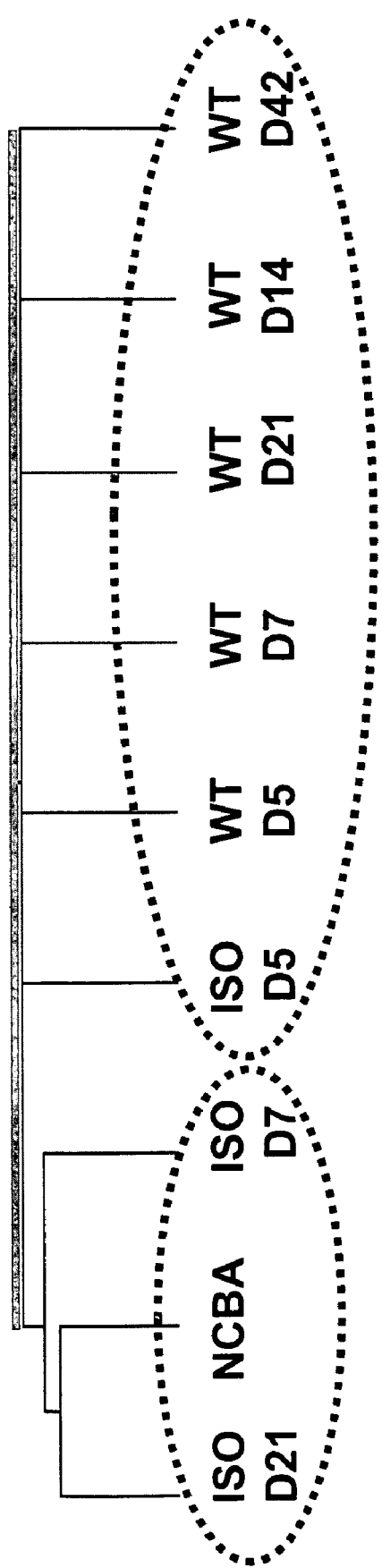
FIG. 2A is a depiction of an unsupervised hierarchical clustering of GRITs.

This description provides methods and materials involved in detecting tissue rejection (e.g., organ rejection). For example, this description provides methods and materials that can be used to diagnose a mammal (e.g., a human) as having transplanted tissue that is being rejected. A mammal can be diagnosed as having transplanted tissue that is being rejected if it is determined that the tissue contains cells that express elevated levels of one or more RITs or that express elevated levels one or more of the nucleic acids listed in Table 2, Table 7, or Table 11. In some embodiments, a mammal can be diagnosed as having transplanted tissue that is being rejected if it is determined that the tissue contains cells that express elevated levels of one or more GRITs, GRIT-like, true GRIT, or occult GRIT transcripts including, without limitation, those listed in Tables 4, 5, 9, or 10, respectively.

The methods and materials provided herein can be used to detect tissue rejection in any mammal such as a human, monkey, horse, dog, cat, cow, pig, mouse, or rat. In addition, the methods and materials provided herein can be used to detect rejection of any type of transplanted tissue including, without limitation, kidney, heart, liver, pancreas, and lung tissue. For example, the methods and materials provided herein can be used to determine whether or not a human who received a kidney transplant is rejecting that transplanted kidney.

Any type of sample containing cells can be used to determine whether or not transplanted tissue contains cells that express one or more RITs or that express one or more of the nucleic acids listed in Table 2, Table 7, or Table 11 at elevated levels. Similarly, any type of sample containing cells can be used to determine whether or not transplanted tissue contains cells that express one or more GRITs, GRIT-like, true GRIT, or occult GRIT transcripts, or that express one or more of the nucleic acids listed in Table 4, Table 5, Table 9, or Table 10 at elevated levels. For example, biopsy (e.g., punch biopsy, aspiration biopsy, excision biopsy, needle biopsy, or shave biopsy), tissue section, lymph fluid, blood, and synovial fluid samples can be used. In some embodiments, a tissue biopsy sample can be obtained directly from the transplanted tissue. In some embodiments, a lymph fluid sample can be obtained from one or more lymph vessels that drain from the transplanted tissue. A sample can contain any type of cell including, without limitation, cytotoxic T lymphocytes, CD4+ T cells, B cells, peripheral blood mononuclear cells, macrophages, kidney cells, lymph node cells, or endothelial cells.

As explained herein, a RIT refers to a transcript that is elevated at least 2-fold in WT kidney allografts at day 5 post transplant in WT hosts vs. normal kidneys. Examples of RITs include, without limitation, those listed in Tables 2, 7, and 11. A GRIT refers to an IFN-γ and rejection induced transcript that is (a) expressed at a level at least 2-fold greater in kidney tissue of mammals treated with IFN-γ than in kidney tissue of untreated mammals, (b) elevated at least 2-fold in tissue from WT kidney allografts at day 5 post transplant in WT hosts as compared to normal kidney tissue, and (c) expressed at levels at least 2-fold lower in kidney tissue from IFN-γ-deficient (GKO) D5 allografts as compared to WT D5 allografts. Examples of GRITs include, without limitation, the nucleic acids listed in Table 4. A GRIT-like transcript refers to a transcript that is (a) expressed at a level at least 2-fold greater in kidney tissue of mammals treated with IFN-γ than in kidney tissue of untreated mammals, (b) elevated at least 2-fold in tissue from WT kidney allografts at day 5 post transplant in WT hosts as compared to normal kidney tissue, and (c) not lower or even increased when IFN-γ is absent in GKO D5 allografts compared to WT D5 allografts. Examples of GRIT-like transcripts include, without limitation, those listed in Table 5. Additional examples of RITs, GRITs, and GRIT-like transcripts can be identified using the procedures described herein. For example, the procedures described in Example 1 can be used to identify RITs, GRITs, and GRIT-like transcripts other than those listed in Tables 2, 4, 5, and 7.

A tGRIT refers to a unique transcript that is rejection-induced and IFN-γ-dependent in rejection, and also is increased at least two-fold by rIFN-γ. Examples of tGRITs include, without limitation, those listed in Table 9. An oGRIT refers to a GRIT that is a unique transcript, but that is not induced at least 2-fold by rIFN-γ in normal kidneys. Examples of oGRITs include, without limitation, those listed in Table 10. An IRIT refers to a transcript that is increased at least two-fold in isografts at least once between day 1 and day 21, as compared to normal kidney, and also increased at least two-fold in CBA allografts at day 5 as compared to normal kidneys. Examples of IRITs include, without limitation, those listed in Table 11. The procedures described in Example 2 can be used to identify RITs, IRITs, GRITs, true GRITs, and occult GRITs other than those listed in Tables 9, 10, and 11.

The expression of any number of RITs, IRITs, GRITs, GRIT-like transcripts, tGRITs, oGRITs, or nucleic acids listed in Tables 2, 4, 5, 7, 9, 10, and/or 11 can be evaluated to determine whether or not transplanted tissue will be rejected. For example, the expression of one or more than one (e.g., two, three, four, five, six, seven, eight, nine, ten, 15, 20, 25, 30, 40, 50, 75, 100, or more than 100) of the nucleic acids listed in Table 2 can be used. In some embodiments, determining that a nucleic acid listed in Table 2 is expressed in a sample at a detectable level can indicate that the transplanted tissue will be rejected. In some embodiments, transplanted tissue can be evaluated by determining whether or not the tissue contains cells that express a nucleic acid listed in Table 2 at an elevated level, i.e., a level that is greater than the average expression level observed in control cells obtained from tissue that has not been transplanted. Typically, a nucleic acid can be classified as being expressed at a level that is greater than the average level observed in control cells if the expression levels differ by at least 1-fold (e.g., 1.5-fold, 2-fold, 3-fold, or more than 3-fold). Control cells typically are the same type of cells as those being evaluated. In some cases, the control cells can be isolated from kidney tissue that has not been transplanted into a mammal. Any number of tissues can be used to obtain control cells. For example, control cells can be obtained from one or more tissue samples (e.g., at least 5, 6, 7, 8, 9, 10, or more tissue samples) obtained from one or more healthy mammals (e.g., at least 5, 6, 7, 8, 9, 10, or more healthy mammals).

Any suitable method can be used to determine whether or not a particular nucleic acid is expressed at a detectable level or at a level that is greater than the average level of expression observed in control cells. For example, expression of a particular nucleic acid can be measured by assessing mRNA expression. mRNA expression can be evaluated using, for example, northern blotting, slot blotting, quantitative reverse transcriptase polymerase chain reaction (RT-PCR), real-time RT-PCR, or chip hybridization techniques. Methods for chip hybridization assays include, without limitation, those described herein. Such methods can be used to determine simultaneously the relative expression levels of multiple mRNAs. Alternatively, expression of a particular nucleic acid can be measured by assessing polypeptide levels. For example, polypeptide levels can be measured using any method such as immuno-based assays (e.g., ELISA), western blotting, or silver staining.

The methods and materials provided herein can be used at any time following a tissue transplantation to determine whether or not the transplanted tissue will be rejected. For example, a sample obtained from transplanted tissue at any time following the tissue transplantation can be assessed for the presence of cells expressing elevated levels of a nucleic acid listed in Table 2. In some cases, a sample can be obtained from transplanted tissue 1, 2, 3, 4, 5, 6, 7, 8, or more hours after the transplanted tissue was transplanted. In some cases, a sample can be obtained from transplanted tissue one or more days (e.g., 2, 3, 4, 5, 6, 7, 8, 9, 10, 15, 20, 25, 30, 40, or more days) after the transplanted tissue was transplanted. Typically, a sample can be obtained from transplanted tissue 2 to 7 days (e.g., 5 to 7 days) after transplantation and assessed for the presence of cells expressing elevated levels of one or more RITs or expressing elevated levels of one or more nucleic acids listed in Table 2.

This description also provides nucleic acid arrays. The arrays provided herein can be two-dimensional arrays, and can contain at least 10 different nucleic acid molecules (e.g., at least 20, at least 30, at least 50, at least 100, or at least 200 different nucleic acid molecules). Each nucleic acid molecule can have any length. For example, each nucleic acid molecule can be between 10 and 250 nucleotides (e.g., between 12 and 200, 14 and 175, 15 and 150, 16 and 125, 18 and 100, 20 and 75, or 25 and 50 nucleotides) in length. In addition, each nucleic acid molecule can have any sequence. For example, the nucleic acid molecules of the arrays provided herein can contain sequences that are present within the nucleic acids listed in Table 2, Table 4, Table 5, Table 7, Table 9, Table 10, and/or Table 11. For the purpose of this document, a sequence is considered present within a nucleic acid listed in, for example, Table 2 when the sequence is present within either the coding or non-coding strand. For example, both sense and anti-sense oligonucleotides designed to human Abp1 nucleic acid are considered present within Abp1 nucleic acid.

Typically, at least 25% (e.g., at least 30%, at least 40%, at least 50%, at least 60%, at least 75%, at least 80%, at least 90%, at least 95%, or 100%) of the nucleic acid molecules of an array provided herein contain a sequence that is (1) at least 10 nucleotides (e.g., at least 11, 12, 13, 14, 15, 16, 17, 18, 19, 20, 25, or more nucleotides) in length and (2) at least about 95 percent (e.g., at least about 96, 97, 98, 99, or 100) percent identical, over that length, to a sequence present within a nucleic acid listed in Table 2, Table 4, Table 5, Table 7, Table 9, Table 10, or Table 11. For example, an array can contain 100 nucleic acid molecules located in known positions, where each of the 100 nucleic acid molecules is 100 nucleotides in length while containing a sequence that is (1) 30 nucleotides in length, and (2) 100 percent identical, over that 30 nucleotide length, to a sequence of one of the nucleic acids listed in Table 2. A nucleic acid molecule of an array provided herein can contain a sequence present within a nucleic acid listed in Table 2, where that sequence contains one or more (e.g., one, two, three, four, or more) mismatches.

The nucleic acid arrays provided herein can contain nucleic acid molecules attached to any suitable surface (e.g., plastic or glass). In addition, any method can be use to make a nucleic acid array. For example, spotting techniques and in situ synthesis techniques can be used to make nucleic acid arrays. Further, the methods disclosed in U.S. Pat. Nos. 5,744, 305 and 5,143,854 can be used to make nucleic acid arrays.

Computer-Readable Medium and an Apparatus for Predicting Rejection

This disclosure further provides a computer-readable storage medium configured with instructions for causing a programmable processor to determine whether a transplanted tissue is being or is likely to be rejected. The determination of whether a transplanted tissue is being or will be rejected can be carried out as described herein; that is, by determining whether one or more of the nucleic acids listed in Table 2 or Table 11 is detected in a sample (e.g., a sample of the tissue), or is expressed at a level that is greater than the level of expression in a corresponding tissue that is not transplanted. The processor also can be designed to perform functions such as removing baseline noise from detection signals.

Instructions carried on a computer-readable storage medium (e.g., for detecting signals) can be implemented in a high level procedural or object oriented programming language to communicate with a computer system. Alternatively, such instructions can be implemented in assembly or machine language. The language further can be compiled or interpreted language.

The nucleic acid detection signals can be obtained using an apparatus (e.g., a chip reader) and a determination of tissue rejection can be generated using a separate processor (e.g., a computer). Alternatively, a single apparatus having a programmable processor can both obtain the detection signals and process the signals to generate a determination of whether rejection is occurring or is likely to occur. In addition, the processing step can be performed simultaneously with the step of collecting the detection signals (e.g., "real-time").

Any suitable process can be used to determine whether a transplanted tissue is being or is likely to be rejected. In some embodiments, for example, a process can include determining whether a pre-determined number (e.g., one, two, three, four, five, six, seven, eight, nine, ten, 15, 20, 25, 30, 40, 50, 75, 100, or more than 100) of the nucleic acids listed in Table 2 or Table 11 is expressed in a sample (e.g., a sample of transplanted tissue) at a detectable level. If the number of nucleic acids that are expressed in the sample is equal to or exceeds the pre-determined number, the transplanted tissue can be predicted to be rejected. If the number of nucleic acids that are expressed in the sample is less than the pre-determined number, the transplanted tissue can be predicted to not be rejected. The steps of this process (e.g., the detection, or non-detection, of each of the nucleic acids listed in Table 2 or Table 11) can be carried out in any suitable order. In some embodiments, a process can include determining whether a pre-determined number of the nucleic acids listed in Table 2 or Table 11 is expressed in a sample at a level that is greater than the average level observed in control cells (e.g., cells obtained from tissue that has not been transplanted. If the number of nucleic acids having increased levels of expression in the sample is equal to or exceeds the pre-determined number, the transplanted tissue can be predicted to be rejected. If the number of nucleic acids having increased expression levels in the sample is less than the pre-determined number, the transplanted tissue can be predicted to not be rejected. Again, the steps of this process can be carried out in any suitable order.

Also provided herein, therefore, is an apparatus for determining whether a transplanted tissue is being or is likely to be rejected. An apparatus for determining whether tissue rejection will occur can include one or more collectors for obtaining signals from a sample (e.g., a sample of nucleic acids hybridized to nucleic acid probes on a substrate such as a chip) and a processor for analyzing the signals and determining whether rejection will occur. By way of example, the collectors can include collection optics for collecting signals (e.g., fluorescence) emitted from the surface of the substrate, separation optics for separating the signal from background focusing the signal, and a recorder responsive to the signal, for recording the amount of signal. The collector can obtain signals representative of the presence of one or more nucleic acids listed in Table 2 or Table 11 (e.g., in samples from transplanted and/or non-transplanted tissue). The apparatus further can generate a visual or graphical display of the signals, such as a digitized representation. The apparatus further can include a display. In some embodiments, the apparatus can be portable.

The invention will be further described in the following examples, which do not limit the scope of the invention described in the claims.

EXAMPLES

Example 1

Interactions Between IFN-γ-Induced Transcripts and Injury Effects

The roles of IFN-γ were investigated in a mouse kidney allograft model that develops the pathologic lesions that are diagnostic in human graft rejection. Basically, a comparison of mouse kidney pathology to the mouse transcriptome was used to guide understanding of the relationship of lesions to transcriptome changes in human rejection. Recombinant IFN-γ (rIFN-γ) was administered to WT mice to identify the GITs in the kidney and examined how the GITs changed during graft rejection, comparing WT to IFN-γ deficient grafts. These experiments have provided insight into some of the complex relationships between IFN-γ inducibility during rejection and in tissue injury and regulation of GITs by non IFN-γ dependent factors during kidney transplantation.

Materials and Methods

Mice: Male CBA/J (CBA) and C57Bl/6 (B6) mice were obtained from the Jackson Laboratory (Bar Harbor, Me.). IFN-γ deficient mice (BALB/c.GKO) and (B6.129S7-IFNg$^{tm1Ts}$; B6.GKO) were bred in the Health Sciences Laboratory Animal Services at the University of Alberta. Mice maintenance and experiments were in conformity with approved animal care protocols. CBA (H-2K, I-A$^k$) into C57Bl/6 (B6; H-2K$^b$D$^b$, I-A$^b$) mice strain combinations, BALB/c.GKO into B6.GKO were studied across full MHC and non-MHC disparities.

Renal transplantation: Renal transplantation was performed as a non life-supporting transplant model. Recovered mice were killed at day 5, 7, 14, 21 or 42 post-transplant. Kidneys were removed, snap frozen in liquid nitrogen and stored at −70° C. No mice received immunosuppressive therapy. Kidneys with technical complications or infection at the time of harvesting were removed from the study.

Treatment with recombinant IFN-γ. CBA mice were injected i.p with 300,000 I.U. of recombinant INF-γ at 0 and 24 hours. rIFN-γ was a generous gift from Dr. T. Stewart at Genentech (South San Francisco, Calif.). Mice were sacrificed after 48 hours.

Microarrays: High-density oligonucleotide Genechip 430A and 430 2.0 arrays, GeneChip T7-Oligo(dT) Promoter Primer Kit, Enzo BioArray HighYield RNA Transcript Labeling Kit, IVT Labeling KIT, GeneChip Sample Cleanup Module, IVT cRNA Cleanup Kit were purchased from Affymetrix (Santa Clara, Calif.). RNeasy Mini Kit was from Qiagen (Ont, Canada), Superscript II, E. coli DNA ligase, E. coli DNA polymerase I, E. coli Rnase H, T4 DNA polymerase, 5x second strand buffer, and dNTPs were from Invitrogen Life Technologies.

RNA preparation and hybridization: Total RNA was extracted from individual kidneys using the guanidinium-cesium chloride method and purified RNA using the RNeasy Mini Kit (Quiagen, Ont. Canada). RNA yields were measured by UV absorbance. The quality was assessed by calculating the absorbance ratio at 260 nm and 280 nm, as well as by using an Agilent BioAnalyzer to evaluate 18S and 28S RNA integrity.

For each array, RNA from 3 mice was pooled. RNA processing, labeling and hybridization to MOE430A or MOE430 2.0 arrays was carried out according to the protocols included in the Affymetrix GeneChip Expression Analysis Technical Manual (available on the World Wide Web at affymetrix.com). cRNA used for Moe 430 2.0 arrays was labeled and fragmented using an IVT Labeling Kit and IVT cRNA Cleanup Kit.

Sample designation: Normal control kidneys were obtained from CBA mice and designated as NCBA. Allografts rejecting in wild type hosts (B6) at day 5 through day 42 post transplant were designated as WT D5, D7, D14, D21 and D42, respectively. Corresponding isografts were designated Iso D5, D7 and D21. Kidneys from mice treated with recombinant IFN-γ and harvested after 48 h were designated rIFN-γ. BALB/c-GKO kidneys (deficient in IFN-7) rejecting in IFN-γ-deficient B6 hosts at day 5 were designated as GKO D5 and corresponding isografts were designated ISO.GKO D5. The following samples (each consisting of RNA pooled from 3 mice) were analyzed by the Moe 430A arrays: two biological replicates of Iso D7, WT (D7, D14, D21 and D42); three replicates for NCBA and WT D5, single samples for Iso D5 and D21. Samples analyzed by the Moe 430 2.0 were NCBA (three replicates), WT D5, GKO D5, ISO.GKO D5 and rIFN-γ (two replicates each).

Sample analysis: Microarray Suite Expression Analysis 5.0 software was used for analysis of Moe 430A arrays (MAS 5.0, Affymetrix), and Gene Chip Operating software (GCOS 2.0, Affymetrix) was used for analysis of Moe 430 2.0 arrays to calculate absolute signal strength and transcripts flagging. Normalization per chip and per gene (GeneSpring™ 7.2, Agilent, Palo Alto Calif.) and to the control samples (NCBA) were described previously. The mean normalized value for further analysis of replicate samples.

Transcripts of interest were selected based on 2-fold differences and significance by Welch's t-test (Anova parametric test, variances not assumed equal). Groups of selected transcripts were then compared for individual time points using the univariate analysis of variance (Unianova with Bonferroni post hoc tests, for log transformed normalized data, SSPS 1.0 statistical package).

Hierarchical cluster analysis was performed using GeneSpring 7.2. Data were log transformed and similarity of transcript expression between experimental groups and between individual transcripts was visualized by a condition and gene tree diagram. Similarity measurements were based on distance. Trajectory clustering (expression pattern comparison, 0.95 correlation coefficient) was performed using the "find similar gene" feature in GeneSpring package.

Results

Terminology: rIFN-γ induced transcripts (GITs) were identified as those increased 48 hours after two injections of rIFN-γ, spaced 24 hours apart. Rejection induced transcripts (RITs) were identified as those increased in allografts at day 5. Injury-induced transcripts were identified as those induced in isografts at days 5 and/or 7. The rejection induced transcripts thus include effects of transplant-related stress as well as alloimmune related changes.

Identification of transcripts induced by IFN-γ in vivo in rejecting kidney allografts. Identification of IFN-γ induced transcripts in kidney allografts was based on data obtained from the Moe 430 2.0 arrays, with cytotoxic T lymphocyte associated transcripts (CATs) deleted from all lists to avoid overlap. First, the rIFN-γ-induced transcripts were identified: 342 transcripts flagged present and increased 2-fold in normal kidneys from mice treated with rIFN-γ (significant by ANOVA) (Table 1). RITs were then selected, defined as transcripts that were elevated 2-fold in WT allografts at day 5 post transplant in WT hosts vs. normal kidneys (significant by Anova). 2040 transcripts, flagged present in the allografts, fulfilled these criteria (Table 2). To determine how many of these transcripts were IFN-γ inducible, they were compared to the GITs. This comparison yielded 163 common transcripts that were induced by rIFN-γ treatment and increased in rejecting kidneys at day 5. Thus, 179 GITs were not significantly induced in rejecting kidneys by these criteria, in spite of the strong IFN-γ response in the allograft.

Validation of IFN-γ induced transcripts in mouse kidney allografts: To verify that the increased expression of 163 transcripts in day 5 allografts was at least partially dependent on IFN-γ, IFN-γ-deficient kidney allografts grafted into IFN-γ-deficient hosts were studied. In these grafts, neither the donor nor the host cells can make IFN-γ. After removing CATs, 570 transcripts were expressed at least 2-fold lower in GKO D5 compared to WT D5 (significant by ANOVA), indicating that the expression of these transcripts was affected by the presence or absence of IFN-γ in allografts (Table 3). Of the 163 previously defined rIFN-γ- and rejection-induced transcripts, 74 were decreased in GKO D5, indicating that they were at least partially dependent on IFN-γ in WT D5 allografts. These were termed IFN-γ and rejection-inducible transcripts (GRITs). On the other hand, 89 transcripts, despite being rIFN-γ-inducible, were not lower or were even increased when IFN-γ was absent in GKO D5 allografts compared to WT D5 allografts. These were termed GRIT-like transcripts. Thus, the GRIT-like transcripts, despite being inducible by rIFN-γ, were increased in allografts by mechanisms largely independent of IFN-γ. The algorithm used for transcript selection is shown in FIG. 1.

Functional classification of GRIT and GRIT-like: The list of GRITs (Table 4) summarizes local effects of IFN-γ on transcription in the isografts and the allografts, as well as systemic effects on the normal rejecting kidney. The transcripts represent genes for several major classes of proteins: (a) MHCs and their related factors (B2m Psmb8-9, Tapbp) and other ubiquitination/proteolysis-related factors (Parp14, Psmb10, Ubd, Ub11); (b) guanylate binding proteins (Gbp2), interferon-induced GTPases (Igtp, Iigp1, Tgtp) and other so called IFN-γ-induced proteins (Ifi1 and Ifi47); (c) cytokines and chemokines: Cc15, Cc18, Cxc19, Cxcl10, interleukin-18 binding protein (I118 bp), Arts1; (d) other immune functions: complement components (C1r, C1s, C2); and (e) transcription factors and activators: Irf7 (ISRE sites), Stat1 (GAS sites), class II transactivator C2ta.

The list of GRIT-like transcripts (Table 5) includes complement components (C1qb, C1qg, Serping1); cytokine, chemokine and receptor related transcripts (Tnfsf13b, Ccr5, Cxcl14, Socs2); some interferon-induced transcripts (Ifi27, Ifitm1, Ifitm6); and Tgfbi, a transcript whose expression is regulated by Tgfb1.

Expression profiles of GRIT and GRIT-like in the isografts and the allografts: The time course of changes in these transcripts post transplant was studied by querying a previously established database from MOE 430A arrays containing the expression values of all transcripts in isografts and allografts, at different times post transplant. Previously identified GRITs were "translated" (using the GeneSpring translation feature) to Moe 430A arrays, and these increased at least 2 fold (significant by Anova) in WT D5 allografts vs NCBA were selected. This permitted creation of a final list of 59 GRITs (Table 4) and 42 GRIT-like transcripts (Table 5). The lower number of transcripts was due to a lack of certain probe sets interrogating Riken sequences in Moe 430A arrays, and perhaps also to the lower sensitivity of the M430A arrays.

Analysis of the expression time course of GRITs and GRIT-like transcripts in isografts and allografts permitted comparison of the impact of transplant-related stress and/or injury on rejection. First, unsupervised clustering of all isografts and allografts was performed based on GRITs and GRIT-like lists (FIG. 2 and FIG. 3). Kidney samples were grouped into two clusters. One powerful cluster included all of the allografts, indicating strong and consistent expression of the GRITs and GRIT-like transcripts in all allografts at all times tested. Surprisingly, ISO D5 clustered with all allografts for the GRITs (FIG. 2). ISO D21 co-clustered with NCBA, indicating recovery of kidneys from injury. ISO D7 was more similar to this group. On the other hand, GRIT-like list yielded good separation of the all isografts from the allografts, clustering ISO D5 and ISO D7 in one subgroup (FIG. 3). This indicated a stronger relation of GRIT expression in ISO D5 to rejecting allografts, compared to GRIT-like expression.

Time course of GRIT expression parallels IFN-γ expression: The time course of GRIT expression supported the cluster organization and the conclusion that there were differences in regulation of GRITs (FIG. 2) versus GRIT-like transcripts (FIG. 3). In the isografts, expression of many GRITs peaked at D5 post transplant and sharply declined at D7 and D21. Thirty-nine and 11 GRITs were increased at least 2-fold at ISO D5 and ISO D7, respectively. Mean expression of GRITs in ISO D5 samples was higher than in ISO D7 and D21 ($p<0.01$). GRIT expression in the allografts, however, was sustained throughout the observation period, with no significant differences among the samples except for a small peak at D14 ($p<0.05$). In addition, GRIT expression in the allografts showed 4-fold higher mean expression compared to ISO D5 ($p<0.02$, corrected for multiple comparisons).

Figure 2B:
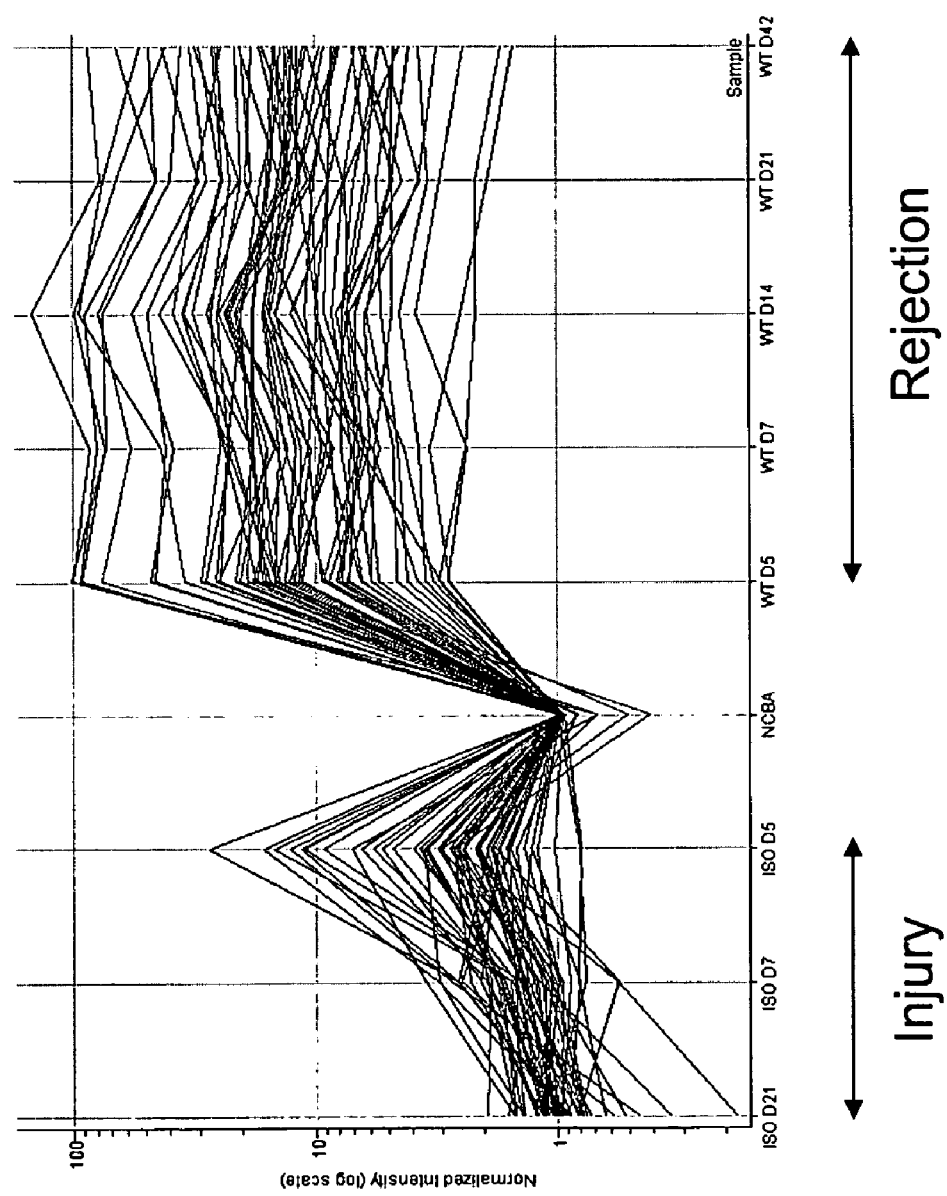
FIG. 2B is a graph showing an expression time course of GRITs in injury and rejection.
Figure 3A:
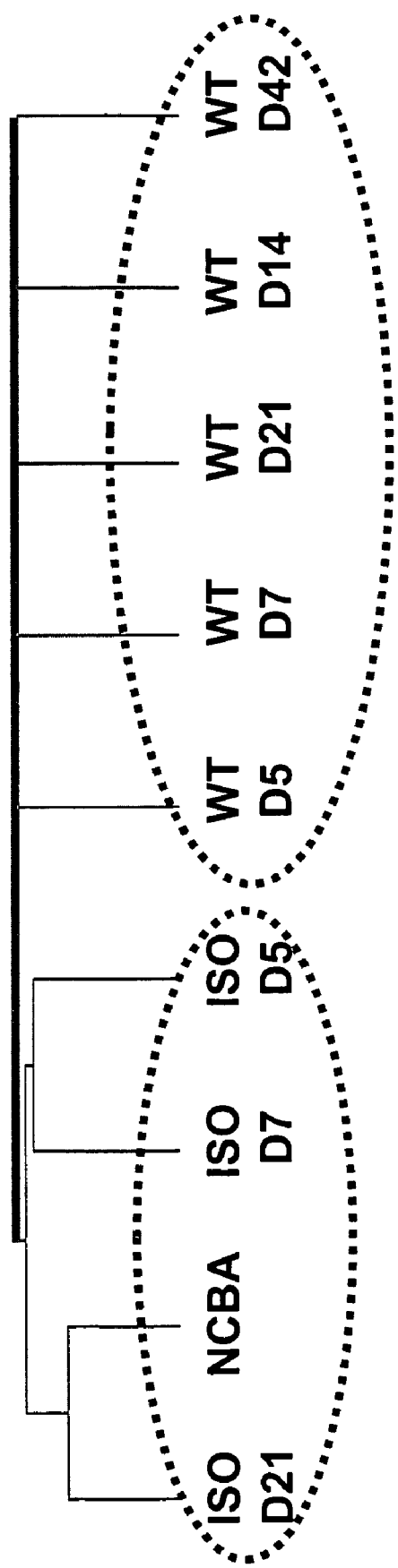
FIG. 3A is a depiction of an unsupervised hierarchical clustering of GRIT-like transcripts.
Figure 3B:
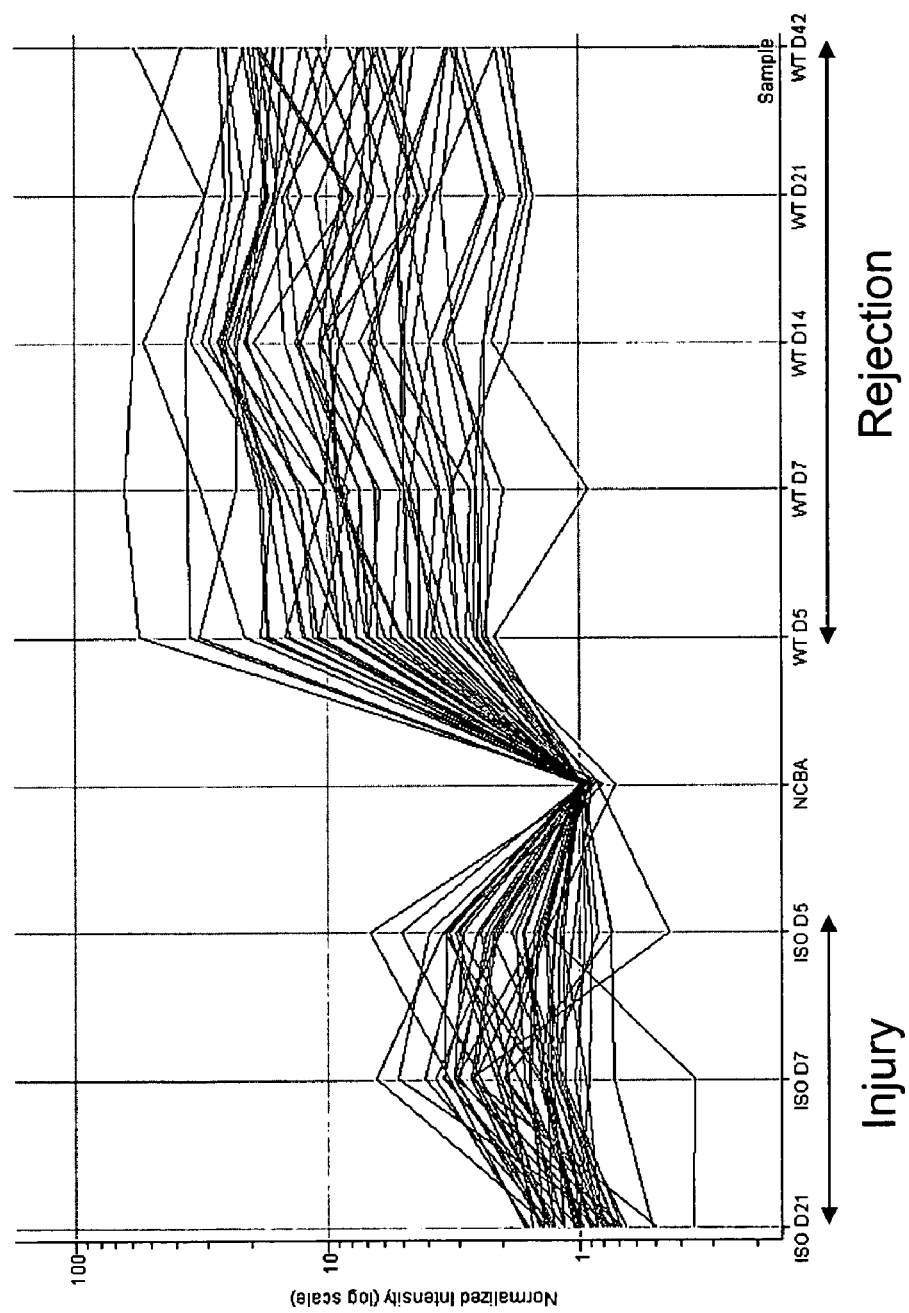
FIG. 3B is a graph showing an expression time course of GRIT-like transcripts in injury and rejection. Normalized values are shown. Clustering was based on distance as the similarity measure. ISO—isografts, WT—allografts, NCBA—control kidneys.

For the comparison, FIG. 2A demonstrates the time course of IFN-γ expression in the isografts D5 throughout D21 and the allografts day 5 throughout day 42. Isograft IFN-γ transcript levels peaked at D5 and declined from D7 on (FIGS. 2B and 2C). However, IFN-γ transcript levels were 5-fold higher in WT D5 allografts compared to ISO D5, and remained high at all allograft time points, with some increase at day 14. Thus GRIT expression parallels that of IFN-γ.

IFN-γ expression also was assessed in WT allografts at early times post transplant. IFN-γ signal strength increased about 8 fold in D5 compared to D3 allografts (FIG. 4A), indicating that the IFN-γ expression was established at D5 post transplant.

Time course of GRIT-like transcripts parallels TGF-β1 expression: GRIT-like transcripts were analyzed over the time course shown in FIG. 3A, and showed consistent expression in all allografts. However, they differed in isografts: there was no statistically significant difference between their mean expression at ISO D5 and ISO D7 (FIG. 3B). 17 GRIT-like allografts were increased at least 2-fold either in ISO D5 or ISO D7 samples. Mean GRIT-like expression was 2 fold higher compared to ISO D5 or ISO D7 (p<0.02, corrected for multiple comparisons). However, GRIT-like mean expression in the isografts and the allografts was lower by 2-fold compared to GRITs.

The appearance of Tgfbi in the GRIT-like list suggests that Tgfb1 may be playing a role in the regulation of some of these transcripts. Moreover, the GRIT-like transcripts, by definition, are not significantly reduced in the absence of IFN-γ, indicating that they are induced by other factors, one candidate being Tgf-β1. The expression profile of Tgfbi was reminiscent of Tgfb1, i.e., it demonstrated a similar peak in ISO D7 and strong increase in the allografts, like many of the GRIT-like transcripts.

Figure 4B:
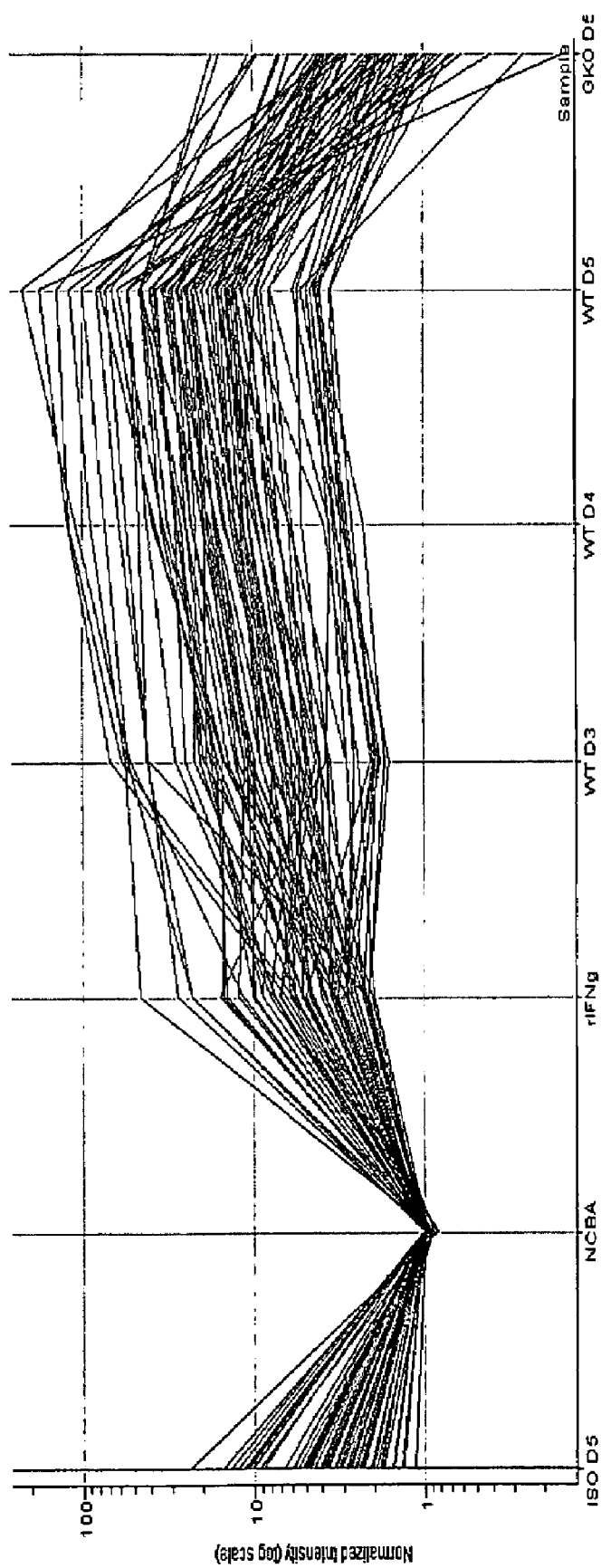
Figure 4C:
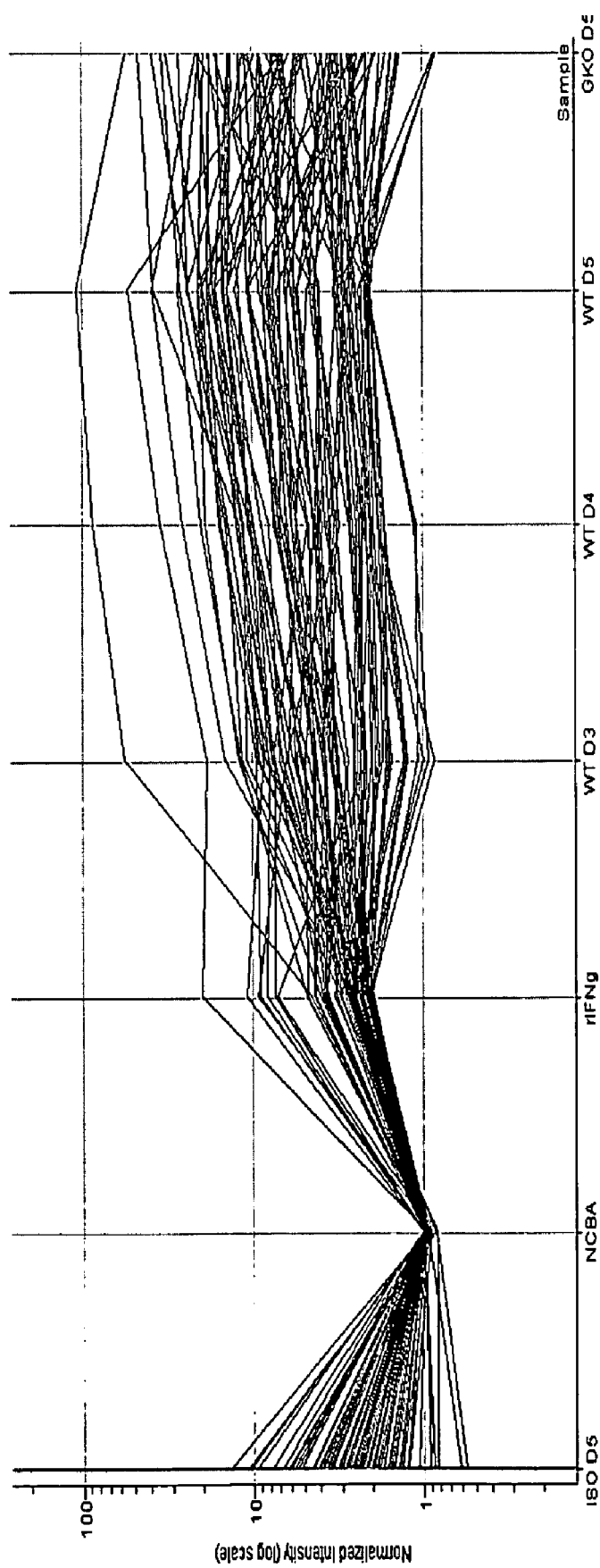

The expression time course of GRIT/GRIT-like in WT allografts at early times post transplant demonstrated a step-wise increase from day 3 to day 4 to day 5 post transplant (FIGS. 4B and 4C).

Expression of GRITs and GRIT-like in the isografts differ in response to IFN-γ: To confirm that the elevated expression of GRIT in wild type isografts is dependent on IFN-7, the expression of GRITs was assessed in the IFN-γ-deficient D5 isografts (ISO.GKO D5) by Moe 430 2.0 arrays and compared to GRIT expression in wild type isografts D5. Transcripts that were increased at least 2-fold in WT D5 vs to ISO.GKO D5 were translated to Moe 430A arrays. It was observed that 36 out of 59 GRITs (Table 4) were expressed at least 2-fold higher in WT D5 isografts compared to ISO.GKO D5. Notably, only 10 GRIT-like transcripts fulfilled these criteria (Table 5). Thus, the majority (66%) of GRITs and only a fraction (25%) of GRIT-like transcripts seemed to be dependent on IFN-γ produced in the isografts.

Regulation of the expression of injury and rejection induced transcripts that are not IFN-γ regulated by these criteria: Due to the uniformity with which the GRITs and GRIT-like transcripts were increased in the isografts (albeit to a varying degree in ISO D5 and ISO D7 samples), the analysis of transplant stress/injury to rejection was extended by analyzing all transcripts flagged present and elevated 2-fold either in isografts at days 5 or 7 and increased 2-fold in WT D5 (significant by Anova). GRITs, GRIT-like and CATs were eliminated from this list. Moreover, transcripts were detected that were decreased 2-fold or more in GKO D5 compared to WT D5, but were not affected by rIFNγ administration. One hundred ten of these transcripts translated to Moe 430A arrays (Table 6) and were eliminated from the RIT list.

Figure 5A:
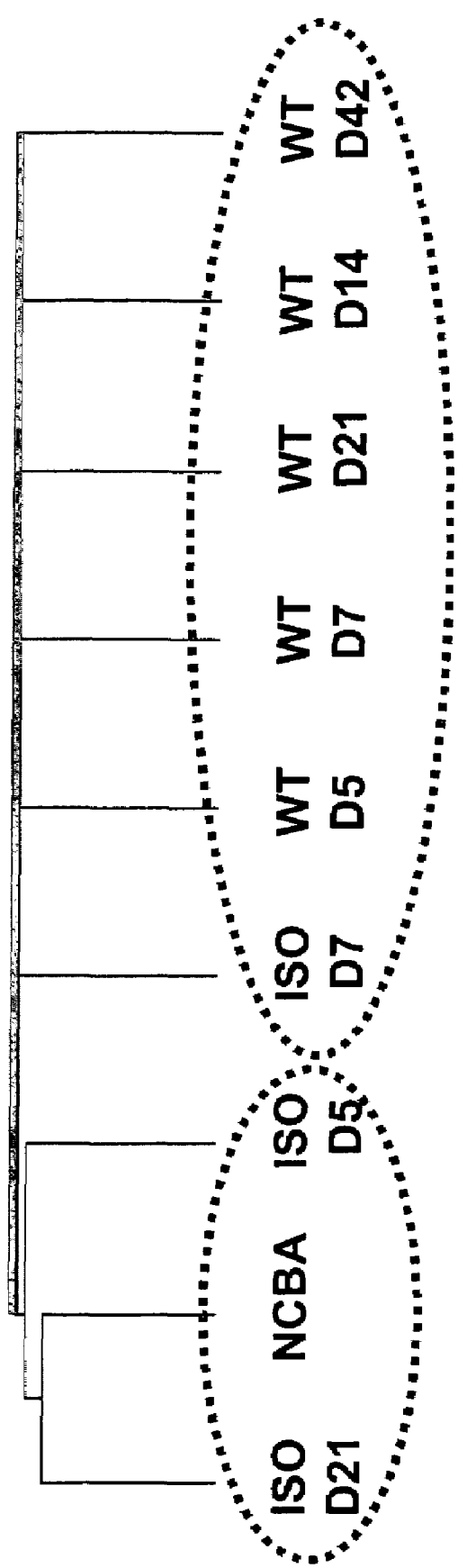
FIG. 5A is a depiction of an unsupervised hierarchical clustering of injury-induced RIT.
Figure 5B:
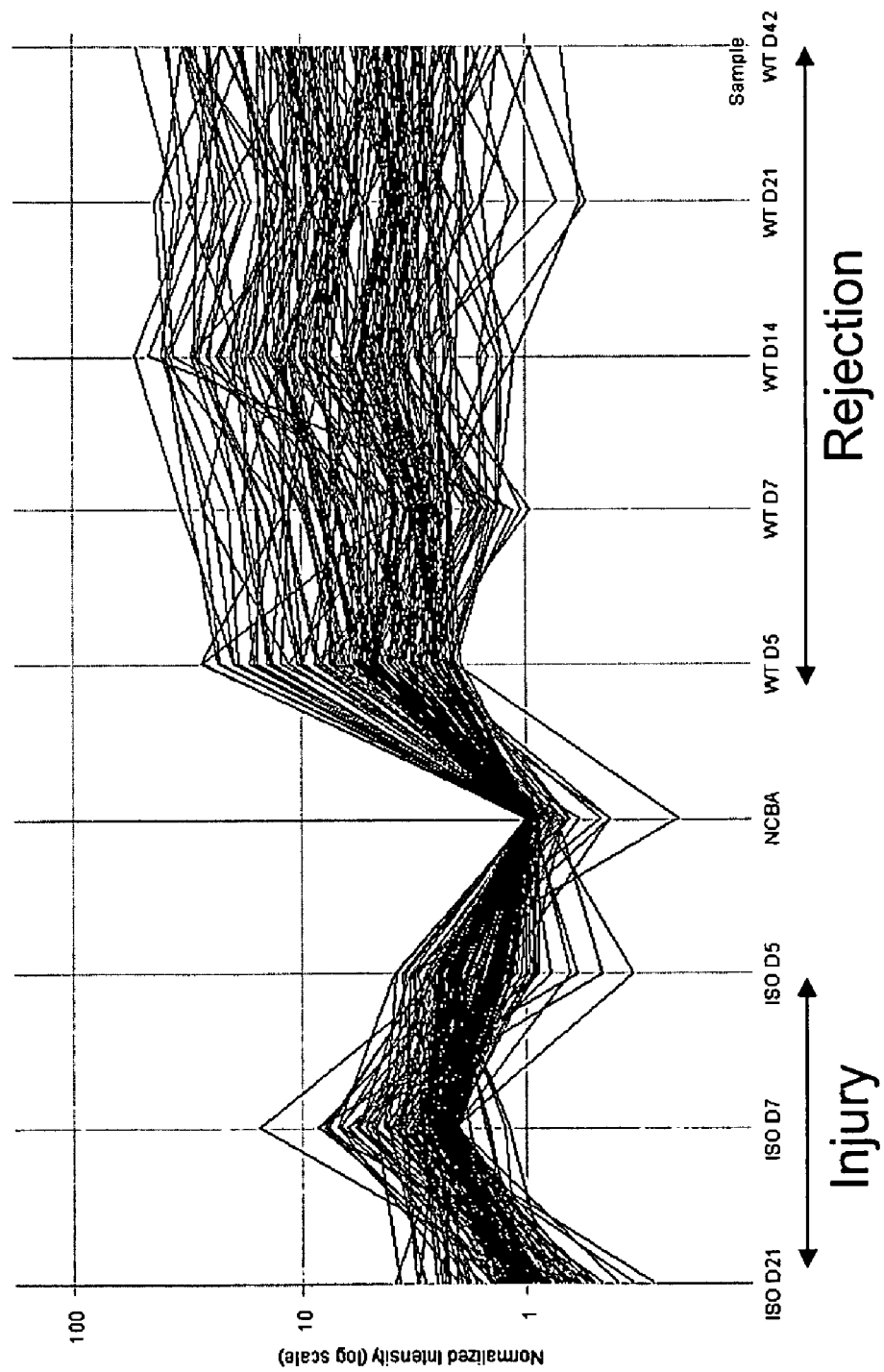
FIG. 5B is a graph showing an expression time course of RIT in injury and rejection. Normalized values are shown. Clustering was based on distance as the similarity measure. ISO—isografts, WT—allografts, NCBA—control kidneys.

The analysis yielded many transcripts that behaved like the GRIT-like transcripts, with a peak at day 7 and consistent high expression in all allografts. As listed in Table 7, 147 injury-induced RITs met these conditions in Moe 430A database. Unsupervised clustering based on this list grouped ISO D7 samples with the allografts (FIG. 5A). Expression pattern of these transcripts confirmed the clustering result. Injury-induced RITs peaked in ISO D7 isografts rather than ISO D5 (FIG. 5B; significant by Anova). One hundred forty RITs were increased 2-fold or more at ISO D7, including the acute-phase response markers: serum amyloids 1-3 and ceruloplasmin, while 54 were increased at ISO D5. The mean expression of RITs was more elevated and sustained in the allografts compared to ISO D7 and ISO D5, with a peak in WT D14 allografts (FIG. 5B, significant by Anova). A Medline-assisted literature search revealed that expression of the injury-induced RITs transcripts could be dependent on either IFN-γ or Tgfb1, or both. IFN-γ control was reported for Vim, Ccl2, Arrb2 (also reported as a possible marker of human heart rejection), ceruloplasmin, Fn1, Fos, Socs3, Timp1, Ncf2, Fcgr3, Plek, and Casp12. Tgfb1 control was reported for transcripts Tgfbi, collagen type 1a2 and 3a1, Socs3, Lox, Cspg2, Fn1, Postn (periostin, homologous to Tgfbi) (Table 8).

Figure 6A:
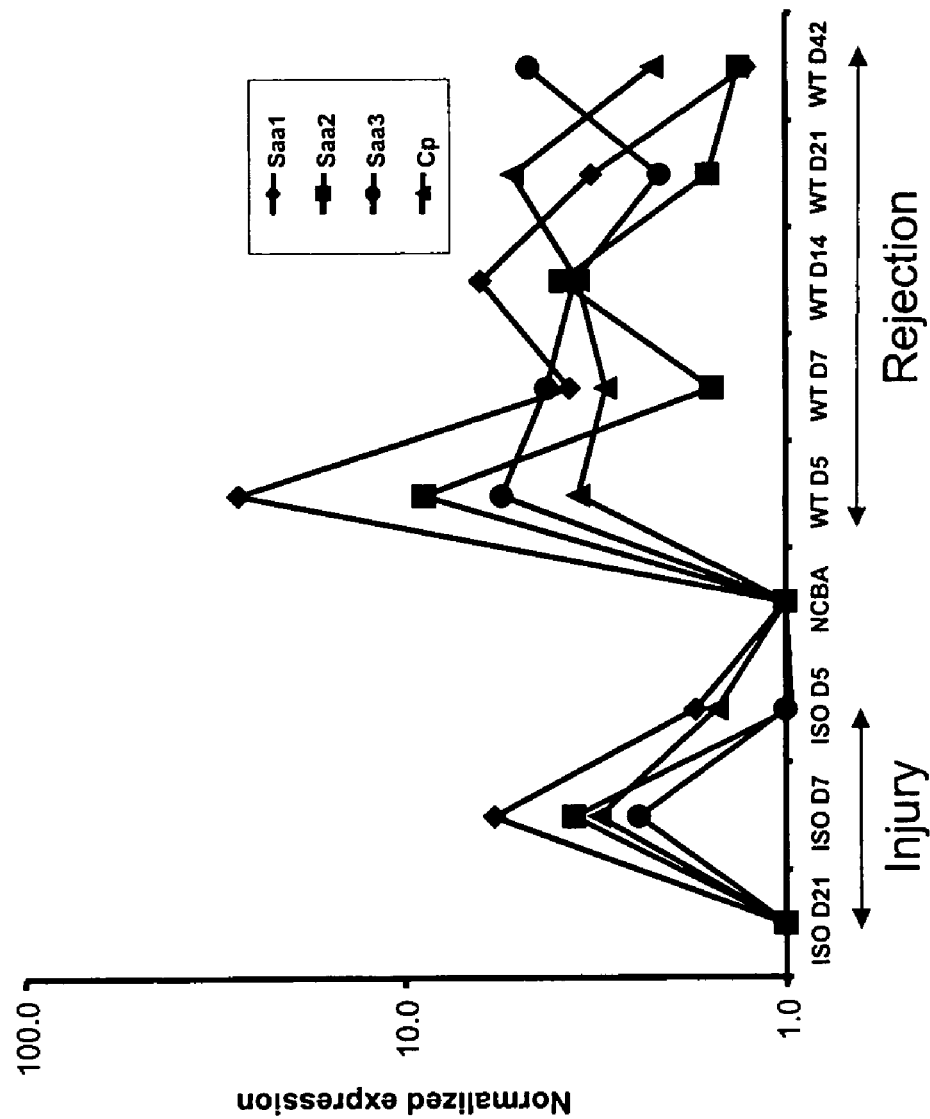
FIG. 6A is a graph showing expression profiles of acute phase markers in isografts and allografts.
Figure 6B:
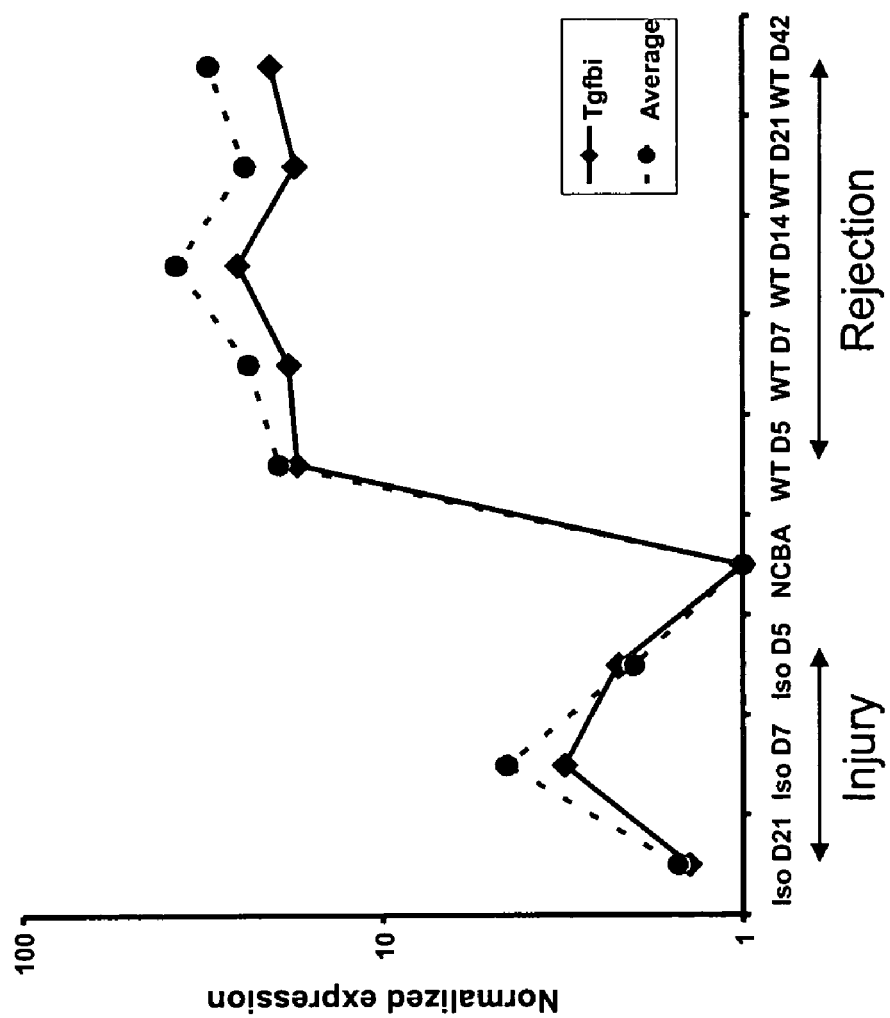
FIG. 6B is a graph showing the expression profiles of Tgfbi and the average expression profile of injury-induced RIT in isografts and allografts. Normalized values are shown in both graphs. ISO—isografts, WT—allografts, NCBA—control kidneys.

The expression profiles of these transcripts were then analyzed, and it was observed that the average expression pattern of injury-induced RITs was significantly similar to the Tgfbi expression profile, as assessed by the trajectory profiling i.e. "find similar gene(s)" feature of GeneSpring (FIGS. 6A and 6B). Next, the expression profiles of a selected prototypic GRIT (Stat1, which was elevated in isografts) and a prototypic GRIT-like transcript (Tgfbi) were compared to the expression profiles of injury-induced RITs. Using the trajectory clustering, 50 transcripts were found with patterns similar to that of Tgfbi (FIG. 7A), and 43 transcripts were found with patterns similar to that of STAT-1 (FIG. 7B). RITs showing Stat-1-like profiles had substantial overlap (39 transcripts) with Tgfbi-like profiles.

TABLE 1 rIFN-γ-induced transcripts (GITs)

| Gene Symbol Affymetrix | Gene Title Affymetrix | NCBA Raw | rIFNg vs NCBA | Genbank |
|---|---|---|---|---|
| — | — | 1241 | 3.2 | AV290571 |
| — | — | 855 | 3.0 | AV227574 |
| — | — | 12 | 2.2 | BB416480 |
| — | — | 127 | 2.0 | BB291656 |
| — | — | 219 | 3.0 | BB533460 |
| — | — | 25 | 2.8 | AW554440 |
| — | — | 83 | 2.3 | BB308208 |
| Oasl2 | 2'-5' oligoadenylate synthetase-like 2 | 209 | 2.2 | BQ033138 |
| Hmgcr | 3-hydroxy-3-methylglutaryl-Coenzyme A reductase | 291 | 2.8 | BB123978 |
| Hmgcs2 | 3-hydroxy-3-methylglutaryl-Coenzyme A synthase 2 | 83 | 5.8 | BC014714 |
| Arf3 | ADP-ribosylation factor 3 | 107 | 2.6 | BQ175059 |
| Akr1c18 | aldo-keto reductase family 1, member C18 | 314 | 7.9 | NM_134066 |
| Akr1c20 | aldo-keto reductase family 1, member C20 | 28 | 15.8 | BC021607 |
| Angptl3 | angiopoietin-like 3 | 253 | 3.7 | BC019491 |
| Arg2 | arginase type II | 85 | 9.3 | AV002218 |

TABLE 1-continued rIFN-γ-induced transcripts (GITs)

| Gene Symbol Affymetrix | Gene Title Affymetrix | NCBA Raw | rIFNg vs NCBA | Genbank |
|---|---|---|---|---|
| Arvcf | armadillo repeat gene deleted in velo-cardio-facial syndrome | 153 | 2.0 | BE947943 |
| Astn1 | astrotactin 1 | 21 | 2.7 | NM_007495 |
| Atp8a1 | ATPase, aminophospholipid transporter (APLT), class I, type 8A, member 1 | 150 | 2.1 | BQ176779 |
| Atp1a2 | ATPase, Na+/K+ transporting, alpha 2 polypeptide | 33 | 3.3 | AV325919 |
| Abcb1a | ATP-binding cassette, sub-family B (MDR/TAP), member 1A | 40 | 3.9 | M30697 |
| Abcb1a | ATP-binding cassette, sub-family B (MDR/TAP), member 1A | 142 | 3.8 | M30697 |
| Abcc3 | ATP-binding cassette, sub-family C (CFTR/MRP), member 3 | 130 | 17.7 | AK006128 |
| Bhlhb5 | basic helix-loop-helix domain containing, class B5 | 113 | 2.0 | NM_021560 |
| B2m | beta-2 microglobulin | 9650 | 2.6 | AI099111 |
| B2m | beta-2 microglobulin | 71 | 3.5 | AA170322 |
| B2m | beta-2 microglobulin | 13469 | 2.0 | BF715219 |
| Bhmt | betaine-homocysteine methyltransferase | 331 | 9.6 | NM_016668 |
| Bace | beta-site APP cleaving enzyme | 152 | 4.1 | BB114336 |
| Baat | bile acid-Coenzyme A: amino acid N-acyltransferase | 17 | 11.2 | NM_007519 |
| Cdh11 | cadherin 11 | 381 | 2.0 | NM_009866 |
| Car5a | carbonic anhydrase 5a, mitochondrial | 98 | 2.2 | NM_007608 |
| Cart1 | cartilage homeo protein 1 | 57 | 2.4 | BB366930 |
| Ctss | cathepsin S | 838 | 2.6 | NM_021281 |
| BC011209 | cDNA sequence BC011209 | 437 | 2.0 | BC011209 |
| BC021340 | cDNA sequence BC021340 | 256 | 2.2 | BC021340 |
| BC060267 | cDNA sequence BC060267 | 59 | 2.2 | BB124106 |
| Ceacam1 | CEA-related cell adhesion molecule 1 | 296 | 3.0 | M77196 |
| Ceacam1 | CEA-related cell adhesion molecule 1 | 377 | 2.3 | BC016891 |
| Ceacam1 | CEA-related cell adhesion molecule 1 | 670 | 2.5 | NM_011926 |
| Ceacam2 | CEA-related cell adhesion molecule 2 | 100 | 3.1 | NM_007543 |
| Ceacam2 | CEA-related cell adhesion molecule 2 | 733 | 2.6 | BC024320 |
| Cp | ceruloplasmin | 232 | 2.1 | BB332449 |
| Ccl21a | chemokine (C—C motif) ligand 21a (serine) | 368 | 2.0 | NM_011335 |
| Ccl5 | chemokine (C—C motif) ligand 5 | 34 | 6.0 | NM_013653 |
| Ccl8 | chemokine (C—C motif) ligand 8 | 115 | 2.3 | NM_021443 |
| Ccr5 | chemokine (C—C motif) receptor 5 | 73 | 2.6 | D83648 |
| Cxcl10 | chemokine (C—X—C motif) ligand 10 | 162 | 2.2 | NM_021274 |
| Cxcl12 | chemokine (C—X—C motif) ligand 12 | 1335 | 2.2 | NM_013655 |
| Cxcl14 | chemokine (C—X—C motif) ligand 14 | 260 | 2.1 | AF252873 |
| Cxcl14 | chemokine (C—X—C motif) ligand 14 | 124 | 2.4 | AF252873 |
| Cxcl9 | chemokine (C—X—C motif) ligand 9 | 125 | 6.5 | NM_008599 |
| CRAD-L | cis-retinol/3alpha hydroxysterol short-chain dehydrogenase-like | 2243 | 4.5 | BC018263 |
| C2ta | class II transactivator | 89 | 2.0 | AF042158 |
| C1qb | complement component 1, q subcomponent, beta polypeptide | 363 | 2.8 | NM_009777 |
| C1qg | complement component 1, q subcomponent, gamma polypeptide | 185 | 4.0 | NM_007574 |
| C1r | complement component 1, r subcomponent | 148 | 2.8 | BB558917 |
| C1r | complement component 1, r subcomponent | 382 | 3.1 | NM_023143 |
| C1s | complement component 1, s subcomponent | 395 | 2.3 | BC022123 |
| C2 | complement component 2 (within H-2S) | 1215 | 2.6 | NM_013484 |
| Coro1a | coronin, actin binding protein 1A | 168 | 2.2 | BB740218 |
| Coro1a | coronin, actin binding protein 1A | 239 | 2.2 | BC002136 |
| Cugbp2 | CUG triplet repeat, RNA binding protein 2 | 161 | 2.1 | BB644164 |
| Cdkn1c | cyclin-dependent kinase inhibitor 1C (P57) | 367 | 2.1 | NM_009876 |
| Cox8b | cytochrome c oxidase, subunit VIIIb | 47 | 6.0 | NM_007751 |
| Cyp4a10 | cytochrome P450, family 4, subfamily a, polypeptide 10 | 573 | 2.0 | BC013476 |
| Cyp4a14 | cytochrome P450, family 4, subfamily a, polypeptide 14 | 47 | 148.5 | AI327006 |
| Dach1 | dachshund 1 (Drosophila) | 91 | 2.0 | BB522228 |
| Dock10 | dedicator of cytokinesis 10 | 145 | 2.6 | BF715043 |
| D10Bwg1379e | DNA segment, Chr 10, Brigham & Women's Genetics 1379 expressed | 25 | 3.9 | BB125269 |
| D12Ertd647e | DNA segment, Chr 12, ERATO Doi 647, expressed | 953 | 4.9 | AW554405 |

TABLE 1-continued rIFN-γ-induced transcripts (GITs)

| Gene Symbol Affymetrix | Gene Title Affymetrix | NCBA Raw | rIFNg vs NCBA | Genbank |
|---|---|---|---|---|
| D12Ertd647e | DNA segment, Chr 12, ERATO Doi 647, expressed | 1414 | 3.4 | BI655075 |
| D3Bwg0562e | DNA segment, Chr 3, Brigham & Women's Genetics 0562 expressed | 52 | 2.4 | BQ175587 |
| D3Bwg0562e | DNA segment, Chr 3, Brigham & Women's Genetics 0562 expressed | 178 | 3.1 | BB238462 |
| D7Bwg0421e | DNA segment, Chr 7, Brigham & Women's Genetics 0421 expressed | 64 | 2.0 | AK017222 |
| Duf6 | DUF6 containing protein | 112 | 2.2 | BB758319 |
| Edaradd | EDAR (ectodysplasin-A receptor)-associated death domain | 28 | 3.1 | NM_133643 |
| Emr4 | EGF-like module containing, mucin-like, hormone receptor-like sequence 4 | 20 | 3.5 | AF396935 |
| Elovl2 | elongation of very long chain fatty acids (FEN1/Elo2, SUR4/Elo3, yeast)-like 2 | 951 | 2.3 | NM_019423 |
| Elovl6 | ELOVL family member 6, elongation of long chain fatty acids (yeast) | 323 | 3.2 | NM_130450 |
| Enah | enabled homolog (Drosophila) | 81 | 2.1 | AV329519 |
| Ednra | endothelin receptor type A | 18 | 3.6 | BC008277 |
| Eva | epithelial V-like antigen | 371 | 2.0 | BC015076 |
| Eva | epithelial V-like antigen | 490 | 2.0 | BC015076 |
| AI481100 | expressed sequence AI481100 | 365 | 5.2 | NM_019440 |
| AI788959 | expressed sequence AI788959 | 914 | 2.8 | BC028826 |
| AI789751 | expressed sequence AI789751 | 326 | 9.9 | AI789751 |
| AI987712 | expressed sequence AI987712 | 92 | 28.2 | AW554594 |
| AU040377 | expressed sequence AU040377 | 141 | 2.1 | AV024806 |
| AW111922 | expressed sequence AW111922 | 361 | 8.0 | BM239828 |
| AW111922 | expressed sequence AW111922 | 885 | 7.5 | BM239828 |
| AW413625 | expressed sequence AW413625 | 80 | 2.7 | NM_026640 |
| Fabp7 | fatty acid binding protein 7, brain | 795 | 2.1 | NM_021272 |
| Facl2 | fatty acid Coenzyme A ligase, long chain 2 | 5896 | 2.3 | BC006927 |
| Facl2 | fatty acid Coenzyme A ligase, long chain 2 | 1417 | 2.1 | BI413218 |
| Fer1l3 | fer-1-like 3, myoferlin (C. elegans) | 208 | 1.9 | BI555209 |
| Fgl2 | fibrinogen-like protein 2 | 114 | 2.5 | BF136544 |
| Foxd1 | forkhead box D1 | 36 | 2.8 | BB662927 |
| Foxq1 | forkhead box Q1 | 219 | 2.5 | NM_008239 |
| Foxq1 | forkhead box Q1 | 142 | 3.8 | AV009267 |
| Gpr135 | G protein-coupled receptor 135 | 45 | 2.9 | AV221890 |
| Gsto1 | glutathione S-transferase omega 1 | 1328 | 2.1 | AV003026 |
| Gpm6b | glycoprotein m6b | 232 | 2.2 | AK016567 |
| Gzma | granzyme A | 68 | 3.6 | NM_010370 |
| Gc | group specific component | 554 | 6.0 | AI195150 |
| Gbp2 | guanylate nucleotide binding protein 2 | 321 | 23.0 | NM_010260 |
| Gbp2 | guanylate nucleotide binding protein 2 | 272 | 22.9 | BE197524 |
| Hck | hemopoietic cell kinase | 117 | 2.1 | NM_010407 |
| Hdgfrp3 | hepatoma-derived growth factor, related protein 3 | 93 | 2.6 | BB291880 |
| H2-Aa | histocompatibility 2, class II antigen A, alpha | 2137 | 4.3 | AF119253 |
| H2-Aa | histocompatibility 2, class II antigen A, alpha | 3501 | 4.3 | BE688749 |
| H2-Ab1 | histocompatibility 2, class II antigen A, beta 1 | 421 | 8.2 | M15848 |
| H2-Ab1 | histocompatibility 2, class II antigen A, beta 1 | 950 | 7.9 | NM_010379 |
| H2-Ab1 | histocompatibility 2, class II antigen A, beta 1 | 659 | 10.9 | M15848 |
| H2-Eb1 | histocompatibility 2, class II antigen E beta | 1760 | 3.7 | NM_010382 |
| H2-DMa | histocompatibility 2, class II, locus DMa | 261 | 9.0 | NM_010386 |
| H2-DMb1 | histocompatibility 2, class II, locus Mb1 | 121 | 14.5 | NM_010388 |
| H2-DMb1 | histocompatibility 2, class II, locus Mb1 | 159 | 15.2 | BB734586 |
| H2-DMb1 | histocompatibility 2, class II, locus Mb1 | 116 | 8.9 | NM_010387 |
| H2-DMb1 | histocompatibility 2, class II, locus Mb1 | 87 | 20.1 | BB734586 |
| H2-DMb1 | histocompatibility 2, class II, locus Mb1 | 347 | 7.4 | NM_010388 |
| H2-K | histocompatibility 2, K region | 626 | 10.3 | L23495 |
| H2-T10 | histocompatibility 2, T region locus 10 | 2355 | 2.3 | NM_010395 |
| H2-T23 | histocompatibility 2, T region locus 23 | 2198 | 5.2 | NM_010398 |
| Hist1h2ae | histone 1, H2ae | 525 | 2.3 | W91024 |
| Hoxd3 | homeo box D3 | 127 | 1.9 | J03770 |
| Hrasls3 | HRAS like suppressor 3 | 504 | 6.9 | BC024581 |
| Hrasls3 | HRAS like suppressor 3 | 372 | 7.1 | BB404920 |
| Hpgd | hydroxyprostaglandin dehydrogenase 15 (NAD) | 556 | 2.7 | AV026552 |

TABLE 1-continued rIFN-γ-induced transcripts (GITs)

| Gene Symbol Affymetrix | Gene Title Affymetrix | NCBA Raw | rIFNg vs NCBA | Genbank |
|---|---|---|---|---|
| 9830126M18 | hypothetical protein 9830126M18 | 113 | 2.0 | BM224662 |
| A330067P21 | hypothetical protein A330067P21 | 65 | 2.0 | BG085812 |
| A330075D07 | hypothetical protein A330075D07 | 34 | 2.7 | BB193024 |
| D630002G06 | hypothetical protein D630002G06 | 712 | 6.1 | AB056443 |
| D630002G06 | hypothetical protein D630002G06 | 650 | 5.4 | AB056443 |
| D630002G06 | hypothetical protein D630002G06 | 136 | 3.6 | NM_134256 |
| D730019B10 | hypothetical protein D730019B10 | 23 | 2.5 | BB508669 |
| MGC6357 | hypothetical protein MGC6357 | 68 | 2.2 | BB667558 |
| Ii | Ia-associated invariant chain | 3790 | 4.3 | BC003476 |
| Idb3 | inhibitor of DNA binding 3 | 1075 | 2.1 | NM_008321 |
| Idb4 | inhibitor of DNA binding 4 | 175 | 2.1 | BB306828 |
| Idb4 | inhibitor of DNA binding 4 | 1179 | 2.2 | BB121406 |
| Igf1 | insulin-like growth factor 1 | 398 | 2.1 | BG092677 |
| Igfals | insulin-like growth factor binding protein, acid labile subunit | 214 | 2.4 | NM_008340 |
| Itga6 | integrin alpha 6 | 2198 | 2.0 | BM935811 |
| Itgax | integrin alpha X | 80 | 2.6 | NM_021334 |
| Igtp | interferon gamma induced GTPase | 905 | 5.6 | NM_018738 |
| Ifi1 | interferon inducible protein 1 | 1151 | 3.8 | NM_008326 |
| Irf7 | interferon regulatory factor 7 | 198 | 4.0 | NM_016850 |
| G1p2 | interferon, alpha-inducible protein | 112 | 3.3 | AK019325 |
| Ifit1 | interferon-induced protein with tetratricopeptide repeats 1 | 93 | 6.2 | NM_008331 |
| Ifit2 | interferon-induced protein with tetratricopeptide repeats 2 | 271 | 2.9 | NM_008332 |
| Il18bp | interleukin 18 binding protein | 122 | 12.2 | AF110803 |
| Kcnip2 | Kv channel-interacting protein 2 | 94 | 2.8 | AW490636 |
| Kcnip2 | Kv channel-interacting protein 2 | 28 | 2.8 | AF439339 |
| Kynu | kynureninase (L-kynurenine hydrolase) | 202 | 4.1 | AV227891 |
| Lrp8 | low density lipoprotein receptor-related protein 8, apolipoprotein e receptor | 84 | 2.8 | BB750940 |
| Ly6e | lymphocyte antigen 6 complex, locus E | 1793 | 3.2 | BM245572 |
| Ly6f | lymphocyte antigen 6 complex, locus F | 24 | 7.1 | NM_008530 |
| — | M. musculus mRNA for testis-specific thymosin beta-10 | 4515 | 2.1 | AV148480 |
| Mpeg1 | macrophage expressed gene 1 | 402 | 4.5 | L20315 |
| Mme | membrane metallo endopeptidase | 2038 | 2.0 | AV174022 |
| Ms4a11 | membrane-spanning 4-domains, subfamily A, member 11 | 50 | 2.3 | NM_026835 |
| Ms4a4d | membrane-spanning 4-domains, subfamily A, member 4D | 96 | 2.6 | NM_025658 |
| Ms4a6b | membrane-spanning 4-domains, subfamily A, member 6B | 126 | 2.8 | NM_027209 |
| — | MHC I = H-2Kd homolog {alternatively spliced, deletion of exon 3} [mice, DBA/2, L1210 lymphoma, mRNA Mutant, 855 nt] | 435 | 10.0 | S70184 |
| Mmd | monocyte to macrophage differentiation-associated | 662 | 2.3 | BC021914 |
| — | Mus musculus 0 day neonate head cDNA, RIKEN full-length enriched library, clone: 4833430O13 product: unknown EST, full insert sequence | 420 | 2.5 | BB109391 |
| — | Mus musculus 0 day neonate kidney cDNA, RIKEN full-length enriched library, clone: D630024M22 product: unclassifiable, full insert sequence | 39 | 2.3 | BB500101 |
| — | Mus musculus 0 day neonate kidney cDNA, RIKEN full-length enriched library, clone: D630033M22 product: hypothetical protein, full insert sequence | 153 | 2.1 | BB820846 |
| — | Mus musculus 0 day neonate kidney cDNA, RIKEN full-length enriched library, clone: D630047M14 product: unclassifiable, full insert sequence | 54 | 2.9 | BB504342 |
| — | Mus musculus 0 day neonate lung cDNA, RIKEN full-length enriched library, clone: E030022N22 product: unclassifiable, full insert sequence | 70 | 2.0 | BI452538 |
| — | Mus musculus 0 day neonate thymus cDNA, RIKEN full-length enriched library, clone: A430110A21 product: unclassifiable, full insert sequence | 112 | 2.7 | AK020789 |

TABLE 1-continued rIFN-γ-induced transcripts (GITs)

| Gene Symbol Affymetrix | Gene Title Affymetrix | NCBA Raw | rIFNg vs NCBA | Genbank |
|---|---|---|---|---|
| — | *Mus musculus* 10 days neonate cerebellum cDNA, RIKEN full-length enriched library, clone: B930059K21 product: unknown EST, full insert sequence | 38 | 2.7 | BM201103 |
| — | *Mus musculus* 12 days embryo spinal ganglion cDNA, RIKEN full-length enriched library, clone: D130028L22 product: unclassifiable, full insert sequence | 56 | 2.0 | BB454099 |
| — | *Mus musculus* 16 days embryo head cDNA, RIKEN full-length enriched library, clone: C130051K14 product: unknown EST, full insert sequence | 110 | 2.3 | BB208251 |
| — | *Mus musculus* 16 days embryo head cDNA, RIKEN full-length enriched library, clone: C130077H22 product: unclassifiable, full insert sequence | 71 | 2.6 | BB374879 |
| — | *Mus musculus* 16 days neonate cerebellum cDNA, RIKEN full-length enriched library, clone: 9630032E14 product: unknown EST, full insert sequence | 128 | 2.1 | AV118079 |
| — | *Mus musculus* 16 days neonate thymus cDNA, RIKEN full-length enriched library, clone: A130086M19 product: unknown EST, full insert sequence | 56 | 2.4 | BB162048 |
| — | *Mus musculus* 18-day embryo whole body cDNA, RIKEN full-length enriched library, clone: 1110059G02 product: unclassifiable, full insert sequence | 157 | 2.2 | BM730637 |
| — | *Mus musculus* 2 days pregnant adult female oviduct cDNA, RIKEN full-length enriched library, clone: E230038I17 product: unknown EST, full insert sequence | 55 | 2.2 | BB053468 |
| — | *Mus musculus* 3 days neonate thymus cDNA, RIKEN full-length enriched library, clone: A630040D01 product: unknown EST, full insert sequence | 172 | 2.8 | BI151331 |
| — | *Mus musculus* 4 days neonate male adipose cDNA, RIKEN full-length enriched library, clone: B430203I24 product: unknown EST, full insert sequence | 87 | 2.0 | BB326079 |
| — | *Mus musculus* 6 days neonate head cDNA, RIKEN full-length enriched library, clone: 5430440L12 product: unknown EST, full insert sequence | 85 | 2.1 | AK017417 |
| — | *Mus musculus* 7 days embryo whole body cDNA, RIKEN full-length enriched library, clone: C430005H19 product: unknown EST, full insert sequence | 124 | 2.2 | BB408240 |
| — | *Mus musculus* adult male bone cDNA, RIKEN full-length enriched library, clone: 9830116N24 product: unclassifiable, full insert sequence | 55 | 2.3 | BB134628 |
| — | *Mus musculus* adult male corpora quadrigemina cDNA, RIKEN full-length enriched library, clone: B230339M22 product: inhibitor of DNA binding 4, full insert sequence | 64 | 2.6 | AI323288 |
| — | *Mus musculus* adult male medulla oblongata cDNA, RIKEN full-length enriched library, clone: 6330531L09 product: unknown EST, full insert sequence | 26 | 2.2 | AV332226 |
| — | *Mus musculus* adult male olfactory brain cDNA, RIKEN full-length enriched library, clone: 6430566E03 product: unknown EST, full insert sequence | 26 | 1.9 | AV237721 |
| — | *Mus musculus* Corpos mRNA, 3' untranslated region | 59 | 2.2 | BM220939 |
| — | *Mus musculus* NOD-derived CD11c +ve dendritic cells cDNA, RIKEN full-length enriched library, clone: F630107D10 product: similar to UBIQUITIN-ACTIVATING ENZYME E1 [*Homo sapiens*], full insert sequence | 223 | 2.1 | AK004894 |

TABLE 1-continued rIFN-γ-induced transcripts (GITs)

| Gene Symbol Affymetrix | Gene Title Affymetrix | NCBA Raw | rIFNg vs NCBA | Genbank |
|---|---|---|---|---|
| — | *Mus musculus* similar to Aldo-keto reductase family 1 member C13 (LOC238465), mRNA | 907 | 2.1 | BG073853 |
| — | *Mus musculus* similar to hypothetical protein (LOC243374), mRNA | 716 | 2.5 | BM243674 |
| — | *Mus musculus* similar to hypothetical protein FLJ31208 (LOC225602), mRNA | 25 | 2.4 | BE197771 |
| — | *Mus musculus* transcribed sequence | 31 | 3.5 | AI790337 |
| — | *Mus musculus* transcribed sequence with strong similarity to protein sp: P00722 (*E. coli*) BGAL__ECOLI Beta-galactosidase (Lactase) | 47 | 3.3 | BG063622 |
| — | *Mus musculus* transcribed sequence with weak similarity to protein ref: NP__036400.1 (*H. sapiens*) similar to vaccinia virus HindIII K4L ORF [Homo sapiens] | 44 | 4.7 | BB210623 |
| — | *Mus musculus* transcribed sequence with weak similarity to protein sp: P32456 (*H. sapiens*) GBP2__HUMAN Interferon-induced guanylate-binding protein 2 (Guanine nucleotide-binding protein 2) | 191 | 45.8 | BM241485 |
| — | *Mus musculus* transcribed sequences | 35 | 2.5 | BB460538 |
| — | *Mus musculus* transcribed sequences | 90 | 2.1 | BB485280 |
| — | *Mus musculus* transcribed sequences | 46 | 2.0 | BM218007 |
| — | *Mus musculus* transcribed sequences | 87 | 3.4 | AV277444 |
| — | *Mus musculus* transcribed sequences | 438 | 4.5 | BE688358 |
| — | *Mus musculus* transcribed sequences | 182 | 2.1 | AW492955 |
| — | *Mus musculus* transcribed sequences | 58 | 4.5 | BI134319 |
| — | *Mus musculus* transcribed sequences | 91 | 2.0 | BB497148 |
| — | *Mus musculus* transcribed sequences | 63 | 2.4 | BG069383 |
| — | *Mus musculus* transcribed sequences | 67 | 2.1 | BM220820 |
| — | *Mus musculus* transcribed sequences | 25 | 2.2 | BB553888 |
| — | *Mus musculus* transcribed sequences | 18 | 2.2 | BB767194 |
| — | *Mus musculus* transcribed sequences | 44 | 2.0 | BM730703 |
| — | *Mus musculus* transcribed sequences | 102 | 1.9 | BG068971 |
| — | *Mus musculus* transcribed sequences | 339 | 27.6 | BG092512 |
| — | *Mus musculus* transcribed sequences | 130 | 2.0 | AW546127 |
| — | *Mus musculus* transcribed sequences | 72 | 2.3 | AW543171 |
| — | *Mus musculus* transcribed sequences | 150 | 2.1 | BI664122 |
| — | *Mus musculus* transcribed sequences | 193 | 2.0 | AV291009 |
| — | *Mus musculus* transcribed sequences | 54 | 2.0 | AU041975 |
| — | *Mus musculus* transcribed sequences | 95 | 2.0 | AV352204 |
| — | *Mus musculus* transcribed sequences | 20 | 2.1 | BB043509 |
| — | *Mus musculus* transcribed sequences | 217 | 2.0 | BM119402 |
| — | *Mus musculus* transcribed sequences | 32 | 2.5 | AV300631 |
| — | *Mus musculus* transcribed sequences | 82 | 4.6 | BG067157 |
| — | *Mus musculus* transcribed sequences | 115 | 2.2 | AW111920 |
| — | *Mus musculus* transcribed sequences | 35 | 3.5 | BM225081 |
| — | *Mus musculus* transcribed sequences | 133 | 2.0 | AW556334 |
| — | *Mus musculus* transcribed sequences | 27 | 3.0 | AI118114 |
| — | *Mus musculus* transcribed sequences | 18 | 3.1 | BB520952 |
| — | *Mus musculus* transcribed sequences | 142 | 2.2 | AV264768 |
| — | *Mus musculus*, clone IMAGE: 4507681, mRNA | 32 | 3.0 | BG071655 |
| Mll | myeloid/lymphoid or mixed-lineage leukemia | 128 | 2.1 | AK017541 |
| Npnt | nephronectin | 1459 | 2.0 | AA223007 |
| Npnt | nephronectin | | | BB433705 |
| Ntf3 | neurotrophin 3 | 49 | 3.3 | NM__008742 |
| Odz3 | odd Oz/ten-m homolog 3 (*Drosophila*) | 9 | 3.2 | BB472509 |
| Olfr56 | olfactory receptor 56 | 336 | 3.4 | NM__008330 |
| Padi2 | peptidyl arginine deiminase, type II | 110 | 3.0 | NM__008812 |
| Ppicap | peptidylprolyl isomerase C-associated protein | 1079 | 3.2 | NM__011150 |
| Pte2a | peroxisomal acyl-CoA thioesterase 2A | 780 | 2.7 | NM__134246 |
| Pck1 | phosphoenolpyruvate carboxykinase 1, cytosolic | 46 | 6.8 | BB225177 |
| Pik3ap1 | phosphoinositide-3-kinase adaptor protein 1 | 64 | 3.0 | BI684288 |
| Pigr | polymeric immunoglobulin receptor | 3030 | 2.1 | AV027632 |
| Kcnk1 | potassium channel, subfamily K, member 1 | 708 | 4.0 | AU043100 |
| Prickle1 | prickle like 1 (*Drosophila*) | 144 | 2.3 | BC022643 |
| Prickle1 | prickle like 1 (*Drosophila*) | 40 | 2.9 | BE992966 |
| Pdcd1lg1 | programmed cell death 1 ligand 1 | 73 | 4.4 | NM__021893 |

TABLE 1-continued rIFN-γ-induced transcripts (GITs)

| Gene Symbol Affymetrix | Gene Title Affymetrix | NCBA Raw | rIFNg vs NCBA | Genbank |
|---|---|---|---|---|
| Prom1 | prominin 1 | 2598 | 2.7 | NM_008935 |
| Psmb10 | proteasome (prosome, macropain) subunit, beta type 10 | 525 | 3.2 | NM_013640 |
| Psmb8 | proteosome (prosome, macropain) subunit, beta type 8 (large multifunctional protease 7) | 17 | 5.1 | AV068122 |
| Psmb8 | proteosome (prosome, macropain) subunit, beta type 8 (large multifunctional protease 7) | 461 | 9.9 | NM_010724 |
| Psmb9 | proteosome (prosome, macropain) subunit, beta type 9 (large multifunctional protease 2) | 298 | 4.5 | NM_013585 |
| Arhgef6 | Rac/Cdc42 guanine nucleotide exchange factor (GEF) 6 | 142 | 2.8 | BM246754 |
| Rai2 | retinoic acid induced 2 | 59 | 2.0 | BB770528 |
| 1110004C05Rik | RIKEN cDNA 1110004C05 gene | 3701 | 2.3 | BC010291 |
| 1110036C17Rik | RIKEN cDNA 1110036C17 gene | 622 | 2.7 | BC027285 |
| 1110036O03Rik | RIKEN cDNA 1110036O03 gene | 115 | 2.0 | BE951265 |
| 1110063G11Rik | RIKEN cDNA 1110063G11 gene | 81 | 2.0 | AK004359 |
| 1190005J19Rik | RIKEN cDNA 1190005J19 gene | 31 | 2.0 | NM_007819 |
| 1200015N20Rik | RIKEN cDNA 1200015N20 gene | 39 | 2.2 | BB461323 |
| 1600020H07Rik | RIKEN cDNA 1600020H07 gene | 1301 | 2.7 | NM_019975 |
| 1700003F17Rik | RIKEN cDNA 1700003F17 gene | 64 | 2.9 | AV220213 |
| 1700007J06Rik | RIKEN cDNA 1700007J06 gene | 27 | 2.2 | AK005720 |
| 1700019D03Rik | RIKEN cDNA 1700019D03 gene | 20 | 2.4 | AK006110 |
| 1810037B05Rik | RIKEN cDNA 1810037B05 gene | 50 | 3.0 | AK007714 |
| 2010204K13Rik | RIKEN cDNA 2010204K13 gene | 249 | 2.3 | NM_023450 |
| 2310007B03Rik | RIKEN cDNA 2310007B03 gene | 78 | 2.3 | AK009193 |
| 2310008H04Rik | RIKEN cDNA 2310008H04 gene | 246 | 5.7 | BC026877 |
| 2310015I10Rik | RIKEN cDNA 2310015I10 gene | 269 | 5.7 | BC008532 |
| 2310022A04Rik | RIKEN cDNA 2310022A04 gene | 327 | 2.0 | AK007542 |
| 2310035M22Rik | RIKEN cDNA 2310035M22 gene | 44 | 2.2 | NM_025863 |
| 2310046K10Rik | RIKEN cDNA 2310046K10 gene | 63 | 2.2 | AK017174 |
| 2310046K10Rik | RIKEN cDNA 2310046K10 gene | 106 | 2.1 | BF020640 |
| 2310061N23Rik | RIKEN cDNA 2310061N23 gene | 219 | 4.2 | AY090098 |
| 2410041A17Rik | RIKEN cDNA 2410041A17 gene | 556 | 3.4 | NM_133348 |
| 2510038N07Rik | RIKEN cDNA 2510038N07 gene | 161 | 2.5 | AW208668 |
| 2610030H06Rik | RIKEN cDNA 2610030H06 gene | 510 | 2.3 | BB429625 |
| 2700038M07Rik | RIKEN cDNA 2700038M07 gene | 786 | 2.0 | BC019601 |
| 2810002E22Rik | RIKEN cDNA 2810002E22 gene | 543 | 2.2 | NM_133859 |
| 2810030E01Rik | RIKEN cDNA 2810030E01 gene | 76 | 2.1 | BB255999 |
| 3300001H21Rik | RIKEN cDNA 3300001H21 gene | 106 | 2.3 | NM_027334 |
| 4631422C05Rik | RIKEN cDNA 4631422C05 gene | 716 | 1.9 | BI648645 |
| 4930513H15Rik | RIKEN cDNA 4930513H15 gene | 49 | 2.4 | AK017117 |
| 4931406H21Rik | RIKEN cDNA 4931406H21 gene | 75 | 2.0 | BG076071 |
| 4931408A02Rik | RIKEN cDNA 4931408A02 gene | 58 | 3.7 | AK016443 |
| 4933402B14Rik | RIKEN cDNA 4933402B14 gene | 45 | 2.2 | AV278444 |
| 5430425C04Rik | RIKEN cDNA 5430425C04 gene | 44 | 2.9 | AK017334 |
| 5830458K16Rik | RIKEN cDNA 5830458K16 gene | 525 | 2.6 | BC024872 |
| 6330407A03Rik | RIKEN cDNA 6330407A03 gene | 60 | 2.2 | AW519657 |
| 6720477E09Rik | RIKEN cDNA 6720477E09 gene | 132 | 2.3 | BB053506 |
| 9230117N10Rik | RIKEN cDNA 9230117N10 gene | 222 | 2.2 | NM_133775 |
| 9330174J19Rik | RIKEN cDNA 9330174J19 gene | 39 | 4.4 | BE687891 |
| A330021E22Rik | RIKEN cDNA A330021E22 gene | 52 | 2.0 | BB561281 |
| A830021K08Rik | RIKEN cDNA A830021K08 gene | 825 | 2.4 | BB291885 |
| A930021H16Rik | RIKEN cDNA A930021H16 gene | 54 | 2.1 | BB513585 |
| B830010L13Rik | RIKEN cDNA B830010L13 gene | 144 | 2.6 | BB333374 |
| C330012H03Rik | RIKEN cDNA C330012H03 gene | 69 | 2.0 | BB098431 |
| D430019H16Rik | RIKEN cDNA D430019H16 gene | 57 | 2.5 | BM116882 |
| D730043B02Rik | RIKEN cDNA D730043B02 gene | 104 | 2.2 | AK021336 |
| E530005C20Rik | RIKEN cDNA E530005C20 gene | 56 | 2.0 | BB662566 |
| Robo2 | roundabout homolog 2 (Drosophila) | 22 | 2.3 | BB366379 |
| Sall1 | sal-like 1 (Drosophila) | 687 | 2.1 | BB739342 |
| Sema3e | sema domain, immunoglobulin domain (Ig), short basic domain, secreted, (semaphorin) 3E | 60 | 2.0 | NM_011348 |
| Serpina10 | serine (or cysteine) proteinase inhibitor, clade A (alpha-1 antiproteinase, antitrypsin), member 10 | 211 | 7.6 | BC018416 |
| Serpina3g | serine (or cysteine) proteinase inhibitor, clade A, member 3G | 92 | 4.5 | BC002065 |
| Serpinb9 | serine (or cysteine) proteinase inhibitor, clade B, member 9 | 323 | 2.1 | BE686716 |

TABLE 1-continued rIFN-γ-induced transcripts (GITs)

| Gene Symbol Affymetrix | Gene Title Affymetrix | NCBA Raw | rIFNg vs NCBA | Genbank |
|---|---|---|---|---|
| Serping1 | serine (or cysteine) proteinase inhibitor, clade G, member 1 | 2372 | 3.8 | NM_009776 |
| Stard13 | serologically defined colon cancer antigen 13 | 151 | 2.0 | BB667840 |
| Stat1 | signal transducer and activator of transcription 1 | 171 | 3.8 | AW214029 |
| Stat1 | signal transducer and activator of transcription 1 | 915 | 2.7 | AW214029 |
| Stat1 | signal transducer and activator of transcription 1 | 808 | 2.8 | AW214029 |
| Slamf8 | SLAM family member 8 | 27 | 3.3 | BC024587 |
| Slc7a12 | solute carrier family 7 (cationic amino acid transporter, y+ system), member 12 | 290 | 29.4 | NM_080852 |
| Slco2a1 | solute carrier organic anion transporter family, member 2a1 | 349 | 2.1 | NM_033314 |
| Stab2 | stabilin 2 | 230 | 1.9 | NM_138673 |
| Scd1 | stearoyl-Coenzyme A desaturase 1 | 2255 | 5.6 | NM_009127 |
| Scd1 | stearoyl-Coenzyme A desaturase 1 | 389 | 3.5 | NM_009127 |
| Socs2 | suppressor of cytokine signaling 2 | 478 | 3.7 | NM_007706 |
| Socs2 | suppressor of cytokine signaling 2 | 354 | 4.7 | NM_007706 |
| Syt13 | synaptotagmin 13 | 37 | 3.3 | BB244585 |
| Tapbp | TAP binding protein | 2304 | 3.5 | AF043943 |
| Tbx3 | T-box 3 | 58 | 2.1 | BB728182 |
| Tgtp | T-cell specific GTPase | 1220 | 8.9 | NM_011579 |
| Thoc1 | THO complex 1 | 33 | 2.2 | BB647938 |
| Thbs1 | thrombospondin 1 | 727 | 2.1 | AI385532 |
| Tmsb10 | thymosin, beta 10 | 941 | 2.4 | NM_025284 |
| Top2a | topoisomerase (DNA) II alpha | 142 | 2.0 | BM211413 |
| Tle2 | transducin-like enhancer of split 2, homolog of Drosophila E(spl) | 150 | 2.1 | AU067681 |
| Tgfbi | transforming growth factor, beta induced | 294 | 2.3 | NM_009369 |
| Tgfbi | transforming growth factor, beta induced | 229 | 2.5 | NM_009369 |
| Tm4sf3 | transmembrane 4 superfamily member 3 | 124 | 2.1 | C76990 |
| Tap1 | transporter 1, ATP-binding cassette, sub-family B (MDR/TAP) | 127 | 5.7 | AW048052 |
| Tmlhe | trimethyllysine hydroxylase, epsilon | 66 | 1.9 | BC005497 |
| Tpm2 | tropomyosin 2, beta | 307 | 2.1 | BC024358 |
| Tubb2 | tubulin, beta 2 | 969 | 2.3 | BC003475 |
| Tnfsf13b | tumor necrosis factor (ligand) superfamily, member 13b | 101 | 2.4 | NM_033622 |
| Arts1 | type 1 tumor necrosis factor receptor shedding aminopeptidase regulator | 444 | 2.3 | NM_030711 |
| Arts1 | type 1 tumor necrosis factor receptor shedding aminopeptidase regulator | 221 | 2.8 | AV287655 |
| Ubd | ubiquitin D | 121 | 11.5 | NM_023137 |
| Utx | ubiquitously transcribed tetratricopeptide repeat gene, X chromosome | 22 | 2.6 | BB306686 |
| Vcam1 | vascular cell adhesion molecule 1 | 268 | 2.6 | BB250384 |
| Was | Wiskott-Aldrich syndrome homolog (human) | 25 | 3.8 | NM_009515 |
| Xdh | xanthine dehydrogenase | 167 | 4.7 | AV286265 |
| Zbp1 | Z-DNA binding protein 1 | 49 | 5.1 | AK008179 |
| Zdhhc6 | zinc finger, DHHC domain containing 6 | 70 | 2.0 | BB251023 |

TABLE 2

Rejection-induced transcripts (RITs)

| Gene Symbol Affymetrix | Common | Gene Title Affymetrix | NCBA Raw | WT D5 vs NCBA | Genbank |
|---|---|---|---|---|---|
| 0610009C03Rik | 0610009C03Rik | RIKEN cDNA 0610009C03 gene | 538 | 2.0 | AK002371 |
| 0610025L06Rik | 0610025L06Rik | RIKEN cDNA 0610025L06 gene | 277 | 5.2 | AK012581 |
| 0610033I05Rik | 0610033I05Rik | RIKEN cDNA 0610033I05 gene | 407 | 3.0 | BC003333 |
| 0610037M15Rik | 0610037M15Rik | RIKEN cDNA 0610037M15 gene | 169 | 15.6 | BG916808 |
| 0610039P13Rik | 0610039P13Rik | RIKEN cDNA 0610039P13 gene | 141 | 3.4 | BC021548 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | 0910001A06Rik | *Mus musculus* 3 days neonate thymus cDNA, RIKEN full-length enriched library, clone: A630020J17 product: unknown EST, full insert sequence | 60 | 4.2 | BB229269 |
| 0910001A06Rik | 0910001A06Rik | RIKEN cDNA 0910001A06 gene | 663 | 6.7 | BC011343 |
| 0910001A06Rik | 0910001A06Rik | RIKEN cDNA 0910001A06 gene | 63 | 2.3 | AV033641 |
| 1100001H23Rik | 1100001H23Rik | RIKEN cDNA 1100001H23 gene | 988 | 4.4 | NM_025806 |
| 1100001I19Rik | 1100001I19Rik | RIKEN cDNA 1100001I19 gene | 288 | 2.1 | BM119324 |
| 1100001I19Rik | 1100001I19Rik | RIKEN cDNA 1100001I19 gene | 219 | 2.8 | BE949451 |
| 1110006O17Rik | 1110006O17Rik | RIKEN cDNA 1110006O17 gene | 199 | 5.1 | BB736636 |
| 1110007F12Rik | 1110007F12Rik | RIKEN cDNA 1110007F12 gene | 30 | 4.0 | BB765808 |
| 1110007F12Rik | 1110007F12Rik | RIKEN cDNA 1110007F12 gene | 1154 | 3.0 | BC020080 |
| — | 1110007H17Rik | *Mus musculus* 0 day neonate lung cDNA, RIKEN full-length enriched library, clone: E030022F06 product: inferred: exchange factor for ARF6 {*Rattus norvegicus*}, full insert sequence | 97 | 2.1 | BI466783 |
| 1110008F13Rik | 1110008F13Rik | RIKEN cDNA 1110008F13 gene | 16 | 6.7 | AV316605 |
| 1110013L07Rik | 1110013L07Rik | RIKEN cDNA 1110013L07 gene | 165 | 3.0 | BB765852 |
| — | 1110033M05Rik | *Mus musculus* transcribed sequences | 34 | 2.1 | BM220862 |
| 1200002N14Rik | 1200002N14Rik | RIKEN cDNA 1200002N14 gene | 470 | 4.3 | BC021433 |
| 1200008O12Rik | 1200008O12Rik | RIKEN cDNA 1200008O12 gene | 44 | 16.3 | AK004655 |
| 1200009I06Rik | 1200009I06Rik | RIKEN cDNA 1200009I06 gene | 270 | 2.0 | AK005443 |
| 1200013B08Rik | 1200013B08Rik | RIKEN cDNA 1200013B08 gene | 183 | 8.3 | AK004734 |
| 1300002K09Rik | 1300002K09Rik | RIKEN cDNA 1300002K09 gene | 141 | 3.6 | AV222559 |
| 1500001L15Rik | 1500001L15Rik | RIKEN cDNA 1500001L15 gene | 921 | 2.1 | BB559925 |
| 1500002B03Rik | 1500002B03Rik | RIKEN cDNA 1500002B03 gene | 175 | 2.4 | AK005105 |
| 1500004A08Rik | 1500004A08Rik | RIKEN cDNA 1500004A08 gene | 219 | 2.3 | BB030508 |
| 1500031M22Rik | 1500031M22Rik | RIKEN cDNA 1500031M22 gene | 119 | 2.1 | AK015145 |
| 1700013H19Rik | 1700013H19Rik | RIKEN cDNA 1700013H19 gene | 144 | 2.3 | AK005954 |
| 1700022C02Rik | 1700022C02Rik | RIKEN cDNA 1700022C02 gene | 24 | 3.9 | AK014919 |
| 1700025G04Rik | 1700025G04Rik | RIKEN cDNA 1700025G04 gene | 110 | 2.0 | AW557527 |
| 1700001M19Rik | 1700029K01Rik | RIKEN cDNA 1700001M19 gene | 59 | 2.0 | BG075808 |
| 1700047I17Rik | 1700047I17Rik | RIKEN cDNA 1700047I17 gene | 65 | 3.8 | BB824055 |
| 1700061I17Rik | 1700061I17Rik | RIKEN cDNA 1700061I17 gene | 27 | 2.5 | AK006854 |
| — | 1700091G21Rik | *Mus musculus* 16 days neonate thymus cDNA, RIKEN full-length enriched library, clone: A130042K22 product: unknown EST, full insert sequence | 97 | 4.3 | BG075562 |
| 1700095N21Rik | 1700095N21Rik | RIKEN cDNA 1700095N21 gene | 151 | 2.3 | NM_029682 |
| — | 1700097N02Rik | *Mus musculus* adult male testis cDNA, RIKEN full-length enriched library, clone: 1700122G02 product: unknown EST, full insert sequence | 16 | 5.0 | AA266367 |
| 1810019A08Rik | 1810019A08Rik | RIKEN cDNA 1810019A08 gene | 80 | 5.1 | AK007540 |
| 1810033B17Rik | 1810033B17Rik | RIKEN cDNA 1810033B17 gene | 38 | 6.4 | BB533148 |
| 1810037B05Rik | 1810037B05Rik | RIKEN cDNA 1810037B05 gene | 50 | 3.1 | AK007714 |
| 1810049K24Rik | 1810049K24Rik | RIKEN cDNA 1810049K24 gene | 484 | 2.4 | BB558800 |
| 1810054D07Rik | 1810054D07Rik | RIKEN cDNA 1810054D07 gene | 40 | 5.0 | AK007856 |
| 1810054D07Rik | 1810054D07Rik | RIKEN cDNA 1810054D07 gene | 45 | 5.4 | BB397062 |
| 1810054D07Rik | 1810054D07Rik | RIKEN cDNA 1810054D07 gene | 99 | 4.5 | BB259628 |
| — | 1810057P16Rik | *Mus musculus* 10 days neonate cortex cDNA, RIKEN full-length enriched library, clone: A830095F23 product: unknown EST, full insert sequence | 94 | 2.6 | BB275943 |
| 1810062O14Rik | 1810062O14Rik | RIKEN cDNA 1810062O14 gene | 99 | 7.4 | AV060417 |
| 2010012C16Rik | 2010012C16Rik | RIKEN cDNA 2010012C16 gene | 187 | 3.0 | AK006303 |
| — | 2010012F05Rik | *Mus musculus* adult male colon cDNA, RIKEN full-length enriched library, clone: 9030607L20 product: weakly similar to MHC CLASS I T7 ANTIGEN (FRAGMENT) [*Mus musculus*], full insert sequence | 54 | 2.2 | AK018542 |
| 2010106G01Rik | 2010106G01Rik | RIKEN cDNA 2010106G01 gene | 1397 | 2.0 | NM_023220 |
| 2010109K11Rik | 2010109K11Rik | RIKEN cDNA 2010109K11 gene | 256 | 3.2 | BB174749 |
| 2010308M01Rik | 2010308M01Rik | RIKEN cDNA 2010308M01 gene | 163 | 2.3 | BC008266 |
| A430106J12Rik | 2010316F05Rik | RIKEN cDNA A430106J12 gene | 41 | 3.5 | BB228331 |
| 2200002D01Rik | 2200002D01Rik | RIKEN cDNA 2200002D01 gene | 189 | 2.3 | AK008617 |
| 2210421G13Rik | 2210421G13Rik | RIKEN cDNA 2210421G13 gene | 19 | 9.3 | AV081797 |
| 2310014H01Rik | 2310014H01Rik | RIKEN cDNA 2310014H01 gene | 331 | 3.3 | AK009340 |
| 2310015N21Rik | 2310015N21Rik | RIKEN cDNA 2310015N21 gene | 300 | 2.9 | AK009372 |
| 2310031L18Rik | 2310031L18Rik | RIKEN cDNA 2310031L18 gene | 76 | 3.4 | BC027435 |
| 2310032F03Rik | 2310032F03Rik | RIKEN cDNA 2310032F03 gene | 36 | 7.7 | BE633038 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| 2310043D08Rik | 2310043D08Rik | RIKEN cDNA 2310043D08 gene | 28 | 5.6 | BF021255 |
| — | 2310047A01Rik | Mus musculus similar to hypothetical protein FLJ90798 (LOC382857), mRNA | 81 | 2.0 | BB813478 |
| 2310047O13Rik | 2310047O13Rik | RIKEN cDNA 2310047O13 gene | 18 | 2.9 | AW554864 |
| 2310061F22Rik | 2310061F22Rik | RIKEN cDNA 2310061F22 gene | 734 | 2.1 | BB253397 |
| 2310067E08Rik | 2310067E08Rik | RIKEN cDNA 2310067E08 gene | 246 | 2.5 | BF168366 |
| 2310075C12Rik | 2310075C12Rik | RIKEN cDNA 2310075C12 gene | 850 | 2.2 | NM_133739 |
| 2400006A19Rik | 2400006A19Rik | RIKEN cDNA 2400006A19 gene | 288 | 7.5 | BC006869 |
| 2410002M20Rik | 2410002M20Rik | RIKEN cDNA 2410002M20 gene | 637 | 2.2 | BM209793 |
| 2410002O22Rik | 2410002O22Rik | RIKEN cDNA 2410002O22 gene | 48 | 2.4 | AK012141 |
| 2410004I17Rik | 2410004I17Rik | RIKEN cDNA 2410004I17 gene | 26 | 6.8 | AK010391 |
| — | 2410006H16Rik | Mus musculus ES cells cDNA, RIKEN full-length enriched library, clone: 2410006H16 product: unknown EST, full insert sequence | 359 | 2.3 | AA939619 |
| 2410012M04Rik | 2410012M04Rik | RIKEN cDNA 2410012M04 gene | 58 | 2.0 | BG229936 |
| B230342M21Rik | 2410024N18Rik | RIKEN cDNA B230342M21 gene | 40 | 3.2 | AK010587 |
| 2410030K01Rik | 2410030K01Rik | RIKEN cDNA 2410030K01 gene | 130 | 2.4 | BF577722 |
| — | 2410129E14Rik | Mus musculus transcribed sequence with strong similarity to protein ref: NP_001060.1 (H. sapiens) tubulin, beta polypeptide [Homo sapiens] | 374 | 3.2 | AA986082 |
| 2600005O03Rik | 2600005O03Rik | RIKEN cDNA 2600005O03 gene | 22 | 5.5 | AK011162 |
| — | 2610002F03Rik | Mus musculus ES cells cDNA, RIKEN full-length enriched library, clone: 2410046H18 product: unknown EST, full insert sequence | 24 | 3.7 | AV011566 |
| 2610028H07Rik | 2610028H07Rik | RIKEN cDNA 2610028H07 gene | 365 | 2.9 | BC006738 |
| 2610029G23Rik | 2610029G23Rik | RIKEN cDNA 2610029G23 gene | 582 | 2.0 | NM_026312 |
| — | 2610036L11Rik | Mus musculus adult male testis cDNA, RIKEN full-length enriched library, clone: 1700015C21 product: unknown EST, full insert sequence | 68 | 3.7 | BF453953 |
| 2610039C10Rik | 2610039C10Rik | RIKEN cDNA 2610039C10 gene | 153 | 3.9 | AK012533 |
| 2610040C18Rik | 2610040C18Rik | RIKEN cDNA 2610040C18 gene | 25 | 4.3 | AU043467 |
| 2610042L04Rik | 2610042L04Rik | RIKEN cDNA 2610042L04 gene | 203 | 5.0 | BM195235 |
| 2610042L04Rik | 2610042L04Rik | RIKEN cDNA 2610042L04 gene | 337 | 4.9 | BM195235 |
| 2610206B13Rik | 2610206B13Rik | RIKEN cDNA 2610206B13 gene | 105 | 2.6 | AK011896 |
| 2610208M17Rik | 2610208M17Rik | RIKEN cDNA 2610208M17 gene | 227 | 2.8 | BI104583 |
| 2610208M17Rik | 2610208M17Rik | RIKEN cDNA 2610208M17 gene | 610 | 3.5 | BI104583 |
| 2610208M17Rik | 2610208M17Rik | RIKEN cDNA 2610208M17 gene | 114 | 3.1 | BQ129438 |
| 2610300B10Rik | 2610300B10Rik | RIKEN cDNA 2610300B10 gene | 87 | 2.6 | BB538449 |
| — | 2610307O08Rik | — | 47 | 18.7 | AV300716 |
| 2610307O08Rik | 2610307O08Rik | RIKEN cDNA 2610307O08 gene | 246 | 6.8 | AK012006 |
| — | 2610318C08Rik | Mus musculus adult male small intestine cDNA, RIKEN full-length enriched library, clone: 2010016H04 product: unknown EST, full insert sequence | 156 | 2.5 | AA197362 |
| 2610318N02Rik | 2610318N02Rik | RIKEN cDNA 2610318N02 gene | 21 | 7.0 | AK012048 |
| 2610510H01Rik | 2610510H01Rik | RIKEN cDNA 2610510H01 gene | 214 | 2.1 | AV122997 |
| 2610510H01Rik | 2610510H01Rik | RIKEN cDNA 2610510H01 gene | 253 | 2.4 | AV122997 |
| 2610510J17Rik | 2610510J17Rik | RIKEN cDNA 2610510J17 gene | 155 | 3.0 | BM230253 |
| 2700019D07Rik | 2700019D07Rik | RIKEN cDNA 2700019D07 gene | 369 | 2.7 | BM937429 |
| — | 2700038G22Rik | Mus musculus adult retina cDNA, RIKEN full-length enriched library, clone: A930033E24 product: unclassifiable, full insert sequence | 141 | 2.3 | AK012332 |
| 2700049P18Rik | 2700049P18Rik | RIKEN cDNA 2700049P18 gene | 73 | 2.4 | AV127670 |
| 2810026P18Rik | 2810026P18Rik | RIKEN cDNA 2810026P18 gene | 209 | 3.1 | AK012825 |
| 2810047L02Rik | 2810047L02Rik | RIKEN cDNA 2810047L02 gene | 19 | 8.8 | AV270035 |
| 2810052M02Rik | 2810052M02Rik | RIKEN cDNA 2810052M02 gene | 99 | 4.6 | NM_023320 |
| 2810406C15Rik | 2810406C15Rik | RIKEN cDNA 2810406C15 gene | 103 | 5.4 | BC025460 |
| 2810417H13Rik | 2810417H13Rik | RIKEN cDNA 2810417H13 gene | 165 | 23.4 | AK017673 |
| 2810417H13Rik | 2810417H13Rik | RIKEN cDNA 2810417H13 gene | 44 | 17.7 | AK017673 |
| 2810418N01Rik | 2810418N01Rik | RIKEN cDNA 2810418N01 gene | 115 | 3.2 | AK013116 |
| A330067P21 | 2810453L12Rik | hypothetical protein A330067P21 | 65 | 2.2 | BG085812 |
| 2810457I06Rik | 2810457I06Rik | RIKEN cDNA 2810457I06 gene | 186 | 2.6 | AK013361 |
| 2810457I06Rik | 2810457I06Rik | RIKEN cDNA 2810457I06 gene | 180 | 3.0 | AW045947 |
| 6720435I21Rik | 2810474O19Rik | RIKEN cDNA 6720435I21 gene | 860 | 2.2 | AA509870 |
| 2900024D24Rik | 2900024D24Rik | RIKEN cDNA 2900024D24 gene | 48 | 10.4 | BB134696 |
| 2900024D24Rik | 2900024D24Rik | RIKEN cDNA 2900024D24 gene | 82 | 4.3 | AI449126 |
| Krc | 2900056N03Rik | kappa B and Rss recognition component | 88 | 5.0 | BB164127 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| 3110010F15Rik | 3110010F15Rik | RIKEN cDNA 3110010F15 gene | 173 | 2.6 | BF320755 |
| 3110010F15Rik | 3110010F15Rik | RIKEN cDNA 3110010F15 gene | 307 | 2.0 | BF320755 |
| 3110037K17Rik | 3110037K17Rik | RIKEN cDNA 3110037K17 gene | 58 | 21.7 | AK014135 |
| 3300001P08Rik | 3300001P08Rik | RIKEN cDNA 3300001P08 gene | 64 | 2.4 | BM213851 |
| 4432406C08Rik | 4432406C08Rik | RIKEN cDNA 4432406C08 gene | 16 | 10.0 | BM247465 |
| 4631422C13Rik | 4631422C13Rik | RIKEN cDNA 4631422C13 gene | 27 | 2.8 | BB154962 |
| AW413625 | 4632417K18Rik | expressed sequence AW413625 | 80 | 15.2 | NM_026640 |
| 4632428N05Rik | 4632428N05Rik | RIKEN cDNA 4632428N05 gene | 139 | 2.6 | BC003967 |
| 4632434I11Rik | 4632434I11Rik | RIKEN cDNA 4632434I11 gene | 20 | 2.8 | BB463610 |
| 4732429D16Rik | 4732429D16Rik | RIKEN cDNA 4732429D16 gene | 130 | 2.0 | BC019814 |
| 4732490P18Rik | 4732490P18Rik | RIKEN cDNA 4732490P18 gene | 31 | 2.1 | BB009703 |
| — | 4833403J16Rik | *Mus musculus* 0 day neonate head cDNA, RIKEN full-length enriched library, clone: 4833403J16 product: unknown EST, full insert sequence | 41 | 2.5 | AK014653 |
| 4833427B12Rik | 4833427B12Rik | RIKEN cDNA 4833427B12 gene | 24 | 7.7 | AW488914 |
| 4921501M20Rik | 4921501M20Rik | RIKEN cDNA 4921501M20 gene | 46 | 3.5 | AF361364 |
| — | 4921511E18Rik | *Mus musculus* adult male testis cDNA, RIKEN full-length enriched library, clone: 4921511E18 product: unclassifiable, full insert sequence | 107 | 2.2 | AK014868 |
| 4930427A07Rik | 4930427A07Rik | RIKEN cDNA 4930427A07 gene | 58 | 2.9 | BE951637 |
| 4930477M19 | 4930477M19 | hypothetical protein 4930477M19 | 66 | 2.4 | BB017021 |
| 4930503L19Rik | 4930503L19Rik | RIKEN cDNA 4930503L19 gene | 42 | 3.5 | AI450962 |
| 4930503L19Rik | 4930503L19Rik | RIKEN cDNA 4930503L19 gene | 27 | 6.4 | AI450962 |
| 4930547N16Rik | 4930547N16Rik | RIKEN cDNA 4930547N16 gene | 10 | 6.9 | BM205349 |
| 4930547N16Rik | 4930547N16Rik | RIKEN cDNA 4930547N16 gene | 25 | 3.5 | BM877490 |
| 4930553M18Rik | 4930553M18Rik | RIKEN cDNA 4930553M18 gene | 83 | 2.1 | BG065617 |
| — | 4930571N24Rik | *Mus musculus* transcribed sequence with moderate similarity to protein sp: P00722 (*E. coli*) BGAL_ECOLI Beta-galactosidase (Lactase) | 20 | 3.5 | BE687174 |
| 4930579G24Rik | 4930579G24Rik | RIKEN cDNA 4930579G24 gene | 99 | 3.0 | BB821996 |
| 4931400A14Rik | 4931400A14Rik | RIKEN cDNA 4931400A14 gene | 533 | 2.8 | AK016419 |
| — | 4933412E12Rik | *Mus musculus* 13 days embryo heart cDNA, RIKEN full-length enriched library, clone: D330011B05 product: unknown EST, full insert sequence | 197 | 2.2 | AK016788 |
| 4933426L22Rik | 4933426L22Rik | RIKEN cDNA 4933426L22 gene | 88 | 3.8 | BB361436 |
| 4933426L22Rik | 4933426L22Rik | RIKEN cDNA 4933426L22 gene | 40 | 5.6 | BB667247 |
| 4933430F08Rik | 4933430F08Rik | RIKEN cDNA 4933430F08 gene | 31 | 37.4 | AK016990 |
| 4933431N12Rik | 4933431N12Rik | RIKEN cDNA 4933431N12 gene | 38 | 4.1 | BE853276 |
| 5033406L14Rik | 5033406L14Rik | RIKEN cDNA 5033406L14 gene | 101 | 3.1 | BB667600 |
| — | 5033413D16Rik | *Mus musculus* 0 day neonate eyeball cDNA, RIKEN full-length enriched library, clone: E130011D04 product: unknown EST, full insert sequence | 144 | 2.4 | AK017164 |
| — | 5230400M03Rik | *Mus musculus* adult male xiphoid cartilage cDNA, RIKEN full-length enriched library, clone: 5230400M03 product: unclassifiable, full insert sequence | 57 | 2.9 | BB312292 |
| A630029F06 | 5330417K06Rik | hypothetical protein A630029F06 | 182 | 3.0 | BB023868 |
| 5430427O19Rik | 5430427O19Rik | RIKEN cDNA 5430427O19 gene | 23 | 7.3 | AI645098 |
| 5430435G22Rik | 5430435G22Rik | RIKEN cDNA 5430435G22 gene | 53 | 7.4 | BB128517 |
| — | 5430437J10Rik | *Mus musculus*, clone IMAGE: 5356629, mRNA | 12 | 4.9 | BF227338 |
| — | 5730405O12Rik | *Mus musculus* 0 day neonate eyeball cDNA, RIKEN full-length enriched library, clone: E130007N07 product: unclassifiable, full insert sequence | 19 | 3.1 | AK017499 |
| 5730466H23Rik | 5730466H23Rik | RIKEN cDNA 5730466H23 gene | 26 | 2.1 | BB079695 |
| — | 5730507H05Rik | *Mus musculus* adult male hypothalamus cDNA, RIKEN full-length enriched library, clone: A230105F24 product: hypothetical protein, full insert sequence | 25 | 10.1 | BB702347 |
| 5730508B09Rik | 5730508B09Rik | RIKEN cDNA 5730508B09 gene | 179 | 3.5 | AK017758 |
| 5730508B09Rik | 5730508B09Rik | RIKEN cDNA 5730508B09 gene | 47 | 11.2 | C80506 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | 5730601F06Rik | *Mus musculus* 16 days embryo head cDNA, RIKEN full-length enriched library, clone: C130077H22 product: unclassifiable, full insert sequence | 71 | 2.2 | BB374879 |
| 5830405N20Rik | 5830405N20Rik | RIKEN cDNA 5830405N20 gene | 49 | 2.5 | BB202848 |
| 5830405N20Rik | 5830405N20Rik | RIKEN cDNA 5830405N20 gene | 19 | 5.9 | AK017900 |
| 9630005B12Rik | 5830411O09Rik | RIKEN cDNA 9630005B12 gene | 139 | 2.4 | BB431654 |
| 9630005812Rik | 5830411O09Rik | RIKEN cDNA 9630005B12 gene | 114 | 2.7 | BB431654 |
| 5830426I05Rik | 5830426I05Rik | RIKEN cDNA 5830426I05 gene | 102 | 6.9 | NM_133762 |
| AI595338 | 5830443L24Rik | expressed sequence AI595338 | 174 | 75.0 | NM_029509 |
| 5830458K16Rik | 5830458K16Rik | RIKEN cDNA 5830458K16 gene | 23 | 4.8 | BC024872 |
| 5830458K16Rik | 5830458K16Rik | RIKEN cDNA 5830458K16 gene | 525 | 9.1 | BC024872 |
| 5830482F20Rik | 5830482F20Rik | RIKEN cDNA 5830482F20 gene | 122 | 3.6 | AW493583 |
| 5830484A20Rik | 5830484A20Rik | RIKEN cDNA 5830484A20 gene | 99 | 4.8 | AW909306 |
| — | 6030405P05Rik | *Mus musculus* 13 days embryo male testis cDNA, RIKEN full-length enriched library, clone: 6030405P05 product: unclassifiable, full insert sequence | 125 | 7.5 | BM244999 |
| 6030423D04Rik | 6030423D04Rik | RIKEN cDNA 6030423D04 gene | 48 | 6.1 | BE986588 |
| 6230416J20Rik | 6230416J20Rik | RIKEN cDNA 6230416J20 gene | 37 | 2.2 | BB794620 |
| 6330406L22Rik | 6330406L22Rik | RIKEN cDNA 6330406L22 gene | 56 | 7.7 | AK018130 |
| 6330407A03Rik | 6330407A03Rik | RIKEN cDNA 6330407A03 gene | 60 | 3.3 | AW519657 |
| 6330412F12Rik | 6330412F12Rik | RIKEN cDNA 6330412F12 gene | 303 | 2.0 | BG066220 |
| 6330442E10Rik | 6330442E10Rik | RIKEN cDNA 6330442E10 gene | 22 | 7.5 | AV328515 |
| — | 6330442E10Rik | — | 82 | 4.2 | BB302103 |
| 6330500D04Rik | 6330500D04Rik | RIKEN cDNA 6330500D04 gene | 87 | 2.8 | BB867666 |
| 6330500D04Rik | 6330500D04Rik | RIKEN cDNA 6330500D04 gene | 104 | 3.9 | BM242294 |
| 6330500D04Rik | 6330500D04Rik | RIKEN cDNA 6330500D04 gene | 66 | 2.3 | AV329070 |
| 6330503K22Rik | 6330503K22Rik | RIKEN cDNA 6330503K22 gene | 182 | 2.3 | BG070835 |
| 6330583I20Rik | 6330583I20Rik | RIKEN cDNA 6330583I20 gene | 43 | 2.5 | BM248637 |
| — | 6430570G24 | *Mus musculus* adult male olfactory brain cDNA, RIKEN full-length enriched library, clone: 6430570G24 product: unknown EST, full insert sequence | 241 | 3.1 | BG069663 |
| — | 6430570G24 | *Mus musculus* adult male olfactory brain cDNA, RIKEN full-length enriched library, clone: 6430570G24 product: unknown EST, full insert sequence | 606 | 3.8 | BG069663 |
| MGC66590 | 6430706D22Rik | Unknown (protein for MGC: 66590) | 24 | 2.3 | BC004768 |
| MGC66590 | 6430706D22Rik | Unknown (protein for MGC: 66590) | 271 | 2.3 | BM248225 |
| 6530401D17Rik | 6530401D17Rik | RIKEN cDNA 6530401D17 gene | 34 | 2.7 | AK013740 |
| 6820428D13 | 6820428D13 | hypothetical protein 6820428D13 | 39 | 2.7 | BG064903 |
| — | 8030448K23Rik | *Mus musculus* transcribed sequences | 98 | 2.1 | BM204579 |
| 8430437G11Rik | 8430437G11Rik | RIKEN cDNA 8430437G11 gene | 271 | 2.2 | BC007160 |
| 9030408N13Rik | 9030408N13Rik | RIKEN cDNA 9030408N13 gene | 66 | 7.0 | NM_025779 |
| 9030625A04Rik | 9030625A04Rik | RIKEN cDNA 9030625A04 gene | 217 | 2.0 | AV373606 |
| 9130002C22Rik | 9130002C22Rik | RIKEN cDNA 9130002C22 gene | 476 | 24.4 | BM243571 |
| 9130017N09Rik | 9130017N09Rik | RIKEN cDNA 9130017N09 gene | 339 | 2.5 | BQ030875 |
| 9130019I15Rik | 9130019I15Rik | RIKEN cDNA 9130019I15 gene | 16 | 46.3 | AK018636 |
| 9130022K13Rik | 9130022K13Rik | RIKEN cDNA 9130022K13 gene | 65 | 5.6 | AK018646 |
| — | 9130211I03Rik | *Mus musculus* similar to Jun dimerization protein 1 gene (LOC381319), mRNA | 64 | 4.9 | AK020278 |
| 9130422G05Rik | 9130422G05Rik | RIKEN cDNA 9130422G05 gene | 177 | 5.0 | AK018685 |
| 9130422G05Rik | 9130422G05Rik | RIKEN cDNA 9130422G05 gene | 195 | 4.4 | AK018685 |
| 9230105E10Rik | 9230105E10Rik | RIKEN cDNA 9230105E10 gene | 108 | 3.6 | BB433710 |
| — | 9230110J10 | *Mus musculus* transcribed sequences | 58 | 4.4 | BG967674 |
| 9230117N10Rik | 9230117N10Rik | RIKEN cDNA 9230117N10 gene | 222 | 7.6 | NM_133775 |
| 9330132E09Rik | 9330132E09Rik | RIKEN cDNA 9330132E09 gene | 189 | 2.3 | AV336691 |
| 9330175E14Rik | 9330175E14Rik | RIKEN cDNA 9330175E14 gene | 11 | 8.0 | BB082472 |
| MGC6357 | 9430034N14Rik | hypothetical protein MGC6357 | 68 | 2.2 | BB667558 |
| — | 9430065F17Rik | *Mus musculus* 12 days embryo embryonic body between diaphragm region and neck cDNA, RIKEN full-length enriched library, clone: 9430065F17 product: unclassifiable, full insert sequence | 30 | 2.1 | AK021377 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| 9430077D24Rik | 9430077D24Rik | RIKEN cDNA 9430077D24 gene | 559 | 2.0 | BG865652 |
| — | 9530028C05 | *Mus musculus* adult male testis cDNA, RIKEN full-length enriched library, clone: 4921508F21 product: similar to HISTOCOMPATIBILITY 2, CLASS II ANTIGEN E BETA [*Mus musculus*], full insert sequence | 278 | 3.9 | BQ175154 |
| — | 9530028C05 | *Mus musculus* adult male testis cDNA, RIKEN full-length enriched library, clone: 4921508F21 product: similar to HISTOCOMPATIBILITY 2, CLASS II ANTIGEN E BETA [*Mus musculus*], full insert sequence | 228 | 4.6 | BQ175154 |
| — | 9530053H05Rik | — | 108 | 4.5 | AK020608 |
| 9630044O09Rik | 9630044O09Rik | RIKEN cDNA 9630044O09 gene | 71 | 3.0 | BB704967 |
| AI645720 | 9630054F20Rik | expressed sequence AI645720 | 106 | 2.1 | BB131620 |
| — | 9630055N22Rik | *Mus musculus* adult retina cDNA, RIKEN full-length enriched library, clone: A930001C09 product: TAIL FIBROBLAST RECEPTOR FOR FELINE LEUKEMIA VIRUS SUBGROUP C homolog [*Mus dunni*], full insert sequence | 523 | 1.9 | BB276950 |
| 9830147J24Rik | 9830147J24Rik | RIKEN cDNA 9830147J24 gene | 83 | 38.2 | BC010229 |
| — | A130052D22 | *Mus musculus* transcribed sequence with strong similarity to protein ref: NP_057365.1 (*H. sapiens*) STE20-like kinase; STE2-like kinase [*Homo sapiens*] | 448 | 2.1 | BB194075 |
| A130092J06Rik | A130092J06Rik | RIKEN cDNA A130092J06 gene | 141 | 3.6 | BI111848 |
| A130096K20 | A130096K20 | hypothetical protein A130096K20 | 576 | 2.5 | AV256780 |
| — | A230061C15Rik | *Mus musculus* adult male hypothalamus cDNA, RIKEN full-length enriched library, clone: A230061C15 product: unknown EST, full insert sequence | 112 | 3.2 | BB153043 |
| A330021E22Rik | A330021E22Rik | RIKEN cDNA A330021E22 gene | 52 | 2.2 | BB561281 |
| A330042H22 | A330042H22 | hypothetical protein A330042H22 | 87 | 11.3 | AW743924 |
| — | A330042I21Rik | *Mus musculus* adult male spinal cord cDNA, RIKEN full-length enriched library, clone: A330042I21 product: unknown EST, full insert sequence | 1523 | 3.6 | AI645293 |
| A330102K04 | A330102K04Rik | hypothetical protein A330102K04 | 35 | 5.5 | AA214835 |
| — | A430093F15Rik | *Mus musculus* 0 day neonate thymus cDNA, RIKEN full-length enriched library, clone: A430093F15 product: hypothetical protein, full insert sequence | 54 | 4.9 | BB209605 |
| A430106J12Rik | A430106J12Rik | RIKEN cDNA A430106J12 gene | 140 | 2.1 | BB498608 |
| A430107D22Rik | A430107D22Rik | RIKEN cDNA A430107D22 gene | 68 | 4.8 | AI481597 |
| A430107D22Rik | A430107D22Rik | RIKEN cDNA A430107D22 gene | 26 | 16.4 | AV312663 |
| — | A530052I06Rik | *Mus musculus* adult male aorta and vein cDNA, RIKEN full-length enriched library, clone: A530052I06 product: unknown EST, full insert sequence | 14 | 3.3 | BM239855 |
| A630077B13Rik | A630077B13Rik | RIKEN cDNA A630077B13 gene | 5 | 183.1 | BB239429 |
| Znfn1a2 | A730095J18Rik | zinc finger protein, subfamily 1A, 2 (Helios) | 59 | 3.6 | BB291816 |
| Znfn1a2 | A730095J18Rik | zinc finger protein, subfamily 1A, 2 (Helios) | 273 | 2.4 | BB319935 |
| — | AA536717 | *Mus musculus* 3 days neonate thymus cDNA, RIKEN full-length enriched library, clone: A630021I17 product: unknown EST, full insert sequence | 31 | 3.2 | BB201845 |
| AA536743 | AA536743 | expressed sequence AA536743 | 368 | 2.6 | BI248354 |
| AA536743 | AA536743 | expressed sequence AA536743 | 543 | 3.0 | BI248354 |
| AA589481 | AA589481 | expressed sequence AA589481 | 123 | 2.1 | BB826899 |
| — | AB124611 | *Mus musculus* 13 days embryo male testis cDNA, RIKEN full-length enriched library, clone: 6030438F01 product: unclassifiable, full insert sequence | 65 | 10.6 | BM246462 |
| Abp1 | Abp1 | amiloride binding protein 1 (amine oxidase, copper-containing) | 188 | 8.7 | BC021880 |
| Facl4 | Acsl4 | fatty acid-Coenzyme A ligase, long chain 4 | 174 | 2.2 | AB033886 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Facl5 | Acsl5; ACS2; ACS5; Facl5; 1700030F05Rik | fatty acid Coenzyme A ligase, long chain 5 | 2295 | 2.1 | AK006541 |
| Strm | Actn1 | striamin | 153 | 2.0 | BC003232 |
| Actr3 | Actr3 | ARP3 actin-related protein 3 homolog (yeast) | 4339 | 2.2 | BE372352 |
| Actr3 | Actr3 | ARP3 actin-related protein 3 homolog (yeast) | 3734 | 2.2 | BE372352 |
| Adam12 | Adam12 | a disintegrin and metalloproteinase domain 12 (meltrin alpha) | 141 | 2.4 | NM_007400 |
| Adam8 | Adam8 | a disintegrin and metalloprotease domain 8 | 54 | 4.4 | NM_007403 |
| Adamts1 | Adamts1 | a disintegrin-like and metalloprotease (reprolysin type) with thrombospondin type 1 motif, 1 | 863 | 4.5 | D67076 |
| Adamts2 | Adamts2 | a disintegrin-like and metalloprotease (reprolysin type) with thrombospondin type 1 motif, 2 | 139 | 2.3 | BM125019 |
| Adamts4 | Adamts4 | a disintegrin-like and metalloprotease (reprolysin type) with thrombospondin type 1 motif, 4 | 60 | 5.6 | BB443585 |
| Adamts6 | Adamts6 | a disintegrin-like and metalloprotease (reprolysin type) with thrombospondin type 1 motif, 6 | 22 | 3.0 | BB227648 |
| — | Adar | *Mus musculus* transcribed sequence with weak similarity to protein ref: NP_081764.1 (*M. musculus*) RIKEN cDNA 5730493B19 [*Mus musculus*] | 103 | 3.5 | BB308291 |
| Adcy7 | Adcy7 | adenylate cyclase 7 | 118 | 17.3 | BB746807 |
| Adfp | Adfp | adipose differentiation related protein | 1090 | 2.7 | NM_007408 |
| Adrbk1 | Adrbk1 | adrenergic receptor kinase, beta 1 | 490 | 2.1 | AF333028 |
| 4833444A01Rik | Adrbk2 | RIKEN cDNA 4833444A01 gene | 235 | 2.0 | BG073639 |
| Agpat4 | Agpat4 | 1-acylglycerol-3-phosphate O-acyltransferase 1 (lysophosphatidic acid acyltransferase, delta) | 241 | 2.5 | BE994529 |
| AI114950 | AI114950 | expressed sequence AI114950 | 244 | 2.7 | BB224153 |
| — | AI132321 | *Mus musculus* transcribed sequence with weak similarity to protein ref: NP_036400.1 (*H. sapiens*) similar to vaccinia virus HindIII K4L ORF [*Homo sapiens*] | 44 | 27.8 | BB210623 |
| AI854251 | AI413582 | expressed sequence AI854251 | 116 | 2.4 | AV039444 |
| — | AI426953 | *Mus musculus* 2 days neonate thymus thymic cells cDNA, RIKEN full-length enriched library, clone: E430023L24 product: unknown EST, full insert sequence | 38 | 2.4 | BE632903 |
| — | AI447881 | *Mus musculus* transcribed sequences | 102 | 2.7 | AI447881 |
| AI447904 | AI447904 | expressed sequence AI447904 | 59 | 26.2 | BM241008 |
| AI447904 | AI447904 | expressed sequence AI447904 | 7 | 70.3 | BM241008 |
| — | AI449310 | *Mus musculus* transcribed sequences | 72 | 2.4 | AW552116 |
| AI449441 | AI449441 | expressed sequence AI449441 | 91 | 2.5 | AV094878 |
| — | AI451557 | *Mus musculus* transcribed sequences | 87 | 24.1 | AV277444 |
| AI452102 | AI452102 | expressed sequence AI452102 | 45 | 3.3 | BB312740 |
| AI467606 | AI467606 | expressed sequence AI467606 | 168 | 10.2 | BB234337 |
| AI467606 | AI467606 | expressed sequence AI467606 | 25 | 9.5 | BB234337 |
| — | AI504062 | *Mus musculus* 9 days embryo whole body cDNA, RIKEN full-length enriched library, clone: D030050E20 product: unclassifiable, full insert sequence | 415 | 2.7 | BM238926 |
| AI504432 | AI504432 | expressed sequence AI504432 | 30 | 15.1 | BB202185 |
| Kcna3 | AI504432 | potassium voltage-gated channel, shaker-related subfamily, member 3 | 23 | 18.8 | AI323624 |
| AI597013 | AI597013 | expressed sequence AI597013 | 47 | 6.1 | BB014626 |
| AI597013 | AI597013 | expressed sequence AI597013 | 77 | 7.9 | BB014626 |
| LOC226691 | AI607873 | interferon-activatable protein | 15 | 28.9 | AI607873 |
| AI661017 | AI661017 | expressed sequence AI661017 | 21 | 15.4 | AV173260 |
| — | AI661384 | *Mus musculus* transcribed sequences | 11 | 14.9 | BB034038 |
| — | AI848100 | *Mus musculus* transcribed sequences | 128 | 2.2 | BB538816 |
| Aif1 | Aif1 | allograft inflammatory factor 1 | 71 | 36.5 | NM_019467 |
| Aim1 | Aim1 | absent in melanoma 1 | 294 | 2.8 | BM233292 |
| Akr1c20 | Akr1c20 | aldo-keto reductase family 1, member C20 | 28 | 8.0 | BC021607 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Akt3 | Akt3 | thymoma viral proto-oncogene 3 | 60 | 3.2 | AF124142 |
| Akt3 | Akt3 | thymoma viral proto-oncogene 3 | 47 | 4.1 | AF124142 |
| Sdccag8 | Akt3 | serologically defined colon cancer antigen 8 | 171 | 3.6 | BB521695 |
| AL024069 | AL024069 | expressed sequence AL024069 | 314 | 2.8 | AI504908 |
| Aldh1a2 | Aldh1a2 | aldehyde dehydrogenase family 1, subfamily A2 | 303 | 5.9 | NM_009022 |
| Aldh1b1 | Aldh1b1 | aldehyde dehydrogenase 1 family, member B1 | 115 | 2.7 | BC020001 |
| Alox5ap | Alox5ap | arachidonate 5-lipoxygenase activating protein | 181 | 13.7 | BC026209 |
| Ankrd1 | Ankrd1 | ankyrin repeat domain 1 (cardiac muscle) | 44 | 5.7 | AK009959 |
| 2900037I21Rik | Anln | RIKEN cDNA 2900037I21 gene | 62 | 7.4 | BI690018 |
| Anp32b | Anp32b | acidic nuclear phosphoprotein 32 family, member B | 1716 | 2.1 | NM_130889 |
| Anxa1 | Anxa1 | annexin A1 | 878 | 2.9 | NM_010730 |
| Anxa2 | Anxa2 | annexin A2 | 2454 | 2.9 | NM_007585 |
| Ap1s2 | Ap1s2 | adaptor-related protein complex 1, sigma 2 subunit | 188 | 2.0 | BE655707 |
| Ap1s2 | Ap1s2; EST1; 1500012A13Rik | adaptor-related protein complex 1, sigma 2 subunit | 151 | 6.4 | AK005223 |
| Apaf1 | Apaf1 | apoptotic protease activating factor 1 | 274 | 2.1 | AK018076 |
| Apob48r | Apob48r | apolipoprotein B48 receptor | 95 | 3.6 | NM_138310 |
| Apobec1 | Apobec1 | apolipoprotein B editing complex 1 | 235 | 3.2 | BC003792 |
| App | App | amyloid beta (A4) precursor protein | 26 | 2.3 | AV348729 |
| Arf3 | Arf3 | ADP-ribosylation factor 3 | 107 | 2.4 | BQ175059 |
| Arf6 | Arf6 | ADP-ribosylation factor 6 | 3548 | 2.1 | BI248938 |
| Arg2 | Arg2 | arginase type II | 85 | 4.3 | AV002218 |
| Arg2 | Arg2 | arginase type II | 145 | 4.3 | NM_009705 |
| 6530401L14Rik | Arhgap11a | RIKEN cDNA 6530401L14 gene | 62 | 8.0 | AV349116 |
| — | Arhgap15 | *Mus musculus* 16 days neonate thymus cDNA, RIKEN full-length enriched library, clone: A130024J05 product: hypothetical protein, full insert sequence | 38 | 5.4 | BB234837 |
| — | Arhgap15 | *Mus musculus* 16 days neonate thymus cDNA, RIKEN full-length enriched library, clone: A130024J05 product: hypothetical protein, full insert sequence | 58 | 3.1 | BB234837 |
| 4933411B03Rik | Arhgap19 | RIKEN cDNA 4933411B03 gene | 35 | 4.1 | BG072763 |
| A130039I20Rik | Arhgap25 | RIKEN cDNA A130039I20 gene | 84 | 3.7 | BM241218 |
| Arhgap4 | Arhgap4 | Rho GTPase activating protein 4 | 117 | 2.6 | NM_138630 |
| AU043488 | Arhgap9 | expressed sequence AU043488 | 84 | 8.7 | BB327418 |
| Gli | Arhgap9 | GLI-Kruppel family member GLI | 24 | 11.5 | AU043488 |
| Gli | Arhgap9 | GLI-Kruppel family member GLI | 12 | 14.6 | AU043488 |
| Arhgdib | Arhgdib | Rho, GDP dissociation inhibitor (GDI) beta | 1160 | 7.7 | AK002516 |
| Arhgef6 | Arhgef6 | Rac/Cdc42 guanine nucleotide exchange factor (GEF) 6 | 142 | 4.5 | BM246754 |
| D430024K22Rik | Arid5a | RIKEN cDNA D430024K22 gene | 56 | 8.3 | BC027152 |
| Desrt | Arid5b | developmentally and sexually retarded with transient immune abnormalities | 19 | 2.7 | BB257077 |
| A630084M22Rik | Arl7 | RIKEN cDNA A630084M22 gene | 254 | 2.8 | BQ176306 |
| 1200015K23Rik | Armc8 | RIKEN cDNA 1200015K23 gene | 115 | 2.2 | BE995635 |
| Arrb2 | Arrb2 | arrestin, beta 2 | 240 | 3.5 | BC016642 |
| Arts1 | Arts1 | type 1 tumor necrosis factor receptor shedding aminopeptidase regulator | 444 | 4.8 | NM_030711 |
| Arts1 | Arts1 | type 1 tumor necrosis factor receptor shedding aminopeptidase regulator | 221 | 4.1 | AV287655 |
| Asf1b | Asf1b | ASF1 anti-silencing function 1 homolog B (*S. cerevisiae*) | 111 | 5.0 | BC003428 |
| Asns | Asns | asparagine synthetase | 329 | 2.3 | BC005552 |
| Asns | Asns | asparagine synthetase | 103 | 4.0 | AV212753 |
| 2610509G12Rik | Atad2 | RIKEN cDNA 2610509G12 gene | 127 | 6.0 | BM206009 |
| Atf3 | Atf3 | activating transcription factor 3 | 109 | 6.6 | BC019946 |
| Atp10a | Atp10a | ATPase, class V, type 10A | 37 | 5.7 | BB487289 |
| Atp10a | Atp10a | ATPase, class V, type 10A | 26 | 3.5 | BM249532 |
| Atp8b2 | Atp8b2 | Atpase, class I, type 8B, member 2 | 248 | 2.6 | BQ178970 |
| — | Atr | *Mus musculus* 16 days neonate thymus cDNA, RIKEN full-length enriched library, clone: A130049K15 product: unclassifiable, full insert sequence | 33 | 2.3 | BM197239 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | AU020206 | *Mus musculus* 3 days neonate thymus cDNA, RIKEN full-length enriched library, clone: A630040D01 product: unknown EST, full insert sequence | 172 | 10.7 | BI151331 |
| Aurkb | Aurkb | aurora kinase B | 21 | 9.6 | BC003261 |
| Aurkb | Aurkb | aurora kinase B | 30 | 11.7 | BC003261 |
| — | AW049306 | *Mus musculus* transcribed sequences | 20 | 3.9 | BE457612 |
| — | AW112010 | *Mus musculus* transcribed sequences | 438 | 32.5 | BE688358 |
| — | AW121567 | *Mus musculus* 12 days embryo spinal ganglion cDNA, RIKEN full-length enriched library, clone: D130071A17 product: unknown EST, full insert sequence | 33 | 2.9 | BB461295 |
| AW212607 | AW212607 | expressed sequence AW212607 | 64 | 3.1 | AV325152 |
| AW212607 | AW212607 | expressed sequence AW212607 | 74 | 5.9 | BB308532 |
| 1810048P08Rik | AW490415 | RIKEN cDNA 1810048P08 gene | 49 | 3.2 | AK010874 |
| — | AW492955 | *Mus musculus* transcribed sequences | 182 | 2.1 | AW492955 |
| — | AW547186 | *Mus musculus* 13 days embryo male testis cDNA, RIKEN full-length enriched library, clone: 6030487A22 product: unclassifiable, full insert sequence | 47 | 3.4 | BB044338 |
| Srr | AW550801 | serine racemase | 191 | 2.3 | BM213835 |
| Axud1 | Axud1 | AXIN1 up-regulated 1 | 100 | 4.5 | BG070296 |
| IkappaBNS | AY078069 | NF-kappa B inhibitor | 26 | 9.0 | AW495632 |
| B230217C12Rik | B230217C12Rik | RIKEN cDNA B230217C12 gene | 24 | 6.2 | BB376573 |
| Cugbp2 | 8230218O03 | CUG triplet repeat, RNA binding protein 2 | 91 | 8.2 | BB644164 |
| Cugbp2 | 8230218O03 | CUG triplet repeat, RNA binding protein 2 | 161 | 7.9 | BB644164 |
| B230315M08Rik | B230315M08Rik | RIKEN cDNA B230315M08 gene | 113 | 2.8 | AI536469 |
| B2m | B2m | beta-2 microglobulin | 71 | 11.6 | AA170322 |
| B2m | B2m | beta-2 microglobulin | 9650 | 2.7 | AI099111 |
| B3gnt5 | B3gnt5 | UDP-GlcNAc: betaGal beta-1,3-N-acetylglucosaminyltransferase 5 | 40 | 3.7 | BM214359 |
| Bak1 | Bak1 | BCL2-antagonist/killer 1 | 113 | 2.1 | AF402617 |
| Bak1 | Bak1 | BCL2-antagonist/killer 1 | 93 | 5.6 | NM_007523 |
| A530094C12Rik | Bank1 | RIKEN cDNA A530094C12 gene | 74 | 2.0 | AI451642 |
| — | Basp1 | *Mus musculus* 10 days neonate medulla oblongata cDNA, RIKEN full-length enriched library, clone: B830039F09 product: BRAIN ACID SOLUBLE PROTEIN 1 (BASP1 PROTEIN) (NEURONAL AXONAL MEMBRANE PROTEIN NAP-22) homolog [*Rattus norvegicus*], full insert sequence | 143 | 9.4 | AK011545 |
| BB146404 | BB146404 | expressed sequence BB146404 | 17 | 4.5 | BC025893 |
| — | BB220380 | *Mus musculus* adult male bone cDNA, RIKEN full-length enriched library, clone: 9830142N16 product: unclassifiable, full insert sequence | 33 | 3.7 | AV281292 |
| BC003236 | BC003236 | cDNA sequence BC003236 | 999 | 2.4 | BB231897 |
| BC004701 | BC004701 | cDNA sequence BC004701 | 41 | 5.9 | BC004701 |
| BC006779 | BC006779 | cDNA sequence BC006779 | 296 | 3.8 | BE853170 |
| BC010462 | BC010462 | cDNA sequence BC010462 | 208 | 3.5 | BC010462 |
| A530020G20Rik | BC010552 | RIKEN cDNA A530020G20 gene | 21 | 3.3 | AV256906 |
| BC010552 | BC010552 | cDNA sequence BC010552 | 133 | 3.6 | BC025548 |
| BC013672 | BC013672 | cDNA sequence BC013672 | 9 | 8.7 | BC013672 |
| BC013712 | BC013712 | cDNA sequence BC013712 | 130 | 12.3 | BB262491 |
| BC023105 | BC023105 | cDNA sequence BC023105 | 46 | 70.3 | BC023105 |
| BC023179 | BC023179 | cDNA sequence BC023179 | 39 | 2.0 | BC023179 |
| BC023741 | BC023741 | cDNA sequence BC023741 | 208 | 11.7 | BB705351 |
| BC023882 | BC023882 | cDNA sequence BC023882 | 238 | 2.8 | BC027393 |
| BC027057 | BC027057 | cDNA sequence BC027057 | 80 | 3.1 | BE133443 |
| BC027057 | BC027057 | cDNA sequence BC027057 | 33 | 8.4 | BB040051 |
| L259 | BC028528 | L259 | 146 | 4.1 | BC028528 |
| BC031748 | BC031748 | cDNA sequence BC031748 | 46 | 2.5 | BB709811 |
| — | BC031781 | — | 246 | 2.0 | AV312901 |
| BC032204 | BC032204 | cDNA sequence BC032204 | 91 | 9.3 | BG066664 |
| — | BC033596 | *Mus musculus* 16 days neonate thymus cDNA, RIKEN full-length enriched library, clone: A130086M19 product: unknown EST, full insert sequence | 56 | 2.6 | BB162048 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| BC037703 | BC037703 | cDNA sequence BC037703 | 87 | 2.5 | AV231983 |
| 9830126M18 | BC052328 | hypothetical protein 9830126M18 | 113 | 6.4 | BM224662 |
| B930060C03 | BC065123 | hypothetical protein B930060C03 | 354 | 3.9 | BM239162 |
| Baz1a | BC065123 | bromodomain adjacent to zinc finger domain 1A | 340 | 2.5 | AV357135 |
| 4732427B05 | BC066140 | hypothetical protein 4732427B05 | 68 | 2.3 | AV114409 |
| — | BC067047 | Mus musculus adult male testis cDNA, RIKEN full-length enriched library, clone: 4930413J11 product: mitochondria located 1 homolog (human), full insert sequence | 142 | 3.6 | BB794978 |
| — | BC068171 | Mus musculus similar to DYSKERIN (LOC245474), mRNA | 501 | 2.2 | BG068512 |
| Bcl11b | Bcl11b | B-cell leukemia/lymphoma 11B | 160 | 2.2 | BM117007 |
| Bcl2l11 | Bcl2l11 | BCL2-like 11 (apoptosis facilitator) | 62 | 2.6 | BB667581 |
| Bcl2l11 | Bcl2l11 | BCL2-like 11 (apoptosis facilitator) | 114 | 3.4 | BM120925 |
| Bcl2l11 | Bcl2l11 | BCL2-like 11 (apoptosis facilitator) | 481 | 2.5 | BM120925 |
| Bcl2l11 | Bcl2l11 | BCL2-like 11 (apoptosis facilitator) | 401 | 3.9 | BB667581 |
| Bcl3 | Bcl3 | B-cell leukemia/lymphoma 3 | 203 | 3.8 | NM_033601 |
| Bcor | Bcor | Bcl6 interacting corepressor | 181 | 2.2 | AK018370 |
| Bgn | Bgn | biglycan | 2040 | 3.2 | AI931862 |
| Bgn | Bgn | biglycan | 2268 | 2.8 | BC019502 |
| Birc1b | Birc1b | baculoviral IAP repeat-containing 1b | 148 | 2.3 | NM_010872 |
| Birc1e | Birc1e | baculoviral IAP repeat-containing 1e | 59 | 2.2 | NM_010870 |
| Birc1f | Birc1f | baculoviral IAP repeat-containing 1f | 79 | 2.5 | AI451585 |
| Birc3 | Birc2 | baculoviral IAP repeat-containing 3 | 824 | 2.3 | NM_007465 |
| Birc2 | Birc3 | baculoviral IAP repeat-containing 2 | 628 | 5.7 | NM_007464 |
| Birc5 | Birc5 | baculoviral IAP repeat-containing 5 | 58 | 18.6 | BC004702 |
| Bnip2 | Bnip2 | BCL2/adenovirus E1B 19 kDa-interacting protein 1, NIP2 | 724 | 2.4 | AV144704 |
| Bnip2 | Bnip2; Nip21; BNIP2beta; 5730523P12Rik | BCL2/adenovirus E1B 19 kDa-interacting protein 1, NIP2 | 667 | 2.2 | AK014659 |
| 2310015I10Rik | Brd4 | RIKEN cDNA 2310015I10 gene | 269 | 13.8 | BC008532 |
| A730011O11Rik | Brrn1 | RIKEN cDNA A730011O11 gene | 204 | 4.6 | BB725358 |
| A730011O11Rik | Brrn1 | RIKEN cDNA A730011O11 gene | 81 | 3.6 | BC021499 |
| Bspry | Bspry | B-box and SPRY domain containing | 552 | 3.3 | NM_138653 |
| Bst1 | Bst1 | bone marrow stromal cell antigen 1 | 167 | 4.5 | AI647987 |
| Btg1 | Btg1 | B-cell translocation gene 1, anti-proliferative | 3872 | 2.3 | L16846 |
| Btk | Btk | Bruton agammaglobulinemia tyrosine kinase | 26 | 8.8 | NM_013482 |
| Btla | Btla | B and T lymphocyte associated | 91 | 7.9 | BM240873 |
| Bub1b | Bub1b | budding uninhibited by benzimidazoles 1 homolog, beta (S. cerevisiae) | 6 | 12.3 | AU045529 |
| Bub3 | Bub3 | budding uninhibited by benzimidazoles 3 homolog (S. cerevisiae) | 20 | 3.6 | BB449877 |
| Bzrp | Bzrp | benzodiazepine receptor, peripheral | 1248 | 2.1 | BB132602 |
| — | C030046G05 | Mus musculus adult male corpus striatum cDNA, RIKEN full-length enriched library, clone: C030046G05 product: unknown EST, full insert sequence | 89 | 3.4 | BE691546 |
| C130032J12Rik | C130032J12Rik | RIKEN cDNA C130032J12 gene | 202 | 2.0 | BB192700 |
| C130036J11 | C130036J11 | hypothetical protein C130036J11 | 8 | 8.1 | BB072624 |
| C1qa | C1qa | complement component 1, q subcomponent, alpha polypeptide | 489 | 8.8 | NM_007572 |
| C1qb | C1qb | complement component 1, q subcomponent, beta polypeptide | 147 | 34.3 | BB111335 |
| C1qb | C1qb | complement component 1, q subcomponent, beta polypeptide | 420 | 6.7 | AW227993 |
| C1qb | C1qb | complement component 1, q subcomponent, beta polypeptide | 363 | 14.1 | NM_009777 |
| C1qg | C1qg | complement component 1, q subcomponent, gamma polypeptide | 185 | 20.8 | NM_007574 |
| C1r | C1r | complement component 1, r subcomponent | 382 | 9.4 | NM_023143 |
| C1s | C1s | complement component 1, s subcomponent | 395 | 12.7 | BC022123 |
| C2 | C2 | complement component 2 (within H-2S) | 1215 | 3.5 | NM_013484 |
| — | C2 | — | 1241 | 4.6 | AV290571 |
| — | C2 | — | 855 | 4.4 | AV227574 |
| C2ta | C2ta | class II transactivator | 43 | 13.2 | AF042158 |
| C2ta | C2ta | class II transactivator | 89 | 10.8 | AF042158 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| C3 | C3 | complement component 3 | 437 | 29.7 | K02782 |
| C330012H03Rik | C330012H03Rik | RIKEN cDNA C330012H03 gene | 69 | 2.8 | BB098431 |
| C330027C09Rik | C330027C09Rik | RIKEN cDNA C330027C09 gene | 53 | 5.5 | AU018569 |
| C3ar1 | C3ar1 | complement component 3a receptor 1 | 113 | 3.5 | NM_009779 |
| C3ar1 | C3ar1 | complement component 3a receptor 1 | 38 | 10.2 | BB333624 |
| C3ar1 | C3ar1 | complement component 3a receptor 1 | 50 | 10.0 | NM_009779 |
| C4 | C4 | complement component 4 (within H-2S) | 894 | 8.4 | NM_009780 |
| C5r1 | C5r1; C5aR; Cd88 | complement component 5, receptor 1 | 41 | 3.4 | NM_007577 |
| C630016B22Rik | C630016B22Rik | RIKEN cDNA C630016B22 gene | 523 | 2.0 | BB711990 |
| C630016B22Rik | C630016B22Rik | RIKEN cDNA C630016B22 gene | 786 | 2.3 | BB771888 |
| — | C730049O14 | *Mus musculus* adult male liver tumor cDNA, RIKEN full-length enriched library, clone: C730049O14 product: unknown EST, full insert sequence | 167 | 4.8 | BB200607 |
| C79407 | C79407 | expressed sequence C79407 | 51 | 3.3 | BB540053 |
| C79407 | C79407 | expressed sequence C79407 | 45 | 6.4 | BE951628 |
| — | C79445 | *Mus musculus* 18-day embryo whole body cDNA, RIKEN full-length enriched library, clone: 1100001P14 product: TUBULIN, BETA 5 homolog [*Homo sapiens*], full insert sequence | 166 | 3.7 | C79445 |
| C80638 | C80638 | expressed sequence C80638 | 38 | 3.5 | AV251613 |
| B130036O03 | C86302 | hypothetical protein B130036O03 | 256 | 2.6 | BB295220 |
| — | C86813; FM2; Ierepo1 | — | 45 | 3.0 | C86813 |
| — | C86813; FM2; Ierepo1 | — | 284 | 5.6 | C86813 |
| — | Cacnb2 | *Mus musculus* adult male hippocampus cDNA, RIKEN full-length enriched library, clone: 2900072G11 product: unknown EST, full insert sequence | 7 | 2.8 | AV154947 |
| Calm1 | Calm1 | calmodulin 1 | 2311 | 2.2 | AU079514 |
| Calmbp1 | Calmbp1 | calmodulin binding protein 1 | 21 | 4.2 | BB648052 |
| E030025C11Rik | Camk1d | RIKEN cDNA E030025C11 gene | 47 | 4.7 | BG071931 |
| Camk2d | Camk2d | calcium/calmodulin-dependent protein kinase II, delta | 69 | 2.0 | BB373572 |
| Capg | Capg | capping protein (actin filament), gelsolin-like | 221 | 7.7 | NM_007599 |
| Capg | Capg | capping protein (actin filament), gelsolin-like | 77 | 2.1 | BB136012 |
| Cappa1 | Capza1 | capping protein alpha 1 | 2195 | 2.5 | AV267494 |
| — | Capza1 | — | 2695 | 2.2 | AI463215 |
| Car13 | Car13 | carbonic anhydrase 13 | 132 | 2.3 | AK010166 |
| Card11 | Card11 | caspase recruitment domain family, member 11 | 24 | 4.6 | AV095659 |
| Card4 | Card4 | caspase recruitment domain 4 | 228 | 3.2 | BB138330 |
| Casp1 | Casp1 | caspase 1 | 94 | 9.4 | BC008152 |
| Casp12 | Casp12 | caspase 12 | 122 | 3.6 | NM_009808 |
| Casp12 | Casp12 | caspase 12 | 145 | 6.8 | NM_009808 |
| Casp3 | Casp3 | caspase 3, apoptosis related cysteine protease | 312 | 2.2 | D86352 |
| Casp3 | Casp3 | caspase 3, apoptosis related cysteine protease | 707 | 2.6 | BG070529 |
| Casp4 | Casp4 | caspase 4, apoptosis-related cysteine protease | 82 | 13.6 | NM_007609 |
| Casp7 | Casp7 | caspase 7 | 234 | 3.7 | U67321 |
| Casp7 | Casp7 | caspase 7 | 528 | 2.8 | NM_007611 |
| Cbfb | Cbfb | core binding factor beta | 1387 | 2.3 | NM_022309 |
| — | Cblb | *Mus musculus* transcribed sequences | 134 | 3.5 | BB205662 |
| Cblb | Cblb | Casitas B-lineage lymphoma b | 258 | 2.1 | AW545867 |
| Ccl11 | Ccl11 | small chemokine (C—C motif) ligand 11 | 21 | 4.7 | NM_011330 |
| Ccl12 | Ccl12 | chemokine (C—C motif) ligand 12 | 11 | 49.6 | U50712 |
| Ccl2 | Ccl2 | chemokine (C—C motif) ligand 2 | 43 | 28.9 | AF065933 |
| Ccl4 | Ccl4 | chemokine (C—C motif) ligand 4 | 95 | 4.5 | AF128218 |
| Ccl5 | Ccl5 | chemokine (C—C motif) ligand 5 | 34 | 140.5 | NM_013653 |
| Ccl6 | Ccl6 | chemokine (C—C motif) ligand 6 | 85 | 8.9 | BC002073 |
| Ccl7 | Ccl7 | chemokine (C—C motif) ligand 7 | 54 | 6.2 | AF128193 |
| Ccl8 | Ccl8 | chemokine (C—C motif) ligand 8 | 115 | 16.0 | NM_021443 |
| Ccl9 | Ccl9 | chemokine (C—C motif) ligand 9 | 25 | 15.6 | AF128196 |
| Ccl9 | Ccl9 | chemokine (C—C motif) ligand 9 | 70 | 9.8 | AF128196 |
| Ccnb1 | Ccnb1 | cyclin B1 | 102 | 7.1 | NM_007629 |
| Ccnb1 | Ccnb1 | cyclin B1 | 55 | 12.1 | NM_007629 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Ccnb1 | Ccnb1 | cyclin B1 | 14 | 22.1 | AU015121 |
| Ccnd2 | Ccnd2 | cyclin D2 | 420 | 2.3 | BQ175880 |
| — | Ccne1 | — | 70 | 3.9 | BB293079 |
| Ccne2 | Ccne2 | cyclin E2 | 47 | 4.5 | AF091432 |
| Ccnf | Ccnf | cyclin F | 11 | 9.5 | NM_007634 |
| Ccr1 | Ccr1 | chemokine (C—C motif) receptor 1 | 81 | 9.2 | AV231648 |
| Ccr2 | Ccr2 | chemokine (C—C) receptor 2 | 123 | 23.0 | BB148128 |
| Ccr2 | Ccr2 | chemokine (C—C) receptor 2 | 87 | 7.6 | BB148128 |
| Ccr2 | Ccr2 | chemokine (C—C) receptor 2 | 70 | 24.5 | BB148128 |
| Ccr5 | Ccr5 | chemokine (C—C motif) receptor 5 | 41 | 16.8 | X94151 |
| Ccr5 | Ccr5 | chemokine (C—C motif) receptor 5 | 31 | 7.6 | X94151 |
| Ccr5 | Ccr5 | chemokine (C—C motif) receptor 5 | 73 | 18.6 | D83648 |
| Ccr9 | Ccr9 | chemokine (C—C motif) receptor 9 | 30 | 4.6 | AJ131357 |
| Ccrl2 | Ccrl2 | chemokine (C—C motif) receptor-like 2 | 138 | 2.5 | AJ318863 |
| Cd14 | Cd14 | CD14 antigen | 359 | 16.5 | NM_009841 |
| Cd160 | Cd160 | CD160 antigen | 121 | 2.4 | NM_018767 |
| Cd160 | Cd160 | CD160 antigen | 16 | 9.7 | AU045688 |
| Cd1d1 | Cd1d1 | CD1d1 antigen | 67 | 4.1 | NM_007639 |
| Mox2 | Cd200 | antigen identified by monoclonal antibody MRC OX-2 | 591 | 2.2 | AF004023 |
| F630003A18Rik | Cd200r1 | RIKEN cDNA F630003A18 gene | 21 | 5.2 | BB770873 |
| Cd22 | Cd22 | CD22 antigen | 97 | 2.0 | AF102134 |
| Cd244 | Cd244 | CD244 natural killer cell receptor 2B4 | 14 | 7.0 | NM_018729 |
| Cd28 | Cd28 | CD28 antigen | 16 | 26.5 | AV313615 |
| Cd28 | Cd28 | CD28 antigen | 43 | 22.1 | NM_007642 |
| Cd38 | Cd38 | CD38 antigen | 191 | 2.7 | NM_007646 |
| Cd38 | Cd38 | CD38 antigen | 455 | 3.7 | BB256012 |
| Cd3e | Cd3e | CD3 antigen, epsilon polypeptide | 31 | 27.4 | NM_007648 |
| Cd44 | Cd44 | CD44 antigen | 117 | 15.9 | AW146109 |
| Cd47 | Cd47 | CD47 antigen (Rh-related antigen, integrin-associated signal transducer) | 1584 | 2.1 | NM_010581 |
| Cd47 | Cd47 | CD47 antigen (Rh-related antigen, integrin-associated signal transducer) | 2922 | 2.4 | NM_010581 |
| Cd48 | Cd48 | CD48 antigen | 82 | 20.7 | BE634960 |
| Cd5 | Cd5 | CD5 antigen | 77 | 6.3 | NM_007650 |
| Cd52 | Cd52 | CD52 antigen | 474 | 28.2 | NM_013706 |
| — | Cd53 | *Mus musculus* transcribed sequences | 13 | 7.7 | BM239715 |
| Cd6 | Cd6 | CD6 antigen | 18 | 11.9 | U12434 |
| Cd68 | Cd68 | CD68 antigen | 189 | 7.9 | BC021637 |
| Cd69 | Cd69 | CD69 antigen | 22 | 13.0 | AK017979 |
| Cd72 | Cd72 | CD72 antigen | 51 | 10.7 | BC003824 |
| Cd79b | Cd79b | CD79B antigen | 54 | 2.7 | NM_008339 |
| Cd83 | Cd83 | CD83 antigen | 94 | 7.4 | NM_009856 |
| Cd84 | Cd84 | CD84 antigen | 44 | 8.2 | NM_013489 |
| Cd86 | Cd86 | CD86 antigen | 53 | 10.4 | NM_019388 |
| Cd86 | Cd86 | CD86 antigen | 38 | 11.2 | NM_019388 |
| Cd8a | Cd8a | CD8 antigen, alpha chain | 96 | 11.3 | BB154331 |
| Cd8a | Cd8a | CD8 antigen, alpha chain | 71 | 18.2 | M12825 |
| Cd8a | Cd8a | CD8 antigen, alpha chain | 60 | 31.2 | M12825 |
| 1700109I12Rik | Cd96 | RIKEN cDNA 1700109I12 gene | 99 | 2.9 | NM_032465 |
| Elovl1 | Cdc20 | elongation of very long chain fatty acids (FEN1/Elo2, SUR4/Elo3, yeast)-like 1 | 307 | 5.7 | BB041150 |
| Cdc20 | Cdc20 | cell division cycle 20 homolog (*S. cerevisiae*) | 302 | 3.1 | NM_023223 |
| Cdc25b | Cdc25b | cell division cycle 25 homolog B (*S. cerevisiae*) | 110 | 2.8 | NM_023117 |
| Cdc2a | Cdc2a | cell division cycle 2 homolog A (*S. pombe*) | 170 | 5.9 | NM_007659 |
| Cdc45l | Cdc45l | cell division cycle 45 homolog (*S. cerevisiae*)-like | 104 | 2.8 | NM_009862 |
| Cdc7 | Cdc7 | cell division cycle 7 (*S. cerevisiae*) | 45 | 5.1 | AB018574 |
| 2610311M19Rik | Cdca2 | RIKEN cDNA 2610311M19 gene | 58 | 5.2 | BG065056 |
| 2610311M19Rik | Cdca2 | RIKEN cDNA 2610311M19 gene | 27 | 6.7 | BG065056 |
| Cdca3 | Cdca3 | cell division cycle associated 3 | 200 | 3.4 | BI081061 |
| Cdca4 | Cdca4 | cell division cycle associated 4 | 200 | 2.1 | BB329505 |
| Cdca4 | Cdca4 | cell division cycle associated 4 | 280 | 3.2 | AF322238 |
| D4Ertd421e | Cdca8 | DNA segment, Chr 4, ERATO Doi 421, expressed | 57 | 12.2 | AV307110 |
| D4Ertd421e | Cdca8 | DNA segment, Chr 4, ERATO Doi 421, expressed | 105 | 8.3 | BB702047 |
| D4Ertd421e | Cdca8 | DNA segment, Chr 4, ERATO Doi 421, expressed | 67 | 4.8 | AV307110 |
| Cdh11 | Cdh11 | cadherin 11 | 381 | 2.8 | NM_009866 |
| Cdk6 | Cdk6 | cyclin-dependent kinase 6 | 16 | 3.0 | NM_009873 |
| Cdkn1a | Cdkn1a | cyclin-dependent kinase inhibitor 1A (P21) | 231 | 3.9 | AK007630 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Cds1 | Cds1 | CDP-diacylglycerol synthase 1 | 324 | 2.0 | BI152841 |
| Cdyl | Cdyl | chromodomain protein, Y chromosome-like | 188 | 2.1 | AF081260 |
| Cebpb | Cebpb | CCAAT/enhancer binding protein (C/EBP), beta | 672 | 3.6 | NM_009883 |
| Cebpb | Cebpb | CCAAT/enhancer binding protein (C/EBP), beta | 214 | 2.9 | AB012278 |
| Cebpd | Cebpd | CCAAT/enhancer binding protein (C/EBP), delta | 236 | 5.5 | BB831146 |
| Cenpa | Cenpa | centromere autoantigen A | 75 | 8.8 | AV132173 |
| BC049989 | Cenpe | cDNA sequence BC049989 | 13 | 2.3 | BG068387 |
| BC049989 | Cenpe | cDNA sequence BC049989 | 136 | 3.1 | BG916502 |
| Lek1 | Cenpf | leucine, glutamic acid, lysine family 1 protein | 89 | 3.4 | BE848253 |
| Cenph | Cenph | centromere autoantigen H | 22 | 5.1 | BC025084 |
| Centb1 | Centb1 | centaurin, beta 1 | 228 | 2.4 | BB757196 |
| Kctd11 | Centb1 | potassium channel tetramerisation domain containing 11 | 110 | 5.9 | BB115902 |
| AA968343 | Cep1 | expressed sequence AA968343 | 166 | 2.2 | BB466021 |
| Cfi | Cfi | complement component factor i | 364 | 3.3 | NM_007686 |
| Ch25h | Ch25h | cholesterol 25-hydroxylase | 90 | 17.6 | NM_009890 |
| Chaf1b | Chaf1b | chromatin assembly factor 1, subunit B (p60) | 81 | 3.3 | BC013532 |
| Chek1 | Chek1 | checkpoint kinase 1 homolog (S. pombe) | 29 | 4.7 | NM_007691 |
| Chi3l3 | Chi3l3 | chitinase 3-like 3 | 15 | 64.7 | NM_009892 |
| Chi3l4 | Chi3l4 | chitinase 3-like 4 | 76 | 13.4 | AY065557 |
| Chsy1 | Chsy1 | carbohydrate (chondroitin) synthase 1 | 640 | 2.0 | BQ174991 |
| Ckap2 | Ckap2 | cytoskeleton associated protein 2 | 121 | 2.8 | BM208103 |
| 1700001C14Rik | Cklf | RIKEN cDNA 1700001C14 gene | 169 | 2.1 | AY047360 |
| Cklfsf7 | Cklfsf7 | chemokine-like factor super family 7 | 48 | 3.2 | BC026773 |
| Cks1 | Cks1b | CDC28 protein kinase 1 | 181 | 4.6 | NM_016904 |
| Cks1 | Cks1b | CDC28 protein kinase 1 | 323 | 6.2 | NM_016904 |
| Clca2 | Clca2 | chloride channel calcium activated 2 | 39 | 3.1 | AF108501 |
| Cldn1 | Cldn1 | claudin 1 | 471 | 3.0 | AV227581 |
| Clecsf10 | Clecsf10 | C-type (calcium dependent, carbohydrate recognition domain) lectin, superfamily member 10 | 68 | 6.8 | NM_020001 |
| Clecsf10 | Clecsf10 | C-type (calcium dependent, carbohydrate recognition domain) lectin, superfamily member 10 | 16 | 11.7 | AF240358 |
| Clecsf12 | Clecsf12 | C-type (calcium dependent, carbohydrate recognition domain) lectin, superfamily member 12 | 197 | 9.5 | NM_020008 |
| Clecsf5 | Clecsf5 | C-type (calcium dependent, carbohydrate-recognition domain) lectin, superfamily member 5 | 56 | 10.9 | NM_021364 |
| 1810046I24Rik | Clecsf6 | RIKEN cDNA 1810046I24 gene | 29 | 7.2 | BC006623 |
| Clecsf6 | Clecsf6 | C-type (calcium dependent, carbohydrate recognition domain) lectin, superfamily member 6 | 65 | 4.6 | NM_011999 |
| Clecsf8 | Clecsf8 | C-type (calcium dependent, carbohydrate recognition domain) lectin, superfamily member 8 | 25 | 4.5 | NM_010819 |
| Clecsf9 | Clecsf9 | C-type (calcium dependent, carbohydrate recognition domain) lectin, superfamily member 9 | 38 | 3.4 | NM_019948 |
| Clecsf9 | Clecsf9 | C-type (calcium dependent, carbohydrate recognition domain) lectin, superfamily member 9 | 17 | 30.6 | NM_019948 |
| Clic1 | Clic1 | chloride intracellular channel 1 | 3468 | 2.6 | NM_033444 |
| E130314M08Rik | Clspn | RIKEN cDNA E130314M08 gene | 40 | 7.0 | BG067086 |
| Cnn2 | Cnn2 | calponin 2 | 626 | 3.8 | BI663014 |
| 4932442K20Rik | Cnot6l | RIKEN cDNA 4932442K20 gene | 322 | 2.0 | BC018506 |
| Cnp1 | Cnp1 | cyclic nucleotide phosphodiesterase 1 | 113 | 2.5 | M58045 |
| Col15a1 | Col15a1 | procollagen, type XV | 247 | 2.1 | AF011450 |
| Col1a2 | Col1a2 | procollagen, type I, alpha 2 | 1460 | 4.5 | BF227507 |
| Col1a2 | Col1a2 | procollagen, type I, alpha 2 | 392 | 8.6 | BF227507 |
| Col3a1 | Col3a1 | procollagen, type III, alpha 1 | 165 | 7.9 | AW550625 |
| Col3a1 | Col3a1 | procollagen, type III, alpha 1 | 1468 | 5.7 | AW550625 |
| Col5a1 | Col5a1 | procollagen, type V, alpha 1 | 242 | 3.6 | AW744319 |
| Col5a2 | Col5a2 | procollagen, type V, alpha 2 | 65 | 3.8 | AV229424 |
| Col5a2 | Col5a2 | procollagen, type V, alpha 2 | 150 | 6.7 | AV229424 |
| Col6a2 | Col6a2 | procollagen, type VI, alpha 2 | 363 | 3.4 | BI455189 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Col6a3 | Col6a3 | procollagen, type VI, alpha 3 | 657 | 2.6 | AF064749 |
| — | Col8a1 | *Mus musculus* 6 days neonate head cDNA, RIKEN full-length enriched library, clone: 5430419M07 product: unknown EST, full insert sequence | 211 | 4.4 | AV292255 |
| Colec12 | Colec12 | collectin sub-family member 12 | 134 | 2.4 | NM_130449 |
| Copeb | Copeb | core promoter element binding protein | 198 | 4.4 | AF072403 |
| Copeb | Copeb | core promoter element binding protein | 501 | 6.3 | AV025472 |
| Copeb | Copeb | core promoter element binding protein | 298 | 5.5 | NM_011803 |
| Coro1a | Coro1a | coronin, actin binding protein 1A | 26 | 3.9 | BB740218 |
| Coro1a | Coro1a | coronin, actin binding protein 1A | 168 | 24.0 | BB740218 |
| 5830400N10Rik | Coro2a | RIKEN cDNA 5830400N10 gene | 69 | 4.1 | AU042532 |
| 5830400N10Rik | Coro2a | RIKEN cDNA 5830400N10 gene | 68 | 4.2 | AI316747 |
| Cp | Cp | ceruloplasmin | 727 | 3.9 | BB009037 |
| Cpne2 | Cpne2 | copine II | 100 | 1.9 | BC023348 |
| Crem | Crem | cAMP responsive element modulator | 373 | 3.3 | AI467599 |
| Crem | Crem | cAMP responsive element modulator | 221 | 3.3 | AI467599 |
| Crip1 | Crip1 | cysteine-rich protein 1 (intestinal) | 1191 | 3.7 | NM_007763 |
| Crlf1 | Crlf1 | cytokine receptor-like factor 1 | 63 | 10.0 | NM_018827 |
| — | Crlf3 | *Mus musculus* transcribed sequences | 110 | 2.8 | BG094104 |
| Crlf3 | Crlf3 | cytokine receptor-like factor 3 | 426 | 2.4 | BB161253 |
| Crtam | Crtam | cytotoxic and regulatory T cell molecule | 54 | 5.0 | NM_019465 |
| Csf1 | Csf1 | colony stimulating factor 1 (macrophage) | 138 | 2.9 | BM233698 |
| Csf1 | Csf1 | colony stimulating factor 1 (macrophage) | 73 | 3.2 | M21149 |
| Csf1 | Csf1 | colony stimulating factor 1 (macrophage) | 213 | 5.5 | BM233698 |
| Csf2rb1 | Csf2rb1 | colony stimulating factor 2 receptor, beta 1, low-affinity (granulocyte-macrophage) | 7 | 11.5 | NM_007780 |
| Csf2rb1 | Csf2rb1 | colony stimulating factor 2 receptor, beta 1, low-affinity (granulocyte-macrophage) | 68 | 14.7 | BB769628 |
| Csf2rb2 | Csf2rb2 | colony stimulating factor 2 receptor, beta 2, low-affinity (granulocyte-macrophage) | 43 | 11.4 | NM_007781 |
| Csf3r | Csf3r | colony stimulating factor 3 receptor (granulocyte) | 26 | 12.4 | NM_007782 |
| Cspg2 | Cspg2 | chondroitin sulfate proteoglycan 2 | 42 | 7.2 | NM_019389 |
| Cspg2 | Cspg2 | chondroitin sulfate proteoglycan 2 | 59 | 8.2 | BM251152 |
| Cstb | Cstb | cystatin B | 5561 | 2.3 | NM_007793 |
| Cstb | Cstb | cystatin B | 2587 | 2.9 | NM_007793 |
| Cstf3 | Cstf3 | cleavage stimulation factor, 3' pre-RNA, subunit 3 | 51 | 2.5 | BM218423 |
| Tpbpb | Ctla2a | trophoblast specific protein beta | 81 | 2.9 | BG064656 |
| Ctla4 | Ctla4 | cytotoxic T-lymphocyte-associated protein 4 | 26 | 21.0 | NM_009843 |
| — | Ctsc | *Mus musculus* transcribed sequences | 11 | 14.6 | BG070233 |
| Ctsc | Ctsc | cathepsin C | 1593 | 8.7 | NM_009982 |
| — | Ctsc | *Mus musculus* transcribed sequences | 32 | 5.3 | AV367948 |
| — | Ctsc | *Mus musculus* transcribed sequences | 98 | 6.5 | BM237633 |
| Ctss | Ctss | cathepsin S | 838 | 16.7 | NM_021281 |
| Cx3cl1 | Cx3cl1 | chemokine (C—X3—C motif) ligand 1 | 705 | 2.4 | AF010586 |
| Cx3cr1 | Cx3cr1 | chemokine (C—X3—C) receptor 1 | 139 | 2.4 | BC012653 |
| Cxcl1 | Cxcl1 | chemokine (C—X—C motif) ligand 1 | 177 | 2.7 | BB554288 |
| Cxcl1 | Cxcl1 | chemokine (C—X—C motif) ligand 1 | 74 | 6.2 | NM_008176 |
| Cxcl10 | Cxcl10 | chemokine (C—X—C motif) ligand 10 | 162 | 81.6 | NM_021274 |
| Cxcl11 | Cxcl11 | chemokine (C—X—C motif) ligand 11 | 46 | 10.5 | NM_019494 |
| Cxcl11 | Cxcl11 | chemokine (C—X—C motif) ligand 11 | 144 | 99.2 | NM_019494 |
| Cxcl13 | Cxcl13 | chemokine (C—X—C motif) ligand 13 | 68 | 4.4 | AF030636 |
| Cxcl14 | Cxcl14 | chemokine (C—X—C motif) ligand 14 | 260 | 3.1 | AF252873 |
| Cxcl14 | Cxcl14 | chemokine (C—X—C motif) ligand 14 | 124 | 9.2 | AF252873 |
| Cxcl16 | Cxcl16 | chemokine (C—X—C motif) ligand 16 | 1027 | 2.9 | BC019961 |
| Cxcl16 | Cxcl16 | chemokine (C—X—C motif) ligand 16 | 1429 | 3.7 | BC019961 |
| Cxcl16 | Cxcl16 | chemokine (C—X—C motif) ligand 16 | 199 | 2.9 | AI662455 |
| Cxcl9 | Cxcl9 | chemokine (C—X—C motif) ligand 9 | 125 | 176.4 | NM_008599 |
| Cxcr3 | Cxcr3 | chemokine (C—X—C motif) receptor 3 | 137 | 10.2 | NM_009910 |
| Cxcr4 | Cxcr4 | chemokine (C—X—C motif) receptor 4 | 133 | 3.6 | D87747 |
| Cybb | Cybb | cytochrome b-245, beta polypeptide | 283 | 21.3 | AV373944 |
| Cybb | Cybb | cytochrome b-245, beta polypeptide | 153 | 14.2 | NM_007807 |
| Cybb | Cybb | cytochrome b-245, beta polypeptide | 161 | 9.1 | AV373944 |
| Cyp1b1 | Cyp1b1 | cytochrome P450, family 1, subfamily b, polypeptide 1 | 259 | 3.4 | BI251808 |
| Cyp4f18 | Cyp4f18 | cytochrome P450, family 4, subfamily f, polypeptide 18 | 19 | 26.1 | NM_024444 |
| Cyp4v3 | Cyp4v3 | cytochrome P450, family 4, subfamily v, polypeptide 3 | 300 | 3.1 | NM_133969 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Cyp4v3 | Cyp4v3 | cytochrome P450, family 4, subfamily v, polypeptide 3 | 137 | 3.9 | NM_133969 |
| Cyr61 | Cyr61 | cysteine rich protein 61 | 384 | 2.5 | BM202770 |
| Cysltr1 | Cysltr1 | cysteinyl leukotriene receptor 1 | 13 | 4.8 | BC027102 |
| Cysltr1 | Cysltr1 | cysteinyl leukotriene receptor 1 | 12 | 4.9 | BC027102 |
| — | D030064D06Rik | Mus musculus 9 days embryo whole body cDNA, RIKEN full-length enriched library, clone: D030064D06 product: unknown EST, full insert sequence | 92 | 2.3 | AW987520 |
| D11Ertd461e | D11Ertd461e | DNA segment, Chr 11, ERATO Doi 461, expressed | 26 | 5.5 | C87579 |
| D11Ertd759e | D11Ertd759e | DNA segment, Chr 11, ERATO Doi 759, expressed | 922 | 4.9 | AW556558 |
| D11Lgp2e | D11Lgp2e | DNA segment, Chr 11, Lothar Hennighausen 2, expressed | 27 | 6.1 | NM_030150 |
| D11Lgp2e | D11Lgp2e | DNA segment, Chr 11, Lothar Hennighausen 2, expressed | 55 | 10.0 | AF316999 |
| D11Wsu99e | D11Wsu99e | DNA segment, Chr 11, Wayne State University 99, expressed | 232 | 2.6 | AV225714 |
| D12Ertd551e | D12Ertd551e | DNA segment, Chr 12, ERATO Doi 551, expressed | 660 | 2.1 | BI102044 |
| — | D12Ertd551e | Mus musculus adult male tongue cDNA, RIKEN full-length enriched library, clone: 2310058N22 product: unknown EST, full insert sequence | 20 | 5.5 | BQ175646 |
| D12Ertd647e | D12Ertd647e | DNA segment, Chr 12, ERATO Doi 647, expressed | 953 | 5.8 | AW554405 |
| D12Ertd647e | D12Ertd647e | DNA segment, Chr 12, ERATO Doi 647, expressed | 1414 | 4.1 | BI655075 |
| 4930513H15Rik | D14Ertd581e | RIKEN cDNA 4930513H15 gene | 49 | 2.1 | AK017117 |
| D16Ertd472e | D16Ertd472e | DNA segment, Chr 16, ERATO Doi 472, expressed | 105 | 4.2 | AV381575 |
| D17H6S56E-5 | D17H6S56E-5 | DNA segment, Chr 17, human D6S56E 5 | 381 | 5.9 | NM_033075 |
| D17H6S56E-5 | D17H6S56E-5 | DNA segment, Chr 17, human D6S56E 5 | 195 | 9.2 | NM_033075 |
| D2Ertd750e | D2Ertd750e | DNA segment, Chr 2, ERATO Doi 750, expressed | 43 | 7.9 | AU019491 |
| — | D330027G24Rik | Mus musculus 13 days embryo heart cDNA, RIKEN full-length enriched library, clone: D330027G24 product: unclassifiable, full insert sequence | 48 | 4.3 | BB449568 |
| Mecp2 | D630021H01Rik | methyl CpG binding protein 2 | 55 | 2.0 | BB499491 |
| D730019B10 | D730019B10 | hypothetical protein D730019B10 | 23 | 12.8 | BB508669 |
| Rpl30 | D730044K07Rik | ribosomal protein L30 | 13 | 2.0 | BB283415 |
| D7Bwg0421e | D7Bwg0421e | DNA segment, Chr 7, Brigham & Women's Genetics 0421 expressed | 31 | 8.1 | BB667693 |
| D7Bwg0421e | D7Bwg0421e | DNA segment, Chr 7, Brigham & Women's Genetics 0421 expressed | 59 | 8.4 | AV370380 |
| Atp8a1 | D830007B15Rik | ATPase, aminophospholipid transporter (APLT), class I, type 8A, member 1 | 124 | 2.7 | BB303874 |
| Atp8a1 | D830007B15Rik | ATPase, aminophospholipid transporter (APLT), class I, type 8A, member 1 | 164 | 4.3 | BB303874 |
| Atp8a1 | D830007B15Rik | ATPase, aminophospholipid transporter (APLT), class I, type 8A, member 1 | 184 | 5.6 | AW610650 |
| Atp8a1 | D830007B15Rik | ATPase, aminophospholipid transporter (APLT), class I, type 8A, member 1 | 150 | 2.9 | BQ176779 |
| Atp8a1 | D830007B15Rik | ATPase, aminophospholipid transporter (APLT), class I, type 8A, member 1 | 213 | 4.3 | AW610650 |
| Dapp1 | Dapp1 | dual adaptor for phosphotyrosine and 3-phosphoinositides 1 | 91 | 3.9 | NM_011932 |
| Dapp1 | Dapp1 | dual adaptor for phosphotyrosine and 3-phosphoinositides 1 | 54 | 4.4 | NM_011932 |
| Dcamkl1 | Dcamkl1 | double cortin and calcium/calmodulin-dependent protein kinase-like 1 | 3 | 4.7 | AW105916 |
| Dcamkl1 | Dcamkl1 | double cortin and calcium/calmodulin-dependent protein kinase-like 1 | 27 | 5.4 | AW105916 |
| Dcamkl1 | Dcamkl1 | double cortin and calcium/calmodulin-dependent protein kinase-like 1 | 18 | 9.8 | AW105916 |
| Dcamkl1 | Dcamkl1 | double cortin and calcium/calmodulin-dependent protein kinase-like 1 | 12 | 19.7 | BB757120 |
| Dck | Dck | deoxycytidine kinase | 54 | 5.3 | BE630687 |
| Dck | Dck | deoxycytidine kinase | 103 | 12.6 | BB030204 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Dck | Dck | deoxycytidine kinase | 105 | 5.1 | NM_007832 |
| Dcn | Dcn | decorin | 2578 | 2.7 | NM_007833 |
| — | Ddef1 | *Mus musculus* transcribed sequences | 29 | 3.6 | BG064109 |
| Ddx21 | Ddx21 | DEAD (Asp-Glu-Ala-Asp) box polypeptide 21 | 293 | 2.1 | BM246099 |
| Ddx39 | Ddx39 | DEAD (Asp-Glu-Ala-Asp) box polypeptide 39 | 940 | 2.6 | BC020134 |
| Ddx39 | Ddx39 | DEAD (Asp-Glu-Ala-Asp) box polypeptide 39 | 1433 | 2.3 | AV214253 |
| 6430573D20Rik | Ddx58 | RIKEN cDNA 6430573D20 gene | 505 | 3.9 | BG063981 |
| Def6 | Def6 | differentially expressed in FDCP 6 | 54 | 4.9 | AK010356 |
| 5830484J08Rik | Depdc1a | RIKEN cDNA 5830484J08 gene | 14 | 8.5 | BC005799 |
| — | Diap1 | *Mus musculus* 7 days embryo whole body cDNA, RIKEN full-length enriched library, clone: C430005H19 product: unknown EST, full insert sequence | 124 | 2.1 | BB408240 |
| Dkk3 | Dkk3 | dickkopf homolog 3 (*Xenopus laevis*) | 354 | 2.5 | AK004853 |
| Dkk3 | Dkk3 | dickkopf homolog 3 (*Xenopus laevis*) | 293 | 2.3 | AK004853 |
| Hurp | Dlg7 | hepatoma up-regulated protein | 24 | 3.2 | BB132734 |
| Hurp | Dlg7 | hepatoma up-regulated protein | 34 | 4.5 | BM250919 |
| E130315B21Rik | Dna2l | RIKEN cDNA E130315B21 gene | 363 | 2.0 | BB546985 |
| 5330419I01Rik | Dnajc9 | RIKEN cDNA 5330419I01 gene | 626 | 2.1 | BM942465 |
| Dnase1l3 | Dnase1l3 | deoxyribonuclease 1-like 3 | 47 | 6.4 | BC012671 |
| Dnase1l3 | Dnase1l3 | deoxyribonuclease 1-like 3 | 12 | 8.8 | BC012671 |
| Npn1 | Dnm3 | neoplastic progression 1 | 86 | 2.5 | BB542096 |
| Dnmt1 | Dnmt1 | DNA methyltransferase (cytosine-5) 1 | 308 | 2.9 | BB165431 |
| — | Dock10 | *Mus musculus* transcribed sequences | 49 | 2.3 | BB211894 |
| Dock10 | Dock10 | dedicator of cytokinesis 10 | 17 | 3.0 | BB763030 |
| Dock10 | Dock10 | dedicator of cytokinesis 10 | 145 | 8.8 | BF715043 |
| — | Dock11 | *Mus musculus* 11 days pregnant adult female ovary and uterus cDNA, RIKEN full-length enriched library, clone: 5033414A21 product: inferred: human CLASP-4 {*Homo sapiens*}, full insert sequence | 106 | 11.1 | AK017170 |
| Dok1 | Dok1 | downstream of tyrosine kinase 1 | 169 | 2.1 | BC013066 |
| Donson | Donson | downstream neighbor of SON | 150 | 2.7 | BQ174742 |
| Dpt | Dpt | dermatopontin | 246 | 2.4 | NM_019759 |
| Dpysl2 | Dpysl2 | dihydropyrimidinase-like 2 | 1968 | 2.0 | BQ174209 |
| — | Dpysl3 | *Mus musculus* transcribed sequence with strong similarity to protein sp: Q14195 (*H. sapiens*) DPY3_HUMAN Dihydropyrimidinase related protein-3 (DRP-3) (Unc-33-like phosphoprotein) (ULIP protein) (Collapsin response mediator protein 4) (CRMP-4) | 78 | 3.7 | AV161550 |
| Dsg2 | Dsg2 | desmoglein 2 | 693 | 2.1 | BG092030 |
| — | Dtx3l | *Mus musculus* transcribed sequence with weak similarity to protein ref: NP_081764.1 (*M. musculus*) RIKEN cDNA 5730493B19 [*Mus musculus*] | 460 | 9.1 | AV327407 |
| BC044798 | Dtx4 | cDNA sequence BC044798 | 589 | 2.5 | AV017487 |
| 2610016C23Rik | Dufd1 | RIKEN cDNA 2610016C23 gene | 53 | 3.7 | AK016786 |
| Dusp10 | Dusp10 | dual specificity phosphatase 10 | 41 | 4.8 | NM_022019 |
| Dusp2 | Dusp2 | dual specificity phosphatase 2 | 54 | 5.0 | L11330 |
| Dutp | Dut | deoxyuridine triphosphatase | 289 | 2.7 | AF091101 |
| — | E030018N11Rik | *Mus musculus* 0 day neonate lung cDNA, RIKEN full-length enriched library, clone: E030018N11 product: hypothetical protein, full insert sequence | 314 | 3.4 | BB794845 |
| E030024M05Rik | E030024M05Rik | RIKEN cDNA E030024M05 gene | 259 | 2.1 | BC025220 |
| — | E130113K08Rik | *Mus musculus* transcribed sequences | 31 | 4.5 | BB491630 |
| E130201N16Rik | E130201N16Rik | RIKEN cDNA E130201N16 gene | 285 | 4.4 | AJ132433 |
| E2f1 | E2f1 | E2F transcription factor 1 | 80 | 2.3 | AK017841 |
| E2f2 | E2f2 | E2F transcription factor 2 | 22 | 4.3 | BB543028 |
| E2f7 | E2f7 | E2F transcription factor 7 | 33 | 3.5 | BG069355 |
| E330016A19Rik | E330016A19Rik | RIKEN cDNA E330016A19 gene | 40 | 5.4 | BB073366 |
| E430004N04Rik | E430004N04Rik | RIKEN cDNA E430004N04 gene | 65 | 7.1 | BE628523 |
| E430004N04Rik | E430004N04Rik | RIKEN cDNA E430004N04 gene | 21 | 3.4 | BB201286 |
| E430019B13Rik | E430019B13Rik | RIKEN cDNA E430019B13 gene | 51 | 2.2 | BE630983 |
| Ebi2 | Ebi2 | Epstein-Barr virus induced gene 2 | 51 | 4.5 | BM242490 |
| Ebi3 | Ebi3 | Epstein-Barr virus induced gene 3 | 70 | 2.9 | NM_015766 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Edg5 | Edg5 | endothelial differentiation, sphingolipid G-protein-coupled receptor, 5 | 152 | 2.5 | AK003144 |
| Edg6 | Edg6 | endothelial differentiation, G-protein-coupled receptor 6 | 87 | 3.1 | AV081616 |
| Ednra | Ednra | endothelin receptor type A | 18 | 4.0 | BC008277 |
| D4Wsu27e | Efhd2 | DNA segment, Chr 4, Wayne State University 27, expressed | 163 | 52.1 | AA409309 |
| Egr1 | Egr1 | early growth response 1 | 317 | 5.3 | NM_007913 |
| Egr2 | Egr2 | early growth response 2 | 3 | 19.6 | X06746 |
| Egr2 | Egr2 | early growth response 2 | 35 | 16.7 | X06746 |
| Egr3 | Egr3 | early growth response 3 | 27 | 10.5 | AV346607 |
| Eif1a | Eif1a | eukaryotic translation initiation factor 1A | 923 | 2.3 | BM200591 |
| Eif1a | Eif1a | eukaryotic translation initiation factor 1A | 1090 | 2.4 | BM200591 |
| 1300018P11Rik | Eif4e3 | RIKEN cDNA 1300018P11 gene | 370 | 4.7 | BC027014 |
| 1300018P11Rik | Eif4e3 | RIKEN cDNA 1300018P11 gene | 464 | 5.1 | BC027014 |
| Pctk2 | Elk3 | PCTAIRE-motif protein kinase 2 | 465 | 2.5 | BM243464 |
| Elk3 | Elk3 | ELK3, member of ETS oncogene family | 425 | 2.0 | BC005686 |
| Elmo1 | Elmo1 | engulfment and cell motility 1, ced-12 homolog (*C. elegans*) | 36 | 3.4 | NM_080288 |
| Elmo1 | Elmo1 | engulfment and cell motility 1, ced-12 homolog (*C. elegans*) | 79 | 3.7 | BC024727 |
| Emb | Emb | embigin | 402 | 2.3 | BG064842 |
| Emb | Emb | embigin | 609 | 2.7 | BG064842 |
| Emilin1 | Emilin1 | elastin microfibril interface located protein 1 | 179 | 2.7 | NM_133918 |
| Emilin2 | Emilin2 | elastin microfibril interface located protein 2 | 92 | 3.8 | BB811788 |
| Emp1 | Emp1 | epithelial membrane protein 1 | 1072 | 2.0 | U25633 |
| Emp3 | Emp3 | epithelial membrane protein 3 | 299 | 5.4 | BC001999 |
| Emr1 | Emr1 | EGF-like module containing, mucin-like, hormone receptor-like sequence 1 | 227 | 3.9 | U66888 |
| Emr4 | Emr4 | EGF-like module containing, mucin-like, hormone receptor-like sequence 4 | 20 | 14.8 | AF396935 |
| Emr4 | Emr4 | EGF-like module containing, mucin-like, hormone receptor-like sequence 4 | 27 | 10.3 | AF396935 |
| Enc1 | Enc1 | ectodermal-neural cortex 1 | 264 | 6.4 | BM120053 |
| Enc1 | Enc1 | ectodermal-neural cortex 1 | 175 | 4.0 | BM120053 |
| Enpp4 | Enpp4 | ectonucleotide pyrophosphatase/phosphodiesterase 4 | 657 | 2.2 | AV280361 |
| Entpd1 | Entpd1 | ectonucleoside triphosphate diphosphohydrolase 1 | 160 | 3.4 | BI151440 |
| Entpd1 | Entpd1 | ectonucleoside triphosphate diphosphohydrolase 1 | 89 | 2.4 | BI151440 |
| Eomes | Eomes | eomesodermin homolog (*Xenopus laevis*) | 69 | 2.1 | BB128925 |
| Epb4.1l2 | Epb4.1l2 | erythrocyte protein band 4.1-like 2 | 528 | 2.0 | BE951907 |
| Eppk1 | Eppk1 | epiplakin 1 | 74 | 2.1 | BC026387 |
| 2310046K10Rik | Epsti1 | RIKEN cDNA 2310046K10 gene | 63 | 13.4 | AK017174 |
| 2310046K10Rik | Epsti1 | RIKEN cDNA 2310046K10 gene | 106 | 14.2 | BF020640 |
| — | Espl1 | *Mus musculus* 10 days neonate skin cDNA, RIKEN full-length enriched library, clone: 4732457F20 product: unknown EST, full insert sequence | 91 | 2.7 | BM200578 |
| Ets1 | Ets1 | E26 avian leukemia oncogene 1, 5' domain | 82 | 2.6 | BC010588 |
| Ets1 | Ets1 | E26 avian leukemia oncogene 1, 5' domain | 564 | 3.2 | BB151715 |
| Ets1 | Ets1 | E26 avian leukemia oncogene 1, 5' domain | 556 | 5.1 | BB151715 |
| Etv3 | Etv3 | ets variant gene 3 | 88 | 2.0 | BM932547 |
| — | Etv6 | *Mus musculus* transcribed sequence with strong similarity to protein sp: P00722 (*E. coli*) BGAL_ECOLI Beta-galactosidase (Lactase) | 73 | 2.4 | BB735884 |
| Evi2a | Evi2a | ecotropic viral integration site 2a | 54 | 7.7 | BB236216 |
| Evi2a | Evi2a | ecotropic viral integration site 2a | 19 | 35.2 | AI122415 |
| Evl | Evl | Ena-vasodilator stimulated phosphoprotein | 96 | 2.5 | AW546029 |
| Evl | Evl | Ena-vasodilator stimulated phosphoprotein | 205 | 4.7 | AW553781 |
| Evl | Evl | Ena-vasodilator stimulated phosphoprotein | 159 | 3.7 | NM_007965 |
| Exo1 | Exo1 | exonuclease 1 | 65 | 2.4 | BE986864 |
| Exo1 | Exo1 | exonuclease 1 | 46 | 2.0 | BE986864 |
| 2310032N20Rik | Exosc8 | RIKEN cDNA 2310032N20 gene | 433 | 3.7 | AK009584 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Ezh2 | Ezh2 | enhancer of zeste homolog 2 (*Drosophila*) | 256 | 4.0 | NM_007971 |
| F10 | F10 | coagulation factor X | 75 | 2.5 | NM_007972 |
| F13a | F13a1 | coagulation factor XIII, alpha subunit | 64 | 4.5 | NM_028784 |
| F2r | F2r | coagulation factor II (thrombin) receptor | 1067 | 3.0 | BQ173958 |
| F2r | F2r | coagulation factor II (thrombin) receptor | 2532 | 2.3 | AV024285 |
| F3 | F3 | coagulation factor III | 542 | 2.8 | BC024886 |
| F730004D16Rik | F730004D16Rik | RIKEN cDNA F730004D16 gene | 100 | 5.4 | BM230330 |
| — | F730047E07Rik | *Mus musculus* hypothetical LOC269515 (LOC269515), mRNA | 37 | 4.7 | BG071041 |
| Fabp5 | Fabp5 | fatty acid binding protein 5, epidermal | 504 | 3.0 | BC002008 |
| Fabp5 | Fabp5 | fatty acid binding protein 5, epidermal | 150 | 3.5 | BC002008 |
| Fabp7 | Fabp7 | fatty acid binding protein 7, brain | 795 | 5.2 | NM_021272 |
| Tnfrsf6 | Fas | tumor necrosis factor receptor superfamily, member 6 | 120 | 6.0 | NM_007987 |
| Fbn1 | Fbn1 | fibrillin 1 | 269 | 3.3 | AF007248 |
| Fbn1 | Fbn1 | fibrillin 1 | 494 | 3.0 | NM_007993 |
| Fbxo5 | Fbxo5 | F-box only protein 5 | 119 | 5.0 | AK011820 |
| Fbxo6b | Fbxo6b | F-box only protein 6b | 455 | 3.0 | NM_015797 |
| 1110064L07Rik | Fbxw17 | RIKEN cDNA 1110064L07 gene | 339 | 4.8 | AV016303 |
| Fcer1g | Fcer1g | Fc receptor, IgE, high affinity I, gamma polypeptide | 225 | 21.7 | NM_010185 |
| Fcgr1 | Fcgr1 | Fc receptor, IgG, high affinity I | 123 | 4.8 | BB075261 |
| Fcgr1 | Fcgr1 | Fc receptor, IgG, high affinity I | 74 | 21.0 | AF143181 |
| Fcgr2b | Fcgr3 | Fc receptor, IgG, low affinity IIb | 161 | 11.4 | NM_010188 |
| Fcrl3 | Fcrl3 | Fc receptor-like 3 | 114 | 20.5 | BC027310 |
| Fen1 | Fen1 | flap structure specific endonuclease 1 | 262 | 3.1 | NM_007999 |
| Fer1l3 | Fer1l3 | fer-1-like 3, myoferlin (*C. elegans*) | 208 | 4.0 | BI555209 |
| Fes | Fes | feline sarcoma oncogene | 105 | 3.0 | BG867327 |
| Fes | Fes | feline sarcoma oncogene | 101 | 3.8 | BG867327 |
| Fga | Fga | fibrinogen, alpha polypeptide | 605 | 6.1 | BC005467 |
| Fgd2 | Fgd2 | FYVE, RhoGEF and PH domain containing 2 | 109 | 2.2 | NM_013710 |
| Fgd3 | Fgd3 | FYVE, RhoGEF and PH domain containing 3 | 66 | 2.7 | AK018025 |
| 1500031J01Rik | Fgfr1op2 | RIKEN cDNA 1500031J01 gene | 82 | 2.2 | AB041650 |
| Fgl2 | Fgl2 | fibrinogen-like protein 2 | 56 | 46.7 | BF136544 |
| Fgl2 | Fgl2 | fibrinogen-like protein 2 | 114 | 28.1 | BF136544 |
| Fgr | Fgr | Gardner-Rasheed feline sarcoma viral (Fgr) oncogene homolog | 120 | 5.4 | NM_010208 |
| Fgr | Fgr | Gardner-Rasheed feline sarcoma viral (Fgr) oncogene homolog | 105 | 4.3 | BB165085 |
| — | Fkbp10 | — | 84 | 2.3 | AI325255 |
| Fli1 | Fli1 | Friend leukemia integration 1 | 228 | 3.5 | BB138212 |
| Fli1 | Fli1 | Friend leukemia integration 1 | 75 | 5.1 | NM_008026 |
| 1110008K06Rik | Fln29 | RIKEN cDNA 1110008K06 gene | 464 | 4.0 | AK003586 |
| 5430425K04Rik | Fmnl2 | RIKEN cDNA 5430425K04 gene | 576 | 2.3 | AK017338 |
| Fnbp1 | Fnbp1 | formin binding protein 1 | 211 | 2.3 | BM244005 |
| Fos | Fos | FBJ osteosarcoma oncogene | 119 | 9.1 | AV026617 |
| Fosl2 | Fosl2 | fos-like antigen 2 | 247 | 4.1 | BM245170 |
| Foxa1 | Foxa1 | forkhead box A1 | 46 | 2.3 | NM_008259 |
| Foxj1 | Foxj1 | forkhead box J1 | 53 | 2.1 | L13204 |
| Foxp1 | Foxp1 | forkhead box P1 | 120 | 2.2 | BG962849 |
| Fprl1 | Fprl1 | formyl peptide receptor-like 1 | 30 | 48.3 | NM_008039 |
| Frk | Frk | fyn-related kinase | 193 | 2.2 | BB787292 |
| Fscn1 | Fscn1 | fascin homolog 1, actin bundling protein (Strongylocentrotus) purpuratus) | 820 | 3.1 | NM_007984 |
| Fshprh1 | Fshprh1 | FSH primary response 1 | 8 | 6.8 | BB258991 |
| Fstl1 | Fstl1 | follistatin-like 1 | 469 | 4.4 | BI452727 |
| Fstl1 | Fstl1 | follistatin-like 1 | 73 | 2.2 | BB540658 |
| Fstl1 | Fstl1 | follistatin-like 1 | 739 | 4.0 | BI452727 |
| Fthfsdc1 | Fthfsdc1 | formyltetrahydrofolate synthetase domain containing 1 | 145 | 3.2 | AV095209 |
| Fus | Fus | fusion, derived from t(12; 16) malignant liposarcoma (human) | 1474 | 2.6 | AF224264 |
| Fut4 | Fut4 | fucosyltransferase 4 | 16 | 6.5 | AV309809 |
| Fxyd5 | Fxyd5 | FXYD domain-containing ion transport regulator 5 | 491 | 7.4 | NM_008761 |
| Fyb | Fyb | FYN binding protein | 73 | 3.8 | BE853428 |
| Fyb | Fyb | FYN binding protein | 64 | 18.3 | BM243379 |
| Fyb | Fyb | FYN binding protein | 70 | 19.2 | BB157866 |
| Fyn | Fyn | Fyn proto-oncogene | 217 | 3.1 | NM_008054 |
| Fyn | Fyn | Fyn proto-oncogene | 369 | 2.9 | NM_008054 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| G430022H21Rik | G430022H21Rik | RIKEN cDNA G430022H21 gene | 108 | 2.6 | BM247306 |
| G430041M01Rik | G430041M01Rik | RIKEN cDNA G430041M01 gene | 602 | 2.1 | BG069073 |
| — | G430041M01Rik | *Mus musculus* adult male corpora quadrigemina cDNA, RIKEN full-length enriched library, clone: B230214O09 product: unknown EST, full insert sequence | 36 | 6.9 | BM211445 |
| Gab3 | Gab3 | growth factor receptor bound protein 2-associated protein 3 | 35 | 2.5 | BB037935 |
| — | Gadd45b | — | 152 | 2.5 | AI323528 |
| Galgt1 | Galgt1 | UDP-N-acetyl-alpha-D-galactosamine: (N-acetylneuraminyl)-galactosylglucosylceramide-beta-1, 4-N-acetylgalactosaminyltransferase | 99 | 8.2 | U18975 |
| Galnt12 | Galnt12 | UDP-N-acetyl-alpha-D-galactosamine: polypeptide N-acetylgalactosaminyltransferase 12 | 92 | 2.6 | AV376137 |
| Galnt6 | Galnt6 | UDP-N-acetyl-alpha-D-galactosamine: polypeptide N-acetylgalactosaminyltransferase 6 | 7 | 11.2 | AV231866 |
| — | Gas2l3 | *Mus musculus* hypothetical LOC237436 (LOC237436), mRNA | 59 | 3.3 | BB770972 |
| — | Gas2l3 | *Mus musculus* hypothetical LOC237436 (LOC237436), mRNA | 52 | 3.7 | BB770972 |
| Gas5 | Gas5 | growth arrest specific 5 | 2282 | 2.0 | NM_013525 |
| Gas5 | Gas5 | growth arrest specific 5 | 288 | 3.0 | BI650268 |
| Gas5 | Gas5 | growth arrest specific 5 | 121 | 5.2 | AW547050 |
| Gas5 | Gas5 | growth arrest specific 5 | 220 | 4.3 | BC004622 |
| Gbp1 | Gbp1 | guanylate nucleotide binding protein 1 | 9 | 54.5 | NM_010259 |
| Gbp2 | Gbp2 | guanylate nucleotide binding protein 2 | 272 | 53.4 | BE197524 |
| Gbp2 | Gbp2 | guanylate nucleotide binding protein 2 | 321 | 100.2 | NM_010260 |
| Gbp3 | Gbp4 | guanylate nucleotide binding protein 3 | 184 | 42.9 | NM_018734 |
| Gch | Gch1 | GTP cyclohydrolase 1 | 54 | 3.3 | NM_008102 |
| Gcnt1 | Gcnt1 | glucosaminyl (N-acetyl) transferase 1, core 2 | 26 | 6.9 | AK017462 |
| Gda | Gda | guanine deaminase | 106 | 11.9 | AW911807 |
| Gda | Gda | guanine deaminase | 33 | 5.4 | NM_010266 |
| Gda | Gda | guanine deaminase | 81 | 12.1 | AW911807 |
| 1110035O14Rik | Gdap10 | RIKEN cDNA 1110035O14 gene | 329 | 4.0 | NM_010268 |
| Gfpt1 | Gfpt1 | glutamine fructose-6-phosphate transaminase 1 | 74 | 2.7 | AF334736 |
| Ggta1 | Ggta1 | glycoprotein galactosyltransferase alpha 1, 3 | 42 | 3.2 | M26925 |
| Ggta1 | Ggta1 | glycoprotein galactosyltransferase alpha 1, 3 | 232 | 3.3 | AF297615 |
| Ian1 | Gimap4 | immune associated nucleotide 1 | 2439 | 3.0 | BC005577 |
| Ian1 | Gimap4 | immune associated nucleotide 1 | 1384 | 2.4 | BC005577 |
| Ian3 | Gimap7 | immune associated nucleotide 3 | 52 | 14.1 | BC026200 |
| Ian3 | Gimap7 | immune associated nucleotide 3 | 9 | 7.7 | BB223831 |
| — | Gimap8 | *Mus musculus* similar to hypothetical protein (LOC243374), mRNA | 716 | 3.2 | BM243674 |
| — | Gimap8 | — | 22 | 7.8 | BB236014 |
| Glipr1 | Glipr1 | GLI pathogenesis-related 1 (glioma) | 144 | 14.8 | BC025083 |
| Glipr2 | Glipr2 | GLI pathogenesis-related 2 | 36 | 12.8 | BM208214 |
| Glipr2 | Glipr2 | GLI pathogenesis-related 2 | 49 | 8.2 | BM208214 |
| — | Gls | *Mus musculus* transcribed sequences | 190 | 2.7 | BM239869 |
| Gmfg | Gmfg | glia maturation factor, gamma | 310 | 5.7 | NM_022024 |
| Gmfg | Gmfg | glia maturation factor, gamma | 76 | 5.9 | NM_022024 |
| — | Gna13 | *Mus musculus* transcribed sequences | 227 | 2.0 | BI180797 |
| Gna13 | Gna13 | guanine nucleotide binding protein, alpha 13 | 1712 | 2.7 | BG073165 |
| Gnb4 | Gnb4 | guanine nucleotide binding protein, beta 4 | 290 | 2.1 | BI713933 |
| Gnb4 | Gnb4 | guanine nucleotide binding protein, beta 4 | 204 | 3.4 | BI713933 |
| Gng10 | Gng10 | guanine nucleotide binding protein (G protein), gamma 10 | 619 | 2.4 | NM_025277 |
| — | Gng2 | *Mus musculus* 15 days embryo male testis cDNA, RIKEN full-length enriched library, clone: 8030491K24 product: unknown EST, full insert sequence | 224 | 2.3 | AV021455 |
| Gng2 | Gng2 | guanine nucleotide binding protein (G protein), gamma 2 subunit | 91 | 7.8 | BB522409 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | Gng2 | *Mus musculus* 15 days embryo male testis cDNA, RIKEN full-length enriched library, clone: 8030491K24 product: unknown EST, full insert sequence | 111 | 2.6 | AV021455 |
| Gp38 | Gp38 | glycoprotein 38 | 383 | 2.6 | NM_010329 |
| Gpm6b | Gpm6b | glycoprotein m6b | 249 | 3.0 | AF254879 |
| Gpm6b | Gpm6b | glycoprotein m6b | 232 | 4.4 | AK016567 |
| Gpr132 | Gpr132 | G protein-coupled receptor 132 | 47 | 3.8 | BB208670 |
| F730001G15Rik | Gpr171 | RIKEN cDNA F730001G15 gene | 17 | 17.5 | BB229616 |
| Gpr18 | Gpr18 | G protein-coupled receptor 18 | 100 | 9.9 | BG145550 |
| Gpr35 | Gpr35 | G protein-coupled receptor 35 | 15 | 14.0 | NM_022320 |
| Gpr43 | Gpr43 | G protein-coupled receptor 43 | 17 | 2.6 | AV370830 |
| Gpr64 | Gpr64 | G protein-coupled receptor 64 | 79 | 2.2 | AV242919 |
| Gpcr25 | Gpr65 | G-protein coupled receptor 25 | 50 | 13.6 | NM_008152 |
| Gpr68 | Gpr68 | G protein-coupled receptor 68 | 24 | 10.0 | BB538372 |
| Gpr84 | Gpr84 | G protein-coupled receptor 84 | 18 | 17.9 | NM_030720 |
| Gprk6 | Gprk6 | G protein-coupled receptor kinase 6 | 556 | 2.5 | BB461269 |
| Gprk6 | Gprk6 | G protein-coupled receptor kinase 6 | 299 | 2.1 | AF040748 |
| 1810036L03Rik | Gsdmdc1 | RIKEN cDNA 1810036L03 gene | 133 | 6.5 | AK007710 |
| Gsg2 | Gsg2 | germ cell-specific gene 2 | 34 | 3.1 | BE457839 |
| Gzma | Gzma | granzyme A | 68 | 14.1 | NM_010370 |
| Gzmk | Gzmk | granzyme K | 24 | 14.1 | AB032200 |
| H28 | H28 | histocompatibility 28 | 343 | 8.9 | NM_031367 |
| H28 | H28 | histocompatibility 28 | 370 | 6.8 | BC024930 |
| H2-Aa | H2-Aa | histocompatibility 2, class II antigen A, alpha | 1265 | 12.3 | AV018723 |
| H2-Aa | H2-Aa | histocompatibility 2, class II antigen A, alpha | 3501 | 7.1 | BE688749 |
| — | H2-Aa | — | 18 | 46.1 | AV086906 |
| H2-Aa | H2-Aa | histocompatibility 2, class II antigen A, alpha | 2137 | 10.8 | AF119253 |
| H2-Ab1 | H2-Ab1 | histocompatibility 2, class II antigen A, beta 1 | 421 | 19.9 | M15848 |
| H2-Ab1 | H2-Ab1 | histocompatibility 2, class II antigen A, beta 1 | 950 | 13.2 | NM_010379 |
| H2-Ab1 | H2-Ab1 | histocompatibility 2, class II antigen A, beta 1 | 659 | 18.5 | M15848 |
| H2afx | H2afx | H2A histone family, member X | 654 | 2.0 | NM_010436 |
| H2-D1 | H2-D1 | histocompatibility 2, D region locus 1 | 87 | 3.5 | X00246 |
| H2-D1 | H2-D1 | histocompatibility 2, D region locus 1 | 76 | 34.3 | M34962 |
| H2-D1 | H2-D1 | histocompatibility 2, D region locus 1 | 43 | 15.6 | M33151 |
| H2-D1 | H2-D1 | histocompatibility 2, D region locus 1 | 437 | 26.3 | M86502 |
| H2-D1 | H2-D1 | histocompatibility 2, D region locus 1 | 43 | 11.3 | M83244 |
| H2-D1 | H2-D1 | histocompatibility 2, D region locus 1 | 2224 | 6.2 | NM_010380 |
| H2-D1 | H2-D1 | histocompatibility 2, D region locus 1 | 228 | 52.6 | L36068 |
| H2-D1 | H2-D1 | histocompatibility 2, D region locus 1 | 152 | 50.7 | M69068 |
| — | H2-DMa | — | 6 | 16.9 | BB425495 |
| H2-DMa | H2-DMa | histocompatibility 2, class II, locus DMa | 261 | 20.9 | NM_010386 |
| H2-DMb1 | H2-DMb1 | histocompatibility 2, class II, locus Mb1 | 121 | 38.0 | NM_010388 |
| H2-DMb1 | H2-DMb1 | histocompatibility 2, class II, locus Mb1 | 159 | 45.2 | BB734586 |
| H2-DMb1 | H2-DMb1 | histocompatibility 2, class II, locus Mb1 | 347 | 16.8 | NM_010388 |
| H2-DMb1 | H2-DMb1 | histocompatibility 2, class II, locus Mb1 | 116 | 19.8 | NM_010387 |
| H2-DMb1 | H2-DMb1 | histocompatibility 2, class II, locus Mb1 | 87 | 53.8 | BB734586 |
| H2-Ea | H2-Ea | histocompatibility 2, class II antigen E alpha | 103 | 3.7 | U13648 |
| H2-Ea | H2-Ea | histocompatibility 2, class II antigen E alpha | 63 | 6.4 | U13648 |
| H2-Eb1 | H2-Eb1 | histocompatibility 2, class II antigen E beta | 1760 | 8.6 | NM_010382 |
| H2-K | H2-K | histocompatibility 2, K region | 136 | 5.9 | J00406 |
| H2-K | H2-K1 | histocompatibility 2, K region | 626 | 22.5 | L23495 |
| — | H2-K1 | MHC l = H-2Kd homolog {alternatively spliced, deletion of exon 3} [mice, DBA/2, L1210 lymphoma, mRNA Mutant, 855 nt] | 435 | 45.5 | S70184 |
| H2-K | H2-K1 | histocompatibility 2, K region | 606 | 23.9 | BC011306 |
| H2-M3 | H2-M3 | histocompatibility 2, M region locus 3 | 261 | 4.8 | NM_013819 |
| H2-Oa | H2-Oa | histocompatibility 2, O region alpha locus | 56 | 6.1 | NM_008206 |
| H2-Ob | H2-Ob | histocompatibility 2, O region beta locus | 38 | 4.4 | BG144448 |
| H2-Q1 | H2-Q1 | histocompatibility 2, Q region locus 1 | 125 | 3.7 | M58156 |
| H2-Q1 | H2-Q1 | histocompatibility 2, Q region locus 1 | 35 | 22.6 | BC010602 |
| H2-K | H2-Q5 | histocompatibility 2, K region | 20 | 18.3 | NM_010393 |
| H2-Q7 | H2-Q7 | histocompatibility 2, Q region locus 7 | 20 | 14.9 | AK013097 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| H2-Q7 | H2-Q7 | histocompatibility 2, Q region locus 7 | 37 | 78.5 | M29881 |
| H2-T10 | H2-T10 | histocompatibility 2, T region locus 10 | 2355 | 4.3 | NM_010395 |
| H2-T23 | H2-T23 | histocompatibility 2, T region locus 23 | 2198 | 8.0 | NM_010398 |
| — | H2-T23 | *Mus musculus* 2 days neonate thymus thymic cells cDNA, RIKEN full-length enriched library, clone: C920026N01 product: weakly similar to H-2 CLASS I HISTOCOMPATIBILITY ANTIGEN, D-37 ALPHA CHAIN PRECURSOR [*Mus musculus*], full insert sequence | 71 | 6.6 | NM_010398 |
| H2-T24 | H2-T24 | histocompatibility 2, T region locus 24 | 109 | 3.1 | L22338 |
| Has2 | Has2 | hyaluronan synthase 2 | 37 | 2.5 | NM_008216 |
| Havcr1 | Havcr1 | hepatitis A virus cellular receptor 1 | 700 | 7.0 | NM_134248 |
| Havcr1 | Havcr1 | hepatitis A virus cellular receptor 1 | 1015 | 7.8 | BM211416 |
| Havcr2 | Havcr2 | hepatitis A virus cellular receptor 2 | 39 | 4.7 | AF450241 |
| — | Hck | *Mus musculus* transcribed sequences | 28 | 2.2 | BM246401 |
| Hck | Hck | hemopoietic cell kinase | 117 | 17.9 | NM_010407 |
| Hcph | Hcph | hemopoietic cell phosphatase | 617 | 4.1 | NM_013545 |
| Hells | Hells | helicase, lymphoid specific | 65 | 10.4 | NM_008234 |
| 4930568P13Rik | Hemp1 | RIKEN cDNA 4930568P13 gene | 36 | 25.3 | BM238906 |
| 4930568P13Rik | Hemp1 | RIKEN cDNA 4930568P13 gene | 147 | 4.8 | BM238906 |
| 2510038N07Rik | Herc5 | RIKEN cDNA 2510038N07 gene | 217 | 12.8 | AI639807 |
| 2510038N07Rik | Herc5 | RIKEN cDNA 2510038N07 gene | 64 | 18.0 | AK015214 |
| 2510038N07Rik | Herc5 | RIKEN cDNA 2510038N07 gene | 161 | 25.4 | AW208668 |
| 2510038N07Rik | Herc5 | RIKEN cDNA 2510038N07 gene | 72 | 20.4 | AI639807 |
| Hesx1 | Hesx1 | homeo box gene expressed in ES cells | 76 | 4.2 | NM_010420 |
| Hgf | Hgf | hepatocyte growth factor | 74 | 2.7 | D10212 |
| Hgf | Hgf | hepatocyte growth factor | 49 | 3.0 | AF042856 |
| Hgf | Hgf | hepatocyte growth factor | 37 | 2.8 | BB476818 |
| — | Hif1a | *Mus musculus* transcribed sequences | 10 | 3.9 | BB409314 |
| Hist1h2ae | Hist1h2ae | histone 1, H2ae | 525 | 24.6 | W91024 |
| Hivep2 | Hivep2 | human immunodeficiency virus type I enhancer binding protein 2 | 138 | 2.0 | AW321867 |
| Hk2 | Hk2 | hexokinase 2 | 79 | 7.1 | NM_013820 |
| Hk3 | Hk3 | hexokinase 3 | 106 | 6.7 | BB334625 |
| — | Hk3 | — | 97 | 14.9 | BB324660 |
| Hmgb2 | Hmgb2 | high mobility group box 2 | 544 | 7.3 | X67668 |
| Hmgb2 | Hmgb2 | high mobility group box 2 | 337 | 9.1 | C85885 |
| Hn1 | Hn1 | hematological and neurological expressed sequence 1 | 327 | 4.3 | NM_008258 |
| Hn1 | Hn1 | hematological and neurological expressed sequence 1 | 236 | 5.6 | NM_008258 |
| — | Hnrpa1 | *Mus musculus* transcribed sequence with strong similarity to protein ref: NP_002127.1 (*H. sapiens*) heterogeneous nuclear ribonucleoprotein A1, isoform a; nuclear ribonucleoprotein particle A1 protein; helix-destabilizing protein; single-strand DNA-binding protein UP1; heterogeneous nuclear ribonucleoprotein core protein A1; heterogeneous nuclear ribonucleoprotein A1B protein; heterogeneous nuclear ribonucleoprotein B2 protein [*Homo sapiens*] | 705 | 3.1 | BI663320 |
| Hnrpa1 | Hnrpa1; Hdp; hnrnp-A1; D15Ertd119e | heterogeneous nuclear ribonucleoprotein A1 | 1077 | 2.1 | AK007802 |
| 2610510D13Rik | Hnrpa3 | RIKEN cDNA 2610510D13 gene | 2441 | 2.0 | BC024454 |
| Hnrpdl | Hnrpdl | heterogeneous nuclear ribonucleoprotein D-like | 787 | 2.3 | NM_016690 |
| Hp | Hp | haptoglobin | 53 | 9.9 | NM_017370 |
| Hpse | Hpse | heparanase | 32 | 22.8 | BG094050 |
| Hrasls3 | Hrasls3 | HRAS like suppressor 3 | 504 | 16.5 | BC024581 |
| Hrb | Hrb | HIV-1 Rev binding protein | 4 | 2.5 | BG068396 |
| 4930534K13Rik | Ibrdc3 | RIKEN cDNA 4930534K13 gene | 280 | 7.3 | AK015966 |
| 4930534K13Rik | Ibrdc3 | RIKEN cDNA 4930534K13 gene | 430 | 6.2 | BG064140 |
| Icam1 | Icam1 | intercellular adhesion molecule | 440 | 10.2 | BC008626 |
| Icos | Icos | inducible T-cell co-stimulator | 68 | 9.8 | AV313923 |
| Icsbp1 | Icsbp1 | interferon consensus sequence binding protein 1 | 228 | 9.9 | BG069095 |
| Icsbp1 | Icsbp1 | interferon consensus sequence binding protein 1 | 432 | 10.0 | BG069095 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Ier5 | Ier5 | immediate early response 5 | 347 | 3.1 | BF147705 |
| Ifi1 | Ifi1 | interferon inducible protein 1 | 1151 | 15.4 | NM_008326 |
| Ifi202b | Ifi202b | interferon activated gene 202B | 118 | 46.5 | NM_011940 |
| Ifi202b | Ifi202b | interferon activated gene 202B | 93 | 42.5 | AV229143 |
| Ifi203 | Ifi203 | interferon activated gene 203 | 63 | 17.8 | NM_008328 |
| Ifi203 | Ifi203 | interferon activated gene 203 | 177 | 9.1 | BC008167 |
| Ifi16 | Ifi204 | interferon, gamma-inducible protein 16 | 22 | 24.8 | NM_008329 |
| Ifi205 | Ifi205 | interferon activated gene 205 | 12 | 140.4 | M74124 |
| Ifi205 | Ifi205 | interferon activated gene 205 | 30 | 151.7 | M74124 |
| Ifi205 | Ifi205 | interferon activated gene 205 | 38 | 79.7 | AI481797 |
| Ifi205 | Ifi205 | interferon activated gene 205 | 76 | 102.7 | AI481797 |
| 2310061N23Rik | Ifi27 | RIKEN cDNA 2310061N23 gene | 219 | 8.2 | AY090098 |
| Ifi30 | Ifi30 | interferon gamma inducible protein 30 | 3381 | 2.4 | NM_023065 |
| 2010008K16Rik | Ifi35 | RIKEN cDNA 2010008K16 gene | 1277 | 6.0 | AW986054 |
| 2010008K16Rik | Ifi35 | RIKEN cDNA 2010008K16 gene | 377 | 4.5 | BC008158 |
| 2010008K16Rik | Ifi35 | RIKEN cDNA 2010008K16 gene | 371 | 2.5 | AW986054 |
| A430056A10Rik | Ifi44 | RIKEN cDNA A430056A10 gene | 439 | 5.0 | BB329808 |
| 9130009C22Rik | Ifih1 | RIKEN cDNA 9130009C22 gene | 506 | 5.4 | AY075132 |
| Ifit1 | Ifit1 | interferon-induced protein with tetratricopeptide repeats 1 | 93 | 18.5 | NM_008331 |
| Ifit2 | Ifit2 | interferon-induced protein with tetratricopeptide repeats 2 | 271 | 33.8 | NM_008332 |
| Ifit3 | Ifit3 | interferon-induced protein with tetratricopeptide repeats 3 | 761 | 6.3 | NM_010501 |
| 1110036C17Rik | Ifitm1 | RIKEN cDNA 1110036C17 gene | 622 | 4.0 | BC027285 |
| 1110004C05Rik | Ifitm3 | RIKEN cDNA 1110004C05 gene | 3701 | 4.2 | BC010291 |
| A330075D07 | Ifitm6 | hypothetical protein A330075D07 | 34 | 10.6 | BB193024 |
| Ifnar2 | Ifnar2 | interferon (alpha and beta) receptor 2 | 107 | 3.0 | Y09864 |
| Ifnar2 | Ifnar2 | interferon (alpha and beta) receptor 2 | 155 | 2.7 | BB522265 |
| Ifnar2 | Ifnar2 | interferon (alpha and beta) receptor 2 | 977 | 2.4 | AF013486 |
| Ifng | Ifng | interferon gamma | 32 | 30.3 | K00083 |
| Ifngr | Ifngr1 | interferon gamma receptor | 572 | 2.0 | NM_010511 |
| Ifrd1 | Ifrd1 | interferon-related developmental regulator 1 | 463 | 3.0 | NM_013562 |
| Igf1 | Igf1 | insulin-like growth factor 1 | 606 | 2.0 | BG075165 |
| Igf1 | Igf1 | insulin-like growth factor 1 | 184 | 2.7 | NM_010512 |
| Igf1 | Igf1 | insulin-like growth factor 1 | 236 | 2.2 | AF440694 |
| Igf1 | Igf1 | insulin-like growth factor 1 | 398 | 3.1 | BG092677 |
| Igh-6 | Igh-6 | immunoglobulin heavy chain 6 (heavy chain of IgM) | 140 | 12.8 | BB226392 |
| Igh-6 | Igh-6 | immunoglobulin heavy chain 6 (heavy chain of IgM) | 269 | 6.0 | AI326478 |
| Igsf6 | Igsf6 | immunoglobulin superfamily, member 6 | 8 | 25.4 | NM_030691 |
| Igsf7 | Igsf7 | immunoglobulin superfamily, member 7 | 101 | 7.0 | AF251705 |
| — | Igtp | Mus musculus 13 days embryo lung cDNA, RIKEN full-length enriched library, clone: D430030N05 product: unknown EST, full insert sequence | 35 | 14.3 | BB485297 |
| Igtp | Igtp | interferon gamma induced GTPase | 905 | 25.9 | NM_018738 |
| AI481100 | Igtp | expressed sequence AI481100 | 365 | 30.9 | NM_019440 |
| Ii | Ii | Ia-associated invariant chain | 3790 | 6.2 | BC003476 |
| AW111922 | Iigp1 | expressed sequence AW111922 | 885 | 36.6 | BM239828 |
| AW111922 | Iigp1 | expressed sequence AW111922 | 361 | 53.7 | BM239828 |
| Il11 | Il11 | interleukin 11 | 43 | 4.4 | NM_008350 |
| Il12b | Il12b | interleukin 12b | 29 | 4.2 | AF128214 |
| Il12rb1 | Il12rb1 | interleukin 12 receptor, beta 1 | 35 | 5.5 | NM_008353 |
| Il18 | Il18 | interleukin 18 | 330 | 2.1 | NM_008360 |
| Il18bp | Il18bp | interleukin 18 binding protein | 122 | 33.6 | AF110803 |
| Il18rap | Il18rap | interleukin 18 receptor accessory protein | 12 | 8.4 | NM_010553 |
| Il1b | Il1b | interleukin 1 beta | 118 | 4.7 | BC011437 |
| Il1rn | Il1rn | interleukin 1 receptor antagonist | 40 | 14.3 | M57525 |
| Il1rn | Il1rn | interleukin 1 receptor antagonist | 99 | 6.6 | NM_031167 |
| Tccr | Il27ra | T cell cytokine receptor | 28 | 8.2 | NM_016671 |
| Il2rb | Il2rb | interleukin 2 receptor, beta chain | 39 | 12.3 | BE634648 |
| Il4i1 | Il4i1 | interleukin 4 induced 1 | 46 | 3.9 | NM_010215 |
| Il4ra | Il4ra | interleukin 4 receptor, alpha | 203 | 2.8 | NM_010557 |
| Il6 | Il6 | interleukin 6 | 15 | 20.8 | NM_031168 |
| Il7r | Il7r | interleukin 7 receptor | 72 | 4.6 | AI573431 |
| Incenp | Incenp | inner centromere protein | 80 | 4.4 | BI410774 |
| Incenp | Incenp | inner centromere protein | 192 | 9.0 | BB418702 |
| Indo | Indo | indoleamine-pyrrole 2,3 dioxygenase | 15 | 6.7 | NM_008324 |
| Inhbb | Inhbb | inhibin beta-B | 98 | 4.2 | BB253137 |
| Inpp5d | Inpp5d | inositol polyphosphate-5-phosphatase D | 170 | 4.7 | U39203 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Irak3 | Irak3 | interleukin-1 receptor-associated kinase 3 | 43 | 2.8 | AV228493 |
| Irak4 | Irak4 | interleukin-1 receptor-associated kinase 4 | 63 | 3.2 | BM220651 |
| B430217B02Rik | Irf1 | RIKEN cDNA B430217B02 gene | 665 | 15.7 | NM_008390 |
| — | Irf2 | — | 53 | 4.9 | AI606908 |
| Irf5 | Irf5 | interferon regulatory factor 5 | 205 | 2.7 | NM_012057 |
| Irf7 | Irf7 | interferon regulatory factor 7 | 198 | 9.8 | NM_016850 |
| Irg1 | Irg1 | immunoresponsive gene 1 | 9 | 80.3 | L38281 |
| Isg20 | Isg20 | interferon-stimulated protein | 119 | 4.7 | BC022751 |
| Isgf3g | Isgf3g | interferon dependent positive acting transcription factor 3 gamma | 327 | 3.6 | NM_008394 |
| Itga4 | Itga4 | integrin alpha 4 | 45 | 4.4 | BB284583 |
| Itga4 | Itga4 | integrin alpha 4 | 19 | 8.5 | NM_010576 |
| — | Itga4 | *Mus musculus* adult retina cDNA, RIKEN full-length enriched library, clone: A930029I05 product: unknown EST, full insert sequence | 138 | 7.9 | BB205589 |
| Itgal | Itgal | integrin alpha L | 118 | 9.3 | BI554446 |
| Itgam | Itgam | integrin alpha M | 16 | 12.4 | NM_008401 |
| Itgax | Itgax | integrin alpha X | 80 | 11.9 | NM_021334 |
| Itgb2 | Itgb2 | integrin beta 2 | 178 | 28.7 | NM_008404 |
| Jak2 | Jak2 | Janus kinase 2 | 882 | 2.4 | NM_008413 |
| Jak2 | Jak2 | Janus kinase 2 | 353 | 3.1 | NM_008413 |
| Smcx | Jarid1c | selected mouse cDNA on the X | 35 | 2.1 | BB165753 |
| Jun | Jun | Jun oncogene | 559 | 2.7 | NM_010591 |
| Kcnab2 | Kcnab2 | potassium voltage-gated channel, shaker-related subfamily, beta member 2 | 35 | 9.0 | U31908 |
| D7Ertd764e | Kcnk6 | DNA segment, Chr 7, ERATO Doi 764, expressed | 139 | 3.5 | BG069589 |
| Kcnn4 | Kcnn4 | potassium intermediate/small conductance calcium-activated channel, subfamily N, member 4 | 45 | 28.2 | BG865910 |
| — | Kcnq5 | *Mus musculus* transcribed sequences | 17 | 2.9 | BB162318 |
| Khdrbs1 | Khdrbs1 | KH domain containing, RNA binding, signal transduction associated 1 | 290 | 7.1 | BB752997 |
| Kif11 | Kif11 | kinesin family member 11 | 41 | 6.6 | BB827235 |
| — | Kif11 | *Mus musculus* transcribed sequences | 68 | 5.0 | BM234447 |
| Kif11 | Kif11 | kinesin family member 11 | 89 | 4.5 | B8827235 |
| Kif18a | Kif18a | kinesin family member 18A | 63 | 2.8 | BC016095 |
| Kif20a | Kif20a | kinesin family member 20A | 65 | 4.3 | NM_009004 |
| Kif21b | Kif21b | kinesin family member 21B | 113 | 3.2 | AV122249 |
| Kif22 | Kif22 | kinesin family member 22 | 248 | 8.4 | BB251322 |
| Kif2c | Kif2c | kinesin family member 2C | 43 | 8.7 | BB104669 |
| Kif2c | Kif2c | kinesin family member 2C | 74 | 4.4 | NM_134471 |
| Kif4 | Kif4 | kinesin family member 4 | 71 | 3.2 | NM_008446 |
| Klf5 | Klf5 | Kruppel-like factor 5 | 164 | 2.4 | BG069607 |
| KLHL6 | Klhl6 | kelch-like 6 | 297 | 3.1 | BM247104 |
| Klra2 | Klra2 | killer cell lectin-like receptor, subfamily A, member 2 | 30 | 14.3 | NM_008462 |
| Klra7 | Klra7 | killer cell lectin-like receptor, subfamily A, member 7 | 7 | 7.9 | U10095 |
| Klra8 | Klra8 | killer cell lectin-like receptor, subfamily A, member 8 | 17 | 5.5 | U12889 |
| Klra3 | Klra9 | killer cell lectin-like receptor, subfamily A, member 3 | 68 | 6.5 | U49865 |
| Klrb1d | Klrb1d | killer cell lectin-like receptor subfamily B member 1D | 11 | 4.2 | AF342896 |
| Klrb1d | Klrb1d | killer cell lectin-like receptor subfamily B member 1D | 25 | 4.6 | AF342896 |
| Klrb1d | Klrb1d | killer cell lectin-like receptor subfamily B member 1D | 20 | 9.8 | NM_008526 |
| Klrb1d | Klrb1d | killer cell lectin-like receptor subfamily B member 1D | 17 | 10.2 | AV294178 |
| Klrc1 | Klrc1 | killer cell lectin-like receptor subfamily C, member 1 | 6 | 19.3 | AF106009 |
| Klre1 | Klre1 | killer cell lectin-like receptor family E member 1 | 33 | 3.2 | BG230222 |
| Klrk1 | Klrk1 | killer cell lectin-like receptor subfamily K, member 1 | 66 | 21.5 | AF039026 |
| Kntc1 | Kntc1 | kinetochore associated 1 | 71 | 4.4 | AW536884 |
| Kpna2 | Kpna2 | karyopherin (importin) alpha 2 | 1340 | 2.6 | NM_010655 |
| Kpna3 | Kpna3 | karyopherin (importin) alpha 3 | 449 | 2.0 | BM213828 |
| Kpnb1 | Kpnb1 | karyopherin (importin) beta 1 | 1298 | 3.3 | BC004096 |
| 9030623C06Rik | Krt20 | RIKEN cDNA 9030623C06 gene | 37 | 4.4 | AF473907 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Laf4 | Laf4 | lymphoid nuclear protein related to AF4 | 37 | 4.3 | BQ177036 |
| D7Bwg0421e | Lair1 | DNA segment, Chr 7, Brigham & Women's Genetics 0421 expressed | 64 | 11.9 | AK017222 |
| Laptm5 | Laptm5 | lysosomal-associated protein transmembrane 5 | 31 | 4.5 | BB264849 |
| Laptm5 | Laptm5 | lysosomal-associated protein transmembrane 5 | 173 | 30.9 | BB218107 |
| — | Lass6 | *Mus musculus* adult male small intestine cDNA, RIKEN full-length enriched library, clone: 2010109K09 product: unclassifiable, full insert sequence | 57 | 2.3 | BG072448 |
| Lbp | Lbp | lipopolysaccharide binding protein | 175 | 3.3 | NM_008489 |
| Lck | Lck | lymphocyte protein tyrosine kinase | 6 | 3.5 | AA867167 |
| Lck | Lck | lymphocyte protein tyrosine kinase | 23 | 2.2 | BB200032 |
| Lck | Lck | lymphocyte protein tyrosine kinase | 93 | 9.2 | AA867167 |
| Lck | Lck | lymphocyte protein tyrosine kinase | 128 | 19.5 | BC011474 |
| Lcn2 | Lcn2 | lipocalin 2 | 176 | 29.2 | X14607 |
| Lcp1 | Lcp1 | lymphocyte cytosolic protein 1 | 231 | 20.8 | NM_008879 |
| Lcp1 | Lcp1 | lymphocyte cytosolic protein 1 | 515 | 15.0 | NM_008879 |
| Lcp2 | Lcp2 | lymphocyte cytosolic protein 2 | 48 | 31.8 | BC006948 |
| Lfng | Lfng | lunatic fringe gene homolog (*Drosophila*) | 146 | 3.0 | NM_008494 |
| Lgals1 | Lgals1 | lectin, galactose binding, soluble 1 | 5227 | 2.9 | AI642438 |
| Lgals1 | Lgals1 | lectin, galactose binding, soluble 1 | 3962 | 2.8 | NM_008495 |
| — | Lgals3 | *Mus musculus* transcribed sequences | 44 | 2.8 | AI426376 |
| Lgals3 | Lgals3 | lectin, galactose binding, soluble 3 | 2066 | 3.2 | X16834 |
| Ppicap | Lgals3bp | peptidylprolyl isomerase C-associated protein | 1079 | 4.7 | NM_011150 |
| Lig1 | Lig1 | ligase I, DNA, ATP-dependent | 193 | 3.6 | NM_010715 |
| Gp49b | Lilrb4 | glycoprotein 49 B | 133 | 22.1 | U05264 |
| Litaf | Litaf | LPS-induced TN factor | 814 | 3.7 | AV360881 |
| Litaf | Litaf | LPS-induced TN factor | 1740 | 4.3 | AV360881 |
| LOC207685 | LOC207685 | hypothetical protein LOC207685 | 66 | 5.0 | AK008551 |
| LOC207685 | LOC207685 | hypothetical protein LOC207685 | 109 | 2.7 | AK008551 |
| LOC209387 | LOC209387 | tripartite motif protein 30-like | 81 | 9.7 | BG068242 |
| LOC209387 | LOC209387 | tripartite motif protein 30-like | 15 | 20.2 | BM241342 |
| LOC223672 | LOC223672 | hypothetical protein LOC223672 | 18 | 25.0 | BC020489 |
| 5830475I06Rik | Loh11cr2a | RIKEN cDNA 5830475I06 gene | 588 | 4.9 | BC004727 |
| Lox | Lox | lysyl oxidase | 87 | 7.5 | M65143 |
| Lox | Lox | lysyl oxidase | 154 | 7.4 | M65143 |
| Loxl3 | Loxl3 | lysyl oxidase-like 3 | 121 | 3.5 | NM_013586 |
| 4832412D13Rik | Lrch1 | RIKEN cDNA 4832412D13 gene | 241 | 2.2 | BB755336 |
| — | Lrch1 | *Mus musculus* transcribed sequences | 22 | 5.8 | AW909485 |
| 1300008B03Rik | Lrg1 | RIKEN cDNA 1300008B03 gene | 81 | 3.7 | NM_029796 |
| Lrmp | Lrmp | lymphoid-restricted membrane protein | 72 | 6.9 | NM_008511 |
| Lrp1 | Lrp1 | low density lipoprotein receptor-related protein 1 | 38 | 2.1 | AV345706 |
| Lrrfip1 | Lrrfip1 | leucine rich repeat (in FLII) interacting protein 1 | 837 | 3.0 | BG069059 |
| AW319595 | Lrrk1 | expressed sequence AW319595 | 233 | 2.3 | BC027199 |
| Lsm5 | Lsm5 | LSM5 homolog, U6 small nuclear RNA associated (*S. cerevisiae*) | 457 | 2.3 | NM_025520 |
| Lsp1 | Lsp1 | lymphocyte specific 1 | 199 | 8.8 | NM_019391 |
| Lst1 | Lst1 | leukocyte specific transcript 1 | 98 | 18.7 | U72644 |
| Lta | Lta | lymphotoxin A | 7 | 5.8 | NM_010735 |
| Ltbp2 | Ltbp2 | latent transforming growth factor beta binding protein 2 | 35 | 14.9 | NM_013589 |
| Ly6c | Ly6c | lymphocyte antigen 6 complex, locus C | 3983 | 2.8 | NM_010741 |
| Ly6e | Ly6e | lymphocyte antigen 6 complex, locus E | 1793 | 6.8 | BM245572 |
| Ly6f | Ly6f | lymphocyte antigen 6 complex, locus F | 24 | 4.3 | NM_008530 |
| Ly6i | Ly6i | lymphocyte antigen 6 complex, locus I | 189 | 15.4 | AF232024 |
| Ly78 | Ly78 | lymphocyte antigen 78 | 77 | 3.2 | NM_008533 |
| Ly86 | Ly86 | lymphocyte antigen 86 | 165 | 24.1 | NM_010745 |
| Lyn | Lyn | Yamaguchi sarcoma viral (v-yes-1) oncogene homolog | 275 | 3.6 | M64608 |
| Lyn | Lyn | Yamaguchi sarcoma viral (v-yes-1) oncogene homolog | 585 | 2.9 | M57697 |
| Lyst | Lyst | lysosomal trafficking regulator | 347 | 2.0 | BB463428 |
| Lyzs | Lyzs | lysozyme | 483 | 27.0 | AW208566 |
| Lyzs | Lyzs | lysozyme | 327 | 56.6 | AV058500 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | Lztfl1 | *Mus musculus* transcribed sequence with strong similarity to protein ref: NP_002127.1 (*H. sapiens*) heterogeneous nuclear ribonucleoprotein A1, isoform a; nuclear ribonucleoprotein particle A1 protein; helix-destabilizing protein; single-strand DNA-binding protein UP1; heterogeneous nuclear ribonucleoprotein core protein A1; heterogeneous nuclear ribonucleoprotein A1B protein; heterogeneous nuclear ribonucleoprotein B2 protein [*Homo sapiens*] | 1043 | 2.1 | BF320908 |
| Mad | Mad | Max dimerization protein | 110 | 2.8 | AV228517 |
| Mad | Mad | Max dimerization protein | 204 | 2.1 | AV228517 |
| Mad2l1 | Mad2l1 | MAD2 (mitotic arrest deficient, homolog)-like 1 (yeast) | 349 | 3.8 | NM_019499 |
| Mafb | Mafb | v-maf musculoaponeurotic fibrosarcoma oncogene family, protein B (avian) | 24 | 2.5 | AW412521 |
| Maff | Maff | v-maf musculoaponeurotic fibrosarcoma oncogene family, protein F (avian) | 91 | 2.7 | BC022952 |
| Map3k1 | Map3k1 | mitogen activated protein kinase kinase kinase 1 | 319 | 2.4 | L13103 |
| Map4k1 | Map4k1 | mitogen activated protein kinase kinase kinase kinase 1 | 17 | 13.9 | BB546619 |
| Marcks | Marcks | myristoylated alanine rich protein kinase C substrate | 1601 | 2.1 | AW546141 |
| Marcks | Marcks | myristoylated alanine rich protein kinase C substrate | 847 | 2.4 | AW546141 |
| Marcks | Marcks | myristoylated alanine rich protein kinase C substrate | 1166 | 2.5 | BB100920 |
| Mbc2 | Mbc2 | membrane bound C2 domain containing protein | 279 | 4.2 | BC011482 |
| — | Mbnl1 | *Mus musculus* transcribed sequences | 96 | 3.8 | BM201095 |
| — | Mbnl3 | *Mus musculus* 0 day neonate lung cDNA, RIKEN full-length enriched library, clone: E030002K20 product: similar to MUSCLEBLIND-LIKE PROTEIN FLJ11316/DKFZP434G2222/DJ842K24.1 [*Homo sapiens*], full insert sequence | 104 | 4.0 | AV306759 |
| Mbtps2 | Mbtps2 | RIKEmembrane-bound transcription factor protease, site 2 | 46 | 4.0 | AV272026 |
| Mcl1 | Mcl1 | myeloid cell leukemia sequence 1 | 3111 | 2.4 | BB374534 |
| Mcl1 | Mcl1 | myeloid cell leukemia sequence 1 | 1844 | 2.4 | BC003839 |
| Mcm2 | Mcm2 | minichromosome maintenance deficient 2 mitotin (*S. cerevisiae*) | 257 | 3.3 | NM_008564 |
| Mcm3 | Mcm3 | minichromosome maintenance deficient 3 (*S. cerevisiae*) | 115 | 5.2 | C80350 |
| Mcm3 | Mcm3 | minichromosome maintenance deficient 3 (*S. cerevisiae*) | 23 | 15.8 | BI658327 |
| Mcm3 | Mcm3 | minichromosome maintenance deficient 3 (*S. cerevisiae*) | 199 | 5.7 | C80350 |
| Mcm3 | Mcm3 | minichromosome maintenance deficient 3 (*S. cerevisiae*) | 39 | 3.2 | C80350 |
| Mcm3 | Mcm3 | minichromosome maintenance deficient 3 (*S. cerevisiae*) | 60 | 9.2 | BI658327 |
| Mcm4 | Mcm4 | minichromosome maintenance deficient 4 homolog (*S. cerevisiae*) | 211 | 4.5 | BB447978 |
| Mcm4 | Mcm4 | minichromosome maintenance deficient 4 homolog (*S. cerevisiae*) | 356 | 4.1 | BC013094 |
| Mcm5 | Mcm5 | minichromosome maintenance deficient 5, cell division cycle 46 (*S. cerevisiae*) | 260 | 9.4 | AI324988 |
| Mcm5 | Mcm5 | minichromosome maintenance deficient 5, cell division cycle 46 (*S. cerevisiae*) | 160 | 6.2 | NM_008566 |
| Mcm6 | Mcm6 | minichromosome maintenance deficient 6 (MIS5 homolog, *S. pombe*) (*S. cerevisiae*) | 304 | 3.7 | BB099487 |
| — | Mcm7 | *Mus musculus* adult male thymus cDNA, RIKEN full-length enriched library, clone: 5830410A10 product: minichromosome maintenance deficient 7 (*S. cerevisiae*), full insert sequence | 766 | 2.0 | NM_008568 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | Mcm7 | *Mus musculus* adult male thymus cDNA, RIKEN full-length enriched library, clone: 5830410A10 product: minichromosome maintenance deficient 7 (*S. cerevisiae*), full insert sequence | 267 | 2.7 | BB407228 |
| — | Mcm7 | *Mus musculus* adult male thymus cDNA, RIKEN full-length enriched library, clone: 5830410A10 product: minichromosome maintenance deficient 7 (*S. cerevisiae*), full insert sequence | 1385 | 2.3 | BB464359 |
| Kdt1 | Mdfid | kidney cell line derived transcript 1 | 889 | 2.2 | U13371 |
| Me2 | Me2 | malic enzyme 2, NAD(+)-dependent, mitochondrial | 51 | 3.4 | BM235734 |
| Me2 | Me2 | malic enzyme 2, NAD(+)-dependent, mitochondrial | 129 | 4.1 | BM235734 |
| Mefv | Mefv | Mediterranean fever | 140 | 3.7 | NM_019453 |
| — | Metap2 | *Mus musculus* transcribed sequences | 44 | 2.1 | BM730703 |
| Mfap5 | Mfap5 | microfibrillar associated protein 5 | 43 | 3.7 | NM_015776 |
| Mfap5 | Mfap5 | microfibrillar associated protein 5 | 67 | 7.2 | NM_015776 |
| — | MGC58382 | *Mus musculus* cDNA clone MGC: 58382 IMAGE: 6774154, complete cds | 58 | 14.2 | BG961961 |
| 1200016D23Rik | MGC65590 | RIKEN cDNA 1200016D23 gene | 5 | 2.8 | BB093351 |
| Mgl1 | Mgl1 | macrophage galactose N-acetyl-galactosamine specific lectin 1 | 35 | 4.5 | NM_010796 |
| Mglap | Mglap | matrix gamma-carboxyglutamate (gla) protein | 4867 | 2.3 | NM_008597 |
| Mki67 | Mki67 | antigen identified by monoclonal antibody Ki 67 | 129 | 11.7 | X82786 |
| — | Mllt3 | *Mus musculus* transcribed sequences | 24 | 3.0 | AV381294 |
| Mllt3 | Mllt3 | myeloid/lymphoid or mixed lineage-leukemia translocation to 3 homolog (*Drosophila*) | 114 | 2.2 | AK019458 |
| Mlp | Mlp | MARCKS-like protein | 92 | 2.2 | BB491008 |
| Mlp | Mlp | MARCKS-like protein | 538 | 3.2 | AV110584 |
| Mmp14 | Mmp14 | matrix metalloproteinase 14 (membrane-inserted) | 97 | 5.1 | NM_008608 |
| Mmp14 | Mmp14 | matrix metalloproteinase 14 (membrane-inserted) | 216 | 5.1 | NM_008608 |
| Mmp19 | Mmp19 | matrix metalloproteinase 19 | 7 | 4.4 | AF153199 |
| Mmp7 | Mmp7 | matrix metalloproteinase 7 | 50 | 6.4 | NM_010810 |
| D930043C02Rik | Mnab | RIKEN cDNA D930043C02 gene | 23 | 2.3 | BM210927 |
| D930043C02Rik | Mnab | RIKEN cDNA D930043C02 gene | 28 | 2.3 | AA709668 |
| Mns1 | Mns1 | meiosis-specific nuclear structural protein 1 | 27 | 3.7 | NM_008613 |
| 4022402H07Rik | Mobk1b | RIKEN cDNA 4022402H07 gene | 1399 | 2.2 | BC011285 |
| — | Mpa2l | *Mus musculus* transcribed sequence with weak similarity to protein sp: P32456 (*H. sapiens*) GBP2_HUMAN Interferon-induced guanylate-binding protein 2 (Guanine nucleotide-binding protein 2) | 191 | 118.4 | BM241485 |
| — | Mpa2l | *Mus musculus* transcribed sequences | 339 | 72.1 | BG092512 |
| Mpeg1 | Mpeg1 | macrophage expressed gene 1 | 402 | 22.7 | L20315 |
| Mre11a | Mre11a | meiotic recombination 11 homolog A (*S. cerevisiae*) | 190 | 2.3 | NM_018736 |
| Ms4a1 | Ms4a1 | membrane-spanning 4-domains, subfamily A, member 1 | 28 | 4.0 | BB236617 |
| Ms4a1 | Ms4a1 | membrane-spanning 4-domains, subfamily A, member 1 | 17 | 3.7 | BB236617 |
| Ms4a4b | Ms4a4b | membrane-spanning 4-domains, subfamily A, member 4B | 88 | 56.0 | BB199001 |
| Ms4a4d | Ms4a4d | membrane-spanning 4-domains, subfamily A, member 4D | 96 | 12.6 | NM_025658 |
| — | Ms4a6b | *Mus musculus* adult male aorta and vein cDNA, RIKEN full-length enriched library, clone: A530066O14 product: unknown EST, full insert sequence | 92 | 3.1 | BB221406 |
| — | Ms4a6b | *Mus musculus* adult male aorta and vein cDNA, RIKEN full-length enriched library, clone: A530066O14 product: unknown EST, full insert sequence | 37 | 4.2 | BB218965 |
| Ms4a6b | Ms4a6b | membrane-spanning 4-domains, subfamily A, member 6B | 126 | 45.7 | NM_027209 |
| Ms4a6c | Ms4a6c | membrane-spanning 4-domains, subfamily A, member 6C | 132 | 14.8 | AF237910 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Ms4a11 | Ms4a6d | membrane-spanning 4-domains, subfamily A, member 11 | 50 | 38.3 | NM_026835 |
| Ms4a11 | Ms4a6d | membrane-spanning 4-domains, subfamily A, member 11 | 57 | 39.2 | NM_026835 |
| A430103C15Rik | Ms4a7 | RIKEN cDNA A430103C15 gene | 105 | 5.4 | BC024402 |
| Msn | Msn | moesin | 1945 | 2.3 | NM_010833 |
| Msn | Msn | moesin | 4591 | 2.1 | NM_010833 |
| Msr1 | Msr1 | macrophage scavenger receptor 1 | 25 | 12.3 | L04274 |
| Msr1 | Msr1 | macrophage scavenger receptor 1 | 44 | 9.9 | AA183642 |
| Msr1 | Msr1 | macrophage scavenger receptor 1 | 58 | 9.8 | BC003814 |
| Mt2 | Mt2 | metallothionein 2 | 3122 | 2.9 | AA796766 |
| Mthfd2 | Mthfd2 | methylenetetrahydrofolate dehydrogenase (NAD+ dependent), methenyltetrahydrofolate cyclohydrolase | 134 | 3.6 | BG076333 |
| Mthfd2 | Mthfd2 | methylenetetrahydrofolate dehydrogenase (NAD+ dependent), methenyltetrahydrofolate cyclohydrolase | 111 | 6.4 | BG076333 |
| Mvp | Mvp | major vault protein | 281 | 3.9 | NM_080638 |
| — | Mvp | — | 396 | 4.1 | BB139464 |
| Mx1 | Mx1 | myxovirus (influenza virus) resistance 1 | 54 | 6.9 | M21039 |
| Myadm | Myadm | myeloid-associated differentiation marker | 716 | 2.1 | BI078799 |
| Myb | Myb | myeloblastosis oncogene | 10 | 26.7 | NM_033597 |
| Myb | Myb | myeloblastosis oncogene | 29 | 7.7 | NM_033597 |
| Myb | Myb | myeloblastosis oncogene | 5 | 7.0 | BC011513 |
| Myc | Myc | myelocytomatosis oncogene | 198 | 3.5 | BC006728 |
| Myd88 | Myd88 | myeloid differentiation primary response gene 88 | 590 | 3.9 | BC005591 |
| — | Myh9 | — | 211 | 2.5 | C80049 |
| Myo1f | Myo1f | myosin IF | 57 | 10.4 | AK021181 |
| Myo1f | Myo1f | myosin IF | 16 | 30.8 | AK021181 |
| Myo1g | Myo1g | myosin IG | 76 | 15.2 | BB235320 |
| Myo9b | Myo9b | myosin IXb | 239 | 2.5 | NM_015742 |
| Nasp | Nasp | nuclear autoantigenic sperm protein (histone-binding) | 470 | 2.3 | BB493242 |
| Ncf1 | Ncf1 | neutrophil cytosolic factor 1 | 155 | 8.1 | AI844633 |
| Ncf2 | Ncf2 | neutrophil cytosolic factor 2 | 121 | 5.7 | NM_010877 |
| Ncor1 | Ncor1 | nuclear receptor co-repressor 1 | 24 | 2.5 | AI481996 |
| — | Nefh | Mus musculus mRNA for mKIAA0845 protein | 18 | 10.0 | M35131 |
| BC034753 | Neil3 | cDNA sequence BC034753 | 29 | 2.1 | AV316939 |
| Nek2 | Nek2 | NIMA (never in mitosis gene a)-related expressed kinase 2 | 112 | 4.2 | C77054 |
| Nek6 | Nek6 | NIMA (never in mitosis gene a)-related expressed kinase 6 | 237 | 2.3 | BC019524 |
| — | Net1 | Mus musculus transcribed sequences | 40 | 4.1 | AV247312 |
| Nfatc1 | Nfatc1 | nuclear factor of activated T-cells, cytoplasmic 1 | 71 | 4.5 | AF239169 |
| Nfatc1 | Nfatc1 | nuclear factor of activated T-cells, cytoplasmic 1 | 187 | 3.6 | NM_016791 |
| Nfatc1 | Nfatc1 | nuclear factor of activated T-cells, cytoplasmic 1 | 204 | 2.6 | BB356861 |
| Nfatc2 | Nfatc2 | nuclear factor of activated T-cells, cytoplasmic 2 | 112 | 3.7 | BM122872 |
| Nfkb1 | Nfkb1 | nuclear factor of kappa light chain gene enhancer in B-cells 1, p105 | 654 | 2.6 | L28118 |
| Nfkb2 | Nfkb2 | nuclear factor of kappa light polypeptide gene enhancer in B-cells 2, p49/p100 | 141 | 3.9 | AF155372 |
| Nfkbia | Nfkbia | nuclear factor of kappa light chain gene enhancer in B-cells inhibitor, alpha | 4502 | 3.1 | AI462015 |
| Nfkbia | Nfkbia | nuclear factor of kappa light chain gene enhancer in B-cells inhibitor, alpha | 666 | 3.2 | AI462015 |
| Nfkbie | Nfkbie | nuclear factor of kappa light polypeptide gene enhancer in B-cells inhibitor, epsilon | 122 | 4.5 | AK011965 |
| — | Nfkbie | — | 194 | 9.7 | BB820441 |
| AA408868 | Nfkbiz | expreexpressed sequence AA408868 | 82 | 10.1 | BM240058 |
| AA408868 | Nfkbiz | expreexpressed sequence AA408868 | 117 | 5.3 | AB026551 |
| AA408868 | Nfkbiz | expreexpressed sequence AA408868 | 169 | 10.8 | AB026551 |
| Ngfr | Ngfr | nerve growth factor receptor (TNFR superfamily, member 16) | 32 | 8.3 | BB151515 |
| Niban | Niban | niban protein | 87 | 3.4 | NM_022018 |
| Nical | Nical | NEDD9 interacting protein with calponin homology and LIM domains | 22 | 6.0 | BB209438 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Nin | Nin | ninein | 190 | 2.3 | AK014241 |
| Nkg7 | Nkg7 | natural killer cell group 7 sequence | 55 | 36.5 | NM_024253 |
| Nktr | Nktr | natural killer tumor recognition sequence | 133 | 2.2 | AW987751 |
| Nmi | Nmi | N-myc (and STAT) interactor | 687 | 6.7 | BC002019 |
| Nnmt | Nnmt | nicotinamide N-methyltransferase | 53 | 6.6 | AK006371 |
| Nol5a | Nol5a | nucleolar protein 5A | 326 | 2.4 | BF660256 |
| Nol5a | Nol5a | nucleolar protein 5A | 436 | 2.2 | BM249243 |
| Npc2 | Npc2 | Niemann Pick type C2 | 100 | 3.9 | BG071996 |
| — | Nr4a3 | *Mus musculus* transcribed sequences | 20 | 7.2 | BE692107 |
| Nr6a1 | Nr6a1 | nuclear receptor subfamily 6, group A, member 1 | 46 | 2.0 | U09563 |
| Nras | Nras; N-ras | neuroblastoma ras oncogene | 462 | 2.4 | AK010412 |
| Nrf1 | Nrf1 | nuclear respiratory factor 1 | 97 | 2.1 | BM221378 |
| 2310014H01Rik | Nrm | RIKEN cDNA 2310014H01 gene | 58 | 3.1 | NM_134122 |
| Nrn1 | Nrn1 | neuritin 1 | 81 | 2.8 | AK003046 |
| — | Nrp1 | *Mus musculus* transcribed sequences | 193 | 2.0 | AV291009 |
| — | Nt5c2 | *Mus musculus* transcribed sequences | 41 | 2.8 | AU017183 |
| AW541137 | Nup107 | expressed sequence AW541137 | 242 | 2.1 | BC004655 |
| Nup153 | Nup153 | nucleoporin 153 | 150 | 2.3 | C88147 |
| Nup210 | Nup210 | nucleoporin 210 | 356 | 3.1 | NM_018815 |
| Nupr1 | Nupr1 | nuclear protein 1 | 743 | 2.1 | NM_019738 |
| Oact1 | Oact1 | O-acyltransferase (membrane bound) domain containing 1 | 84 | 3.8 | AV366860 |
| Oas1g | Oas1a | 2'-5' oligoadenylate synthetase 1G | 345 | 6.9 | BC018470 |
| Oasl1 | Oasl1 | 2'-5' oligoadenylate synthetase-like 1 | 174 | 4.0 | AB067533 |
| Oasl2 | Oasl2 | 2'-5' oligoadenylate synthetase-like 2 | 209 | 17.4 | BQ033138 |
| Olfr56 | Olfr56 | olfactory receptor 56 | 336 | 39.5 | NM_008330 |
| Olr1 | Olr1 | oxidized low density lipoprotein (lectin-like) receptor 1 | 8 | 7.9 | NM_138648 |
| A130090K04Rik | Oprm1 | RIKEN cDNA A130090K04 gene | 347 | 3.1 | BQ176089 |
| Osmr | Osmr | oncostatin M receptor | 96 | 5.0 | AB015978 |
| Osmr | Osmr | oncostatin M receptor | 286 | 4.7 | AB015978 |
| — | P2rx7 | *Mus musculus* transcribed sequences | 46 | 2.7 | AI552982 |
| P2ry10 | P2ry10 | purinergic receptor P2Y, G-protein coupled 10 | 19 | 18.0 | AK020001 |
| P2ry12 | P2ry12 | purinergic receptor P2Y, G-protein coupled 12 | 32 | 3.2 | AK013804 |
| Gpr86 | P2ry13 | G protein-coupled receptor 86 | 68 | 4.5 | AK008013 |
| Gpr105 | P2ry14 | G protein-coupled receptor 105 | 220 | 2.2 | AF177211 |
| P2ry6 | P2ry6 | pyrimidinergic receptor P2Y, G-protein coupled, 6 | 110 | 5.1 | BC027331 |
| — | Pabpc1 | *Mus musculus* 0 day neonate thymus cDNA, RIKEN full-length enriched library, clone: A430039M01 product: unknown EST, full insert sequence | 63 | 2.0 | AW552076 |
| Padi2 | Padi2 | peptidyl arginine deiminase, type II | 110 | 2.1 | NM_008812 |
| Panx1 | Panx1 | pannexin 1 | 88 | 3.2 | NM_019482 |
| 5330431N24Rik | Parp11 | RIKEN cDNA 5330431N24 gene | 264 | 3.1 | BB026163 |
| BC021340 | Parp14 | cDNA sequence BC021340 | 256 | 16.1 | BC021340 |
| Adprtl3 | Parp3 | ADP-ribosyltransferase (NAD+; poly (ADP-ribose) polymerase)-like 3 | 527 | 2.1 | AW990611 |
| Adprtl3 | Parp3 | ADP-ribosyltransferase (NAD+; poly (ADP-ribose) polymerase)-like 3 | 1373 | 2.6 | BC014870 |
| — | Parp8 | *Mus musculus* 13 days embryo forelimb cDNA, RIKEN full-length enriched library, clone: 5930433N17 product: unknown EST, full insert sequence | 123 | 2.3 | C85455 |
| BC003281 | Parp9 | cDNA sequence BC003281 | 460 | 12.0 | NM_030253 |
| 1110035O14Rik | Pbef1 | RIKEN cDNA 1110035O14 gene | 2754 | 2.4 | AW989410 |
| D14Ertd732e | Pbk | DNA segment, Chr 14, ERATO Doi 732, expressed | 200 | 3.2 | NM_023209 |
| Pcna | Pcna | proliferating cell nuclear antigen | 3700 | 2.3 | BC010343 |
| Arpc1b | Pdap1 | actin related protein 2/3 complex, subunit 1B | 690 | 6.1 | BE979985 |
| Pdcd1lg1 | Pdcd1lg1 | programmed cell death 1 ligand 1 | 73 | 45.1 | NM_021893 |
| Pdcd1lg2 | Pdcd1lg2 | programmed cell death 1 ligand 2 | 57 | 5.6 | NM_021396 |
| Pde4b | Pde4b | phosphodiesterase 4B, cAMP specific | 76 | 2.9 | BG793493 |
| Pdk4 | Pdk4 | pyruvate dehydrogenase kinase, isoenzyme 4 | 283 | 3.1 | NM_013743 |
| Pdlim1 | Pdlim1 | PDZ and LIM domain 1 (elfin) | 272 | 2.6 | NM_016861 |
| Ril | Pdlim4 | reversion induced LIM gene | 63 | 3.6 | NM_019417 |
| Peli1 | Peli1 | pellino 1 | 476 | 2.8 | BC016515 |
| Per1 | Per1 | period homolog 1 (*Drosophila*) | 62 | 3.9 | AF022992 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Pfc | Pfc | properdin factor, complement | 24 | 16.5 | BB800282 |
| Pfkfb3 | Pfkfb3 | 6-phosphofructo-2-kinase/fructose-2,6-biphosphatase 3 | 164 | 3.4 | NM_133232 |
| Pfkp | Pfkp | phosphofructokinase, platelet | 1402 | 2.7 | NM_019703 |
| Phemx | Phemx | pan hematopoietic expression | 41 | 3.8 | AF175771 |
| 4933417L10Rik | Phf11 | RIKEN cDNA 4933417L10 gene | 301 | 4.8 | AV280841 |
| E130113K22Rik | Phf20l1 | RIKEN cDNA E130113K22 gene | 114 | 2.1 | AV349060 |
| B2m | Phf20l1 | beta-2 microglobulin | 13469 | 2.0 | BF715219 |
| 4931428F02Rik | Phf6 | RIKEN cDNA 4931428F02 gene | 187 | 2.5 | AA275278 |
| 4931428F02Rik | Phf6 | RIKEN cDNA 4931428F02 gene | 151 | 2.4 | BG073473 |
| Pigr | Pigr | polymeric immunoglobulin receptor | 3030 | 4.4 | AV027632 |
| Pigr | Pigr | polymeric immunoglobulin receptor | 2667 | 3.0 | NM_011082 |
| Pik3ap1 | Pik3ap1 | phosphoinositide-3-kinase adaptor protein 1 | 64 | 7.8 | BI684288 |
| Pik3cd | Pik3cd | phosphatidylinositol 3-kinase catalytic delta polypeptide | 111 | 4.7 | BB700084 |
| Pik3cg | Pik3cg | phosphoinositide-3-kinase, catalytic, gamma polypeptide | 146 | 2.6 | BB205102 |
| Pik3r1 | Pik3r1 | phosphatidylinositol 3-kinase, regulatory subunit, polypeptide 1 (p85 alpha) | 564 | 2.8 | M60651 |
| — | Pik3r5 | *Mus musculus* transcribed sequences | 41 | 5.0 | AV230647 |
| Pilra | Pilra | paired immunoglobin-like type 2 receptor alpha | 108 | 4.3 | BB775785 |
| Pim1 | Pim1 | proviral integration site 1 | 546 | 4.2 | BE631223 |
| Pip5k2a | Pip5k2a | phosphatidylinositol-4-phosphate 5-kinase, type II, alpha | 104 | 2.6 | AK012196 |
| Pip5k2a | Pip5k2a | phosphatidylinositol-4-phosphate 5-kinase, type II, alpha | 420 | 3.0 | AK012196 |
| Pira10 | Pira6 | paired-Ig-like receptor A10 | 69 | 15.0 | NM_011093 |
| — | Pira6 | — | 10 | 15.5 | NM_011087 |
| Pirb | Pirb | paired-Ig-like receptor B | 13 | 47.9 | U96693 |
| Pitpnm | Pitpnm1 | phosphatidylinositol membrane-associated | 461 | 2.1 | BB206460 |
| Pkib | Pkib | protein kinase inhibitor beta, cAMP dependent, testis specific | 44 | 3.8 | AV047342 |
| Pla2g4a | Pla2g4a | phospholipase A2, group IVA (cytosolic, calcium-dependent) | 270 | 4.4 | NM_008869 |
| Pla2g7 | Pla2g7 | phospholipase A2, group VII (platelet-activating factor acetylhydrolase, plasma) | 338 | 5.8 | AK005158 |
| Plac8 | Plac8 | placenta-specific 8 | 756 | 14.2 | AF263458 |
| — | Plagl2 | *Mus musculus* transcribed sequence with weak similarity to protein ref: NP_081764.1 (*M. musculus*) RIKEN cDNA 5730493B19 [*Mus musculus*] | 33 | 2.6 | BF584971 |
| Plagl2 | Plagl2 | pleiomorphic adenoma gene-like 2 | 49 | 3.4 | NM_018807 |
| Plcg2 | Plcg2 | phospholipase C, gamma 2 | 521 | 2.1 | AW546508 |
| Plcl2 | Plcl2 | phospholipase C-like 2 | 144 | 5.4 | BM207017 |
| Plekha2 | Plekha2 | pleckstrin homology domain-containing, family A (phosphoinositide binding specific) member 2 | 346 | 2.3 | NM_031257 |
| Plekha2 | Plekha2 | pleckstrin homology domain-containing, family A (phosphoinositide binding specific) member 2 | 139 | 2.0 | BE852755 |
| Plekha2 | Plekha2 | pleckstrin homology domain-containing, family A (phosphoinositide binding specific) member 2 | 611 | 3.1 | NM_031257 |
| 2410005C22Rik | Plekha4 | RIKEN cDNA 2410005C22 gene | 46 | 3.2 | BC024961 |
| Cnk | Plk3 | cytokine inducible kinase | 117 | 2.2 | BM947855 |
| Stk18 | Plk4 | serine/threonine kinase 18 | 128 | 2.7 | BB706079 |
| Stk18 | Plk4 | serine/threonine kinase 18 | 116 | 4.9 | AI385771 |
| Plp2 | Plp2 | proteolipid protein 2 | 1503 | 2.0 | AK012816 |
| Plxnc1 | Plxnc1 | plexin C1 | 30 | 3.2 | BB476707 |
| Plxnc1 | Plxnc1 | plexin C1 | 126 | 2.9 | BB476707 |
| Plxnc1 | Plxnc1 | plexin C1 | 48 | 5.5 | BB476707 |
| Pnp | Pnp | purine-nucleoside phosphorylase | 4116 | 2.2 | AK008143 |
| Pola1 | Pola1 | polymerase (DNA directed), alpha 1 | 155 | 2.6 | NM_008892 |
| Pold1 | Pold1 | polymerase (DNA directed), delta 1, catalytic subunit | 164 | 2.1 | BC009128 |
| Pold3 | Pold3 | polymerase (DNA-directed), delta 3, accessory subunit | 223 | 1.9 | AK010805 |
| Pole2 | Pole2 | polymerase (DNA directed), epsilon 2 (p59 subunit) | 181 | 3.2 | AF036898 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Polh | Polh | polymerase (DNA directed), eta (RAD 30 related) | 150 | 3.5 | BB066090 |
| Pou2af1 | Pou2af1 | POU domain, class 2, associating factor 1 | 15 | 9.4 | NM_011136 |
| Ppfia4 | Ppfia4; 1110008G13Rik | protein tyrosine phosphatase, receptor type, f polypeptide (PTPRF), interacting protein (liprin), alpha 4 | 24 | 4.5 | AK003571 |
| 2410005L11Rik | Ppil5 | RIKEN cDNA 2410005L11 gene | 9 | 3.0 | BG067404 |
| Ppp1r12a | Ppp1r12a | protein phosphatase 1, regulatory (inhibitor) subunit 12A | 1000 | 2.3 | AV309184 |
| — | Ppp1r12a | Mus musculus 7 days embryo whole body cDNA, RIKEN full-length enriched library, clone: C430016H01 product: unknown EST, full insert sequence | 86 | 2.7 | BB410003 |
| Ppp1r12a | Ppp1r12a | protein phosphatase 1, regulatory (inhibitor) subunit 12A | 550 | 2.0 | BI653999 |
| Ppp1r12a | Ppp1r12a | protein phosphatase 1, regulatory (inhibitor) subunit 12A | 641 | 2.2 | AV309184 |
| — | Ppt1 | Mus musculus 12 days embryo spinal ganglion cDNA, RIKEN full-length enriched library, clone: D130070K05 product: unknown EST, full insert sequence | 60 | 3.0 | BB461203 |
| Prdm1 | Prdm1 | PR domain containing 1, with ZNF domain | 157 | 2.1 | NM_007548 |
| Prg | Prg1 | proteoglycan, secretory granule | 2020 | 4.9 | NM_011157 |
| Prim2 | Prim2 | DNA primase, p58 subunit | 137 | 2.2 | NM_008922 |
| Prkcb | Prkcb1 | protein kinase C, beta | 27 | 5.8 | BF660388 |
| Prkch | Prkch | protein kinase C, eta | 412 | 2.7 | BM243756 |
| Prkch | Prkch | protein kinase C, eta | 259 | 3.4 | NM_008856 |
| Prkcq | Prkcq | protein kinase C, theta | 159 | 3.0 | AB062122 |
| AI325941 | Prkd2 | expressed sequence AI325941 | 151 | 2.2 | BB204677 |
| AI325941 | Prkd2 | expressed sequence AI325941 | 103 | 2.7 | AW557946 |
| Prkr | Prkr | protein kinase, interferon-inducible double stranded RNA dependent | 165 | 5.0 | BE911144 |
| Procr | Procr | protein C receptor, endothelial | 163 | 4.7 | NM_011171 |
| Pros1 | Pros1 | protein S (alpha) | 445 | 2.0 | Z25469 |
| Prrx1 | Prrx1 | paired related homeobox 1 | 24 | 2.0 | BB051738 |
| Pscd4 | Pscd4 | pleckstrin homology, Sec7 and coiled/coil domains 4 | 22 | 18.8 | AK010908 |
| Pscdbp | Pscdbp | pleckstrin homology, Sec7 and coiled-coil domains, binding protein | 682 | 3.6 | BC007144 |
| BC046518 | Psd4 | cDNA sequence BC046518 | 122 | 2.2 | BM221809 |
| Psma6 | Psma6 | proteasome (prosome, macropain) subunit, alpha type 6 | 12 | 2.8 | AA189256 |
| Psmb10 | Psmb10 | proteasome (prosome, macropain) subunit, beta type 10 | 525 | 14.7 | NM_013640 |
| — | Psmb2 | Mus musculus 10 days neonate cerebellum cDNA, RIKEN full-length enriched library, clone: B930059K21 product: unknown EST, full insert sequence | 38 | 2.4 | BM201103 |
| Psmb8 | Psmb8 | proteosome (prosome, macropain) subunit, beta type 8 (large multifunctional protease 7) | 461 | 27.5 | NM_010724 |
| Psmb8 | Psmb8 | proteosome (prosome, macropain) subunit, beta type 8 (large multifunctional protease 7) | 17 | 24.0 | AV068122 |
| Tap1 | Psmb9 | transporter 1, ATP-binding cassette, sub-family B (MDR/TAP) | 127 | 29.5 | AW048052 |
| Psmb9 | Psmb9 | proteosome (prosome, macropain) subunit, beta type 9 (large multifunctional protease 2) | 298 | 30.2 | NM_013585 |
| Psme1 | Psme1 | proteasome (prosome, macropain) 28 subunit, alpha | 2901 | 3.1 | NM_011189 |
| Psme2 | Psme2 | proteasome (prosome, macropain) 28 subunit, beta | 1669 | 5.3 | NM_011190 |
| Ptger2 | Ptger2 | prostaglandin E receptor 2 (subtype EP2) | 19 | 13.1 | BC005440 |
| Ptger4 | Ptger4 | prostaglandin E receptor 4 (subtype EP4) | 51 | 2.8 | NM_008965 |
| Ptger4 | Ptger4 | prostaglandin E receptor 4 (subtype EP4) | 259 | 5.0 | BC011193 |
| Ptgs2 | Ptgs2 | prostaglandin-endoperoxide synthase 2 | 32 | 4.4 | M94967 |
| Ptgs2 | Ptgs2 | prostaglandin-endoperoxide synthase 2 | 31 | 9.3 | M94967 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Ptk9l | Ptk9l | protein tyrosine kinase 9-like (A6-related protein) | 125 | 3.4 | AK002699 |
| Ptk9l | Ptk9l | protein tyrosine kinase 9-like (A6-related protein) | 328 | 3.8 | BB397672 |
| Ptpn12 | Ptpn12 | protein tyrosine phosphatase, non-receptor type 12 | 1107 | 2.2 | X63440 |
| Ptpn18 | Ptpn18 | protein tyrosine phosphatase, non-receptor type 18 | 338 | 2.9 | NM_011206 |
| Ptprc | Ptprc | protein tyrosine phosphatase, receptor type, C | 516 | 18.2 | NM_011210 |
| — | Ptprc | Mus musculus 16 days neonate thymus cDNA, RIKEN full-length enriched library, clone: A130082N01 product: unclassifiable, full insert sequence | 28 | 10.1 | BM239436 |
| Ptprcap | Ptprcap | protein tyrosine phosphatase, receptor type, C polypeptide-associated protein | 140 | 7.5 | NM_016933 |
| Ptpre | Ptpre | protein tyrosine phosphatase, receptor type, E | 102 | 4.5 | U35368 |
| Ptpre | Ptpre | protein tyrosine phosphatase, receptor type, E | 73 | 3.6 | U35368 |
| Pttg1 | Pttg1 | pituitary tumor-transforming 1 | 408 | 2.3 | AF069051 |
| 9130417A21Rik | Pycard | RIKEN cDNA 9130417A21 gene | 396 | 6.5 | BG084230 |
| Pycs | Pycs | pyrroline-5-carboxylate synthetase (glutamate gamma-semialdehyde synthetase) | 136 | 2.9 | BF148128 |
| Pycs | Pycs | pyrroline-5-carboxylate synthetase (glutamate gamma-semialdehyde synthetase) | 99 | 6.6 | BB251523 |
| 2010317E03Rik | Pyp | RIKEN cDNA 2010317E03 gene | 1519 | 2.9 | NM_026438 |
| Qpct | Qpct | glutaminyl-peptide cyclotransferase (glutaminyl cyclase) | 27 | 3.8 | BB150720 |
| Rab19 | Rab19 | RAB19, member RAS oncogene family | 108 | 2.8 | BM241400 |
| Rab32 | Rab32 | RAB32, member RAS oncogene family | 564 | 2.6 | NM_026405 |
| Rab37 | Rab37 | RAB37, member of RAS oncogene family | 43 | 2.1 | BB433704 |
| D330025I23Rik | Rab8b | RIKEN cDNA D330025I23 gene | 840 | 4.1 | BM214169 |
| Rac2 | Rac2 | RAS-related C3 botulinum substrate 2 | 169 | 10.9 | NM_009008 |
| Rad18 | Rad18 | RAD18 homolog (S. cerevisiae) | 73 | 2.3 | BC011120 |
| Rad18 | Rad18 | RAD18 homolog (S. cerevisiae) | 18 | 4.2 | BB530954 |
| Rad23b | Rad23b | RAD23b homolog (S. cerevisiae) | 21 | 2.4 | BB482313 |
| Rad54l | Rad54l | RAD54 like (S. cerevisiae) | 17 | 8.1 | AV310220 |
| Ramp1 | Ramp1 | receptor (calcitonin) activity modifying protein 1 | 66 | 2.3 | NM_016894 |
| Ranbp2 | Ranbp2 | RAN binding protein 2 | 61 | 2.6 | BB208180 |
| Rap2b | Rap2b | RAP2B, member of RAS oncogene family | 60 | 3.4 | BB390705 |
| Rap2b | Rap2b | RAP2B, member of RAS oncogene family | 196 | 2.7 | BB645629 |
| Rap2c | Rap2c | RAP2C, member of RAS oncogene family | 464 | 2.0 | AK008416 |
| Rap2c | Rap2c | RAP2C, member of RAS oncogene family | 415 | 2.2 | AK008416 |
| Rasa3 | Rasa3 | RAS p21 protein activator 3 | 142 | 4.6 | NM_009025 |
| Rasd1 | Rasd1 | RAS, dexamethasone-induced 1 | 136 | 4.7 | BB217136 |
| Rasgrp1 | Rasgrp1 | RAS guanyl releasing protein 1 | 181 | 3.2 | BE691356 |
| Rassf4 | Rassf4 | Ras association (RalGDS/AF-6) domain family 4 | 28 | 10.0 | AV291679 |
| Rbl1 | Rbl1 | retinoblastoma-like 1 (p107) | 314 | 5.8 | U27177 |
| Rbl1 | Rbl1 | retinoblastoma-like 1 (p107) | 59 | 3.2 | U27178 |
| Rbm3 | Rbm3 | RNA binding motif protein 3 | 193 | 2.5 | AK011224 |
| Rbmxrt | Rbmxrt | RNA binding motif protein, X chromosome retrogene | 887 | 2.1 | NM_009033 |
| Rcn | Rcn1 | reticulocalbin | 286 | 4.2 | NM_009037 |
| Refbp2 | Refbp2 | RNA and export factor binding protein 2 | 611 | 2.1 | NM_019484 |
| Rel | Rel | reticuloendotheliosis oncogene | 24 | 3.8 | NM_009044 |
| Relb | Relb | avian reticuloendotheliosis viral (v-rel) oncogene related B | 109 | 3.0 | NM_009046 |
| Rfc3 | Rfc3 | replication factor C (activator 1) 3 | 132 | 2.3 | BC026795 |
| Rfc3 | Rfc3 | replication factor C (activator 1) 3 | 128 | 2.9 | AK013095 |
| Eif4a2 | Rfc4 | eukaryotic translation initiation factor 4A2 | 105 | 2.9 | BB251459 |
| Rfc4 | Rfc4 | replication factor C (activator 1) 4 | 188 | 3.0 | BC003335 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | Rfwd2 | *Mus musculus* 9.5 days embryo parthenogenote cDNA, RIKEN full-length enriched library, clone: B130031H03 product: unclassifiable, full insert sequence | 40 | 2.0 | BB294853 |
| Rgs19 | Rgs19 | regulator of G-protein signaling 19 | 73 | 6.2 | BB233670 |
| Rgs2 | Rgs2 | regulator of G-protein signaling 2 | 425 | 2.0 | AF215668 |
| Rgs2 | Rgs2 | regulator of G-protein signaling 2 | 303 | 2.6 | BB034265 |
| Rgs2 | Rgs2 | regulator of G-protein signaling 2 | 454 | 2.6 | AF215668 |
| Arhb | Rhob | ras homolog gene family, member B | 2877 | 2.9 | BC018275 |
| Arhg | Rhog | ras homolog gene family, member G | 467 | 2.0 | NM_019566 |
| Arhh | Rhoh | ras homolog gene family, member H | 67 | 5.0 | BM243660 |
| — | Rims2 | *Mus musculus* transcribed sequences | 285 | 2.1 | C79043 |
| Ripk2 | Ripk2 | receptor (TNFRSF)-interacting serine-threonine kinase 2 | 225 | 2.0 | NM_138952 |
| Ris2 | Ris2 | retroviral integration site 2 | 631 | 2.6 | AF477481 |
| Ris2 | Ris2 | retroviral integration site 2 | 228 | 2.0 | AF477481 |
| 9530043P15Rik | Rnase6 | RIKEN cDNA 9530043P15 gene | 66 | 6.5 | AW825994 |
| Rnaset2 | Rnaset2; RNASE6PL; 0610007O07Rik; 4833423A10Rik; 4930532K22Rik | ribonuclease T2 | 154 | 2.2 | AK015947 |
| Trpc2 | Rnf121 | transient receptor potential cation channel, subfamily C, member 2 | 35 | 2.5 | AW324327 |
| Rnpc2 | Rnpc2 | RNA-binding region (RNP1, RRM) containing 2 | 162 | 2.2 | BB203348 |
| Rnpc2 | Rnpc2 | RNA-binding region (RNP1, RRM) containing 2 | 305 | 2.5 | C79248 |
| Rnpc2 | Rnpc2 | RNA-binding region (RNP1, RRM) containing 2 | 233 | 2.3 | C79248 |
| — | Rnu22 | *Mus musculus* 9 days embryo whole body cDNA, RIKEN full-length enriched library, clone: D030060F23 product: Mus musculus U22 snoRNA host gene (UHG) gene, complete sequence, full insert sequence | 352 | 2.3 | BQ177137 |
| — | Rnu22 | *Mus musculus* 9 days embryo whole body cDNA, RIKEN full-length enriched library, clone: D030060F23 product: Mus musculus U22 snoRNA host gene (UHG) gene, complete sequence, full insert sequence | 155 | 7.0 | BB493265 |
| Rp2h | Rp2h | retinitis pigmentosa 2 homolog (human) | 185 | 2.3 | BB431808 |
| Rp2h | Rp2h | retinitis pigmentosa 2 homolog (human) | 672 | 2.4 | BB431808 |
| Rpa2 | Rpa2 | replication protein A2 | 238 | 2.5 | BC004578 |
| Rpa2 | Rpa2; Rf-A2 | replication protein A2 | 208 | 2.2 | AK011530 |
| Rpgrip1 | Rpgrip1 | retinitis pigmentosa GTPase regulator interacting protein 1 | 45 | 35.9 | NM_023879 |
| Rpl12 | Rpl12 | ribosomal protein L12 | 82 | 3.2 | BG807990 |
| Rps25 | Rps25 | ribosomal protein S25 | 250 | 2.1 | BM729504 |
| 3010033P07Rik | Rps9 | RIKEN cDNA 3010033P07 gene | 188 | 16.9 | AA762498 |
| Rrad | Rrad | Ras-related associated with diabetes | 33 | 6.6 | NM_019662 |
| Rrm1 | Rrm1 | ribonucleotide reductase M1 | 383 | 3.3 | BB758819 |
| Rrm1 | Rrm1 | ribonucleotide reductase M1 | 380 | 3.3 | BB758819 |
| 2510004L01Rik | Rsad2 | RIKEN cDNA 2510004L01 gene | 1215 | 2.5 | BB132493 |
| — | Rtn4 | *Mus musculus* 16 days embryo head cDNA, RIKEN full-length enriched library, clone: C130026I10 product: unknown EST, full insert sequence | 158 | 3.4 | BB648600 |
| — | Rtn4 | *Mus musculus* 16 days embryo head cDNA, RIKEN full-length enriched library, clone: C130026I10 product: unknown EST, full insert sequence | 109 | 2.9 | BG072267 |
| Runx3 | Runx3 | runt related transcription factor 3 | 19 | 9.3 | AV233043 |
| S100a10 | S100a10 | S100 calcium binding protein A10 (calpactin) | 103 | 1.9 | BB450829 |
| S100a4 | S100a4 | S100 calcium binding protein A4 | 120 | 13.7 | D00208 |
| S100a6 | S100a6 | S100 calcium binding protein A6 (calcyclin) | 1217 | 2.8 | NM_011313 |
| S100a8 | S100a8 | S100 calcium binding protein A8 (calgranulin A) | 24 | 9.4 | NM_013650 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| S100a9 | S100a9 | S100 calcium binding protein A9 (calgranulin B) | 29 | 8.9 | NM_009114 |
| Saa1 | Saa1 | serum amyloid A 1 | 18 | 20.0 | NM_009117 |
| Saa2 | Saa2 | serum amyloid A 2 | 33 | 3.0 | NM_011314 |
| Saa2 | Saa2 | serum amyloid A 2 | 62 | 7.0 | NM_011314 |
| Saa3 | Saa3 | serum amyloid A 3 | 110 | 8.6 | NM_011315 |
| Samhd1 | Samhd1 | SAM domain and HD domain, 1 | 418 | 11.3 | NM_018851 |
| Samhd1 | Samhd1 | SAM domain and HD domain, 1 | 185 | 11.4 | BF148012 |
| Samhd1 | Samhd1 | SAM domain and HD domain, 1 | 8 | 16.3 | AV376100 |
| Samsn1 | Samsn1 | SAM domain, SH3 domain and nuclear localisation signals, 1 | 49 | 9.1 | NM_023380 |
| B130024B19Rik | Sart2 | RIKEN cDNA B130024B19 gene | 62 | 5.7 | BM207218 |
| Satb1 | Satb1 | special AT-rich sequence binding protein 1 | 52 | 5.0 | AV172776 |
| Satb1 | Satb1 | special AT-rich sequence binding protein 1 | 68 | 2.9 | AV172776 |
| Scarb2 | Scarb2 | scavenger receptor class B, member 2 | 783 | 2.0 | NM_007644 |
| Sdc1 | Sdc1 | syndecan 1 | 337 | 2.9 | BB533095 |
| Sdccag8 | Sdccag8 | serologically defined colon cancer antigen 8 | 114 | 3.5 | BG695418 |
| — | Sec8l1 | *Mus musculus* transcribed sequence with strong similarity to protein sp: P00722 (*E. coli*) BGAL_ECOLI Beta-galactosidase (Lactase) | 59 | 2.3 | BM941583 |
| Sectm1 | Sectm1 | secreted and transmembrane 1 | 516 | 2.9 | AI481997 |
| Sectm1 | Sectm1 | secreted and transmembrane 1 | 3261 | 3.0 | AI481997 |
| Sell | Sell | selectin, lymphocyte | 69 | 14.0 | M36005 |
| Sell | Sell | selectin, lymphocyte | 86 | 9.7 | M36005 |
| E330036L07Rik | Senp1 | RIKEN cDNA E330036L07 gene | 75 | 2.2 | BC023129 |
| Sepw1 | Sepw1 | selenoprotein W, muscle 1 | 1468 | 2.0 | BB464434 |
| Serpina10 | Serpina10 | serine (or cysteine) proteinase inhibitor, clade A (alpha-1 antiproteinase, antitrypsin), member 10 | 211 | 44.0 | BC018416 |
| Serpina1a | Serpina1a | serine (or cysteine) proteinase inhibitor, clade A, member 1a | 156 | 6.4 | NM_009243 |
| Serpina1b | Serpina1b | serine (or cysteine) proteinase inhibitor, clade A, member 1b | 2182 | 2.0 | NM_009244 |
| Serpina3g | Serpina3g | serine (or cysteine) proteinase inhibitor, clade A, member 3G | 92 | 107.8 | BC002065 |
| Serpina3n | Serpina3n | serine (or cysteine) proteinase inhibitor, clade A, member 3N | 18 | 10.9 | NM_009252 |
| Serpinb1a | Serpinb1a | serine (or cysteine) proteinase inhibitor, clade B, member 1a | 78 | 2.7 | AF426024 |
| Serpinb1a | Serpinb1a | serine (or cysteine) proteinase inhibitor, clade B, member 1a | 256 | 3.2 | AF426024 |
| Serpinb6a | Serpinb6a | serine (or cysteine) proteinase inhibitor, clade B, member 6a | 679 | 2.3 | NM_009254 |
| Serpinb6b | Serpinb6b | serine (or cysteine) proteinase inhibitor, clade B, member 6b | 375 | 4.2 | NM_011454 |
| Serpinb9 | Serpinb9 | serine (or cysteine) proteinase inhibitor, clade B, member 9 | 972 | 6.3 | NM_009256 |
| Serpinb9 | Serpinb9 | serine (or cysteine) proteinase inhibitor, clade B, member 9 | 323 | 5.3 | BE686716 |
| Serpine1 | Serpine1 | serine (or cysteine) proteinase inhibitor, clade E, member 1 | 80 | 4.3 | NM_008871 |
| Serping1 | Serping1 | serine (or cysteine) proteinase inhibitor, clade G, member 1 | 2372 | 5.4 | NM_009776 |
| — | Sertad4 | *Mus musculus* 16 days embryo head cDNA, RIKEN full-length enriched library, clone: C130018M11 product: unclassifiable, full insert sequence | 96 | 5.2 | BQ174721 |
| Sfpi1 | Sfpi1 | SFFV proviral integration 1 | 116 | 5.5 | NM_011355 |
| Sfrs3 | Sfrs3 | splicing factor, arginine/serine-rich 3 (SRp20) | 1401 | 2.2 | BB492363 |
| Sfrs7 | Sfrs7 | splicing factor, arginine/serine-rich 7 | 1701 | 2.1 | BC027391 |
| 3300001M08Rik | Sgol1 | RIKEN cDNA 3300001M08 gene | 16 | 3.9 | BB410537 |
| Sh3bgrl | Sh3bgrl | SH3-binding domain glutamic acid-rich protein like | 1195 | 2.0 | AK004519 |
| Sh3bgrl | Sh3bgrl | SH3-binding domain glutamic acid-rich protein like | 14 | 4.7 | BB548587 |
| Sh3bgrl3 | Sh3bgrl3 | SH3 domain binding glutamic acid-rich protein-like 3 | 1255 | 4.7 | NM_080559 |
| Sh3bp2 | Sh3bp2 | SH3-domain binding protein 2 | 296 | 2.3 | BC010198 |
| Sh3kbp1 | Sh3kbp1 | SH3-domain kinase binding protein 1 | 18 | 3.8 | BB766215 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Sh3kbp1 | Sh3kbp1 | SH3-domain kinase binding protein 1 | 161 | 6.3 | BB326929 |
| Shcbp1 | Shcbp1 | Shc SH2-domain binding protein 1 | 35 | 12.4 | NM_011369 |
| — | Siat4c | — | 32 | 3.4 | BE954474 |
| Siat8d | Siat8d | sialyltransferase 8 (alpha-2, 8-sialyltransferase) D | 166 | 4.6 | NM_009183 |
| Sil | Sil | Tal1 interrupting locus | 30 | 3.0 | BC004585 |
| Sit | Sit | SHP2 interacting transmembrane adaptor | 57 | 2.2 | NM_019436 |
| Slamf1 | Slamf1 | signaling lymphocytic activation molecule family member 1 | 72 | 3.0 | BB132695 |
| Slamf1 | Slamf1 | signaling lymphocytic activation molecule family member 1 | 12 | 7.9 | BB132695 |
| Slamf7 | Slamf7 | SLAM family member 7 | 58 | 5.4 | AK016183 |
| Slamf8 | Slamf8 | SLAM family member 8 | 27 | 65.9 | BC024587 |
| Slamf9 | Slamf9 | SLAM family member 9 | 135 | 5.9 | NM_029612 |
| Slbp | Slbp | stem-loop binding protein | 1160 | 2.3 | NM_009193 |
| Slc11a1 | Slc11a1 | solute carrier family 11 (proton-coupled divalent metal ion transporters), member 1 | 177 | 6.5 | NM_013612 |
| Slc15a3 | Slc15a3 | solute carrier family 15, member 3 | 38 | 24.8 | NM_023044 |
| Slc20a1 | Slc20a1 | solute carrier family 20, member 1 | 890 | 2.6 | NM_015747 |
| 2610016M12Rik | Slc25a24 | RIKEN cDNA 2610016M12 gene | 93 | 3.1 | BF578055 |
| 2610016M12Rik | Slc25a24 | RIKEN cDNA 2610016M12 gene | 261 | 4.6 | BM230959 |
| Slc28a2 | Slc28a2 | solute carrier family 28 (sodium-coupled nucleoside transporter), member 2 | 9 | 21.0 | NM_021520 |
| Slc2a3 | Slc2a3 | solute carrier family 2 (facilitated glucose transporter), member 3 | 68 | 4.2 | BB414515 |
| Slc2a6 | Slc2a6 | solute carrier family 2 (facilitated glucose transporter), member 6 | 14 | 15.4 | BB196807 |
| Slc31a2 | Slc31a2 | solute carrier family 31, member 2 | 350 | 2.5 | NM_025286 |
| Tramd1 | Slc36a2 | tramdorin 1 (transmembrane domain rich protein) | 26 | 3.3 | AI596194 |
| Slc38a1 | Slc38a1 | solute carrier family 38, member 1 | 193 | 2.4 | NM_134086 |
| Slc38a1 | Slc38a1 | solute carrier family 38, member 1 | 35 | 18.6 | BF165681 |
| F730005G13 | Slc39a2 | hypothetical protein F730005G13 | 23 | 5.0 | BB049001 |
| Slc39a6 | Slc39a6 | solute carrier family 39 (metal ion transporter), member 6 | 375 | 2.4 | BB825002 |
| A230035L05Rik | Slc41a2 | RIKEN cDNA A230035L05 gene | 765 | 2.3 | BC026874 |
| Eeg1 | Slc43a3 | embryonic epithelial gene 1 | 452 | 2.2 | NM_021398 |
| Slc4a7 | Slc4a7 | solute carrier family 4, sodium bicarbonate cotransporter, member 7 | 81 | 2.2 | BB454531 |
| — | Slc7a1 | *Mus musculus* 7 days neonate cerebellum cDNA, RIKEN full-length enriched library, clone: A730046J11 product: unclassifiable, full insert sequence | 215 | 2.7 | BB264620 |
| — | Slc7a1 | *Mus musculus* 7 days neonate cerebellum cDNA, RIKEN full-length enriched library, clone: A730046J11 product: unclassifiable, full insert sequence | 331 | 2.7 | BB264620 |
| Slfn2 | Slfn2 | schlafen 2 | 190 | 12.0 | NM_011408 |
| Slfn8 | Slfn8 | schlafen 8 | 72 | 8.6 | BC024709 |
| Smc2l1 | Smc2l1 | SMC2 structural maintenance of chromosomes 2-like 1 (yeast) | 16 | 2.1 | BI684556 |
| Smc2l1 | Smc2l1 | SMC2 structural maintenance of chromosomes 2-like 1 (yeast) | 25 | 3.4 | BI684556 |
| Smc2l1 | Smc2l1 | SMC2 structural maintenance of chromosomes 2-like 1 (yeast) | 243 | 5.2 | NM_008017 |
| Smc4l1 | Smc4l1 | SMC4 structural maintenance of chromosomes 4-like 1 (yeast) | 699 | 3.3 | AV172948 |
| — | Smc4l1 | *Mus musculus* transcribed sequence with weak similarity to protein ref: NP_081764.1 (*M. musculus*) RIKEN cDNA 5730493B19 [*Mus musculus*] | 56 | 6.7 | BM244144 |
| Smc4l1 | Smc4l1 | SMC4 structural maintenance of chromosomes 4-like 1 (yeast) | 196 | 4.0 | BI665568 |
| Smc4l1 | Smc4l1 | SMC4 structural maintenance of chromosomes 4-like 1 (yeast) | 243 | 5.3 | BI665568 |
| 1110054A24Rik | Smpdl3b | RIKEN cDNA 1110054A24 gene | 108 | 10.0 | NM_133888 |
| Snrpa1 | Snrpa1 | small nuclear ribonucleoprotein polypeptide A' | 790 | 2.1 | BC013777 |
| Snrpb2 | Snrpb2 | U2 small nuclear ribonucleoprotein B | 906 | 2.2 | AW537796 |
| Snrpb2 | Snrpb2 | U2 small nuclear ribonucleoprotein B | 1003 | 2.4 | AV066554 |
| Snx10 | Snx10 | sorting nexin 10 | 203 | 20.8 | AK010399 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| 2410003C09Rik | Soat1 | RIKEN cDNA 2410003C09 gene | 197 | 3.1 | BC025091 |
| — | Socs2 | — | 75 | 3.3 | BB022048 |
| Socs2 | Socs2 | suppressor of cytokine signaling 2 | 478 | 5.8 | NM_007706 |
| Socs2 | Socs2 | suppressor of cytokine signaling 2 | 354 | 5.5 | NM_007706 |
| Socs3 | Socs3 | suppressor of cytokine signaling 3 | 60 | 17.5 | NM_007707 |
| Socs3 | Socs3 | suppressor of cytokine signaling 3 | 153 | 22.3 | BB241535 |
| Socs3 | Socs3 | suppressor of cytokine signaling 3 | 98 | 17.8 | BB831725 |
| Solt | Solt | SoxLZ/Sox6 leucine zipper binding protein in testis | 95 | 3.8 | NM_021790 |
| — | Spata5 | *Mus musculus* transcribed sequences | 30 | 2.9 | BG069359 |
| Spata5 | Spata5 | spermatogenesis associated 5 | 180 | 2.4 | NM_021343 |
| — | Spata5 | *Mus musculus* transcribed sequences | 74 | 2.0 | BG074352 |
| Spata5 | Spata5 | spermatogenesis associated 5 | 32 | 5.6 | BB819052 |
| Sphk1 | Sphk1 | sphingosine kinase 1 | 171 | 2.1 | AF068749 |
| Spib | Spib | Spi-B transcription factor (Spi-1/PU.1 related) | 78 | 2.4 | BM244106 |
| Spn | Spn | sialophorin | 130 | 2.3 | NM_009259 |
| Spop | Spop | speckle-type POZ protein | 45 | 2.6 | AA688828 |
| Spred1 | Spred1 | sprouty protein with EVH-1 domain 1, related sequence | 890 | 2.0 | BQ044290 |
| Ssb | Ssb | Sjogren syndrome antigen B | 427 | 2.0 | BG796845 |
| Ssbp2 | Ssbp2 | single-stranded DNA binding protein 2 | 19 | 1.9 | AK005150 |
| BC030940 | Ssh2 | cDNA sequence BC030940 | 373 | 2.1 | BB038915 |
| 0610038P07Rik | Ssr3 | RIKEN cDNA 0610038P07 gene | 1890 | 2.7 | AU022074 |
| Stat1 | Stat1 | signal transducer and activator of transcription 1 | 171 | 23.0 | AW214029 |
| — | Stat1 | *Mus musculus* transcribed sequences | 85 | 19.6 | BB229853 |
| Stat1 | Stat1 | signal transducer and activator of transcription 1 | 915 | 14.1 | AW214029 |
| Stat1 | Stat1 | signal transducer and activator of transcription 1 | 808 | 22.7 | AW214029 |
| Stat2 | Stat2 | signal transducer and activator of transcription 2 | 145 | 3.2 | AF088862 |
| Stat2 | Stat2 | signal transducer and activator of transcription 2 | 138 | 6.1 | AF088862 |
| Stat3 | Stat3 | signal transducer and activator of transcription 3 | 746 | 3.3 | AK004083 |
| Steap | Steap | six transmembrane epithelial antigen of the prostate | 391 | 2.8 | AF297098 |
| Steap | Steap | six transmembrane epithelial antigen of the prostate | 176 | 3.9 | AF297098 |
| Stk17b | Stk17b | serine/threonine kinase 17b (apoptosis-inducing) | 240 | 9.3 | AV173139 |
| Stk17b | Stk17b | serine/threonine kinase 17b (apoptosis-inducing) | 364 | 9.3 | AV173139 |
| Stk17b | Stk17b | serine/threonine kinase 17b (apoplosis-inducing) | 70 | 4.9 | AI661948 |
| Epb7.2 | Stom | erythrocyte protein band 7.2 | 83 | 2.4 | AF093620 |
| Strm | Strm | striamin | 713 | 3.2 | BE853286 |
| Stx11 | Stx11 | syntaxin 11 | 59 | 10.1 | AK017897 |
| Sulf1 | Sulf1 | sulfalase 1 | 24 | 3.3 | BB751459 |
| Sulf1 | Sulf1 | sulfalase 1 | 42 | 5.3 | BB065799 |
| Suv39h1 | Suv39h1 | suppressor of variegation 3-9 homolog 1 (*Drosophila*) | 184 | 3.3 | AF193862 |
| Suv39h2 | Suv39h2 | suppressor of variegation 3-9 homolog 2 (*Drosophila*) | 29 | 3.1 | NM_022724 |
| Syk | Syk | spleen tyrosine kinase | 39 | 2.7 | U36776 |
| Syk | Syk | spleen tyrosine kinase | 98 | 3.4 | AW907526 |
| Syk | Syk | spleen tyrosine kinase | 20 | 11.5 | AW907526 |
| Syncrip | Syncrip | synaptotagmin binding, cytoplasmic RNA interacting protein | 303 | 2.1 | BG920261 |
| Syt1 | Syt1 | synaptotagmin 1 | 64 | 2.1 | BM118245 |
| Syt13 | Syt13 | synaptotagmin 13 | 37 | 3.3 | BB244585 |
| T2bp | T2bp | Traf2 binding protein | 317 | 3.7 | BB277065 |
| Tacc3 | Tacc3 | transforming, acidic coiled-coil containing protein 3 | 47 | 3.8 | BB787809 |
| Tank | Tank | TRAF family member-associated Nf-kappa B activator | 23 | 5.5 | BB040938 |
| Tap2 | Tap2 | transporter 2, ATP-binding cassette, sub-family B (MDR/TAP) | 389 | 11.2 | BE691515 |
| Tapbp | Tapbp | TAP binding protein | 917 | 4.6 | AF043943 |
| Tapbp | Tapbp | TAP binding protein | 2304 | 5.5 | AF043943 |
| LOC213233 | Tapbpl | similar to hypothetical protein FLJ10143 | 255 | 7.4 | BC017613 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| LOC213233 | Tapbpl | similar to hypothetical protein FLJ10143 | 36 | 5.3 | BC017613 |
| Tbc1d8 | Tbc1d8 | TBC1 domain family, member 8 | 135 | 2.2 | BC005421 |
| Tbk1 | Tbk1 | TANK-binding kinase 1 | 546 | 2.1 | NM_019786 |
| Tbx21 | Tbx21 | T-box 21 | 19 | 12.6 | NM_019507 |
| Tcerg1 | Tcerg1 | transcription elongation regulator 1 (CA150) | 29 | 3.7 | AW046403 |
| Tcf7 | Tcf7 | transcription factor 7, T-cell specific | 58 | 13.5 | AI323642 |
| — | TCR beta-chain | M. musculus mRNA for Tcell receptor, V-J beta junctional region (clone T1CRP8) | 22 | 8.2 | M87849 |
| — | Tcra | Mus musculus adult male thymus cDNA, RIKEN full-length enriched library, clone: 5830404G23 product: T-cell receptor alpha chain precursor V-J region (TA72) (fragment) homolog [Mus musculus], full insert sequence | 54 | 2.9 | AV312643 |
| — | Tcra | Mus musculus adult male thymus cDNA, RIKEN full-length enriched library, clone: 5830404G23 product: T-cell receptor alpha chain precursor V-J region (TA72) (fragment) homolog [Mus musculus], full insert sequence | 567 | 8.8 | U95921 |
| — | Tcra | Mus musculus adult male thymus cDNA, RIKEN full-length enriched library, clone: 5830404G23 product: T-cell receptor alpha chain precursor V-J region (TA72) (fragment) homolog [Mus musculus], full insert sequence | 697 | 7.7 | U07662 |
| — | Tcra | Mus musculus T cell receptor alpha chain variable region (TCRAV3S9) mRNA, partial cds | 612 | 9.2 | X01134 |
| — | Tcra | Mus musculus adult male thymus cDNA, RIKEN full-length enriched library, clone: 5830404G23 product: T-cell receptor alpha chain precursor V-J region (TA72) (fragment) homolog [Mus musculus], full insert sequence | 27 | 7.5 | BM243643 |
| — | Tcrb-J; 5830405F06Rik | — | 31 | 3.1 | AK018014 |
| Tcrb-V13 | Tcrb-V13 | T-cell receptor beta, variable 13 | 21 | 4.0 | U63547 |
| Tcrb-V13 | Tcrb-V13 | T-cell receptor beta, variable 13 | 68 | 55.0 | U07661 |
| Tcrb-V13 | Tcrb-V13 | T-cell receptor beta, variable 13 | 22 | 7.0 | AI021643 |
| Tcrb-V13 | Tcrb-V13 | T-cell receptor beta, variable 13 | 41 | 75.1 | X67128 |
| Tcrb-V13 | Tcrb-V13 | T-cell receptor beta, variable 13 | 16 | 4.2 | BF318536 |
| Tcrb-V13 | Tcrb-V13 | T-cell receptor beta, variable 13 | 28 | 7.5 | M31648 |
| Tcrb-V13 | Tcrb-V13 | T-cell receptor beta, variable 13 | 217 | 28.7 | U46841 |
| Tcrb-V13 | Tcrb-V13 | T-cell receptor beta, variable 13 | 12 | 6.8 | U46841 |
| Tcrb-V13 | Tcrb-V13 | T-cell receptor beta, variable 13 | 17 | 24.4 | X14388 |
| Tcrb-V13 | Tcrb-V13 | T-cell receptor beta, variable 13 | 65 | 55.9 | M11456 |
| Tcrb-V13 | Tcrb-V13 | T-cell receptor beta, variable 13 | 170 | 29.2 | M16120 |
| Tes | Tes | testis derived transcript | 400 | 2.8 | BC010465 |
| Tfdp1 | Tfdp1 | transcription factor Dp 1 | 709 | 2.1 | BG075396 |
| Tgfb1i1 | Tgfb1i1 | transforming growth factor beta 1 induced transcript 1 | 268 | 2.0 | NM_009365 |
| Tgfbi | Tgfbi | transforming growth factor, beta induced | 294 | 24.1 | NM_009369 |
| — | Tgfbi | — | 219 | 27.0 | BB533460 |
| Tgfbi | Tgfbi | transforming growth factor, beta induced | 229 | 19.6 | NM_009369 |
| Tgfbi | Tgfbi | transforming growth factor, beta induced | 556 | 6.1 | BB532080 |
| — | Tgfbr2 | Mus musculus transcribed sequences | 105 | 2.4 | BB465968 |
| 5730599O09Rik | Tgif2 | RIKEN cDNA 5730599O09 gene | 93 | 2.4 | AW556273 |
| Tgm2 | Tgm2 | transglutaminase 2, C polypeptide | 4344 | 2.1 | BB550124 |
| Tgm2 | Tgm2 | transglutaminase 2, C polypeptide | 3210 | 2.7 | BB041811 |
| — | Tgn | Mus musculus transcribed sequences | 16 | 5.8 | AI451480 |
| Tgtp | Tgtp | T-cell specific GTPase | 1220 | 24.4 | NM_011579 |
| Thbs1 | Thbs1 | thrombospondin 1 | 337 | 2.8 | AI385532 |
| Thbs1 | Thbs1 | thrombospondin 1 | 727 | 2.7 | AI385532 |
| Thbs2 | Thbs2 | thrombospondin 2 | 74 | 2.2 | NM_011581 |
| — | Thrap2 | Mus musculus transcribed sequences | 18 | 4.5 | C79489 |
| Thy1 | Thy1 | thymus cell antigen 1, theta | 53 | 28.3 | AV028402 |
| Timeless | Timeless | timeless homolog (Drosophila) | 43 | 3.1 | BM230269 |
| Timeless | Timeless | timeless homolog (Drosophila) | 117 | 3.4 | BM230269 |
| Timp1 | Timp1 | tissue inhibitor of metalloproteinase 1 | 69 | 61.5 | BC008107 |
| 1110005A05Rik | Tipin | RIKEN cDNA 1110005A05 gene | 507 | 2.3 | AK011357 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Tle4 | Tle4 | transducin-like enhancer of split 4, E(spl) homolog (Drosophila) | 208 | 2.1 | AU045006 |
| Tlr1 | Tlr1 | toll-like receptor 1 | 40 | 12.4 | AF316985 |
| Tlr2 | Tlr2 | toll-like receptor 2 | 145 | 11.9 | NM_011905 |
| Tlr3 | Tlr3 | toll-like receptor 3 | 252 | 2.3 | NM_126166 |
| Tlr3 | Tlr3 | toll-like receptor 3 | 129 | 3.9 | NM_126166 |
| Tlr4 | Tlr4 | toll-like receptor 4 | 19 | 3.1 | BB148728 |
| Tlr4 | Tlr4 | toll-like receptor 4 | 152 | 2.3 | AF185285 |
| Tlr4 | Tlr4 | toll-like receptor 4 | 91 | 2.2 | AF185285 |
| Tlr6 | Tlr6 | toll-like receptor 6 | 48 | 5.4 | NM_011604 |
| Tlr7 | Tlr7 | toll-like receptor 7 | 16 | 9.1 | AY035889 |
| Tm4sf7 | Tm4sf7 | transmembrane 4 superfamily member 7 | 1349 | 2.0 | NM_053082 |
| Tm6sf1 | Tm6sf1 | transmembrane 6 superfamily member 1 | 116 | 5.3 | AV378394 |
| Tm6sf1 | Tm6sf1 | transmembrane 6 superfamily member 1 | 280 | 2.8 | AV378394 |
| Mtf2 | Tmed5 | metal response element binding transcription factor 2 | 283 | 2.0 | BG066919 |
| Tmod3 | Tmod3 | tropomodulin 3 | 447 | 2.1 | BB224629 |
| Tmod3 | Tmod3 | tropomodulin 3 | 452 | 2.1 | AK017725 |
| Tmpo | Tmpo | thymopoietin | 1030 | 2.5 | AA153892 |
| Tmprss4 | Tmprss4 | transmembrane protease, serine 4 | 36 | 11.7 | BC021368 |
| — | Tmsb10 | M. musculus mRNA for testis-specific thymosin beta-10 | 4515 | 5.7 | AV148480 |
| Tmsb10 | Tmsb10 | thymosin, beta 10 | 941 | 10.4 | NM_025284 |
| — | Tmsb10 | M. musculus mRNA for testis-specific thymosin beta-10 | 1945 | 7.8 | BB096368 |
| Tmsb4x | Tmsb4x | thymosin, beta 4, X chromosome | 9065 | 2.7 | NM_021278 |
| Tnfaip2 | Tnfaip2 | tumor necrosis factor, alpha-induced protein 2 | 749 | 1.9 | NM_009396 |
| Tnfaip3 | Tnfaip3 | tumor necrosis factor, alpha-induced protein 3 | 77 | 4.8 | NM_009397 |
| Tnfaip3 | Tnfaip3 | tumor necrosis factor, alpha-induced protein 3 | 236 | 4.3 | BM241351 |
| Abcb1a | Tnfaip9 | ATP-binding cassette, sub-family B (MDR/TAP), member 1A | 95 | 5.7 | NM_054098 |
| Tnfrsf11b | Tnfrsf11b | tumor necrosis factor receptor superfamily, member 11b (osteoprotegerin) | 3 | 4.0 | AB013898 |
| Tnfrsf12a | Tnfrsf12a | tumor necrosis factor receptor superfamily, member 12a | 810 | 2.5 | NM_013749 |
| Tnfrsf12a | Tnfrsf12a | tumor necrosis factor receptor superfamily, member 12a | 693 | 3.0 | NM_013749 |
| Tnfrsf14 | Tnfrsf14 | tumor necrosis factor receptor superfamily, member 14 (herpesvirus entry mediator) | 14 | 10.0 | BC022125 |
| Tnfrsf18 | Tnfrsf18 | tumor necrosis factor receptor superfamily, member 18 | 81 | 5.5 | AF229434 |
| Tnfrsf1b | Tnfrsf1b | tumor necrosis factor receptor superfamily, member 1b | 182 | 3.2 | M60469 |
| Tnfrsf4 | Tnfrsf4 | tumor necrosis factor receptor superfamily, member 4 | 163 | 4.7 | NM_011659 |
| Tnfrsf5 | Tnfrsf5 | tumor necrosis factor receptor superfamily, member 5 | 46 | 18.8 | NM_011611 |
| Tnfrsf5 | Tnfrsf5 | tumor necrosis factor receptor superfamily, member 5 | 48 | 20.4 | BB220422 |
| Tnfrsf5 | Tnfrsf5 | tumor necrosis factor receptor superfamily, member 5 | 95 | 15.7 | AI385482 |
| Tnfrsf7 | Tnfrsf7 | tumor necrosis factor receptor superfamily, member 7 | 20 | 9.6 | L24495 |
| Tnfsf10 | Tnfsf10 | tumor necrosis factor (ligand) superfamily, member 10 | 293 | 5.1 | NM_009425 |
| Tnfsf13b | Tnfsf13b | tumor necrosis factor (ligand) superfamily, member 13b | 48 | 3.0 | BB079466 |
| Tnfsf13b | Tnfsf13b | tumor necrosis factor (ligand) superfamily, member 13b | 101 | 7.4 | NM_033622 |
| Tnfsf9 | Tnfsf9 | tumor necrosis factor (ligand) superfamily, member 9 | 29 | 5.3 | NM_009404 |
| Tnip1 | Tnip1 | TNFAIP3 interacting protein 1 | 724 | 2.4 | AJ242777 |
| Top2a | Top2a | topoisomerase (DNA) II alpha | 39 | 3.9 | BB749838 |
| Top2a | Top2a | topoisomerase (DNA) II alpha | 142 | 14.7 | BM211413 |
| 2810429C13Rik | Topbp1 | RIKEN cDNA 2810429C13 gene | 334 | 2.5 | BC007170 |
| Tor3a | Tor3a | torsin family 3, member A | 226 | 2.4 | NM_023141 |
| Tor3a | Tor3a | torsin family 3, member A | 180 | 4.1 | AK009693 |
| Tor3a | Tor3a | torsin family 3, member A | 287 | 3.3 | NM_023141 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | Tox | Mus musculus transcribed sequences | 24 | 4.1 | BM124834 |
| Tox | Tox | thymocyte selection-associated HMG box gene | 6 | 10.5 | BB547854 |
| Tox | Tox | thymocyte selection-associated HMG box gene | 89 | 4.7 | BB547854 |
| 5430425C04Rik | Tp53i5 | RIKEN cDNA 5430425C04 gene | 44 | 3.5 | AK017334 |
| Tpm2 | Tpm2 | tropomyosin 2, beta | 307 | 2.5 | BC024358 |
| Tpm2 | Tpm2 | tropomyosin 2, beta | 977 | 2.2 | AK003186 |
| — | Tpm4 | Mus musculus 7 days embryo whole body cDNA, RIKEN full-length enriched library, clone: C430002D13 product: TROPOMYOSIN 4 homolog [Homo sapiens], full insert sequence | 1905 | 2.9 | AV122663 |
| Tpst1 | Tpst1 | protein-tyrosine sulfotransferase 1 | 130 | 4.8 | NM_013837 |
| Tpt1h | Tpt1h | tRNA splicing 2' phosphotransferase 1 homolog (S. cerevisiae) | 181 | 16.0 | BB113173 |
| 2610005B21Rik | Tpx2 | RIKEN cDNA 2610005B21 gene | 132 | 3.4 | AK011311 |
| 2610005B21Rik | Tpx2 | RIKEN cDNA 2610005B21 gene | 9 | 6.5 | AK011311 |
| Traf1 | Traf1 | Tnf receptor-associated factor 1 | 40 | 6.1 | BB218245 |
| Traf1 | Traf1 | Tnf receptor-associated factor 1 | 34 | 10.8 | BG064103 |
| Trem3 | Trem3 | triggering receptor expressed on myeloid cells 3 | 96 | 2.4 | NM_021407 |
| 5031403H21Rik | Treml4 | RIKEN cDNA 5031403H21 gene | 5 | 14.6 | BB740529 |
| — | Trex1 | Mus musculus adult female vagina cDNA, RIKEN full-length enriched library, clone: 9930022F21 product: similar to G PROTEIN COUPLED RECEPTOR [Mus musculus], full insert sequence | 26 | 6.3 | AF140709 |
| Ifld2 | Trib3 | induced in fatty liver dystrophy 2 | 34 | 6.6 | BB508622 |
| Trim12 | Trim12 | tripartite motif protein 12 | 13 | 8.3 | BM244351 |
| Trim21 | Trim21 | tripartite motif protein 21 | 341 | 2.3 | BC010580 |
| Trim21 | Trim21 | tripartite motif protein 21 | 325 | 3.9 | BC010580 |
| Trim27 | Trim27 | tripartite motif protein 27 | 783 | 2.2 | BB290427 |
| Trim30 | Trim30 | tripartite motif protein 30 | 215 | 7.9 | AF220015 |
| Trim30 | Trim30 | tripartite motif protein 30 | 252 | 9.4 | BM240719 |
| 9230105E10Rik | Trim34 | RIKEN cDNA 9230105E10 gene | 427 | 4.5 | BI653857 |
| Trip13 | Trip13 | thyroid hormone receptor interactor 13 | 31 | 4.5 | AK010336 |
| Trip13 | Trip13 | thyroid hormone receptor interactor 13 | 56 | 9.0 | AK010336 |
| Tslpr | Tslpr | thymic stromal-derived lymphopoietin, receptor | 313 | 3.7 | NM_016715 |
| Ttk | Ttk | Ttk protein kinase | 30 | 7.1 | NM_009445 |
| Tuba1 | Tuba1 | tubulin, alpha 1 | 1848 | 3.7 | NM_011653 |
| Tuba2 | Tuba2 | tubulin, alpha 2 | 9060 | 2.2 | BC008117 |
| Tuba8 | Tuba8 | tubulin, alpha 8 | 67 | 2.9 | BB047533 |
| Tubb2 | Tubb2 | tubulin, beta 2 | 969 | 2.9 | BC003475 |
| Tubb5 | Tubb5 | tubulin, beta 5 | 568 | 3.6 | BG064086 |
| Tubb5 | Tubb5 | tubulin, beta 5 | 2009 | 3.3 | NM_011655 |
| 2310057H16Rik | Tubb6 | RIKEN cDNA 2310057H16 gene | 204 | 4.2 | NM_026473 |
| Tube1 | Tube1 | epsilon-tubulin 1 | 27 | 2.7 | AK010005 |
| Txk | Txk | TXK tyrosine kinase | 31 | 4.2 | U19607 |
| Tyki | Tyki | thymidylate kinase family LPS-inducible member | 406 | 3.0 | AK004595 |
| Tyrobp | Tyrobp | TYRO protein tyrosine kinase binding protein | 261 | 17.8 | NM_011662 |
| C330001M22 | Ubash3a | hypothetical protein C330001M22 | 89 | 3.1 | BB397001 |
| Ubd | Ubd | ubiquitin D | 121 | 223.5 | NM_023137 |
| Ube2c | Ube2c | ubiquitin-conjugating enzyme E2C | 133 | 10.5 | AV162459 |
| Ubce8 | Ube2l6 | ubiquitin-conjugating enzyme 8 | 85 | 8.7 | BC008238 |
| Ugcg | Ugcg | UDP-glucose ceramide glucosyltransferase | 203 | 2.2 | BF682223 |
| Ugcg | Ugcg | UDP-glucose ceramide glucosyltransferase | 229 | 2.5 | AA591863 |
| Np95 | Uhrf1 | nuclear protein 95 | 60 | 12.5 | BB702754 |
| Np95 | Uhrf1 | nuclear protein 95 | 43 | 6.5 | BB702754 |
| 2510009H09Rik | Unc5cl | RIKEN cDNA 2510009H09 gene | 71 | 2.5 | AK010945 |
| Unc93b | Unc93b1 | unc-93 homolog B (C. elegans) | 424 | 3.3 | BC018388 |
| Upp1 | Upp1 | uridine phosphorylase 1 | 391 | 8.2 | NM_009477 |
| Usp18 | Usp18 | ubiquitin specific protease 18 | 165 | 20.6 | NM_011909 |
| — | Usp32 | Mus musculus transcribed sequence with weak similarity to protein ref: NP_081764.1 (M. musculus) RIKEN cDNA 5730493B19 [Mus musculus] | 34 | 2.1 | BB740339 |
| Vasp | Vasp | vasodilator-stimulated phosphoprotein | 705 | 3.1 | BC015289 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | Vcam1 | *Mus musculus* transcribed sequences | 49 | 20.6 | AV280637 |
| Vcam1 | Vcam1 | vascular cell adhesion molecule 1 | 152 | 25.4 | L08431 |
| 1300011C24Rik | Vdp | RIKEN cDNA 1300011C24 gene | 3412 | 2.0 | AV139821 |
| Vim | Vim | vimentin | 1185 | 8.9 | AV147875 |
| Vim | Vim | vimentin | 1376 | 8.7 | M24849 |
| Vim | Vim | vimentin | 570 | 10.5 | AV147875 |
| Vps54 | Vps54 | vacuolar protein sorting 54 (yeast) | 8 | 2.9 | BB201271 |
| Vrk1 | Vrk1 | vaccinia related kinase 1 | 243 | 2.0 | BC016676 |
| Vrk2 | Vrk2 | vaccinia related kinase 2 | 87 | 3.3 | BC013520 |
| Vrk2 | Vrk2 | vaccinia related kinase 2 | 154 | 3.0 | AK012664 |
| Wars | Wars | tryptophanyl-tRNA synthetase | 387 | 2.4 | BC003450 |
| Wars | Wars | tryptophanyl-tRNA synthetase | 791 | 2.7 | BB785450 |
| Wars | Wars | tryptophanyl-tRNA synthetase | 193 | 4.6 | AK004541 |
| Wars | Wars | tryptophanyl-tRNA synthetase | 768 | 2.9 | AI528863 |
| Was | Was | Wiskott-Aldrich syndrome homolog (human) | 25 | 17.0 | NM_009515 |
| Waspip | Waspip | Wiskott-Aldrich syndrome protein interacting protein | 249 | 4.9 | C76969 |
| Waspip | Waspip | Wiskott-Aldrich syndrome protein interacting protein | 195 | 4.6 | C76969 |
| Wbp5 | Wbp5 | WW domain binding protein 5 | 3473 | 2.1 | BC007478 |
| — | Wbscr1 | *Mus musculus* transcribed sequences | 43 | 2.5 | BI499987 |
| Wbscr5 | Wbscr5 | Williams-Beuren syndrome chromosome region 5 homolog (human) | 67 | 5.7 | AF257136 |
| D630024B06Rik | Wdhd1 | RIKEN cDNA D630024B06 gene | 71 | 5.0 | C77437 |
| Whsc1 | Whsc1 | Wolf-Hirschhorn syndrome candidate 1 (human) | 104 | 2.8 | AK017992 |
| Wisp1 | Wisp1 | WNT1 inducible signaling pathway protein 1 | 145 | 2.4 | NM_018865 |
| 2700038M07Rik | Wsb1 | RIKEN cDNA 2700038M07 gene | 786 | 2.1 | BC019601 |
| Xcl1 | Xcl1 | chemokine (C motif) ligand 1 | 32 | 18.1 | NM_008510 |
| Xdh | Xdh | xanthine dehydrogenase | 167 | 16.7 | AV286265 |
| Ywhah | Ywhah | tyrosine 3-monooxygenase/tryptophan 5-monooxygenase activation protein, eta polypeptide | 2590 | 2.2 | NM_011738 |
| Zap70 | Zap70 | zeta-chain (TCR) associated protein kinase | 45 | 6.2 | BB204558 |
| Zbp1 | Zbp1 | Z-DNA binding protein 1 | 49 | 78.0 | AK008179 |
| Zbp1 | Zbp1 | Z-DNA binding protein 1 | 14 | 118.4 | NM_021394 |
| Zc3hav1 | Zc3hav1 | zinc finger CCCH type, antiviral 1 | 174 | 2.0 | AK004770 |
| Zc3hav1 | Zc3hav1 | zinc finger CCCH type, antiviral 1 | 465 | 4.0 | BB757349 |
| Zc3hdc1 | Zc3hdc1 | zinc finger CCCH type domain containing 1 | 462 | 6.7 | BM227980 |
| A430104C18Rik | Zc3hdc7 | RIKEN cDNA A430104C18 gene | 193 | 2.4 | AW556219 |
| 2410141K03Rik | Zcchc10 | RIKEN cDNA 2410141K03 gene | 159 | 2.1 | BC025078 |
| — | Zcchc6 | *Mus musculus* transcribed sequences | 113 | 2.1 | BI695361 |
| 1110051N18Rik | Zcwcc3 | RIKEN cDNA 1110051N18 gene | 343 | 3.5 | AI452146 |
| 1110051N18Rik | Zcwcc3 | RIKEN cDNA 1110051N18 gene | 224 | 3.2 | BC026506 |
| — | Zfhx1b | *Mus musculus* transcribed sequence with moderate similarity to protein sp: P00722 (*E. coli*) BGAL_ECOLI Beta-galactosidase (Lactase) | 65 | 2.3 | BG061923 |
| — | Zfhx1b | *Mus musculus* Corpos mRNA, 3' untranslated region | 59 | 3.1 | BM220939 |
| — | Zfhx1b | *Mus musculus* transcribed sequences | 65 | 2.3 | BB488200 |
| Zfhx1b | Zfhx1b | zinc finger homeobox 1b | 226 | 2.4 | NM_015753 |
| Zfp118 | Zfp118 | Zinc finger protein 118 | 59 | 2.2 | BB176857 |
| Zfp313 | Zfp313 | zinc finger protein 313 | 1410 | 2.0 | BB251247 |
| 3732412P20 | Zfp455 | hypothetical protein 3732412P20 | 37 | 3.6 | AV172851 |
| Zfp472 | Zfp472 | zinc finger protein 472 | 149 | 2.1 | BC023090 |
| Zfp52 | Zfp52 | zinc finger protein 52 | 68 | 2.7 | BM225280 |
| Zfp52 | Zfp52 | zinc finger protein 52 | 263 | 2.4 | BM225280 |
| Zfp118 | Zfp53 | Zinc finger protein 118 | 132 | 2.3 | NM_013843 |
| Znfn1a1 | Zfpn1a1 | zinc finger protein, subfamily 1A, 1 (Ikaros) | 85 | 19.8 | AV317621 |
| — | Zfpn1a1 | *Mus musculus*, clone IMAGE: 1263252, mRNA | 40 | 2.6 | BM237812 |
| Znfn1a3 | Zfpn1a3 | zinc finger protein, subfamily 1A, 3 (Aiolos) | 42 | 4.4 | BB202216 |
| Znfn1a3 | Zfpn1a3 | zinc finger protein, subfamily 1A, 3 (Aiolos) | 34 | 21.1 | BB151746 |
| Zfr | Zfr | zinc finger RNA binding protein | 54 | 2.5 | BB214490 |
| Zfr | Zfr | zinc finger RNA binding protein | 71 | 2.6 | BM119505 |
| Zipro1 | Zipro1 | zinc finger proliferation 1 | 185 | 3.0 | AI326272 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| B830022L21Rik | Znrf1 | RIKEN cDNA B830022L21 gene | 190 | 2.4 | BC006765 |
| — | Zswim6 | *Mus musculus* transcribed sequences | 116 | 2.0 | AI427602 |
| D10Ertd749e | Zwint | DNA segment, Chr 10, ERATO Doi 749, expressed | 143 | 2.6 | BC013559 |
| Brd7 | | bromodomain containing 7 | 14 | 2.4 | BB022341 |
| — | | *Mus musculus* transcribed sequence with strong similarity to protein sp: P00722 (*E. coli*) BGAL_ECOLI Beta-galactosidase (Lactase) | 229 | 2.5 | BG143461 |
| — | | *Mus musculus* transcribed sequences | 24 | 2.9 | BB066105 |
| Crsp9 | | cofactor required for Sp1 transcriptional activation, subunit 9, 33 kDa | 59 | 2.2 | AK009549 |
| — | | — | 104 | 2.6 | BQ033755 |
| — | | *Mus musculus* transcribed sequences | 8 | 3.1 | BE686253 |
| — | | *Mus musculus* 0 day neonate eyeball cDNA, RIKEN full-length enriched library, clone: E130307M10 product: unclassifiable, full insert sequence | 40 | 2.6 | BB710625 |
| — | | *Mus musculus* transcribed sequence with weak similarity to protein pir: I58401 (*M. musculus*) I58401 protein-tyrosine kinase (EC 2.7.1.112) JAK3 - mouse | 223 | 3.8 | AW556821 |
| — | | | 1919 | 3.2 | AY052560 |
| Srrm1 | | serine/arginine repetitive matrix 1 | 43 | 2.5 | BB254130 |
| — | | *Mus musculus* adult male aorta and vein cDNA, RIKEN full-length enriched library, clone: A530086D01 product: unknown EST, full insert sequence | 54 | 2.3 | BB224338 |
| — | | — | 78 | 4.4 | BB116018 |
| — | | *Mus musculus* transcribed sequences | 37 | 2.5 | BE691393 |
| — | | *Mus musculus* transcribed sequences | 57 | 3.1 | BE943672 |
| — | | *Mus musculus* transcribed sequences | 12 | 5.8 | BE447255 |
| Loxl2 | | lysyl oxidase-like 2 | 231 | 2.2 | AI415741 |
| — | | *Mus musculus* 16 days neonate heart cDNA, RIKEN full-length enriched library, clone: D830032E20 product: similar to ENVELOPE PROTEIN (FRAGMENT) [Friend spleen focus-forming virus], full insert sequence | 24 | 3.1 | BB042982 |
| Pfkp | | phosphofructokinase, platelet | 438 | 2.3 | BB076574 |
| Itgb4bp | | integrin beta 4 binding protein | 174 | 2.0 | AK018313 |
| — | | *Mus musculus* 2 days neonate thymus thymic cells cDNA, RIKEN full-length enriched library, clone: E430008K23 product: unknown EST, full insert sequence | 102 | 3.3 | BI076809 |
| — | | *Mus musculus* 12 days embryo embryonic body between diaphragm region and neck cDNA, RIKEN full-length enriched library, clone: 9430088I02 product: unknown EST, full insert sequence | 54 | 2.2 | BM239026 |
| — | | *Mus musculus* adult male thymus cDNA, RIKEN full-length enriched library, clone: 5830404C02 product: unknown EST, full insert sequence | 5 | 8.8 | BB241847 |
| — | | — | 12 | 2.2 | BB800744 |
| Cp | | ceruloplasmin | 232 | 2.0 | BB332449 |
| — | | *Mus musculus* transcribed sequence with strong similarity to protein sp: Q9NZJ4 (*H. sapiens*) SACS_HUMAN Sacsin | 55 | 3.5 | BG075163 |
| Etv3 | | ets variant gene 3 | 284 | 2.5 | BI456953 |
| Strn3 | | striatin, calmodulin binding protein 3 | 114 | 2.0 | BB228907 |
| — | | *Mus musculus* 2 days pregnant adult female ovary cDNA, RIKEN full-length enriched library, clone: E330027C07 product: weakly similar to ZINC FINGER PROTEIN 43 (HTF6) [*Homo sapiens*], full insert sequence | 61 | 5.5 | BE989616 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | | *Mus musculus* 9 days embryo whole body cDNA, RIKEN full-length enriched library, clone: D030060F23 product: Mus musculus U22 snoRNA host gene (UHG) gene, complete sequence, full insert sequence | 69 | 4.3 | BF163381 |
| — | | *Mus musculus* transcribed sequences | 32 | 2.6 | AV300631 |
| — | | — | 104 | 2.7 | AV084904 |
| Zfp295 | | zinc finger protein 295 | 102 | 2.2 | BB091040 |
| — | | *Mus musculus* transcribed sequences | 62 | 2.3 | BB230267 |
| H2afz | | H2A histone family, member Z | 765 | 1.9 | AV215230 |
| — | | *Mus musculus* similar to FLJ14075 protein (LOC217431), mRNA | 80 | 2.1 | BG071110 |
| — | | *Mus musculus* 0 day neonate skin cDNA, RIKEN full-length enriched library, clone: 4632424N07 product: unknown EST, full insert sequence | 47 | 2.3 | AV233462 |
| — | | *Mus musculus* adult male thymus cDNA, RIKEN full-length enriched library, clone: 5830404C02 product: unknown EST, full insert sequence | 55 | 2.8 | AV312603 |
| — | | *Mus musculus* transcribed sequences | 134 | 2.8 | BI466416 |
| — | | *Mus musculus* transcribed sequence with weak similarity to protein ref: NP_061226.1 (*M. musculus*) 2-cell-stage, variable group, member 1; variable group of 2-cell-stage gene family [*Mus musculus*] | 20 | 2.8 | AI452166 |
| 1700029I01Rik | | RIKEN cDNA 1700029I01 gene | 81 | 3.5 | AV047635 |
| — | | *Mus musculus* transcribed sequences | 62 | 5.9 | AV247387 |
| — | | *Mus musculus* cDNA clone MGC: 6071 IMAGE: 3492410, complete cds | 130 | 3.3 | BC022776 |
| — | | — | 68 | 4.0 | BB256262 |
| Smc6l1 | | SMC6 structural maintenance of chromosomes 6-like 1 (yeast) | 43 | 3.0 | BB056038 |
| — | | *Mus musculus* transcribed sequences | 63 | 2.1 | BB473548 |
| — | | *Mus musculus* transcribed sequences | 36 | 2.7 | AU040162 |
| — | | *Mus musculus* 0 day neonate eyeball cDNA, RIKEN full-length enriched library, clone: E130112O04 product: unknown EST, full insert sequence | 48 | 2.1 | BB541236 |
| — | | — | 6 | 9.3 | BB030365 |
| — | | *Mus musculus* transcribed sequences | 79 | 2.5 | BG069527 |
| — | | — | 8 | 3.4 | AI661342 |
| — | | *Mus musculus* transcribed sequences | 229 | 2.2 | BM218086 |
| 2210023K21Rik | | RIKEN cDNA 2210023K21 gene | 125 | 4.7 | BI106821 |
| — | | — | 94 | 2.1 | BG074662 |
| Igsf6 | | immunoglobulin superfamily, member 6 | 23 | 2.8 | AV078837 |
| — | | *Mus musculus* transcribed sequence with weak similarity to protein pir: S12207 (*M. musculus*) S12207 hypothetical protein (B2 element) - mouse | 29 | 2.4 | BB449580 |
| Rp2h | | retinitis pigmentosa 2 homolog (human) | 209 | 2.2 | BF168611 |
| — | | *Mus musculus* transcribed sequences | 37 | 3.9 | BE634580 |
| Stk4 | | serine/threonine kinase 4 | 1036 | 2.0 | BB141897 |
| Ccr7 | | chemokine (C—C motif) receptor 7 | 4 | 9.9 | BB204380 |
| — | | *Mus musculus* adult male thymus cDNA, RIKEN full-length enriched library, clone: 5830443J22 product: unknown EST, full insert sequence | 28 | 3.1 | BB165850 |
| — | | *Mus musculus* 0 day neonate eyeball cDNA, RIKEN full-length enriched library, clone: E130013E11 product: unknown EST, full insert sequence | 67 | 2.1 | BB538708 |
| — | | *Mus musculus* similar to Elongation factor 1-alpha 1 (EF-1-alpha-1) (Elongation factor 1 A-1) (eEF1A-1) (Elongation factor Tu) (EF-Tu) (LOC381109), mRNA | 154 | 4.1 | AV328340 |
| 2610018G03Rik | | RIKEN cDNA 2610018G03 gene | 123 | 2.0 | AW556821 |
| — | | *Mus musculus* transcribed sequences | 36 | 3.5 | BB208080 |
| — | | *Mus musculus* transcribed sequences | 21 | 3.0 | BB271581 |
| Atf4 | | activating transcription factor 4 | 398 | 2.4 | AV314773 |
| — | | *Mus musculus* transcribed sequences | 52 | 2.3 | BB458874 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| 2610039C10Rik | | RIKEN cDNA 2610039C10 gene | 113 | 3.5 | AK012762 |
| — | | *Mus musculus* transcribed sequence with moderate similarity to protein ref: NP_038602.1 (*M. musculus*) L1 repeat, Tf subfamily, member 18 [*Mus musculus*] | 42 | 2.1 | AV372127 |
| — | | *Mus musculus* transcribed sequences | 224 | 3.0 | AA266723 |
| — | | — | 388 | 2.0 | AV368189 |
| E430036I04Rik | | RIKEN cDNA E430036I04 gene | 85 | 6.8 | BB329408 |
| — | | — | 98 | 2.4 | BQ266693 |
| Rp2h | | retinitis pigmentosa 2 homolog (human) | 188 | 2.2 | BF168611 |
| — | | *Mus musculus* similar to DYSKERIN (LOC245474), mRNA | 190 | 4.4 | BB779105 |
| 0610025L06Rik | | RIKEN cDNA 0610025L06 gene | 1362 | 6.2 | AV010467 |
| — | | *Mus musculus*, clone IMAGE: 5066616, mRNA | 72 | 3.7 | BE373131 |
| — | | *Mus musculus* transcribed sequences | 21 | 2.4 | BM196689 |
| — | | — | 157 | 2.2 | BG976607 |
| — | | *Mus musculus* transcribed sequences | 9 | 5.0 | BB534560 |
| C330006D17Rik | | RIKEN cDNA C330006D17 gene | 191 | 2.4 | BB397948 |
| — | | — | 169 | 4.7 | BG976607 |
| — | | *Mus musculus* transcribed sequence with weak similarity to protein pir: S12207 (*M. musculus*) S12207 hypothetical protein (82 element) - mouse | 96 | 2.2 | BB667685 |
| — | | *Mus musculus* transcribed sequences | 53 | 12.1 | BM246630 |
| — | | *Mus musculus* transcribed sequence with weak similarity to protein pir: S12207 (*M. musculus*) S12207 hypothetical protein (B2 element) - mouse | 29 | 3.8 | AI451538 |
| — | | — | 299 | 2.3 | BG976607 |
| — | | *Mus musculus* mRNA similar to interferon-inducible GTPase (cDNA clone MGC: 49532 IMAGE: 3495064), complete cds | 33 | 5.1 | BC020118 |
| Mll | | myeloid/lymphoid or mixed-lineage leukemia | 128 | 2.0 | AK017541 |
| — | | *Mus musculus* transcribed sequences | 46 | 2.5 | BG073023 |
| Cp | | ceruloplasmin | 1596 | 3.9 | BB332449 |
| — | | *Mus musculus* similar to 2-cell-stage, variable group, member 3; 2-cell-stage, variable group, member 1 (LOC236374), mRNA | 96 | 2.1 | BG070246 |
| — | | — | 28 | 5.3 | BC003855 |
| — | | *Mus musculus* similar to Ig delta chain C region, membrane-bound form - mouse (LOC382646), mRNA | 29 | 3.5 | BE686052 |
| 3010033P07Rik | | RIKEN cDNA 3010033P07 gene | 114 | 2.5 | AK013903 |
| — | | *Mus musculus* transcribed sequences | 94 | 3.6 | BB376947 |
| — | | *Mus musculus* transcribed sequences | 182 | 2.8 | BB829165 |
| Pscdbp | | pleckstrin homology, Sec7 and coiled-coil domains, binding protein | 1081 | 3.1 | BB503614 |
| — | | — | 1108 | 2.5 | BB145101 |
| Hmmr | | hyaluronan mediated motility receptor (RHAMM) | 82 | 3.0 | X64550 |
| — | | *Mus musculus* 0 day neonate thymus cDNA, RIKEN full-length enriched library, clone: A430110E23 product: unknown EST, full insert sequence | 25 | 3.8 | AI840829 |
| Nr4a2 | | nuclear receptor subfamily 4, group A, member 2 | 23 | 2.8 | BB703394 |
| Rod1 | | ROD1 regulator of differentiation 1 (*S. pombe*) | 130 | 3.4 | BB519382 |
| Eif4ebp1 | | eukaryotic translation initiation factor 4E binding protein 1 | 393 | 2.6 | AV216412 |
| — | | *Mus musculus* transcribed sequences | 94 | 2.5 | BE634878 |
| — | | *Mus musculus* adult male tongue cDNA, RIKEN full-length enriched library, clone: 2310050P20 product: unknown EST, full insert sequence | 19 | 3.3 | BG061080 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| Col1a1 | | procollagen, type I, alpha 1 | 138 | 5.9 | BI794771 |
| — | | Mus musculus 18 days pregnant adult female placenta and extra embryonic tissue cDNA, RIKEN full-length enriched library, clone: 3830421G02 product: unknown EST, full insert sequence | 136 | 2.4 | BI082172 |
| — | | — | 512 | 2.9 | BG976607 |
| — | | — | 244 | 3.7 | BM941868 |
| — | | — | 1603 | 3.3 | BF719154 |
| Ncf1 | | neutrophil cytosolic factor 1 | 35 | 15.5 | BE370703 |
| — | | Mus musculus diabetic nephropathy-related gene 1 mRNA, partial sequence | 118 | 58.3 | BM241271 |
| — | | Mus musculus transcribed sequence with moderate similarity to protein pir: A39822 (H. sapiens) A39822 leukosialin precursor - human | 148 | 6.7 | BB160586 |
| — | | Mus musculus transcribed sequences | 125 | 3.9 | BB667149 |
| Rrm2 | | ribonucleotide reductase M2 | 412 | 8.2 | AV301324 |
| — | | Mus musculus transcribed sequences | 96 | 2.4 | BM243375 |
| — | | — | 138 | 2.1 | BI155210 |
| Ddx39 | | DEAD (Asp-Glu-Ala-Asp) box polypeptide 39 | 1234 | 2.5 | AV111502 |
| — | | — | 17 | 4.6 | AV340322 |
| Cp | | ceruloplasmin | 915 | 4.3 | BB332449 |
| — | | Mus musculus transcribed sequence with moderate similarity to protein sp: P00722 (E. coli) BGAL_ECOLI Beta-galactosidase (Lactase) | 91 | 3.0 | BB281100 |
| — | | — | 230 | 5.3 | U29539 |
| Gna13 | | guanine nucleotide binding protein, alpha 13 | 1362 | 2.3 | BI662324 |
| — | | Mus musculus transcribed sequences | 66 | 2.5 | AA267568 |
| — | | Mus musculus 16 days neonate heart cDNA, RIKEN full-length enriched library, clone: D830028N22 product: unclassifiable, full insert sequence | 19 | 4.3 | BB518323 |
| Rp2h | | retinitis pigmentosa 2 homolog (human) | 202 | 2.2 | BF168611 |
| — | | Mus musculus adult male cecum cDNA, RIKEN full-length enriched library, clone: 9130208D14 product: unknown EST, full insert sequence | 28 | 4.8 | AI506672 |
| — | | Mus musculus transcribed sequences | 96 | 3.3 | BB767243 |
| 9930027N05Rik | | RIKEN cDNA 9930027N05 gene | 41 | 39.3 | AI662854 |
| — | | Mus musculus transcribed sequence with weak similarity to protein ref: NP_081764.1 (M. musculus) RIKEN cDNA 5730493B19 [Mus musculus] | 35 | 9.3 | BB740904 |
| — | | Mus musculus transcribed sequences | 35 | 2.6 | BM239760 |
| — | | Mus musculus transcribed sequence with moderate similarity to protein ref: NP_081764.1 (M. musculus) RIKEN cDNA 5730493B19 [Mus musculus] | 68 | 2.9 | BF714880 |
| — | | Mus musculus transcribed sequences | 110 | 3.5 | BM222853 |
| Cp | | ceruloplasmin | 838 | 4.2 | BB332449 |
| Ncf1 | | neutrophil cytosolic factor 1 | 60 | 7.0 | BE370703 |
| — | | — | 59 | 37.3 | BE688410 |
| Hn1 | | hematological and neurological expressed sequence 1 | 194 | 7.9 | AV067695 |
| — | | — | 986 | 20.1 | AV066625 |
| Myadm | | myeloid-associated differentiation marker | 1120 | 2.1 | BB500055 |
| Vcam1 | | vascular cell adhesion molecule 1 | 296 | 19.2 | BB250384 |
| Cugbp2 | | CUG triplet repeat, RNA binding protein 2 | 148 | 6.0 | BB667096 |
| — | | Mus musculus 3 days neonate thymus cDNA, RIKEN full-length enriched library, clone: A630020E03 product: unknown EST, full insert sequence | 41 | 40.5 | BB207611 |

TABLE 2-continued

Rejection-induced transcripts (RITs)

| Gene Symbol Affymetrix | Common | Gene Title Affymetrix | NCBA Raw | WT D5 vs NCBA | Genbank |
|---|---|---|---|---|---|
| — | | *Mus musculus* transcribed sequence with strong similarity to protein sp: Q61753 (*M. musculus*) SERA_MOUSE D-3-phosphoglycerate dehydrogenase (3-PGDH) (A10) | 510 | 2.3 | AV216768 |
| Cxcl9 | | chemokine (C—X—C motif) ligand 9 | 33 | 69.4 | BI104444 |
| Rod1 | | ROD1 regulator of differentiation 1 (*S. pombe*) | 138 | 4.6 | BB519382 |
| — | | — | 19 | 17.8 | BC003855 |
| — | | *Mus musculus* transcribed sequence with strong similarity to protein sp: P10660 (*H. sapiens*) RS6_HUMAN 40S ribosomal protein S6 (Phosphoprotein NP33) | 536 | 3.9 | C76675 |
| — | | *Mus musculus* transcribed sequences | 28 | 33.7 | BB224524 |
| — | | *Mus musculus* adult male aorta and vein cDNA, RIKEN full-length enriched library, clone: A530049N04 product: unknown EST, full insert sequence | 18 | 23.4 | BE692425 |
| — | | *Mus musculus* similar to toll-like receptor (LOC279572), mRNA | 32 | 15.8 | BI655907 |
| — | | *Mus musculus* transcribed sequences | 196 | 3.2 | AW543723 |
| — | | — | 31 | 17.1 | BG072508 |
| Etv3 | | ets variant gene 3 | 198 | 2.1 | BI456953 |
| — | | *Mus musculus* transcribed sequences | 12 | 2.3 | BF321297 |
| — | | — | 19 | 67.1 | NM_022429 |
| — | | *Mus musculus* similar to AIM2 protein (LOC383619), mRNA | 15 | 4.0 | BE685969 |
| Cnp1 | | cyclic nucleotide phosphodiesterase 1 | 354 | 6.3 | BB251922 |
| — | | — | 286 | 2.9 | BC004065 |
| Tpm3 | | tropomyosin 3, gamma | 621 | 3.8 | AV311925 |
| 2210023K21Rik | | RIKEN cDNA 2210023K21 gene | 381 | 5.8 | BI106821 |
| — | | *Mus musculus* transcribed sequences | 115 | 61.7 | AW111920 |
| — | | — | 172 | 12.6 | BB668084 |
| — | | — | 24 | 7.8 | AV247013 |
| — | | — | 38 | 29.1 | BE688410 |
| — | | *Mus musculus* transcribed sequence with weak similarity to protein ref: NP_081764.1 (*M. musculus*) RIKEN cDNA 5730493B19 [*Mus musculus*] | 21 | 6.6 | BB535821 |
| Rps3 | | ribosomal protein S3 | 138 | 2.0 | BG069767 |
| — | | *Mus musculus* adult male aorta and vein cDNA, RIKEN full-length enriched library, clone: A530023D22 product: unclassifiable, full insert sequence | 6 | 5.5 | BB214834 |
| — | | — | 55 | 6.8 | BB135602 |
| — | | *Mus musculus*, clone IMAGE: 1348774, mRNA | 11 | 28.8 | AA666504 |
| Cnn3 | | calponin 3, acidic | 943 | 4.2 | BB490338 |
| Hrasls3 | | HRAS like suppressor 3 | 372 | 21.7 | BB404920 |
| — | | *Mus musculus* similar to surface protein MCA-32 (LOC380732), mRNA | 17 | 7.5 | BE629676 |
| — | | Mouse non-productive mRNA for T-cell receptor gamma V5-J1-C1 | 6 | 23.2 | NM_011558 |
| G1p2 | | interferon, alpha-inducible protein | 112 | 16.7 | AK019325 |
| Pim1 | | proviral integration site 1 | 261 | 4.9 | AI323550 |
| Vcam1 | | vascular cell adhesion molecule 1 | 268 | 39.1 | BB250384 |
| 1200008O12Rik | | RIKEN cDNA 1200008O12 gene | 7 | 6.5 | AV126179 |
| — | | *Mus musculus* adult male cortex cDNA, RIKEN full-length enriched library, clone: B530033B21 product: unknown EST, full insert sequence | 336 | 10.9 | BB645745 |
| — | | *Mus musculus* transcribed sequences | 12 | 7.8 | BB552085 |
| G1p2 | | interferon, alpha-inducible protein | 17 | 10.3 | AK019325 |
| Nfkbia | | nuclear factor of kappa light chain gene enhancer in B-cells inhibitor, alpha | 1311 | 4.1 | BB096843 |

TABLE 3

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| BC027231 | 0610037H22Rik | cDNA sequence BC027231 | 1.0 | 0.4 | AU051504 |
| 0610037M15Rik | 0610037M15Rik | RIKEN cDNA 0610037M15 gene | 15.6 | 3.2 | BG916808 |
| 1110007F12Rik | 1110007F12Rik | RIKEN cDNA 1110007F12 gene | 3.0 | 0.6 | BC020080 |
| 1110013L07Rik | 1110013L07Rik | RIKEN cDNA 1110013L07 gene | 3.0 | 1.5 | BB765852 |
| 1110032F04Rik | 1110032F04Rik | RIKEN cDNA 1110032F04 gene | 1.3 | 0.4 | BE985708 |
| 1200015F23Rik | 1200015F23Rik | RIKEN cDNA 1200015F23 gene | 1.1 | 0.5 | AK004786 |
| 1200015F23Rik | 1200015F23Rik | RIKEN cDNA 1200015F23 gene | 1.8 | 0.6 | AK004786 |
| 1500004A08Rik | 1500004A08Rik | RIKEN cDNA 1500004A08 gene | 2.3 | 1.1 | BB030508 |
| 1700008D07Rik | 1700008D07Rik | RIKEN cDNA 1700008D07 gene | 0.9 | 0.4 | AK005758 |
| 1700012B18Rik | 1700012B18Rik | RIKEN cDNA 1700012B18 gene | 0.7 | 0.4 | BC022135 |
| — | 1700091G21Rik | *Mus musculus* 16 days neonate thymus cDNA, RIKEN full-length enriched library, clone: A130042K22 product: unknown EST, full insert sequence | 4.3 | 2.1 | BG075562 |
| 1810054D07Rik | 1810054D07Rik | RIKEN cDNA 1810054D07 gene | 5.4 | 1.9 | BB397062 |
| 1810054D07Rik | 1810054D07Rik | RIKEN cDNA 1810054D07 gene | 4.5 | 2.1 | BB259628 |
| 1810054D07Rik | 1810054D07Rik | RIKEN cDNA 1810054D07 gene | 5.0 | 2.2 | AK007856 |
| 1810062O14Rik | 1810062O14Rik | RIKEN cDNA 1810062O14 gene | 7.4 | 3.5 | AV060417 |
| — | 2010001M06Rik | *Mus musculus* adult male small intestine cDNA, RIKEN full-length enriched library, clone: 2010001M06 product: unknown EST, full insert sequence | 0.9 | 0.3 | BE200030 |
| 2210019E14Rik | 2210019E14Rik | RIKEN cDNA 2210019E14 gene | 1.5 | 0.8 | BB771921 |
| 2210421G13Rik | 2210421G13Rik | RIKEN cDNA 2210421G13 gene | 9.3 | 0.8 | AV081797 |
| Elk4 | 2310011G17Rik | ELK4, member of ETS oncogene family | 0.4 | 0.2 | AW046689 |
| 2310047C04Rik | 2310047C04Rik | RIKEN cDNA 2310047C04 gene | 1.2 | 0.3 | BM231657 |
| 2600014C01Rik | 2600014C01Rik | RIKEN cDNA 2600014C01 gene | 0.6 | 0.2 | BC027339 |
| 2610042L04Rik | 2610042L04Rik | RIKEN cDNA 2610042L04 gene | 5.0 | 0.9 | BM195235 |
| 2610042L04Rik | 2610042L04Rik | RIKEN cDNA 2610042L04 gene | 4.9 | 0.9 | BM195235 |
| 2610305D13Rik | 2610305D13Rik | RIKEN cDNA 2610305D13 gene | 0.7 | 0.1 | AK011986 |
| 2610528J11Rik | 2610528J11Rik | RIKEN cDNA 2610528J11 gene | 0.3 | 0.1 | AK012175 |
| 2700007P21Rik | 2700007P21Rik | RIKEN cDNA 2700007P21 gene | 1.1 | 0.4 | BB552785 |
| LOC217820 | 2700069A02Rik | hypothetical protein LOC217820 | 0.8 | 0.4 | BM198642 |
| 2810022L02Rik | 2810022L02Rik | RIKEN cDNA 2810022L02 gene | 0.9 | 0.3 | BC014764 |
| 2810429K17Rik | 2810429K17Rik | RIKEN cDNA 2810429K17 gene | 0.7 | 0.2 | AK013194 |
| 2900024C23Rik | 2900024C23Rik | RIKEN cDNA 2900024C23 gene | 1.3 | 0.5 | AK013580 |
| 4631426E05Rik | 4631426E05Rik | RIKEN cDNA 4631426E05 gene | 0.2 | 0.1 | BB739558 |
| — | 4921504P05Rik | — | 0.8 | 0.4 | AK014814 |
| 4930402H24Rik | 4930402H24Rik | RIKEN cDNA 4930402H24 gene | 1.1 | 0.4 | AK015050 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| 4930413O22Rik | 4930413O22Rik | RIKEN cDNA 4930413O22 gene | 1.1 | 0.5 | NM_026493 |
| — | 4930420O11Rik | *Mus musculus* 4 days neonate male adipose cDNA, RIKEN full-length enriched library, clone: B430318O09 product: CDNA FLJ33039 FIS, CLONE THYMU2000369, MODERATELY SIMILAR TO *MUS MUSCULUS* SYNTROPHIN-ASSOCIATED SERINE-THREONINE PROTEIN KINASE MRNA homolog [. . .] | 1.8 | 0.7 | BB328498 |
| 4930422I07Rik | 4930422I07Rik | RIKEN cDNA 4930422I07 gene | 0.9 | 0.3 | BG068263 |
| — | 4930488P18Rik | — | 1.4 | 0.2 | AV057155 |
| 4930562F07Rik | 4930523C07Rik | RIKEN cDNA 4930562F07 gene | 1.3 | 0.6 | AV032877 |
| 4930550C14Rik | 4930550C14Rik | RIKEN cDNA 4930550C14 gene | 1.9 | 0.6 | AK016083 |
| — | 4930556N09Rik | *Mus musculus* adult male testis cDNA, RIKEN full-length enriched library, clone: 4930556N09 product: unclassifiable, full insert sequence | 1.3 | 0.5 | AK016152 |
| 1810010E01Rik | 4930579G22Rik | RIKEN cDNA 1810010E01 gene | 1.0 | 0.4 | BI202437 |
| 4933409L06Rik | 4933409L06Rik | RIKEN cDNA 4933409L06 gene | 1.3 | 0.6 | BB645791 |
| — | 4933412E12Rik | *Mus musculus* 13 days embryo heart cDNA, RIKEN full-length enriched library, clone: D330011B05 product: unknown EST, full insert sequence | 2.2 | 0.5 | AK016788 |
| — | 4933412E12Rik | — | 1.5 | 0.4 | BB265147 |
| 4933415L06Rik | 4933415L06Rik | RIKEN cDNA 4933415L06 gene | 1.0 | 0.4 | AW554226 |
| — | 4933417N07Rik | *Mus musculus* adult male testis cDNA, RIKEN full-length enriched library, clone: 4933417N07 product: unknown EST, full insert sequence | 1.1 | 0.6 | AK016849 |
| — | 4933422E07Rik | *Mus musculus* adult male bone cDNA, RIKEN full-length enriched library, clone: 9830114D01 product: hypothetical protein, full insert sequence | 1.2 | 0.6 | BE630630 |
| 5133401N09Rik | 5133401N09Rik | RIKEN cDNA 5133401N09 gene | 1.9 | 0.7 | BC026742 |
| 5830405N20Rik | 5830405N20Rik | RIKEN cDNA 5830405N20 gene | 2.5 | 0.8 | BB202848 |
| 9630005B12Rik | 5830411O09Rik | RIKEN cDNA 9630005B12 gene | 2.4 | 0.8 | BB431654 |
| AI595338 | 5830443L24Rik | expressed sequence AI595338 | 75.0 | 0.4 | NM_029509 |
| 5830458K16Rik | 5830458K16Rik | RIKEN cDNA 5830458K16 gene | 9.1 | 1.6 | BC024872 |
| 5830484A20Rik | 5830484A20Rik | RIKEN cDNA 5830484A20 gene | 1.2 | 0.5 | BG072319 |
| 5830484A20Rik | 5830484A20Rik | RIKEN cDNA 5830484A20 gene | 4.8 | 2.0 | AW909306 |
| 9130002C22Rik | 9130002C22Rik | RIKEN cDNA 9130002C22 gene | 24.4 | 6.4 | BM243571 |
| 9130019I15Rik | 9130019I15Rik | RIKEN cDNA 9130019I15 gene | 46.3 | 13.7 | AK018636 |
| 9130022K13Rik | 9130022K13Rik | RIKEN cDNA 9130022K13 gene | 5.6 | 1.3 | AK018646 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| — | 9130430L19Rik | *Mus musculus* adult male cecum cDNA, RIKEN full-length enriched library, clone: 9130430L19 product: unknown EST, full insert sequence | 1.5 | 0.7 | AK020296 |
| 9230105E10Rik | 9230105E10Rik | RIKEN cDNA 9230105E10 gene | 3.6 | 0.6 | BB433710 |
| 9330177P20Rik | 9330177P20Rik | RIKEN cDNA 9330177P20 gene | 1.3 | 0.6 | BB375580 |
| — | 9530028C05 | *Mus musculus* adult male testis cDNA, RIKEN full-length enriched library, clone: 4921508F21 product: similar to HISTOCOMPATIBILITY 2, CLASS II ANTIGEN E BETA [*Mus musculus*], full insert sequence | 3.9 | 1.7 | BQ175154 |
| — | 9530028C05 | *Mus musculus* adult male testis cDNA, RIKEN full-length enriched library, clone: 4921508F21 product: similar to HISTOCOMPATIBILITY 2, CLASS II ANTIGEN E BETA [*Mus musculus*], full insert sequence | 4.6 | 2.0 | BQ175154 |
| A030012M09Rik | A030012M09Rik | RIKEN cDNA A030012M09 gene | 0.9 | 0.4 | BB549335 |
| A130015N09Rik | A130015N09Rik | RIKEN cDNA A130015N09 gene | 0.5 | 0.2 | AI647939 |
| — | A330042I21Rik | *Mus musculus* adult male spinal cord cDNA, RIKEN full-length enriched library, clone: A330042I21 product: unknown EST, full insert sequence | 3.6 | 0.4 | BB187486 |
| — | A330042I21Rik | *Mus musculus* adult male spinal cord cDNA, RIKEN full-length enriched library, clone: A330042I21 product: unknown EST, full insert sequence | 3.6 | 0.4 | AI645293 |
| A530088I07Rik | A530088I07Rik | RIKEN cDNA A530088I07 gene | 1.8 | 0.3 | BB637972 |
| A630024B12Rik | A630024B12Rik | RIKEN cDNA A630024B12 gene | 1.2 | 0.3 | BB240995 |
| A630077B13Rik | A630077B13Rik | RIKEN cDNA A630077B13 gene | 183.1 | 1.5 | BB239429 |
| AA960558 | AA960558 | expressed sequence AA960558 | 1.4 | 0.7 | BB277078 |
| Abca13 | Abca13 | ATP-binding cassette, sub-family A (ABC1), member 13 | 0.9 | 0.2 | BB503961 |
| Abcc2 | Abcc2 | ATP-binding cassette, sub-family C (CFTR/MRP), member 2 | 0.4 | 0.1 | NM_013806 |
| Acas2 | Acas2 | acetyl-Coenzyme A synthetase 2 (ADP forming) | 0.3 | 0.1 | NM_019811 |
| Adamts15 | Adamts15 | a disintegrin-like and metalloprotease (reprolysin type) with thrombospondin type 1 motif, 15 | 0.3 | 0.1 | AV228731 |
| Agtrap | Agtrap | angiotensin II, type I receptor-associated protein | 0.8 | 0.2 | NM_009642 |
| AI447904 | AI447904 | expressed sequence AI447904 | 70.3 | 9.7 | BM241008 |
| AI447904 | AI447904 | expressed sequence AI447904 | 26.2 | 7.6 | BM241008 |
| — | AI451557 | *Mus musculus* transcribed sequences | 24.1 | 3.1 | AV277444 |
| LOC226691 | AI607873 | interferon-activatable protein | 28.9 | 9.7 | AI607873 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| AI649392 | AI649392 | expressed sequence AI649392 | 0.9 | 0.4 | BB496366 |
| AI788959 | AI788959 | expressed sequence AI788959 | 0.7 | 0.1 | BC028826 |
| AI848100 | AI848100 | expressed sequence AI848100 | 0.9 | 0.4 | BB148987 |
| Aif1 | Aif1 | allograft inflammatory factor 1 | 36.5 | 9.1 | NM_019467 |
| 4930502N02Rik | Ak7 | RIKEN cDNA 4930502N02 gene | 2.5 | 0.4 | AV256298 |
| Akr1c20 | Akr1c20 | aldo-keto reductase family 1, member C20 | 8.0 | 2.0 | BC021607 |
| Akr1c21 | Akr1c21 | aldo-keto reductase family 1, member C21 | 0.5 | 0.1 | AW146041 |
| Aldh1a1 | Aldh1a1 | aldehyde dehydrogenase family 1, subfamily A1 | 0.5 | 0.1 | NM_013467 |
| Aldh1b1 | Aldh1b1 | aldehyde dehydrogenase 1 family, member B1 | 2.7 | 1.2 | BC020001 |
| Aldh8a1 | Aldh8a1 | aldehyde dehydrogenase 8 family, member A1 | 0.3 | 0.1 | BC013511 |
| 2810455B10Rik | Als2cr19 | RIKEN cDNA 2810455B10 gene | 1.0 | 0.4 | AK008055 |
| Amacr | Amacr | alpha-methylacyl-CoA racemase | 0.2 | 0.0 | NM_008537 |
| — | Ankib1 | *Mus musculus* 16 days embryo head cDNA, RIKEN full-length enriched library, clone: C130072C03 product: hypothetical protein, full insert sequence | 0.9 | 0.3 | BB373816 |
| Apg12l | Apg12l | autophagy 12-like (*S. cerevisiae*) | 0.9 | 0.4 | AK016474 |
| App | App | amyloid beta (A4) precursor protein | 2.3 | 0.7 | AV348729 |
| Arhgap15 | Arhgap15 | Rho GTPase activating protein 15 | 1.9 | 0.8 | AK018058 |
| Arhgap18 | Arhgap18 | Rho GTPase activating protein 18 | 0.4 | 0.2 | BE307291 |
| Arl2bp | Arl2bp | ADP-ribosylation factor-like 2 binding protein | 0.9 | 0.4 | NM_024191 |
| 1200015K23Rik | Armc8 | RIKEN cDNA 1200015K23 gene | 1.2 | 0.5 | BE995635 |
| Arts1 | Arts1 | type 1 tumor necrosis factor receptor shedding aminopeptidase regulator | 4.8 | 1.9 | NM_030711 |
| Arts1 | Arts1 | type 1 tumor necrosis factor receptor shedding aminopeptidase regulator | 4.1 | 1.2 | AV287655 |
| Asb13 | Asb13 | ankyrin repeat and SOCS box-containing protein 13 | 0.8 | 0.4 | AF403041 |
| Asb13 | Asb13 | ankyrin repeat and SOCS box-containing protein 13 | 0.9 | 0.4 | AF403041 |
| A330005H02Rik | Atp11c | RIKEN cDNA A330005H02 gene | 0.7 | 0.2 | BB184010 |
| Atp1a3 | Atp1a3 | ATPase, Na+/K+ transporting, alpha 3 polypeptide | 1.2 | 0.5 | BC020177 |
| Atp6v1e1 | Atp6v1e1 | ATPase, H+ transporting, V1 subunit E isoform 1 | 0.7 | 0.4 | C85064 |
| — | AW112010 | *Mus musculus* transcribed sequences | 32.5 | 4.1 | BE688358 |
| B230106I24Rik | B230106I24Rik | RIKEN cDNA B230106I24 gene | 0.8 | 0.3 | AV369935 |
| B230106I24Rik | B230106I24Rik | RIKEN cDNA B230106I24 gene | 1.0 | 0.5 | AV369935 |
| B2m | B2m | beta-2 microglobulin | 11.6 | 2.0 | AA170322 |
| B3galt5 | B3galt5 | UDP-Gal: betaGlcNAc beta 1,3-galactosyltransferase, polypeptide 5 | 0.4 | 0.2 | NM_033149 |
| Bak1 | Bak1 | BCL2-antagonist/killer 1 | 2.1 | 0.5 | AF402617 |
| BC005471 | BC005471 | cDNA sequence BC005471 | 1.5 | 0.7 | BC005471 |
| BC010462 | BC010462 | cDNA sequence BC010462 | 3.5 | 0.3 | BC010462 |
| BC013712 | BC013712 | cDNA sequence BC013712 | 12.3 | 4.1 | BB262491 |
| BC014805 | BC014805 | cDNA sequence BC014805 | 0.7 | 0.2 | AJ132857 |
| BC022687 | BC022687 | cDNA sequence BC022687 | 0.3 | 0.2 | BC022687 |
| BC023105 | BC023105 | cDNA sequence BC023105 | 70.3 | 0.7 | BC023105 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| BC026585 | BC026585 | cDNA sequence BC026585 | 0.2 | 0.1 | BC026585 |
| L259 | BC028528 | L259 | 4.1 | 1.8 | BC028528 |
| 2310015I10Rik | Brd4 | RIKEN cDNA 2310015I10 gene | 13.8 | 2.8 | BC008532 |
| C1r | C1r | complement component 1, r subcomponent | 9.4 | 3.8 | NM_023143 |
| C1s | C1s | complement component 1, s subcomponent | 12.7 | 2.8 | BC022123 |
| C2 | C2 | complement component 2 (within H-2S) | 3.5 | 0.9 | NM_013484 |
| — | C2 | — | 4.6 | 0.9 | AV290571 |
| — | C2 | — | 4.4 | 1.1 | AV227574 |
| C230080I20Rik | C230080I20Rik | RIKEN cDNA C230080I20 gene | 0.6 | 0.2 | BB795533 |
| C2ta | C2ta | class II transactivator | 13.2 | 1.6 | AF042158 |
| C2ta | C2ta | class II transactivator | 10.8 | 1.5 | AF042158 |
| C330005L02Rik | C330005L02Rik | RIKEN cDNA C330005L02 gene | 0.9 | 0.4 | BE134115 |
| C6.1A | C6.1A | c6.1a protein | 0.9 | 0.5 | AI462244 |
| — | C730040L01Rik | *Mus musculus* 10 days neonate cortex cDNA, RIKEN full-length enriched library, clone: A830089I03 product: hypothetical KRAB box containing protein, full insert sequence | 1.3 | 0.2 | BB391874 |
| Car5b | Car5b | carbonic anhydrase 5b, mitochondrial | 1.1 | 0.4 | NM_019513 |
| Card11 | Card11 | caspase recruitment domain family, member 11 | 4.6 | 2.0 | AV095659 |
| Casp1 | Casp1 | caspase 1 | 9.4 | 2.2 | BC008152 |
| Casp12 | Casp12 | caspase 12 | 3.6 | 1.7 | NM_009808 |
| Casp4 | Casp4 | caspase 4, apoptosis-related cysteine protease | 13.6 | 6.8 | NM_007609 |
| Cbs | Cbs | cystathionine beta-synthase | 0.6 | 0.1 | BC026595 |
| Cbx5 | Cbx5 | chromobox homolog 5 (*Drosophila* HP1a) | 0.9 | 0.4 | NM_007626 |
| Ccl19 | Ccl19 | chemokine (C—C motif) ligand 19 | 1.8 | 0.1 | NM_011888 |
| Ccl21a | Ccl21a | chemokine (C—C motif) ligand 21a (serine) | 0.9 | 0.1 | NM_011335 |
| — | Ccl27 | — | 0.7 | 0.1 | BQ174669 |
| Ccl27 | Ccl27 | chemokine (C—C motif) ligand 27 | 0.6 | 0.2 | NM_011336 |
| Ccl28 | Ccl28 | chemokine (C—C motif) ligand 28 | 0.9 | 0.0 | BG867337 |
| Ccl28 | Ccl28 | chemokine (C—C motif) ligand 28 | 1.1 | 0.3 | BE196980 |
| Ccl28 | Ccl28 | chemokine (C—C motif) ligand 28 | 0.9 | 0.1 | BG867337 |
| Ccl5 | Ccl5 | chemokine (C—C motif) ligand 5 | 140.5 | 9.6 | NM_013653 |
| Ccl8 | Ccl8 | chemokine (C—C motif) ligand 8 | 16.0 | 6.2 | NM_021443 |
| Ccr9 | Ccr9 | chemokine (C—C motif) receptor 9 | 2.1 | 0.6 | NM_009913 |
| Mox2 | Cd200 | antigen identified by monoclonal antibody MRC OX-2 | 2.2 | 1.0 | AF004023 |
| Cd86 | Cd86 | CD86 antigen | 10.4 | 4.5 | NM_019388 |
| — | Cdca3 | — | 1.7 | 0.7 | AV352659 |
| Cds1 | Cds1 | CDP-diacylglycerol synthase 1 | 2.0 | 0.9 | BI152841 |
| 4932437H03 | Cenpj | hypothetical protein 4932437H03 | 1.2 | 0.6 | BG068259 |
| Chpt1 | Chpt1 | choline phosphotransferase 1 | 0.5 | 0.2 | BC016251 |
| Clrf | Clec2h; Clrf | C-type lectin related f | 0.1 | 0.0 | AK017207 |
| Clic5 | Clic5 | chloride intracellular channel 5 | 0.7 | 0.1 | BB610000 |
| Clic5 | Clic5 | chloride intracellular channel 5 | 0.8 | 0.2 | AA210377 |
| Clic5 | Clic5 | chloride intracellular channel 5 | 1.1 | 0.2 | BB028501 |
| Clrf | Clrf | C-type lectin related f | 0.2 | 0.0 | AF350410 |
| Cml5 | Cml5 | camello-like 5 | 0.6 | 0.2 | BC024605 |
| Arvcf | Comt | armadillo repeat gene deleted in velo-cardio-facial syndrome | 0.8 | 0.2 | NM_007744 |
| Cpeb4 | Cpeb4 | cytoplasmic polyadenylation element binding protein 4 | 0.9 | 0.4 | NM_026252 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| — | Cpt2 | — | 1.1 | 0.5 | AV236319 |
| Csprs | Csprs | component of Sp100-rs | 1.4 | 0.1 | NM_033616 |
| Csprs | Csprs | component of Sp100-rs | 1.8 | 0.1 | BB148221 |
| 2210401K11Rik | Ctbs | RIKEN cDNA 2210401K11 gene | 0.6 | 0.3 | BC022594 |
| 2210401K11Rik | Ctbs | RIKEN cDNA 2210401K11 gene | 0.8 | 0.4 | BC022594 |
| Cxcl10 | Cxcl10 | chemokine (C—X—C motif) ligand 10 | 81.6 | 3.1 | NM_021274 |
| Cxcl11 | Cxcl11 | chemokine (C—X—C motif) ligand 11 | 99.2 | 3.6 | NM_019494 |
| Cxcl9 | Cxcl9 | chemokine (C—X—C motif) ligand 9 | 176.4 | 0.2 | NM_008599 |
| Cxcr3 | Cxcr3 | chemokine (C—X—C motif) receptor 3 | 10.2 | 2.6 | NM_009910 |
| Cybb | Cybb | cytochrome b-245, beta polypeptide | 14.2 | 5.9 | NM_007807 |
| Cyp4v3 | Cyp4v3 | cytochrome P450, family 4, subfamily v, polypeptide 3 | 3.9 | 1.8 | NM_133969 |
| — | D030011O10Rik | Mus musculus transcribed sequence with weak similarity to protein pir: T17242 (H. sapiens) T17242 hypothetical protein DKFZp586B1417.1 - human (fragment) | 0.6 | 0.3 | BE994639 |
| D11Ertd759e | D11Ertd759e | DNA segment, Chr 11, ERATO Doi 759, expressed | 4.9 | 1.8 | AW556558 |
| D11Lgp2e | D11Lgp2e | DNA segment, Chr 11, Lothar Hennighausen 2, expressed | 6.1 | 0.6 | NM_030150 |
| D11Lgp2e | D11Lgp2e | DNA segment, Chr 11 Lothar Hennighausen 2, expressed | 10.0 | 2.3 | AF316999 |
| — | D12Ertd551e | Mus musculus adult male tongue cDNA, RIKEN full-length enriched library, clone: 2310058N22 product: unknown EST, full insert sequence | 5.5 | 2.3 | BQ175646 |
| D12Ertd647e | D12Ertd647e | DNA segment, Chr 12, ERATO Doi 647, expressed | 5.8 | 1.8 | AW554405 |
| D12Ertd647e | D12Ertd647e | DNA segment, Chr 12, ERATO Doi 647, expressed | 4.1 | 1.4 | BI655075 |
| — | D12Ertd771e | Mus musculus 13 days embryo male testis cDNA, RIKEN full-length enriched library, clone: 6030490B17 product: unknown EST, full insert sequence | 1.3 | 0.6 | BB392503 |
| D5Ertd135e | D5Ertd135e | DNA segment, Chr 5, ERATO Doi 135, expressed | 0.5 | 0.3 | BB401993 |
| D7Bwg0421e | D7Bwg0421e | DNA segment, Chr 7, Brigham & Women's Genetics 0421 expressed | 8.1 | 2.7 | BB667693 |
| 2210404A22Rik | D8Ertd594e | RIKEN cDNA 2210404A22 gene | 0.9 | 0.3 | AK008821 |
| Ddx47 | Ddx47 | DEAD (Asp-Glu-Ala-Asp) box polypeptide 47 | 0.4 | 0.1 | BB305306 |
| Defcr9 | Defcr9 | defensin related cryptdin 9 | 1.4 | 0.5 | U03065 |
| Dnase1l3 | Dnase1l3 | deoxyribonuclease 1-like 3 | 6.4 | 0.4 | BC012671 |
| Dnase1l3 | Dnase1l3 | deoxyribonuclease 1-like 3 | 8.8 | 0.9 | BC012671 |
| D14Wsu89e | Dock9 | DNA segment, Chr 14, Wayne State University 89, expressed | 0.6 | 0.2 | BB795072 |
| Dsg2 | Dsg2 | desmoglein 2 | 1.9 | 0.9 | C79957 |
| Dsg2 | Dsg2 | desmoglein 2 | 1.3 | 0.6 | AB072269 |
| — | Dtx3l | Mus musculus transcribed sequence with weak similarity to protein ref: NP_081764.1 (M. musculus) RIKEN cDNA 5730493B19 [Mus musculus] | 9.1 | 2.1 | AV327407 |
| E130309F12Rik | E130309F12Rik | RIKEN cDNA E130309F12 gene | 0.7 | 0.0 | BB523550 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| E430019B13Rik | E430019B13Rik | RIKEN cDNA E430019B13 gene | 2.2 | 0.9 | BE630983 |
| 1300018P11Rik | Eif4e3 | RIKEN cDNA 1300018P11 gene | 5.1 | 2.4 | BC027014 |
| 2810013J18Rik | Eme2 | RIKEN cDNA 2810013J18 gene | 1.0 | 0.4 | AK012738 |
| Entpd5 | Entpd5 | ectonucleoside triphosphate diphosphohydrolase 5 | 0.4 | 0.2 | NM_007647 |
| Entpd5 | Entpd5 | ectonucleoside triphosphate diphosphohydrolase 5 | 0.4 | 0.2 | NM_007647 |
| Entpd5 | Entpd5 | ectonucleoside triphosphate diphosphohydrolase 5 | 0.4 | 0.2 | AF136571 |
| Entpd5 | Entpd5 | ectonucleoside triphosphate diphosphohydrolase 5 | 0.5 | 0.2 | NM_007647 |
| 2310046K10Rik | Epsti1 | RIKEN cDNA 2310046K10 gene | 13.4 | 3.8 | AK017174 |
| Etv1 | Etv1 | ets variant gene 1 | 0.4 | 0.1 | NM_007960 |
| 2610104C07Rik | Exosc1 | RIKEN cDNA 2610104C07 gene | 1.2 | 0.6 | BC024423 |
| Fabp7 | Fabp7 | fatty acid binding protein 7, brain | 5.2 | 0.3 | NM_021272 |
| 1110064L07Rik | Fbxw17 | RIKEN cDNA 1110064L07 gene | 4.8 | 2.3 | AV016303 |
| Fcrl3 | Fcrl3 | Fc receptor-like 3 | 20.5 | 5.4 | BC027310 |
| Fgl2 | Fgl2 | fibrinogen-like protein 2 | 28.1 | 3.9 | BF136544 |
| Fgl2 | Fgl2 | fibrinogen-like protein 2 | 46.7 | 5.6 | BF136544 |
| 1110008K06Rik | Fln29 | RIKEN cDNA 1110008K06 gene | 4.0 | 1.6 | AK003586 |
| Fmo4 | Fmo4 | flavin containing monooxygenase 4 | 0.4 | 0.0 | AF461145 |
| Fmo5 | Fmo5 | flavin containing monooxygenase 5 | 0.3 | 0.1 | NM_010232 |
| Fmr1 | Fmr1 | fragile X mental retardation syndrome 1 homolog | 1.2 | 0.6 | AF461114 |
| 6030440G05Rik | Frmd4b | RIKEN cDNA 6030440G05 gene | 0.7 | 0.3 | BM119551 |
| — | Gabra2 | *Mus musculus* transcribed sequences | 0.9 | 0.4 | BB433285 |
| A530057M15Rik | Galm | RIKEN cDNA A530057M15 gene | 0.6 | 0.3 | AV307219 |
| Gbp2 | Gbp2 | guanylate nucleotide binding protein 2 | 53.4 | 2.3 | BE197524 |
| Gbp2 | Gbp2 | guanylate nucleotide binding protein 2 | 100.2 | 2.9 | NM_010260 |
| Gbp3 | Gbp4 | guanylate nucleotide binding protein 3 | 42.9 | 7.5 | NM_018734 |
| Gca | Gca | grancalcin | 1.2 | 0.5 | BC021450 |
| Gca | Gca | grancalcin | 1.5 | 0.4 | BC021450 |
| Ghr | Ghr | growth hormone receptor | 0.5 | 0.2 | M33324 |
| Ian1 | Gimap4 | immune associated nucleotide 1 | 3.0 | 1.1 | BC005577 |
| Ian1 | Gimap4 | immune associated nucleotide 1 | 2.4 | 0.9 | BC005577 |
| Ian3 | Gimap7 | immune associated nucleotide 3 | 14.1 | 5.4 | BC026200 |
| Glipr1 | Glipr1 | GLI pathogenesis-related 1 (glioma) | 14.8 | 7.4 | BC025083 |
| Gnb4 | Gnb4 | guanine nucleotide binding protein, beta 4 | 2.1 | 1.0 | BI713933 |
| Gpr1 | Gpr1 | G protein-coupled receptor 1 | 1.2 | 0.5 | AW541072 |
| Gpr18 | Gpr18 | G protein-coupled receptor 18 | 9.9 | 3.4 | BG145550 |
| 1810036L03Rik | Gsdmdc1 | RIKEN cDNA 1810036L03 gene | 6.5 | 2.5 | AK007710 |
| Gstt2 | Gstt2 | glutathione S-transferase, theta 2 | 0.7 | 0.3 | BC012707 |
| Gzmk | Gzmk | granzyme K | 14.1 | 3.9 | AB032200 |
| H28 | H28 | histocompatibility 28 | 1.6 | 0.5 | NM_031367 |
| H28 | H28 | histocompatibility 28 | 6.8 | 1.1 | BC024930 |
| H28 | H28 | histocompatibility 28 | 8.9 | 1.1 | NM_031367 |
| — | H2-Aa | — | 46.1 | 10.5 | AV086906 |
| H2-Ab1 | H2-Ab1 | histocompatibility 2, class II antigen A, beta 1 | 13.2 | 4.0 | NM_010379 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| H2-BI | H2-BI | histocompatibility 2, blastocyst | 1.6 | 0.5 | NM_008199 |
| H2-D1 | H2-D1 | histocompatibility 2, D region locus 1 | 6.2 | 0.0 | NM_010380 |
| H2-DMb1 | H2-DMb1 | histocompatibility 2, class II, locus Mb1 | 19.8 | 3.8 | NM_010387 |
| H2-DMb1 | H2-DMb1 | histocompatibility 2, class II, locus Mb1 | 38.0 | 4.3 | NM_010388 |
| H2-DMb1 | H2-DMb1 | histocompatibility 2, class II, locus Mb1 | 45.2 | 4.8 | BB734586 |
| H2-K | H2-K1 | histocompatibility 2, K region | 22.5 | 7.1 | L23495 |
| — | H2-K1 | MHC I = H-2Kd homolog {alternatively spliced, deletion of exon 3} [mice, DBA/2, L1210 lymphoma, mRNA Mutant, 855 nt] | 45.5 | 10.8 | S70184 |
| H2-M3 | H2-M3 | histocompatibility 2, M region locus 3 | 4.8 | 2.0 | NM_013819 |
| H2-Oa | H2-Oa | histocompatibility 2, O region alpha locus | 6.1 | 1.4 | NM_008206 |
| H2-Ob | H2-Ob | histocompatibility 2, O region beta locus | 4.4 | 1.1 | BG144448 |
| H2-Q1 | H2-Q1 | histocompatibility 2, Q region locus 1 | 22.6 | 3.1 | BC010602 |
| H2-Q7 | H2-Q7 | histocompatibility 2, Q region locus 7 | 78.5 | 24.8 | M29881 |
| H2-T10 | H2-T10 | histocompatibility 2, T region locus 10 | 4.3 | 0.7 | NM_010395 |
| H2-T23 | H2-T23 | histocompatibility 2, T region locus 23 | 8.0 | 0.9 | NM_010398 |
| — | H2-T23 | Mus musculus 2 days neonate thymus thymic cells cDNA, RIKEN full-length enriched library, clone: C920026N01 product: weakly similar to H-2 CLASS I HISTOCOMPATIBILITY ANTIGEN, D-37 ALPHA CHAIN PRECURSOR [Mus musculus], full insert sequence | 6.6 | 1.3 | NM_010398 |
| H2-T24 | H2-T24 | histocompatibility 2, T region locus 24 | 3.1 | 0.6 | L22338 |
| Hadhsc | Hadhsc | L-3-hydroxyacyl-Coenzyme A dehydrogenase, short chain | 0.4 | 0.1 | BB114220 |
| Hdc | Hdc | histidine decarboxylase | 0.9 | 0.1 | BG072171 |
| Hdc | Hdc | histidine decarboxylase | 0.9 | 0.1 | AF109137 |
| Helic1 | Helic1 | helicase, ATP binding 1 | 1.4 | 0.6 | BB501662 |
| 2510038N07Rik | Herc5 | RIKEN cDNA 2510038N07 gene | 20.4 | 1.2 | AI639807 |
| 2510038N07Rik | Herc5 | RIKEN cDNA 2510038N07 gene | 18.0 | 2.0 | AK015214 |
| 2510038N07Rik | Herc5 | RIKEN cDNA 2510038N07 gene | 12.8 | 1.0 | AI639807 |
| 2510038N07Rik | Herc5 | RIKEN cDNA 2510038N07 gene | 25.4 | 1.9 | AW208668 |
| — | Hk3 | — | 14.9 | 4.0 | BB324660 |
| — | Hnrpm | Mus musculus transcribed sequences | 0.9 | 0.4 | AW493461 |
| Hpse | Hpse | heparanase | 22.8 | 11.4 | BG094050 |
| Hrasls3 | Hrasls3 | HRAS like suppressor 3 | 16.5 | 0.8 | BC024581 |
| Hsd11b1 | Hsd11b1 | hydroxysteroid 11-beta dehydrogenase 1 | 0.3 | 0.2 | NM_008288 |
| Hsf2bp | Hsf2bp | heat shock transcription factor 2 binding protein | 0.6 | 0.2 | AK016553 |
| Icsbp1 | Icsbp1 | interferon consensus sequence binding protein 1 | 9.9 | 2.8 | BG069095 |
| Icsbp1 | Icsbp1 | interferon consensus sequence binding protein 1 | 10.0 | 3.7 | BG069095 |
| Idh1 | Idh1 | isocitrate dehydrogenase 1 (NADP+), soluble | 0.8 | 0.3 | AI788952 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| Ifi1 | Ifi1 | interferon inducible protein 1 | 15.4 | 1.1 | NM_008326 |
| Ifi202b | Ifi202b | interferon activated gene 202B | 42.5 | 5.8 | AV229143 |
| Ifi202b | Ifi202b | interferon activated gene 202B | 46.5 | 3.2 | NM_011940 |
| Ifi203 | Ifi203 | interferon activated gene 203 | 17.8 | 8.8 | NM_008328 |
| Ifi203 | Ifi203 | interferon activated gene 203 | 9.1 | 2.7 | BC008167 |
| Ifi16 | Ifi204 | interferon, gamma-inducible protein 16 | 24.8 | 5.5 | NM_008329 |
| Ifi205 | Ifi205 | interferon activated gene 205 | 151.7 | 40.3 | M74124 |
| Ifi205 | Ifi205 | interferon activated gene 205 | 102.7 | 10.1 | AI481797 |
| Ifi205 | Ifi205 | interferon activated gene 205 | 79.7 | 13.6 | AI481797 |
| 2010008K16Rik | Ifi35 | RIKEN cDNA 2010008K16 gene | 4.5 | 1.7 | BC008158 |
| 2010008K16Rik | Ifi35 | RIKEN cDNA 2010008K16 gene | 6.0 | 2.3 | AW986054 |
| A430056A10Rik | Ifi44 | RIKEN cDNA A430056A10 gene | 5.0 | 0.7 | BB329808 |
| 9130009C22Rik | Ifih1 | RIKEN cDNA 9130009C22 gene | 5.4 | 1.7 | AY075132 |
| Ifit1 | Ifit1 | interferon-induced protein with tetratricopeptide repeats 1 | 18.5 | 3.5 | NM_008331 |
| Ifit2 | Ifit2 | interferon-induced protein with tetratricopeptide repeats 2 | 33.8 | 2.0 | NM_008332 |
| Ifit3 | Ifit3 | interferon-induced protein with tetratricopeptide repeats 3 | 6.3 | 0.6 | NM_010501 |
| Ifng | Ifng | interferon gamma | 30.3 | 2.5 | K00083 |
| Igf1 | Igf1 | insulin-like growth factor 1 | 2.7 | 1.1 | NM_010512 |
| Igf1 | Igf1 | insulin-like growth factor 1 | 2.0 | 0.9 | BG075165 |
| Igh-6 | Igh-6 | immunoglobulin heavy chain 6 (heavy chain of IgM) | 6.0 | 1.9 | AI326478 |
| Igk-V1 | Igk-V1 | immunoglobulin kappa chain variable 1 (V1) | 1.4 | 0.2 | U29768 |
| Igk-V8 | Igk-V8 | immunoglobulin kappa chain variable 8 (V8) | 1.5 | 0.2 | BI107286 |
| Igsf7 | Igsf7 | immunoglobulin superfamily, member 7 | 7.0 | 3.4 | AF251705 |
| Igtp | Igtp | interferon gamma induced GTPase | 25.9 | 0.8 | NM_018738 |
| — | Igtp | *Mus musculus* 13 days embryo lung cDNA, RIKEN full-length enriched library, clone: D430030N05 product: unknown EST, full insert sequence | 14.3 | 1.0 | BB485297 |
| AI481100 | Igtp | expressed sequence AI481100 | 30.9 | 1.2 | NM_019440 |
| AW111922 | Iigp1 | expressed sequence AW111922 | 36.6 | 0.6 | BM239828 |
| AW111922 | Iigp1 | expressed sequence AW111922 | 53.7 | 0.7 | BM239828 |
| Il12b | Il12b | interleukin 12b | 1.7 | 0.3 | AF128214 |
| Il12rb1 | Il12rb1 | interleukin 12 receptor, beta 1 | 5.5 | 2.6 | NM_008353 |
| Il15 | Il15 | interleukin 15 | 1.0 | 0.2 | NM_008357 |
| Il18 | Il18 | interleukin 18 | 2.1 | 0.9 | NM_008360 |
| Il18bp | Il18bp | interleukin 18 binding protein | 33.6 | 1.5 | AF110803 |
| Temt | Inmt | thioether S-methyltransferase | 0.2 | 0.0 | NM_009349 |
| B430217B02Rik | Irf1 | RIKEN cDNA B430217B02 gene | 15.7 | 2.2 | NM_008390 |
| Irf7 | Irf7 | interferon regulatory factor 7 | 9.8 | 2.9 | NM_016850 |
| Irg1 | Irg1 | immunoresponsive gene 1 | 80.3 | 31.1 | L38281 |
| Itga4 | Itga4 | integrin alpha 4 | 8.5 | 3.3 | NM_010576 |
| Itm2a | Itm2a | integral membrane protein 2A | 1.1 | 0.5 | BI966443 |
| Itm2a | Itm2a | integral membrane protein 2A | 1.0 | 0.4 | BI966443 |
| Itpka | Itpka | inositol 1,4,5-trisphosphate 3-kinase A | 1.7 | 0.9 | BC027291 |
| Klra2 | Klra2 | killer cell lectin-like receptor, subfamily A, member 2 | 14.3 | 2.5 | NM_008462 |
| Klra7 | Klra7 | killer cell lectin-like receptor, subfamily A, member 7 | 7.9 | 1.8 | U10095 |
| Klra8 | Klra8 | killer cell lectin-like receptor, subfamily A, member 8 | 5.5 | 0.9 | U12889 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| Klra3 | Klra9 | killer cell lectin-like receptor, subfamily A, member 3 | 6.5 | 1.9 | U49865 |
| Klrb1d | Klrb1d | killer cell lectin-like receptor subfamily B member 1D | 4.6 | 1.3 | AF342896 |
| Klrb1d | Klrb1d | killer cell lectin-like receptor subfamily B member 1D | 9.8 | 3.3 | NM_008526 |
| Klrc1 | Klrc1 | killer cell lectin-like receptor subfamily C, member 1 | 19.3 | 7.6 | AF106009 |
| Klrk1 | Klrk1 | killer cell lectin-like receptor subfamily K, member 1 | 21.5 | 3.5 | AF039026 |
| D7Bwg0421e | Lair1 | DNA segment, Chr 7, Brigham & Women's Genetics 0421 expressed | 11.9 | 4.0 | AK017222 |
| — | Leprel1 | *Mus musculus* 12 days embryo embryonic body between diaphragm region and neck cDNA, RIKEN full-length enriched library, clone: 9430093N11 product: unknown EST, full insert sequence | 0.9 | 0.4 | BB105009 |
| Letm1 | Letm1 | leucine zipper-EF-hand containing transmembrane protein 1 | 0.6 | 0.3 | BG060855 |
| Lgals8 | Lgals8 | lectin, galactose binding, soluble 8 | 1.1 | 0.5 | AI987967 |
| — | Lmtk2 | *Mus musculus* transcribed sequence with strong similarity to protein sp: P00722 (*E. coli*) BGAL_ECOLI Beta-galactosidase (Lactase) | 1.2 | 0.3 | BB449235 |
| LOC207685 | LOC207685 | hypothetical protein LOC207685 | 2.7 | 0.5 | AK008551 |
| LOC209387 | LOC209387 | tripartite motif protein 30-like | 20.2 | 7.5 | BM241342 |
| LOC223672 | LOC223672 | hypothetical protein LOC223672 | 25.0 | 0.7 | BC020489 |
| Ly6c | Ly6c | lymphocyte antigen 6 complex, locus C | 2.8 | 1.0 | NM_010741 |
| Ly6i | Ly6i | lymphocyte antigen 6 complex, locus I | 15.4 | 0.4 | AF232024 |
| Ly86 | Ly86 | lymphocyte antigen 86 | 24.1 | 11.6 | NM_010745 |
| 2410018D16Rik | Mat2b | RIKEN cDNA 2410018D16 gene | 1.0 | 0.5 | NM_134017 |
| — | MDABG2-4 | *Mus musculus* nucleosome-reactive monoclonal antibody PR1-3, Ig light chain variable region mRNA, partial cds. | 2.0 | 0.6 | AB007986 |
| Mgat3 | Mgat3 | mannoside acetylglucosaminyltransferase 3 | 0.2 | 0.1 | NM_010795 |
| MGC25972 | MGC25972 | similar to cytochrome P450, 4a10 | 0.4 | 0.1 | BC025936 |
| Mia2 | Mia2 | melanoma inhibitory activity 2 | 0.9 | 0.3 | AF390177 |
| — | Mpa2l | *Mus musculus* transcribed sequences | 72.1 | 1.7 | BG092512 |
| — | Mpa2l | *Mus musculus* transcribed sequence with weak similarity to protein sp: P32456 (*H. sapiens*) GBP2_HUMAN Interferon-induced guanylate-binding protein 2 (Guanine nucleotide-binding protein 2) | 118.4 | 1.5 | BM241485 |
| Mpeg1 | Mpeg1 | macrophage expressed gene 1 | 22.7 | 6.9 | L20315 |
| Ms4a1 | Ms4a1 | membrane-spanning 4-domains, subfamily A, member 1 | 4.0 | 2.0 | BB236617 |
| Ms4a4b | Ms4a4b | membrane-spanning 4-domains, subfamily A, member 4B | 56.0 | 11.5 | BB199001 |
| Ms4a4d | Ms4a4d | membrane-spanning 4-domains, subfamily A, member 4D | 12.6 | 0.7 | NM_025658 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| Ms4a6b | Ms4a6b | membrane-spanning 4-domains, subfamily A, member 6B | 45.7 | 15.7 | NM_027209 |
| Ms4a6c | Ms4a6c | membrane-spanning 4-domains, subfamily A, member 6C | 14.8 | 5.8 | AF237910 |
| Mtac2d1 | Mtac2d1 | membrane targeting (tandem) C2 domain containing 1 | 0.4 | 0.1 | BB548141 |
| Mtap7 | Mtap7 | microtubule-associated protein 7 | 1.2 | 0.6 | AK006385 |
| Mx1 | Mx1 | myxovirus (influenza virus) resistance 1 | 6.9 | 1.8 | M21039 |
| — | Net1 | *Mus musculus* transcribed sequences | 4.1 | 1.2 | AV247312 |
| Ngfr | Ngfr | nerve growth factor receptor (TNFR superfamily, member 16) | 8.3 | 3.1 | BB151515 |
| Nmi | Nmi | N-myc (and STAT) interactor | 6.7 | 1.4 | BC002019 |
| Nt5c2 | Nt5c2 | 5'-nucleotidase, cytosolic II | 1.1 | 0.4 | BI202534 |
| Nt5c2 | Nt5c2; GMP; NT5B; PNT5; cN-II; 2010002I23Rik | 5'-nucleotidase, cytosolic II | 1.6 | 0.7 | BC006028 |
| Oas1g | Oas1a | 2'-5' oligoadenylate synthetase 1G | 6.9 | 2.4 | BC018470 |
| Oasl2 | Oasl2 | 2'-5' oligoadenylate synthetase-like 2 | 17.4 | 1.9 | BQ033138 |
| Og9x | Og9x | OG9 homeobox gene | 0.7 | 0.4 | BB705267 |
| BC047207 | Olfml1 | cDNA sequence BC047207 | 0.7 | 0.3 | BB055163 |
| Olfr56 | Olfr56 | olfactory receptor 56 | 39.5 | 2.3 | NM_008330 |
| A130090K04Rik | Oprm1 | RIKEN cDNA A130090K04 gene | 1.3 | 0.4 | BB703415 |
| A130090K04Rik | Oprm1 | RIKEN cDNA A130090K04 gene | 3.1 | 1.1 | BQ176089 |
| Osbpl6 | Osbpl6 | oxysterol binding protein-like 6 | 0.5 | 0.2 | BG070848 |
| Paip1 | Paip1 | polyadenylate binding protein-interacting protein 1 | 0.8 | 0.1 | BB381990 |
| Paip1 | Paip1 | polyadenylate binding protein-interacting protein 1 | 0.9 | 0.0 | BC019726 |
| 5330431N24Rik | Parp11 | RIKEN cDNA 5330431N24 gene | 3.1 | 1.3 | BB026163 |
| BC021340 | Parp14 | cDNA sequence BC021340 | 16.1 | 3.0 | BC021340 |
| Adprtl3 | Parp3 | ADP-ribosyltransferase (NAD+; poly (ADP-ribose) polymerase)-like 3 | 2.6 | 0.8 | BC014870 |
| Adprtl3 | Parp3 | ADP-ribosyltransferase (NAD+; poly (ADP-ribose) polymerase)-like 3 | 2.1 | 1.0 | AW990611 |
| BC003281 | Parp9 | cDNA sequence BC003281 | 12.0 | 2.9 | NM_030253 |
| 1110035O14Rik | Pbef1 | RIKEN cDNA 1110035O14 gene | 2.4 | 1.0 | AW989410 |
| Pclo | Pclo | piccolo (presynaptic cytomatrix protein) | 0.6 | 0.1 | AW493746 |
| Pdcd1lg1 | Pdcd1lg1 | programmed cell death 1 ligand 1 | 45.1 | 4.7 | NM_021893 |
| Pde9a | Pde9a | phosphodiesterase 9A | 0.6 | 0.3 | NM_008804 |
| Pdzk1 | Pdzk1; Pdzd1; mPDZK1; D3Ertd537e; 1700023D20Rik; 2610507N21Rik; 4921513F16Rik | PDZ domain containing 1 | 0.4 | 0.2 | AK006269 |
| Peli1 | Peli1 | pellino 1 | 2.1 | 1.0 | BC016515 |
| 4933417L10Rik | Phf11 | RIKEN cDNA 4933417L10 gene | 4.8 | 1.1 | AV280841 |
| Phip | Phip | pleckstrin homology domain interacting protein | 1.3 | 0.5 | BI737352 |
| Pigr | Pigr | polymeric immunoglobulin receptor | 4.4 | 1.7 | AV027632 |
| Pigr | Pigr | polymeric immunoglobulin receptor | 3.0 | 1.2 | NM_011082 |
| — | Pink1 | — | 0.4 | 0.2 | AV371921 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| — | Plec1 | *Mus musculus* similar to Plec1 protein (LOC381010), mRNA | 1.4 | 0.5 | BI525140 |
| Pnp | Pnp | purine-nucleoside phosphorylase | 2.2 | 0.8 | AK008143 |
| Mt1a | Polr2k | metallothionein-I activator | 0.9 | 0.4 | AA175187 |
| Ppargc1 | Ppargc1a | peroxisome proliferative activated receptor, gamma, coactivator 1 | 0.5 | 0.2 | BB745167 |
| — | Ppt1 | *Mus musculus* 12 days embryo spinal ganglion cDNA, RIKEN full-length enriched library, clone: D130070K05 product: unknown EST, full insert sequence | 3.0 | 0.6 | BB461203 |
| Ppt1 | Ppt1 | palmitoyl-protein thioesterase 1 | 1.0 | 0.5 | AF326558 |
| Prkr | Prkr | protein kinase, interferon-inducible double stranded RNA dependent | 5.0 | 2.0 | BE911144 |
| — | Prok1 | *Mus musculus* 3 days neonate thymus cDNA, RIKEN full-length enriched library, clone: A630076J17 product: unclassifiable, full insert sequence | 0.6 | 0.3 | BE651535 |
| Psmb10 | Psmb10 | proteasome (prosome, macropain) subunit, beta type 10 | 14.7 | 3.6 | NM_013640 |
| Psmb8 | Psmb8 | proteosome (prosome, macropain) subunit, beta type 8 (large multifunctional protease 7) | 27.5 | 4.1 | NM_010724 |
| Psmb8 | Psmb8 | proteosome (prosome, macropain) subunit, beta type 8 (large multifunctional protease 7) | 24.0 | 3.4 | AV068122 |
| Psmb9 | Psmb9 | proteosome (prosome, macropain) subunit, beta type 9 (large multifunctional protease 2) | 30.2 | 2.1 | NM_013585 |
| Tap1 | Psmb9 | transporter 1, ATP-binding cassette, sub-family B (MDR/TAP) | 29.5 | 3.9 | AW048052 |
| Psme1 | Psme1 | proteasome (prosome, macropain) 28 subunit, alpha | 3.1 | 1.5 | NM_011189 |
| Psme2 | Psme2 | proteasome (prosome, macropain) 28 subunit, beta | 5.3 | 1.9 | NM_011190 |
| Psme4 | Psme4 | proteasome (prosome, macropain) activator subunit 4 | 0.8 | 0.3 | BG075584 |
| — | Ptbp2 | *Mus musculus* 16 days neonate thymus cDNA, RIKEN full-length enriched library, clone: A130023P20 product: unclassifiable, full insert sequence | 1.3 | 0.6 | BB155176 |
| Ptprcap | Ptprcap | protein tyrosine phosphatase, receptor type, C polypeptide-associated protein | 7.5 | 3.5 | NM_016933 |
| — | Ptprk | *Mus musculus* transcribed sequences | 1.0 | 0.4 | BG802688 |
| 2410027J01Rik | Qprt | RIKEN cDNA 2410027J01 gene | 0.6 | 0.1 | AI195046 |
| — | Rab11fip3 | *Mus musculus* 0 day neonate kidney cDNA, RIKEN full-length enriched library, clone: D630036H09 product: similar to EFERIN [*Homo sapiens*], full insert sequence | 0.4 | 0.2 | BQ266518 |
| Rab17 | Rab17 | RAB17, member RAS oncogene family | 0.6 | 0.3 | NM_008998 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| Rab19 | Rab19 | RAB19, member RAS oncogene family | 2.8 | 0.9 | BM241400 |
| Rbl1 | Rbl1 | retinoblastoma-like 1 (p107) | 5.8 | 2.2 | U27177 |
| — | Rkhd2 | *Mus musculus* 16 days embryo head cDNA, RIKEN full-length enriched library, clone: C130049H14 product: unknown EST, full insert sequence | 0.8 | 0.2 | BB369687 |
| 4930474F22Rik | Rnase10 | RIKEN cDNA 4930474F22 gene | 1.2 | 0.3 | AK015573 |
| Rnaset2 | Rnaset2; RNASE6PL; 0610007O07Rik; 4833423A10Rik; 4930532K22Rik | ribonuclease T2 | 2.2 | 0.6 | AK015947 |
| Samhd1 | Samhd1 | SAM domain and HD domain, 1 | 16.3 | 5.3 | AV376100 |
| Samhd1 | Samhd1 | SAM domain and HD domain, 1 | 11.4 | 4.1 | BF148012 |
| Samhd1 | Samhd1 | SAM domain and HD domain, 1 | 11.3 | 2.7 | NM_018851 |
| D11Moh48 | Scrn2 | DNA segment, Chr 11, KL Mohlke 48 | 0.3 | 0.1 | BC021346 |
| D11Moh48 | Scrn2 | DNA segment, Chr 11, KL Mohlke 48 | 0.3 | 0.1 | BB735480 |
| Sec8 | Sec8l1 | SEC8 (*S. cerevisiae*) | 0.9 | 0.4 | AK010695 |
| Sectm1 | Sectm1 | secreted and transmembrane 1 | 3.0 | 0.0 | AI481997 |
| Sell | Sell | selectin, lymphocyte | 14.0 | 6.5 | M36005 |
| Sell | Sell | selectin, lymphocyte | 9.7 | 4.7 | M36005 |
| Serpina10 | Serpina10 | serine (or cysteine) proteinase inhibitor, clade A (alpha-1 antiproteinase, antitrypsin), member 10 | 44.0 | 17.5 | BC018416 |
| Sfrp1 | Sfrp1 | secreted frizzled-related sequence protein 1 | 0.5 | 0.2 | BI658627 |
| Sfrp1 | Sfrp1 | secreted frizzled-related sequence protein 1 | 0.5 | 0.2 | BI658627 |
| Sgcb | Sgcb | sarcoglycan, beta (dystrophin-associated glycoprotein) | 0.9 | 0.3 | AK014381 |
| Slamf7 | Slamf7 | SLAM family member 7 | 5.4 | 1.1 | AK016183 |
| Slamf8 | Slamf8 | SLAM family member 8 | 65.9 | 9.5 | BC024587 |
| 1200003C15Rik | Slc16a9 | RIKEN cDNA 1200003C15 gene | 0.3 | 0.1 | AK004684 |
| 1200003C15Rik | Slc16a9 | RIKEN cDNA 1200003C15 gene | 0.4 | 0.1 | AK004684 |
| Slc18a1 | Slc18a1 | solute carrier family 18 (vesicular monoamine), member 1 | 0.3 | 0.1 | BB011871 |
| Slc1a1 | Slc1a1 | solute carrier family 1, member 1 | 0.5 | 0.2 | AF087578 |
| Slc1a4 | Slc1a4 | solute carrier family 1 (glutamate/neutral amino acid transporter), member 4 | 1.8 | 0.6 | BB277461 |
| Slc1a4 | Slc1a4 | solute carrier family 1 (glutamate/neutral amino acid transporter), member 4 | 1.5 | 0.6 | BB277461 |
| Slc22a5 | Slc22a5 | solute carrier family 22 (organic cation transporter), member 5 | 0.4 | 0.2 | NM_011396 |
| Slc26a7 | Slc26a7 | solute carrier family 26, member 7 | 0.5 | 0.2 | AV292356 |
| Slc2a5 | Slc2a5 | solute carrier family 2 (facilitated glucose transporter), member 5 | 0.2 | 0.0 | NM_019741 |
| A230035L05Rik | Slc41a2 | RIKEN cDNA A230035L05 gene | 2.3 | 1.0 | BC026874 |
| AI315119 | Slc5a12 | expressed sequence AI315119 | 0.3 | 0.1 | BB503566 |
| Xtrp2 | Slc6a18 | X transporter protein 2 | 0.7 | 0.3 | AF075266 |
| 4632401C08Rik | Slc6a19 | RIKEN cDNA 4632401C08 gene | 0.4 | 0.1 | AK014544 |
| 4632401C08Rik | Slc6a19 | RIKEN cDNA 4632401C08 gene | 0.4 | 0.1 | BM119683 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| Slco1a1 | Slco1a1 | solute carrier organic anion transporter family, member 1a1 | 0.2 | 0.0 | AB031813 |
| Slfn8 | Slfn8 | schlafen 8 | 8.6 | 2.7 | BC024709 |
| Smpdl3a | Smpdl3a | sphingomyelin phosphodiesterase, acid-like 3A | 0.6 | 0.2 | NM_020561 |
| Snx10 | Snx10 | sorting nexin 10 | 20.8 | 8.4 | AK010399 |
| Sod3 | Sod3 | superoxide dismutase 3, extracellular | 0.3 | 0.1 | NM_011435 |
| Sostdc1 | Sostdc1 | sclerostin domain containing 1 | 0.4 | 0.2 | BC021458 |
| Srd5a2l | Srd5a2l | steroid 5 alpha-reductase 2-like | 1.1 | 0.4 | BB825787 |
| — | Ss18 | *Mus musculus* transcribed sequences | 1.1 | 0.5 | BB199855 |
| — | Stat1 | *Mus musculus* transcribed sequences | 19.6 | 1.4 | BB229853 |
| Stat1 | Stat1 | signal transducer and activator of transcription 1 | 22.7 | 1.1 | AW214029 |
| Stat1 | Stat1 | signal transducer and activator of transcription 1 | 14.1 | 1.1 | AW214029 |
| Stat1 | Stat1 | signal transducer and activator of transcription 1 | 23.0 | 2.0 | AW214029 |
| Stat2 | Stat2 | signal transducer and activator of transcription 2 | 6.1 | 1.7 | AF088862 |
| Stat2 | Stat2 | signal transducer and activator of transcription 2 | 3.2 | 1.3 | AF088862 |
| 4921538B17Rik | Steap2 | RIKEN cDNA 4921538B17 gene | 1.2 | 0.5 | BB529332 |
| Mrpl16 | Stx3 | mitochondrial ribosomal protein L16 | 0.6 | 0.1 | D29800 |
| Sult1c1 | Sult1c2 | sulfotransferase family, cytosolic, 1C, member 1 | 0.5 | 0.2 | NM_026935 |
| Syn2 | Syn2 | synapsin II | 0.3 | 0.1 | NM_013681 |
| Syt1 | Syt1 | synaptotagmin 1 | 2.1 | 0.9 | BM118245 |
| Tap2 | Tap2 | transporter 2, ATP-binding cassette, sub-family B (MDR/TAP) | 11.2 | 2.5 | BE691515 |
| Tapbp | Tapbp | TAP binding protein | 4.6 | 1.0 | AF043943 |
| Tapbp | Tapbp | TAP binding protein | 5.5 | 2.1 | AF043943 |
| LOC213233 | Tapbpl | similar to hypothetical protein FLJ10143 | 5.3 | 1.5 | BC017613 |
| 4432405K22Rik | Tbc1d15 | RIKEN cDNA 4432405K22 gene | 1.2 | 0.6 | BF577643 |
| Tcf7 | Tcf7 | transcription factor 7, T-cell specific | 13.5 | 4.5 | AI323642 |
| — | TCR beta-chain | *M. musculus* mRNA for Tcell receptor, V-J beta junctional region (clone T1CRP8) | 8.2 | 2.4 | M87849 |
| — | Tcra | *Mus musculus* T cell receptor alpha chain variable region (TCRAV3S9) mRNA, partial cds | 9.2 | 3.9 | X01134 |
| — | Tcra | *Mus musculus* adult male thymus cDNA, RIKEN full-length enriched library, clone: 5830404G23 product: T-cell receptor alpha chain precursor V-J region (TA72) (fragment) homolog [*Mus musculus*], full insert sequence | 7.7 | 3.0 | U07662 |
| — | Tcra | *Mus musculus* adult male thymus cDNA, RIKEN full-length enriched library, clone: 5830474E17 product: T-cell receptor alpha chain precursor V-J region (TA72) (fragment) homolog [*Mus musculus*], full insert sequence | 1.7 | 0.7 | BB032962 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| — | Tcrb-J; 5830405F06Rik | — | 3.1 | 0.5 | AK018014 |
| Tcrb-V13 | Tcrb-V13 | T-cell receptor beta, variable 13 | 55.0 | 25.2 | U07661 |
| Tcrb-V13 | Tcrb-V13 | T-cell receptor beta, variable 13 | 55.9 | 21.5 | M11456 |
| Tcrb-V13 | Tcrb-V13 | T-cell receptor beta, variable 13 | 6.8 | 1.0 | U46841 |
| Tcrb-V13 | Tcrb-V13 | T-cell receptor beta, variable 13 | 75.1 | 29.5 | X67128 |
| Tex9 | Tex9 | testis expressed gene 9 | 1.3 | 0.4 | AK008505 |
| — | Tgfbr2 | *Mus musculus* transcribed sequences | 2.4 | 0.6 | BB465968 |
| Tgtp | Tgtp | T-cell specific GTPase | 24.4 | 1.7 | NM_011579 |
| Timp3 | Timp3 | tissue inhibitor of metalloproteinase 3 | 0.5 | 0.2 | BI111620 |
| Syn2 | Timp4 | synapsin II | 0.5 | 0.2 | AK013810 |
| Tlr3 | Tlr3 | toll-like receptor 3 | 3.9 | 1.2 | NM_126166 |
| 1810015P03Rik | Tmed6 | RIKEN cDNA 1810015P03 gene | 0.5 | 0.2 | NM_025458 |
| 2810428F02Rik | Tmem19 | RIKEN cDNA 2810428F02 gene | 0.8 | 0.4 | AK018383 |
| Tmprss4 | Tmprss4 | transmembrane protease, serine 4 | 11.7 | 2.0 | BC021368 |
| Tnfrsf14 | Tnfrsf14 | tumor necrosis factor receptor superfamily, member 14 (herpesvirus entry mediator) | 10.0 | 0.9 | BC022125 |
| Tnfrsf5 | Tnfrsf5 | tumor necrosis factor receptor superfamily, member 5 | 15.7 | 4.4 | AI385482 |
| Tnfrsf5 | Tnfrsf5 | tumor necrosis factor receptor superfamily, member 5 | 18.8 | 7.6 | NM_011611 |
| Tnfrsf5 | Tnfrsf5 | tumor necrosis factor receptor superfamily, member 5 | 20.4 | 6.6 | BB220422 |
| Tnfsf10 | Tnfsf10 | tumor necrosis factor (ligand) superfamily, member 10 | 5.1 | 0.4 | NM_009425 |
| Top2b | Top2b | topoisomerase (DNA) II beta | 1.8 | 0.6 | BB166592 |
| 5430425C04Rik | Tp53i5 | RIKEN cDNA 5430425C04 gene | 3.5 | 1.2 | AK017334 |
| — | Trex1 | *Mus musculus* adult female vagina cDNA, RIKEN full-length enriched library, clone: 9930022F21 product: similar to G PROTEIN COUPLED RECEPTOR [*Mus musculus*], full insert sequence | 6.3 | 2.9 | AF140709 |
| Trim12 | Trim12 | tripartite motif protein 12 | 8.3 | 2.5 | BM244351 |
| Trim21 | Trim21 | tripartite motif protein 21 | 2.3 | 1.0 | BC010580 |
| Trim21 | Trim21 | tripartite motif protein 21 | 3.9 | 1.1 | BC010580 |
| Trim25 | Trim25 | tripartite motif protein 25 | 1.2 | 0.5 | AI746456 |
| Trim30 | Trim30 | tripartite motif protein 30 | 7.9 | 2.8 | AF220015 |
| 9230105E10Rik | Trim34 | RIKEN cDNA 9230105E10 gene | 4.5 | 1.7 | BI653857 |
| Gtl6 | Trip12 | gene trap locus 6 | 0.9 | 0.4 | BG923744 |
| E130308C19Rik | Tspyl5 | RIKEN cDNA E130308C19 gene | 1.6 | 0.4 | AV332105 |
| Tuba8 | Tuba8 | tubulin, alpha 8 | 2.9 | 1.0 | BB047533 |
| Tyki | Tyki | thymidylate kinase family LPS-inducible member | 1.9 | 0.5 | AK004595 |
| C330001M22 | Ubash3a | hypothetical protein C330001M22 | 3.1 | 1.3 | BB397001 |
| Ubd | Ubd | ubiquitin D | 223.5 | 3.3 | NM_023137 |
| Ubce8 | Ube2l6 | ubiquitin-conjugating enzyme 8 | 8.7 | 1.2 | BC008238 |
| — | Ubr1 | *Mus musculus* transcribed sequence with weak similarity to protein pir: RGECDW (*E. coli*) RGECDW transcription activator of D-serine dehydratase —*Escherichia coli* | 0.9 | 0.4 | AV299235 |
| Ugt8 | Ugt8 | UDP-glucuronosyltransferase 8 | 0.5 | 0.2 | NM_011674 |
| Upb1 | Upb1 | ureidopropionase, beta | 0.4 | 0.1 | NM_133995 |
| Upp1 | Upp1 | uridine phosphorylase 1 | 8.2 | 2.1 | NM_009477 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| Usp18 | Usp18 | ubiquitin specific protease 18 | 20.6 | 1.6 | NM_011909 |
| Wars | Wars | tryptophanyl-tRNA synthetase | 2.4 | 0.9 | BC003450 |
| Wars | Wars | tryptophanyl-tRNA synthetase | 2.7 | 0.8 | BB785450 |
| — | Wld | — | 0.8 | 0.3 | AF260924 |
| Wrn | Wrn | Werner syndrome homolog (human) | 1.6 | 0.5 | D86527 |
| Xdh | Xdh | xanthine dehydrogenase | 16.7 | 6.1 | AV286265 |
| — | Ywhaq | *Mus musculus* 16 days neonate thymus cDNA, RIKEN full-length enriched library, clone: A130046D12 product: 14-3-3 PROTEIN TAU (14-3-3 PROTEIN THETA), full insert sequence | 1.3 | 0.5 | AV024540 |
| Zbp1 | Zbp1 | Z-DNA binding protein 1 | 78.0 | 3.9 | AK008179 |
| Zbp1 | Zbp1 | Z-DNA binding protein 1 | 118.4 | 3.0 | NM_021394 |
| 9430083K24Rik | Zbtb5 | RIKEN cDNA 9430083K24 gene | 1.3 | 0.6 | AI267092 |
| Zc3hdc1 | Zc3hdc1 | zinc finger CCCH type domain containing 1 | 6.7 | 2.2 | BM227980 |
| Zfp287 | Zfp287 | zinc finger protein 287 | 1.4 | 0.6 | BI714160 |
| AI839779 | Zfp365 | expressed sequence AI839779 | 0.5 | 0.2 | AV327248 |
| Zfp386 | Zfp386 | zinc finger protein 386 (Kruppel-like) | 1.8 | 0.8 | NM_019565 |
| 4633401C23Rik | Zfp84 | RIKEN cDNA 4633401C23 gene | 1.3 | 0.6 | AI465811 |
| Znfn1a3 | Zfpn1a3 | zinc finger protein, subfamily 1A, 3 (Aiolos) | 4.4 | 1.9 | BB202216 |
| Zfr | Zfr | zinc finger RNA binding protein | 2.6 | 1.0 | BM119505 |
| — | | *Mus musculus* similar to 2-cell-stage, variable group, member 3; 2-cell-stage, variable group, member 1 (LOC236374), mRNA | 2.1 | 0.9 | BG070246 |
| — | — | — | 0.4 | 0.2 | AK016021 |
| — | — | — | 9.3 | 3.4 | BB030365 |
| — | — | — | 6.8 | 0.6 | BB135602 |
| — | | *Mus musculus* transcribed sequences | 0.7 | 0.2 | BG071026 |
| 2210023K21Rik | | RIKEN cDNA 2210023K21 gene | 4.7 | 2.3 | BI106821 |
| — | — | — | 3.6 | 1.5 | AV340322 |
| — | | *Mus musculus* transcribed sequences | 1.3 | 0.2 | BB738659 |
| — | | *Mus musculus* transcribed sequence with moderate similarity to protein ref: NP_114409.1 (*H. sapiens*) hypothetical protein MGC1314 similar to fucosidase, alpha-L-1, tissue [*Homo sapiens*] | 0.3 | 0.1 | BM054266 |
| Vcam1 | | vascular cell adhesion molecule 1 | 19.2 | 8.8 | BB250384 |
| — | | *Mus musculus* anti-MUC1 antibody SM3 Ig heavy chain variable region mRNA, partial cds | 1.5 | 0.5 | AY058911 |
| — | | *Mus musculus* LOC380741 (LOC380741), mRNA | 1.6 | 0.5 | BB323723 |
| — | | *Mus musculus* cDNA clone IMAGE: 5151706, partial cds | 0.8 | 0.2 | BB553937 |
| — | | *Mus musculus* transcribed sequence with moderate similarity to protein pir: A47643 (*M. musculus*) A47643 hypothetical protein - mouse (fragment) | 1.5 | 0.1 | BG862223 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| — | | *Mus musculus* adult male pituitary gland cDNA, RIKEN full-length enriched library, clone: 5330412J20 product: unknown EST, full insert sequence | 1.6 | 0.7 | BB022773 |
| — | | — | 1.4 | 0.3 | BG065699 |
| — | | *Mus musculus* 0 day neonate head cDNA, RIKEN full-length enriched library, clone: 4833429G05 product: unknown EST, full insert sequence | 1.5 | 0.7 | AV251099 |
| — | | *Mus musculus* transcribed sequences | 1.1 | 0.5 | BB378649 |
| — | | *Mus musculus* similar to transmembrane protein SHREW1 (LOC230959), mRNA | 1.9 | 0.7 | AW123234 |
| — | | *Mus musculus* transcribed sequence with strong similarity to protein sp: P00722 (*E. coli*) BGAL_ECOLI Beta-galactosidase (Lactase) | 0.8 | 0.3 | AV370837 |
| — | | — | 0.6 | 0.2 | AW319988 |
| — | | *Mus musculus* 0 day neonate kidney cDNA, RIKEN full-length enriched library, clone: D630022F07 product: hypothetical protein, full insert sequence | 0.5 | 0.2 | BB750877 |
| — | | *Mus musculus* cDNA clone MGC: 6071 IMAGE: 3492410, complete cds | 3.3 | 0.8 | BC022776 |
| — | | Mouse non-productive mRNA for T-cell receptor gamma V5-J1-C1 | 2.1 | 0.6 | NM_011558 |
| — | | — | 67.1 | 8.6 | NM_022429 |
| — | | *Mus musculus* transcribed sequence with strong similarity to protein sp: P00722 (*E. coli*) BGAL_ECOLI Beta-galactosidase (Lactase) | 0.7 | 0.3 | AW124641 |
| — | | *Mus musculus* transcribed sequence with moderate similarity to protein ref: NP_079184.1 (*H. sapiens*) hypothetical protein FLJ12973 [*Homo sapiens*] | 1.5 | 0.3 | BB436326 |
| — | | *Mus musculus* transcribed sequence with weak similarity to protein ref: NP_443092.1 (*H. sapiens*) kruppel-like zinc finger protein [*Homo sapiens*] | 1.1 | 0.1 | C77501 |
| — | | *Mus musculus* transcribed sequence with moderate similarity to protein pir: R5HU35 (*H. sapiens*) R5HU35 ribosomal protein L35a —human | 1.2 | 0.4 | BB201888 |
| — | | *Mus musculus* transcribed sequences | 1.4 | 0.6 | BB343967 |
| Rnaset2 | | ribonuclease T2 | 1.7 | 0.8 | AV101824 |
| — | | *Mus musculus* diabetic nephropathy-related gene 1 mRNA, partial sequence | 58.3 | 13.4 | BM241271 |
| — | | *Mus musculus* transcribed sequences | 0.7 | 0.3 | BE979870 |
| — | | *Mus musculus* transcribed sequences | 5.0 | 1.2 | BB534560 |
| — | | *Mus musculus* transcribed sequences | 1.1 | 0.4 | AV230978 |

TABLE 3-continued

Transcripts decreased in GKO D5

| Gene Symbol Affymetrix | Common | Gene Title Affymetrix | WT D5 vs NCBA | GKO D5 vs NCBA | Genbank |
|---|---|---|---|---|---|
| Cxcl9 | | chemokine (C—X—C motif) ligand 9 | 69.4 | 0.7 | BI104444 |
| — | | *Mus musculus* adult male aorta and vein cDNA, RIKEN full-length enriched library, clone: A530023D22 product: unclassifiable, full insert sequence | 5.5 | 2.6 | BB214834 |
| Nalp6 | | NACHT, leucine rich repeat and PYD containing 6 | 0.6 | 0.2 | BB071996 |
| — | | *Mus musculus* 9 days embryo whole body cDNA, RIKEN full-length enriched library, clone: D030030M01 product: unknown EST, full insert sequence | 1.1 | 0.5 | BB442202 |
| — | | *Mus musculus* transcribed sequences | 61.7 | 0.4 | AW111920 |
| Clic5 | | chloride intracellular channel 5 | 0.9 | 0.2 | BB236747 |
| — | | *Mus musculus* adult male cortex cDNA, RIKEN full-length enriched library, clone: B530033B21 product: unknown EST, full insert sequence | 10.9 | 1.4 | BB645745 |
| — | | — | 1.5 | 0.1 | BG297038 |
| G1p2 | | interferon, alpha-inducible protein | 16.7 | 3.0 | AK019325 |
| — | | *Mus musculus* adult male testis cDNA, RIKEN full-length enriched library, clone: 4921513I01 product: unknown EST, full insert sequence | 1.4 | 0.5 | AV254764 |
| — | | — | 12.6 | 1.0 | BB668084 |
| — | | — | 17.1 | 0.5 | BG072508 |
| — | | *Mus musculus* mRNA similar to interferon-inducible GTPase (cDNA clone MGC: 49532 IMAGE: 3495064), complete cds | 5.1 | 0.7 | BC020118 |
| — | | *Mus musculus* adult male hippocampus cDNA, RIKEN full-length enriched library, clone: C630020O05 product: unknown EST, full insert sequence | 0.9 | 0.1 | BB428710 |
| — | | *Mus musculus* 0 day neonate eyeball cDNA, RIKEN full-length enriched library, clone: E130009O20 product: unknown EST, full insert sequence | 1.5 | 0.7 | BB313276 |
| — | | *Mus musculus* adult male aorta and vein cDNA, RIKEN full-length enriched library, clone: A530086D01 product: unknown EST, full insert sequence | 2.3 | 0.3 | BB224338 |
| Hrasls3 | | HRAS like suppressor 3 | 21.7 | 1.0 | BB404920 |
| — | | — | 4.6 | 0.8 | AV340322 |

TABLE 4

GRIT expression in WT and GKO grafts

| Gene Symbol | Gene Title Affymetrix | ISO D5 vs NCBA | ISO D5 vs ISO.GKO D5 | WT D5 vs NCBA |
|---|---|---|---|---|
| Iigp1 | interferon inducible GTPase 1 | 27.5 | 8.1 | 45.7 |
| Tgtp | T-cell specific GTPase | 16.6 | 8.1 | 28.4 |
| Mpa2l | macrophage activation 2 like | 14.9 | 12.5 | 92.9 |
| Gbp2 | guanylate nucleotide binding protein 2 | 12.8 | 33.2 | 47.7 |
| Gbp2 | guanylate nucleotide binding protein 2 | 11.5 | 8.6 | 76.1 |
| Iigp1 | interferon inducible GTPase 1 | 11.2 | 7.4 | 20.4 |
| Igtp | interferon gamma induced GTPase | 9.3 | 4.8 | 17.8 |
| Cxcl10 | chemokine (C—X—C motif) ligand 10 | 7.0 | | 100.9 |
| H2-DMb1 | histocompatibility 2, class II, locus Mb1 | 6.5 | 2.6 | 11.3 |
| Gtpi-pending | interferon-g induced GTPase | 5.8 | 5.0 | 24.7 |
| Ubd | ubiquitin D | 5.3 | 4.5 | 91.8 |
| Psmb8 | proteosome (prosome, macropain) subunit, beta type 8 (large multifunctional protease 7) | 4.8 | 2.0 | 25.5 |
| Stat1 | signal transducer and activator of transcription 1 | 3.9 | 3.3 | 11.7 |
| Cxcl9 | chemokine (C—X—C motif) ligand 9 | 3.7 | 14.7 | 99.8 |
| Mpeg1 | macrophage expressed gene 1 | 3.6 | | 16.4 |
| Psmb9 | proteosome (prosome, macropain) subunit, beta type 9 (large multifunctional protease 2) | 3.6 | 3.9 | 19.1 |
| H2-DMb2 | histocompatibility 2, class II, locus Mb2 | 3.4 | 6.3 | 13.3 |
| Psmb10 | proteasome (prosome, macropain) subunit, beta type 10 | 3.4 | 3.0 | 14.5 |
| Ifi1 | interferon inducible protein 1 | 3.1 | 3.9 | 8.2 |
| Ifi47 | interferon gamma inducible protein | 3.1 | 3.7 | 21.4 |
| Brd4 | bromodomain containing 4 | 3.0 | | 9.4 |
| Ifit2 | interferon-induced protein with tetratricopeptide repeats 2 | 2.8 | 2.1 | 25.1 |
| Pdcd1lg1 | programmed cell death 1 ligand 1 | 2.7 | 4.5 | 29.6 |
| Fgl2 | fibrinogen-like protein 2 | 2.7 | | 14.4 |
| 5033415K03Rik | RIKEN cDNA 5033415K03 gene | 2.7 | | 17.5 |
| Il18bp | interleukin 18 binding protein | 2.6 | 6.6 | 17.3 |
| Stat1 | signal transducer and activator of transcription 1 | 2.6 | 7.1 | 7.7 |
| H2-K | histocompatibility 2, K region | 2.6 | 4.7 | 9.0 |
| Xdh | xanthine dehydrogenase | 2.6 | | 11.7 |
| Pigr | polymeric immunoglobulin receptor | 2.4 | | 6.5 |
| Parp14 | poly (ADP-ribose) polymerase family, member 14 | 2.4 | 2.7 | 11.4 |
| Ccl5 | chemokine (C—C motif) ligand 5 | 2.4 | 62.5 | 34.8 |
| BE688358NCBI | ESTs | 2.2 | 3.5 | 16.0 |
| 5830458K16Rik | RIKEN cDNA 5830458K16 gene | 2.2 | 2.1 | 9.2 |
| H2-T23 | histocompatibility 2, T region locus 23 | 2.2 | 2.7 | 7.3 |
| Arts1-pending | type 1 tumor necrosis factor receptor shedding aminopeptidase regulator | 2.1 | | 2.8 |
| C2ta | class II transactivator | 2.1 | 3.8 | 7.7 |
| Fabp7 | fatty acid binding protein 7, brain | 2.1 | | 2.8 |
| G1p2 | interferon, alpha-inducible protein | 2.1 | | 8.0 |
| Oasl2 | 2'-5' oligoadenylate synthetase-like 2 | 1.9 | | 14.7 |
| Ms4a6b | membrane-spanning 4-domains, subfamily A, member 6B | 1.9 | | 14.1 |
| Tapbp | TAP binding protein | 1.9 | 2.4 | 4.6 |
| H2-Ab1 | histocompatibility 2, class II antigen A, beta 1 | 1.9 | 5.0 | 5.9 |
| Ms4a4d | membrane-spanning 4-domains, subfamily A, member 4D | 1.8 | | 3.8 |
| Zbp1 | Z-DNA binding protein 1 | 1.8 | 2.9 | 12.2 |
| C1s | complement component 1, s subcomponent | 1.7 | | 12.7 |
| Lair1 | leukocyte-associated Ig-like receptor 1 | 1.7 | | 3.3 |
| Ccl8 | chemokine (C—C motif) ligand 8 | 1.6 | 3.1 | 3.1 |
| Slamf8 | Slamf8 | 1.6 | 3.4 | 15.4 |
| H2-T10 | histocompatibility 2, T region locus 10 | 1.6 | | 3.5 |
| Serpina10 | hypothetical protein MGC25863 | 1.5 | | 8.8 |
| H2-K | histocompatibility 2, K region | 1.5 | 2.1 | 14.5 |
| Irf7 | interferon regulatory factor 7 | 1.4 | | 6.4 |
| C1r | complement component 1, r subcomponent | 1.3 | | 7.4 |
| Ifit1 | interferon-induced protein with tetratricopeptide repeats 1 | 1.3 | 4.2 | 5.9 |
| Ube1l | Ube1l | 1.2 | | 4.2 |

TABLE 4-continued

GRIT expression in WT and GKO grafts

| Gene Symbol | Gene Title Affymetrix | ISO D5 vs NCBA | ISO D5 vs ISO.GKO D5 | WT D5 vs NCBA |
|---|---|---|---|---|
| Hrasls3 | HRAS like suppressor 3 | 1.0 | | 7.2 |
| C2 | complement component 2 (within H-2S) | 0.8 | | 3.1 |
| B2m | Beta-2 microglobulin | 0.8 | | 5.5 |

TABLE 5

GRIT-like transcript expression in WT and GKO grafts

| Gene Symbol | Gene Title Affymetrix | ISO D5 vs NCBA | ISO D5 vs ISO.GKO | WT D5 vs NCBA |
|---|---|---|---|---|
| H2-Aa | histocompatibility 2, class II antigen A, alpha | 5.1 | 3.8 | 10.8 |
| Ms4a6d | membrane-spanning 4-domains, subfamily A, member 6D | 4.0 | | 21.2 |
| Hist1h2ad | histone 1, H2ad | 3.4 | | 32.4 |
| H2-DMa | histocompatibility 2, class II, locus DMa | 3.4 | 3.6 | 11.3 |
| Top2a | topoisomerase (DNA) II alpha | 3.4 | | 8.5 |
| H2-Aa | histocompatibility 2, class II antigen A, alpha | 3.3 | 3.0 | 6.8 |
| Ii | Ia-associated invariant chain | 3.1 | 3.5 | 5.5 |
| Ctss | cathepsin S | 2.9 | | 8.9 |
| Tgfbi | transforming growth factor, beta induced, 68 kDa | 2.9 | | 17.3 |
| Ccr5 | chemokine (C—C motif) receptor 5 | 2.5 | | 12.1 |
| H2-Eb1 | histocompatibility 2, class II antigen E beta | 2.5 | 3.5 | 6.8 |
| C1qb | complement component 1, q subcomponent, beta polypeptide | 2.3 | | 8.7 |
| Ifi27 | interferon, alpha-inducible protein 27 | 2.2 | | 3.2 |
| Tgfbi | transforming growth factor, beta induced, 68 kDa | 2.2 | | 17.2 |
| Coro1a | coronin, actin binding protein 1A | 2.1 | | 35.2 |
| C1qg | complement component 1, q subcomponent, gamma polypeptide | 2.1 | | 8.8 |
| Coro1a | coronin, actin binding protein 1A | 2.0 | | 55.3 |
| Gzma | granzyme A | 1.9 | 2.7 | 4.6 |
| Hck | hemopoietic cell kinase | 1.8 | | 7.0 |
| Ppicap | peptidylprolyl isomerase C-associated protein | 1.7 | | 4.8 |
| Serping1 | serine (or cysteine) proteinase inhibitor, clade G, member 1 | 1.7 | | 4.3 |
| Itgax | integrin alpha X | 1.5 | 2.0 | 5.9 |
| Was | Wiskott-Aldrich syndrome homolog (human) | 1.4 | | 5.9 |
| Tmsb10 | thymosin, beta 10 | 1.4 | | 6.3 |
| Tgfbi | transforming growth factor, beta induced, 68 kDa | 1.4 | | 14.0 |
| Tmsb10 | thymosin, beta 10 | 1.4 | | 4.1 |
| Epsti1 | epithelial stromal interaction 1 (breast) | 1.4 | | 7.6 |
| Ly6f | lymphocyte antigen 6 complex, locus F | 1.3 | | 2.6 |
| Ifitm3 | interferon induced transmembrane protein 3 | 1.3 | | 2.4 |
| Ifitm6 | interferon induced transmembrane protein 6 | 1.3 | | 2.6 |
| AW413625 | expressed sequence AW413625 | 1.2 | 2.3 | 3.7 |
| Tnfsf13b | tumor necrosis factor (ligand) superfamily, member 13b | 1.2 | | 2.8 |
| AU020206 | *Mus musculus* 3 days neonate thymus cDNA, RIKEN full-length enriched library, clone: A630040D01 | 1.2 | | 5.1 |
| Ifitm1 | interferon induced transmembrane protein 1 | 1.2 | 2.4 | 2.5 |
| AI132321 | *Mus musculus* 0 day neonate thymus cDNA, RIKEN full-length enriched library, clone: A430098J23 | 1.1 | 2.3 | 5.1 |
| Gpm6b | glycoprotein m6b | 1.1 | | 2.3 |
| Cugbp2 | CUG triplet repeat, RNA binding protein 2 | 0.9 | | 3.5 |

TABLE 5-continued

GRIT-like transcript expression in WT and GKO grafts

| Gene Symbol | Gene Title Affymetrix | ISO D5 vs NCBA | ISO D5 vs ISO.GKO | WT D5 vs NCBA |
|---|---|---|---|---|
| Emr4 | EGF-like module containing, mucin-like, hormone receptor-like sequence 4 | 0.9 | | 3.0 |
| Cxcl14 | chemokine (C—X—C motif) ligand 14 | 0.8 | | 3.0 |
| Socs2 | suppressor of cytokine signaling 2 | 0.8 | | 2.2 |
| 9230117N10Rik | RIKEN cDNA 9230117N10 gene | 0.7 | | 3.8 |
| Cxcl14 | chemokine (C—X—C motif) ligand 14 | 0.4 | | 7.6 |

TABLE 6

Transcripts decreased in GKO D5 but not induced by rIFNγ

| Gene Symbol | Title_Affy | ISO D5 vs NCBA | ISO D5 vs ISO.GKO | WT D5 vs NCBA |
|---|---|---|---|---|
| 5830443L24Rik | RIKEN cDNA 5830443L24 gene | 8.1 | 6.8 | 74.8 |
| BC023105 | cDNA sequence BC023105 | 7.5 | 20.0 | 10.9 |
| Cxcl11 | chemokine (C—X—C motif) ligand 11 | 5.8 | 2.5 | 70.4 |
| Ifi202b | interferon activated gene 202B | 4.9 | | 33.1 |
| Ly86 | lymphocyte antigen 86 | 3.4 | | 12.9 |
| Dnr12 | Diabetic nephropathy-like protein (Dnr12) mRNA, partial sequence | 3.1 | 3.2 | 20.4 |
| Ubce8 | ubiquitin-conjugating enzyme 8 | 3.0 | | 5.7 |
| H2-D1 | histocompatibility 2, D region locus 1 | 3.0 | 5.1 | 7.7 |
| Trim34 | tripartite motif protein 34 | 3.0 | | 9.9 |
| Aif1 | allograft inflammatory factor 1 | 2.8 | | 16.5 |
| Klra2 | killer cell lectin-like receptor, subfamily A, member 2 | 2.7 | | 7.3 |
| Ptprcap | protein tyrosine phosphatase, receptor type, C polypeptide-associated protein | 2.4 | | 15.9 |
| Ms4a4c | membrane-spanning 4-domains, subfamily A, member 4C | 2.4 | 3.2 | 14.0 |
| H28 | histocompatibility 28 | 2.3 | | 6.5 |
| BC013712 | cDNA sequence BC013712 | 2.2 | 2.4 | 7.1 |
| Ms4a6c | membrane-spanning 4-domains, subfamily A, member 6C | 2.2 | | 7.3 |
| H28 | Histocompatibility 28 | 2.2 | | 4.4 |
| H2-Q1 | histocompatibility 2, Q region locus 1 | 2.1 | 5.8 | 10.9 |
| Tnfrsf5 | tumor necrosis factor receptor superfamily, member 5 | 2.1 | 2.6 | 6.7 |
| Ifi205 | interferon activated gene 205 | 2.1 | 3.6 | 25.4 |
| Vcam1 | vascular cell adhesion molecule 1 | 2.1 | 2.4 | 12.5 |
| Sell | selectin, lymphocyte | 2.0 | | 7.8 |
| Tap2 | transporter 2, ATP-binding cassette, sub-family B (MDR/TAP) | 1.9 | 2.9 | 7.4 |
| Icsbp | interferon concensus sequence binding protein | 1.9 | | 8.4 |
| Nmi | N-myc (and STAT) interactor | 1.9 | | 5.4 |
| Tnfsf10 | tumor necrosis factor (ligand) superfamily, member 10 | 1.8 | | 6.7 |
| Gbp4 | guanylate nucleotide binding protein 4 | 1.8 | | 12.6 |
| Parp9 | poly (ADP-ribose) polymerase family, member 9 | 1.7 | 2.3 | 8.7 |
| Ifi205 | interferon activated gene 205 | 1.7 | 3.3 | 15.9 |
| Casp1 | caspase 1 | 1.7 | | 6.6 |
| Irf1 | interferon regulatory factor 1 | 1.7 | 2.5 | 8.7 |
| Igh-6 | immunoglobulin heavy chain 6 (heavy chain of IgM) | 1.7 | 2.2 | 4.2 |
| Ifit3 | interferon-induced protein with tetratricopeptide repeats 3 | 1.7 | | 5.4 |
| Casp11 | caspase 11, apoptosis-related cysteine protease (caspase 4 precursor) | 1.7 | | 8.4 |
| Usp18 | ubiquitin specific protease 18 | 1.7 | | 8.5 |
| Zc3hdc1 | hypothetical protein 9930021O16 | 1.7 | | 5.2 |
| Samhd1 | SAM domain and HD domain, 1 | 1.7 | | 8.5 |
| Fcrl3 | Fc receptor-like 3 | 1.7 | | 6.6 |
| Oas1g | 2'-5' oligoadenylate synthetase 1G | 1.6 | | 3.3 |
| Snx10 | sorting nexin 10 | 1.6 | | 14.0 |
| 0610037M15Rik | RIKEN cDNA 0610037M15 gene | 1.6 | | 6.4 |
| Ifi203 | interferon activated gene 203 | 1.6 | | 5.7 |

TABLE 6-continued

Transcripts decreased in GKO D5 but not induced by rIFNγ

| Gene Symbol | Title__Affy | ISO D5 vs NCBA | ISO D5 vs ISO.GKO | WT D5 vs NCBA |
|---|---|---|---|---|
| Stat2 | signal transducer and activator of transcription 2 | 1.6 | | 4.4 |
| Gzmk | granzyme K | 1.6 | | 2.5 |
| Ifi44 | interferon-induced protein 44 | 1.5 | | 4.2 |
| IFNg | interferon gamma | 1.5 | | 8.2 |
| Slamf6 | SLAM family member 6 | 1.5 | | 2.2 |
| H2-Q7 | histocompatibility 2, Q region locus 7 | 1.5 | 3.3 | 11.2 |
| Il12rb1 | interleukin 12 receptor, beta 1 | 1.5 | | 4.6 |
| Ifi35 | interferon-induced protein 35 | 1.5 | | 4.2 |
| Trim30 | tripartite motif protein 30 | 1.5 | | 4.4 |
| Cybb | cytochrome b-245, beta polypeptide | 1.5 | | 5.1 |
| H2-M3 | histocompatibility 2, M region locus 3 | 1.5 | | 4.4 |
| Glipr1 | GLI pathogenesis-related 1 (glioma) | 1.4 | | 5.6 |
| Slfn8 | schlafen 8 | 1.4 | | 3.0 |
| Ifih1 | interferon induced with helicase C domain 1 | 1.4 | | 3.5 |
| Trim21 | tripartite motif protein 21 | 1.4 | | 3.0 |
| Trim21 | tripartite motif protein 21 | 1.4 | | 2.3 |
| Stat2 | signal transducer and activator of transcription 2 | 1.4 | | 8.5 |
| Parp3 | poly (ADP-ribose) polymerase family, member 3 | 1.3 | | 4.4 |
| 2610042L04Rik | RIKEN cDNA 2610042L04 gene | 1.3 | | 4.7 |
| H2-T24 | histocompatibility 2, T region locus 24 | 1.3 | | 2.5 |
| Slc41a2 | solute carrier family 41, member 2 | 1.3 | | 3.2 |
| Sectm1 | secreted and transmembrane 1 | 1.3 | | 3.2 |
| Gimap7 | GTPase, IMAP family member 7 | 1.3 | 2.7 | 6.0 |
| Cyp4v3 | cytochrome P450, family 4, subfamily v, polypeptide 3 | 1.3 | | 2.0 |
| Psme2 | proteasome (prosome, macropain) 28 subunit, beta | 1.3 | | 4.2 |
| Mx1 | myxovirus (influenza virus) resistance 1 | 1.3 | | 4.5 |
| Dnase1l3 | deoxyribonuclease 1-like 3 | 1.3 | | 23.9 |
| Ifi204 | interferon activated gene 204 | 1.2 | 2.9 | 9.0 |
| Tnfrsf5 | tumor necrosis factor receptor superfamily, member 5 | 1.2 | 2.8 | 3.9 |
| Wars | tryptophanyl-tRNA synthetase | 1.2 | | 3.5 |
| Ly6c | lymphocyte antigen 6 complex, locus C | 1.2 | | 2.2 |
| Psme1 | proteasome (prosome, macropain) 28 subunit, alpha | 1.2 | | 2.8 |
| 4930422C14 | hypothetical protein 4930422C14 | 1.2 | | 8.2 |
| D11Lgp2e | DNA segment, Chr 11, Lothar Hennighausen 2, expressed | 1.2 | | 16.8 |
| Samhd1 | SAM domain and HD domain, 1 | 1.1 | | 6.9 |
| Dnase1l3 | deoxyribonuclease 1-like 3 | 1.1 | | 2.4 |
| Gimap4 | GTPase, IMAP family member 4 | 1.1 | | 2.4 |
| 1110007F12Rik | RIKEN cDNA 1110007F12 gene | 1.1 | | 3.9 |
| H2-Oa | histocompatibility 2, O region alpha locus | 1.1 | | 2.7 |
| Pnp | purine-nucleoside phosphorylase | 1.1 | | 2.4 |
| Rbl1 | retinoblastoma-like 1 (p107) | 1.1 | | 4.1 |
| C920025E04Rik | RIKEN cDNA C920025E04 gene | 1.1 | | 3.0 |
| Cxcr3 | chemokine (C—X—C motif) receptor 3 | 1.1 | | 4.1 |
| Klrk1 | killer cell lectin-like receptor subfamily K, member 1 | 1.1 | | 3.9 |
| Icsbp | interferon concensus sequence binding protein | 1.0 | 2.0 | 8.1 |
| Klra7 | killer cell lectin-like receptor, subfamily A, member 7 | 1.0 | | 2.7 |
| BC010462 | cDNA sequence BC010462 | 1.0 | | 2.9 |
| Pbef-pending | pre-B-cell colony-enhancing factor | 1.0 | | 2.1 |
| Prkr | protein kinase, interferon-inducible double stranded RNA dependent | 1.0 | | 3.0 |
| Wars | tryptophanyl-tRNA synthetase | 1.0 | | 4.0 |
| Asahl | N-acylsphingosine amidohydrolase (acid ceramidase)-like | 1.0 | | 2.5 |
| Tlr3 | toll-like receptor 3 | 1.0 | | 2.4 |
| 1810054D07Rik | RIKEN cDNA 1810054D07 gene | 1.0 | | 4.6 |
| 9530028C05 | product: similar to HISTOCOMPATIBILITY 2, CLASS II ANTIGEN E BETA [*Mus musculus*], full insert sequence. | 0.9 | | 2.9 |
| Sell | selectin, lymphocyte | 0.9 | | 3.7 |

TABLE 6-continued

Transcripts decreased in GKO D5 but not induced by rIFNγ

| Gene Symbol | Title__Affy | ISO D5 vs NCBA | ISO D5 vs ISO.GKO | WT D5 vs NCBA |
|---|---|---|---|---|
| Eif4e3 | eukaryotic translation initiation factor 4E member 3 | 0.9 | | 3.1 |
| 2310016F22Rik | RIKEN cDNA 2310016F22 gene | 0.9 | | 17.4 |
| Irg1 | immunoresponsive gene 1 | 0.9 | | 34.6 |
| Klrb1b | killer cell lectin-like receptor subfamily B member 1B | 0.9 | | 2.7 |
| Tcf7 | transcription factor 7, T-cell specific | 0.9 | | 10.1 |
| Slamf7 | SLAM family member 7 | 0.8 | | 4.2 |
| Ifi203 | interferon activated gene 203 | 0.8 | | 4.4 |
| Cd3z | CD3 antigen, zeta polypeptide | 0.8 | | 6.9 |
| MGI: 1923551 | FLN29 gene product | 0.7 | | 3.0 |
| Trim34 | tripartite motif protein 34 | 0.7 | | 2.2 |
| Upp | uridine phosphorylase | 0.6 | | 6.5 |
| Ngfr | nerve growth factor receptor | 0.5 | 9.9 | 2.3 |
| Ifi203 | interferon activated gene 203 | 0.3 | | 23.6 |

TABLE 7

Injury-induced RITs in rejection

| Gene Symbol | Gene Title | ISO D21 | ISO D7 | ISO D5 | WT D5 | WT D7 | WT D14 | WT D21 | WT D42 | Genbank |
|---|---|---|---|---|---|---|---|---|---|---|
| 1110028E10Rik | RIKEN cDNA 1110028E10 gene | 1.5 | 2.1 | 0.9 | 2.4 | 2.2 | 2.7 | 2.7 | 3.1 | BB478892 |
| 1200016E24Rik | RIKEN cDNA 1200016E24 gene | 0.9 | 2.6 | 0.9 | 2.8 | 1.9 | 2.0 | 2.8 | 2.5 | BF719154 |
| 1200016E24Rik | RIKEN cDNA 1200016E24 gene | 1.1 | 2.4 | 1.0 | 2.6 | 2.4 | 1.5 | 3.2 | 1.6 | AU018141 |
| 2610042L04Rik | RIKEN cDNA 2610042L04 gene | 1.2 | 1.5 | 2.2 | 4.9 | 3.0 | 6.7 | 3.8 | 4.2 | BM195235 |
| 9030408N13Rik | RIKEN cDNA 9030408N13 gene | 1.1 | 2.5 | 1.6 | 6.2 | 9.2 | 11.9 | 11.9 | 11.1 | NM_025779 |
| Abp1 | amiloride binding protein 1 (amine oxidase, copper-containing) | 0.8 | 3.1 | 0.9 | 4.0 | 2.6 | 10.0 | 8.0 | 5.0 | BC021880 |
| Adamts1 | a disintegrin-like and metalloprotease (reprolysin type) with thrombospondin type 1 motif, 1 | 1.1 | 2.9 | 1.5 | 4.2 | 2.2 | 5.4 | 4.0 | 4.7 | D67076 |
| Adamts4 | a disintegrin-like and metalloprotease (reprolysin type) with thrombospondin type 1 motif, 4 | 1.1 | 3.3 | 1.1 | 3.2 | 2.7 | 4.4 | 4.1 | 5.6 | BB443585 |
| Aldh1a2 | aldehyde dehydrogenase family 1, subfamily A2 | 0.5 | 4.0 | 1.3 | 4.1 | 2.7 | 2.6 | 3.7 | 4.5 | NM_009022 |
| Anln | anillin, actin binding protein (scraps homolog, *Drosophila*) | 1.3 | 2.3 | 1.9 | 2.3 | 3.3 | 4.0 | 3.3 | 3.6 | BI690018 |
| Arrb2 | similar to Beta-arrestin 2 (Arrestin, beta 2) | 0.9 | 2.1 | 1.0 | 5.2 | 8.6 | 11.4 | 10.8 | 9.8 | BC016642 |
| Asns | asparagine synthetase | 0.6 | 2.2 | 1.1 | 3.0 | 1.5 | 3.6 | 3.2 | 5.0 | AV212753 |
| Basp1 | brain abundant, membrane attached signal protein 1 | 1.0 | 2.2 | 1.4 | 4.9 | 6.0 | 14.2 | 13.6 | 18.3 | AK011545 |
| Bcl3 | B-cell leukemia/lymphoma 3 | 1.7 | 3.6 | 1.8 | 7.2 | 8.0 | 4.8 | 7.0 | 4.7 | NM_033601 |
| Bcl6 | B-cell leukemia/lymphoma 6 | 3.9 | 2.3 | 2.3 | 2.1 | 2.5 | 2.3 | 2.4 | 2.1 | BB183854 |
| Birc1b | baculoviral IAP repeat-containing 1b | 0.9 | 1.5 | 2.1 | 2.5 | 2.8 | 6.2 | 4.0 | 5.9 | NM_010872 |
| Bsf3-pending | B-cell stimulating factor 3 | 0.6 | 2.0 | 2.1 | 2.1 | 2.2 | 3.5 | 5.0 | 3.3 | BB825816 |
| C1qa | complement component 1, q subcomponent, alpha polypeptide | 1.4 | 3.9 | 2.8 | 10.3 | 15.7 | 29.2 | 24.1 | 28.8 | NM_007572 |
| C1qb | complement component 1, q subcomponent, beta polypeptide | 2.3 | 2.2 | 2.0 | 3.4 | 5.0 | 10.2 | 6.6 | 7.7 | AW227993 |
| C79673 | expressed sequence C79673 | 1.4 | 2.7 | 1.4 | 19.9 | 24.5 | 41.2 | 33.5 | 38.1 | BG066664 |
| Car13 | carbonic anhydrase 13 | 0.6 | 2.1 | 1.5 | 4.2 | 2.2 | 4.5 | 3.7 | 3.3 | NM_024495 |
| Casp12 | caspase 12 | 1.1 | 1.5 | 2.3 | 3.0 | 2.5 | 9.1 | 6.6 | 7.0 | NM_009808 |
| Ccl2 | chemokine (C—C motif) ligand 2 | 1.1 | 2.9 | 1.2 | 7.4 | 7.5 | 10.7 | 9.3 | 10.5 | AF065933 |
| Ccl9 | chemokine (C—C motif) ligand 9 | 0.7 | 2.4 | 1.2 | 3.1 | 5.0 | 6.4 | 11.4 | 12.1 | NM_011338 |
| Ccl9 | chemokine (C—C motif) ligand 9 | 1.0 | 5.8 | 1.1 | 8.6 | 12.1 | 18.2 | 23.3 | 33.2 | AF128196 |
| Ccnb1 | cyclin B1 | 1.0 | 2.7 | 2.4 | 9.9 | 6.7 | 8.6 | 5.6 | 5.5 | X58708 |
| Ccr2 | chemokine (C—C) receptor 2 | 1.0 | 6.9 | 3.9 | 23.1 | 30.9 | 39.4 | 22.4 | 9.4 | U47035 |
| Ccr2 | chemokine (C—C) receptor 2 | 1.9 | 3.2 | 3.6 | 13.4 | 17.7 | 17.5 | 14.1 | 7.8 | NM_009915 |
| Cd14 | CD14 antigen | 0.9 | 3.6 | 1.3 | 7.3 | 2.8 | 5.4 | 4.2 | 4.6 | NM_009841 |
| Cd44 | CD44 antigen | 1.1 | 3.7 | 2.1 | 9.8 | 14.3 | 29.6 | 28.9 | 25.0 | BC005676 |
| Cdc2a | cell division cycle 2 homolog A (*S. pombe*) | 0.3 | 3.4 | 1.3 | 5.1 | 5.0 | 5.3 | 3.6 | 3.7 | NM_007659 |
| Ch25h | cholesterol 25-hydroxylase | 1.0 | 2.1 | 1.4 | 6.7 | 8.0 | 12.3 | 6.7 | 12.7 | NM_009890 |
| Clca2 | chloride channel calcium activated 2 | 0.7 | 2.2 | 2.2 | 2.2 | 1.4 | 3.7 | 2.1 | 5.3 | AF108501 |
| Clca2 | chloride channel calcium activated 2 | 1.1 | 2.8 | 2.6 | 2.1 | 1.3 | 1.1 | 1.8 | 2.0 | AF108501 |
| Clecsf10 | C-type (calcium dependent, carbohydrate recognition domain) lectin, superfamily member 10 | 1.0 | 3.6 | 1.5 | 4.8 | 7.0 | 8.1 | 8.8 | 13.4 | NM_020001 |
| Clecsf10 | C-type (calcium dependent, carbohydrate recognition domain) lectin, superfamily member 10 | 1.0 | 4.0 | 1.3 | 5.0 | 6.8 | 16.5 | 10.4 | 19.5 | AF240358 |

TABLE 7-continued

Injury-induced RITs in rejection

| Gene Symbol | Gene Title | ISO D21 | ISO D7 | ISO D5 | WT D5 | WT D7 | WT D14 | WT D21 | WT D42 | Genbank |
|---|---|---|---|---|---|---|---|---|---|---|
| Clecsf6 | C-type (calcium dependent, carbohydrate recognition domain) lectin, superfamily member 6 | 1.1 | 4.3 | 3.8 | 4.7 | 7.0 | 12.8 | 14.3 | 14.4 | NM_011999 |
| Clecsf6 | C-type (calcium dependent, carbohydrate recognition domain) lectin, superfamily member 6 | 1.4 | 3.4 | 1.8 | 3.5 | 6.0 | 16.3 | 14.1 | 13.4 | BC006623 |
| Clecsf8 | C-type (calcium dependent, carbohydrate recognition domain) lectin, superfamily member 8 | 1.1 | 2.4 | 1.6 | 2.1 | 2.9 | 2.9 | 3.1 | 7.4 | NM_010819 |
| Clecsf9 | C-type (calcium dependent, carbohydrate recognition domain) lectin, superfamily member 9 | 1.0 | 4.3 | 2.8 | 16.2 | 18.5 | 12.2 | 7.5 | 11.6 | BC003218 |
| Col1a1 | procollagen, type I, alpha 1 | 0.4 | 2.0 | 1.3 | 5.0 | 8.4 | 4.8 | 9.1 | 3.4 | BI794771 |
| Col1a1 | procollagen, type I, alpha 1 | 2.0 | 6.8 | 1.9 | 11.3 | 26.7 | 18.9 | 31.4 | 17.8 | U08020 |
| Col1a2 | procollagen, type I, alpha 2 | 1.0 | 2.4 | 1.5 | 4.3 | 6.3 | 8.9 | 7.0 | 7.6 | BF227507 |
| Col1a2 | procollagen, type I, alpha 2 | 1.1 | 3.7 | 2.6 | 6.3 | 9.4 | 14.7 | 12.0 | 8.9 | AW545978 |
| Col3a1 | procollagen, type III, alpha 1 | 1.1 | 4.8 | 2.6 | 5.4 | 6.8 | 15.5 | 8.9 | 11.0 | BG968894 |
| Col3a1 | procollagen, type III, alpha 1 | 1.2 | 3.8 | 2.4 | 4.8 | 6.7 | 16.3 | 9.3 | 9.6 | AW550625 |
| Cp | ceruloplasmin | 0.5 | 2.6 | 1.6 | 2.8 | 1.2 | 2.9 | 2.6 | 1.6 | BB531328 |
| Cp | ceruloplasmin | 0.7 | 2.8 | 1.2 | 4.0 | 1.7 | 3.0 | 3.8 | 2.4 | BB009037 |
| Cp | ceruloplasmin | 0.9 | 3.1 | 1.5 | 3.5 | 2.9 | 3.5 | 5.2 | 2.2 | NM_007752 |
| Cp | ceruloplasmin | 0.9 | 3.1 | 1.7 | 4.4 | 1.8 | 3.0 | 4.1 | 2.3 | NM_007752 |
| Cp | ceruloplasmin | 1.0 | 2.9 | 1.7 | 3.8 | 1.6 | 3.1 | 3.6 | 2.1 | NM_007752 |
| Cpe | carboxypeptidase E | 1.3 | 2.5 | 2.5 | 2.2 | 1.3 | 1.3 | 1.6 | 0.9 | BC010197 |
| Crap | cardiac responsive adriamycin protein | 0.6 | 2.2 | 1.2 | 2.1 | 1.3 | 4.0 | 4.0 | 4.1 | AK009959 |
| Crap | cardiac responsive adriamycin protein | 0.7 | 3.5 | 1.8 | 3.3 | 1.6 | 7.4 | 6.3 | 9.3 | NM_013468 |
| Crlf1 | cytokine receptor-like factor 1 | 1.9 | 5.2 | 1.2 | 10.6 | 12.2 | 11.5 | 13.4 | 18.1 | NM_018827 |
| Cspg2 | chondroitin sulfate proteoglycan 2 | 0.7 | 2.2 | 1.3 | 4.0 | 3.7 | 11.3 | 5.2 | 11.1 | BI692925 |
| Cx3cr1 | chemokine (C—X3—C) receptor 1 | 1.3 | 2.0 | 1.8 | 2.5 | 3.0 | 4.7 | 7.2 | 4.1 | BC012653 |
| Cxcl13 | chemokine (C—X—C motif) ligand 13 | 1.2 | 2.9 | 1.3 | 3.6 | 2.3 | 1.3 | 2.0 | 1.8 | NM_018866 |
| Ddx3y | DEAD (Asp-Glu-Ala-Asp) box polypeptide 3, Y-linked | 3.0 | 2.5 | 3.2 | 2.1 | 2.5 | 3.0 | 3.0 | 2.9 | BB667072 |
| Ddx3y | DEAD (aspartate-glutamate-alanine-aspartate) box polypeptide, Y chromosome | 2.5 | 2.9 | 3.2 | 2.4 | 2.2 | 2.1 | 2.3 | 2.9 | AJ007376 |
| Ddx3y | DEAD (aspartate-glutamate-alanine-aspartate) box polypeptide, Y chromosome | 3.1 | 3.5 | 3.3 | 3.1 | 3.1 | 4.1 | 3.2 | 3.8 | AA210261 |
| Dpysl3 | dihydropyrimidinase-like 3 | 1.5 | 2.2 | 2.0 | 3.6 | 1.9 | 4.7 | 4.1 | 3.0 | AV161550 |
| Egr2 | early growth response 2 | 0.6 | 2.0 | 1.3 | 3.7 | 4.6 | 6.2 | 7.7 | 6.6 | X06746 |
| Eif2s3y | eukaryotic translation initiation factor 2, subunit 3, structural gene Y-linked | 2.4 | 2.8 | 2.4 | 2.9 | 2.4 | 3.6 | 2.9 | 3.0 | NM_012011 |
| Emr1 | EGF-like module containing, mucin-like, hormone receptor-like sequence 1 | 1.2 | 2.4 | 1.8 | 2.9 | 5.0 | 10.0 | 10.4 | 11.3 | U66888 |
| Evi2 | ecotropic viral integration site 2 | 1.1 | 2.2 | 2.3 | 5.8 | 7.7 | 12.8 | 9.4 | 8.9 | NM_010161 |
| F13a | coagulation factor XIII, alpha subunit | 1.2 | 2.5 | 1.7 | 2.8 | 2.9 | 3.7 | 3.2 | 9.3 | NM_028784 |
| Fbn1 | fibrillin 1 | 1.1 | 2.3 | 2.0 | 2.5 | 2.8 | 5.6 | 4.1 | 5.4 | NM_007993 |
| Fcgr1 | Fc receptor, IgG, high affinity I | 1.2 | 2.2 | 2.0 | 7.0 | 9.7 | 23.7 | 11.0 | 21.4 | AF143181 |
| Fcgr3 | Fc receptor, IgG, low affinity III | 1.2 | 3.0 | 2.1 | 5.2 | 8.3 | 25.9 | 17.6 | 30.6 | NM_010188 |
| Fga | fibrinogen, alpha polypeptide | 1.0 | 3.9 | 0.8 | 7.3 | 2.7 | 1.1 | 0.6 | 0.7 | BC005467 |
| Fn1 | fibronectin 1 | 1.1 | 2.3 | 1.6 | 2.1 | 3.1 | 7.6 | 7.6 | 7.8 | BC004724 |
| Fos | FBJ osteosarcoma oncogene | 0.9 | 2.1 | 1.2 | 5.3 | 5.6 | 9.6 | 5.7 | 7.6 | AV026617 |
| G7e-pending | G7e protein | 1.0 | 2.3 | 1.3 | 4.6 | 3.7 | 6.0 | 5.2 | 4.5 | NM_033075 |
| G7e-pending | G7e protein | 1.1 | 2.5 | 1.4 | 4.9 | 3.8 | 6.2 | 6.3 | 3.8 | BC027314 |
| Gm1549 | gene model 1549, (NCBI) | 1.1 | 1.2 | 2.2 | 2.6 | 2.2 | 2.7 | 1.1 | 2.6 | AJ319753 |
| Gp49b | glycoprotein 49 B | 1.4 | 5.2 | 2.6 | 10.1 | 13.9 | 28.0 | 17.8 | 32.0 | U05264 |
| Havcr1 | hepatitis A virus cellular receptor 1 | 0.5 | 4.2 | 1.4 | 3.1 | 1.0 | 3.1 | 0.7 | 1.3 | NM_134248 |
| Hmmr | hyaluronan mediated motility receptor (RHAMM) | 0.6 | 2.2 | 1.4 | 2.8 | 2.9 | 2.0 | 1.9 | 1.8 | NM_013552 |
| Igl-V1 | immunoglobulin lambda chain, variable 1 | 3.7 | 4.6 | 2.1 | 3.3 | 3.3 | 36.1 | 40.9 | 32.9 | AK008145 |
| Igsf6 | immunoglobulin superfamily, member 6 | 1.0 | 2.6 | 0.9 | 13.7 | 18.5 | 30.5 | 22.4 | 25.3 | NM_030691 |
| Il1b | interleukin 1 beta | 1.2 | 3.7 | 1.1 | 2.1 | 2.2 | 5.1 | 3.5 | 5.2 | BC011437 |
| Il1rn | interleukin 1 receptor antagonist | 0.9 | 3.1 | 1.7 | 4.7 | 3.9 | 11.8 | 5.5 | 12.5 | M57525 |
| Itgam | integrin alpha M (CD11b) | 1.2 | 3.8 | 2.1 | 5.5 | 7.9 | 11.0 | 8.8 | 10.8 | NM_008401 |
| Kif20a | kinesin family member 20A | 1.3 | 2.2 | 2.6 | 3.4 | 3.9 | 4.2 | 2.9 | 3.4 | NM_009004 |
| Kif22-ps | kinesin family member 22, pseudogene | 0.9 | 2.8 | 2.2 | 5.8 | 5.3 | 5.7 | 3.8 | 4.0 | BB251322 |
| Krt20 | keratin 20 | 1.1 | 2.4 | 1.5 | 2.9 | 1.5 | 8.7 | 7.8 | 11.8 | AF473907 |
| Lcn2 | lipocalin 2 | 1.0 | 15.4 | 2.2 | 27.6 | 11.8 | 40.9 | 35.8 | 53.0 | X14607 |
| Lcp1 | lymphocyte cytosolic protein 1 | 0.9 | 2.3 | 1.5 | 14.1 | 15.8 | 20.0 | 15.2 | 18.3 | BC022943 |
| Lgals1 | lectin, galactose binding, soluble 1 | 0.7 | 2.0 | 1.3 | 2.6 | 2.5 | 4.1 | 2.8 | 4.1 | AI642438 |
| Lgals1 | lectin, galactose binding, soluble 1 | 0.9 | 2.0 | 1.1 | 3.0 | 2.8 | 3.6 | 3.1 | 3.1 | NM_008495 |
| Lif | leukemia inhibitory factor | 1.8 | 3.3 | 1.4 | 4.5 | 3.8 | 3.8 | 3.7 | 4.7 | BB235045 |
| Lox | lysyl oxidase | 0.6 | 5.8 | 2.3 | 8.0 | 6.3 | 22.5 | 12.5 | 31.2 | M65143 |
| Lox | lysyl oxidase | 0.8 | 2.5 | 1.3 | 4.1 | 3.1 | 9.8 | 6.8 | 12.9 | NM_010728 |
| Lrg1 | leucine-rich alpha-2-glycoprotein | 1.3 | 6.3 | 0.5 | 8.3 | 2.5 | 5.3 | 5.2 | 4.2 | NM_029796 |
| Lyzs | lysozyme | 1.4 | 7.7 | 2.7 | 22.8 | 26.8 | 39.5 | 43.7 | 22.1 | AV058500 |
| Lyzs | lysozyme | 1.5 | 4.9 | 1.8 | 13.6 | 19.0 | 25.2 | 21.3 | 25.9 | AW208566 |
| Lyzs | lysozyme | 1.6 | 7.9 | 2.7 | 19.0 | 20.9 | 38.2 | 19.1 | 32.7 | AV066625 |
| Mad2l1 | MAD2 (mitotic arrest deficient, homolog)-like 1 (yeast) | 0.9 | 2.2 | 1.6 | 4.6 | 3.8 | 4.5 | 2.8 | 2.8 | NM_019499 |
| Mcmd | mini chromosome maintenance deficient (*S. cerevisiae*) | 1.3 | 1.8 | 2.2 | 6.1 | 5.7 | 5.1 | 5.0 | 3.6 | C80350 |

TABLE 7-continued

Injury-induced RITs in rejection

| Gene Symbol | Gene Title | ISO D21 | ISO D7 | ISO D5 | WT D5 | WT D7 | WT D14 | WT D21 | WT D42 | Genbank |
|---|---|---|---|---|---|---|---|---|---|---|
| Mcmd6 | mini chromosome maintenance deficient 6 (S. cerevisiae) | 1.0 | 2.0 | 1.8 | 4.5 | 5.2 | 4.4 | 3.7 | 3.0 | BB099487 |
| Mki67 | antigen identified by monoclonal antibody Ki 67 | 0.8 | 2.6 | 2.2 | 9.8 | 11.3 | 7.8 | 8.8 | 3.7 | X82786 |
| Ms4a6d | membrane-spanning 4-domains, subfamily A, member 6D | 0.9 | 5.6 | 3.3 | 19.7 | 33.6 | 53.6 | 29.3 | 39.4 | NM_026835 |
| Ms4a7 | membrane-spanning 4-domains, subfamily A, member 7 | 1.3 | 2.5 | 2.1 | 2.9 | 5.5 | 13.9 | 15.4 | 15.4 | BC024402 |
| Msn | moesin | 1.2 | 2.0 | 1.3 | 2.9 | 2.6 | 3.4 | 2.4 | 2.9 | NM_010833 |
| Ncf2 | neutrophil cytosolic factor 2 | 1.3 | 2.1 | 2.0 | 4.6 | 5.7 | 13.6 | 9.3 | 11.5 | NM_010877 |
| Osmr | oncostatin receptor | 1.0 | 2.4 | 1.8 | 3.5 | 2.7 | 4.3 | 5.5 | 4.7 | NM_011019 |
| Pira6 | paired-Ig-like receptor A6 | 1.2 | 2.4 | 2.2 | 6.9 | 9.6 | 16.9 | 9.2 | 8.4 | NM_011093 |
| Plac8 | placenta-specific 8 | 0.8 | 2.0 | 1.3 | 7.5 | 7.1 | 6.5 | 5.9 | 5.0 | AF263458 |
| Plek | pleckstrin | 0.9 | 2.6 | 2.3 | 8.3 | 11.9 | 18.2 | 12.5 | 15.4 | AF181829 |
| Postn | periostin, osteoblast specific factor | 1.0 | 2.8 | 2.5 | 2.7 | 2.9 | 8.0 | 7.2 | 14.4 | BI110565 |
| Prc1 | protein regulator of cytokinesis 1 | 0.7 | 2.4 | 3.1 | 5.4 | 4.3 | 6.0 | 3.7 | 3.6 | BC005475 |
| Ptgs2 | prostaglandin-endoperoxide synthase 2 | 0.8 | 4.8 | 2.0 | 4.1 | 6.9 | 13.4 | 5.6 | 9.3 | M88242 |
| Rad51ap1 | RAD51 associated protein 1 | 0.7 | 2.1 | 0.6 | 4.7 | 3.4 | 2.2 | 2.6 | 2.5 | BC003738 |
| Rarres2 | retinoic acid receptor responder (tazarotene induced) 2 | 2.2 | 2.4 | 1.3 | 3.6 | 2.7 | 7.4 | 5.9 | 6.5 | AV012073 |
| Rrm2 | ribonucleotide reductase M2 | 0.9 | 2.3 | 1.4 | 5.1 | 3.4 | 3.9 | 2.4 | 3.2 | NM_009104 |
| Rrm2 | ribonucleotide reductase M2 | 1.0 | 2.2 | 1.5 | 4.8 | 3.9 | 4.8 | 3.1 | 2.5 | AV301324 |
| Runx1 | runt related transcription factor 1 | 0.9 | 2.3 | 1.3 | 3.8 | 3.2 | 7.5 | 7.8 | 8.8 | BI696226 |
| S100a8 | S100 calcium binding protein A8 (calgranulin A) | 0.5 | 8.6 | 0.6 | 4.8 | 2.4 | 2.5 | 3.6 | 3.6 | NM_013650 |
| Saa1 | serum amyloid A 1 | 1.0 | 5.8 | 1.7 | 27.3 | 3.7 | 6.3 | 3.2 | 1.3 | NM_009117 |
| Saa2 | serum amyloid A 2 | 0.8 | 3.6 | 1.0 | 8.9 | 1.6 | 3.9 | 1.6 | 1.3 | NM_011314 |
| Saa3 | serum amyloid A 3 | 0.8 | 2.4 | 0.9 | 5.5 | 4.2 | 3.6 | 2.1 | 4.7 | NM_011315 |
| Serpine1 | serine (or cysteine) proteinase inhibitor, clade E, member 1 | 1.1 | 5.6 | 0.9 | 6.5 | 10.0 | 23.4 | 11.0 | 32.2 | NM_008871 |
| Slc25a24 | solute carrier family 25 (mitochondrial carrier, phosphate carrier), member 24 | 0.8 | 2.0 | 1.5 | 2.3 | 2.2 | 5.4 | 3.5 | 4.1 | BF578055 |
| Smcy | selected mouse cDNA on the Y | 2.2 | 2.5 | 2.4 | 2.3 | 2.8 | 2.3 | 2.7 | 2.1 | AF127244 |
| Smpdl3b | sphingomyelin phosphodiesterase, acid-like 3B | 1.0 | 2.5 | 1.6 | 4.9 | 3.4 | 8.8 | 5.5 | 5.7 | NM_133888 |
| Socs3 | suppressor of cytokine signaling 3 | 0.7 | 6.8 | 2.5 | 16.9 | 12.9 | 19.2 | 13.5 | 18.9 | BB241535 |
| Socs3 | suppressor of cytokine signaling 3 | 1.4 | 6.2 | 1.2 | 12.4 | 11.4 | 9.4 | 11.6 | 12.9 | BB831725 |
| Sprr2f | small proline-rich protein 2F | 0.8 | 5.8 | 1.4 | 2.4 | 1.1 | 46.4 | 26.1 | 22.6 | NM_011472 |
| Stk17b | serine/threonine kinase 17b (apoptosis-inducing) | 1.4 | 2.0 | 1.5 | 5.7 | 7.7 | 11.4 | 7.7 | 7.1 | BG064688 |
| Syncrip | synaptotagmin binding, cytoplasmic RNA interacting protein | 3.1 | 3.6 | 2.7 | 4.0 | 3.4 | 4.7 | 3.2 | 4.0 | BG920261 |
| Tapbpl | TAP binding protein-like | 0.8 | 1.2 | 2.3 | 8.7 | 7.4 | 7.4 | 6.9 | 5.1 | BC017613 |
| Tgfbi | transforming growth factor, beta induced, 68 kDa | 1.0 | 2.5 | 2.1 | 4.6 | 4.6 | 8.0 | 6.0 | 5.3 | BB532080 |
| Tiarp-pending | Tnfa-induced adipose-related protein | 1.0 | 3.4 | 1.4 | 4.1 | 1.4 | 1.3 | 2.4 | 2.1 | NM_054098 |
| Timd2 | T-cell immunoglobulin and mucin domain containing 2 | 1.8 | 2.7 | 2.4 | 2.5 | 1.6 | 1.6 | 0.5 | 1.0 | BC025096 |
| Timd2 | T-cell immunoglobulin and mucin domain containing 2 | 2.8 | 4.1 | 3.5 | 5.2 | 3.3 | 3.3 | 1.7 | 2.4 | BC028829 |
| Timp1 | tissue inhibitor of metalloproteinase 1 | 1.3 | 8.3 | 1.9 | 15.5 | 15.3 | 29.1 | 16.6 | 26.4 | BC008107 |
| Tnc | tenascin C | 0.3 | 3.3 | 1.4 | 2.4 | 3.3 | 4.4 | 5.5 | 10.4 | NM_011607 |
| Tnfrsf12a | tumor necrosis factor receptor superfamily, member 12a | 1.2 | 3.1 | 1.2 | 5.6 | 3.1 | 5.6 | 4.4 | 4.1 | NM_013749 |
| Tnfrsf12a | tumor necrosis factor receptor superfamily, member 12a | 1.2 | 2.3 | 1.2 | 4.9 | 2.7 | 4.8 | 4.3 | 2.9 | NM_013749 |
| Tpte | transmembrane phosphatase with tensin homology | 2.5 | 3.0 | 3.2 | 2.6 | 1.1 | 2.1 | 2.8 | 1.4 | AJ311312 |
| Tubb6 | tubulin, beta 6 | 0.8 | 5.8 | 1.0 | 13.5 | 12.0 | 13.0 | 11.2 | 21.8 | NM_026473 |
| Ugcg | UDP-glucose ceramide glucosyltransferase | 2.1 | 2.0 | 1.3 | 2.4 | 3.0 | 6.0 | 3.9 | 4.5 | NM_011673 |
| Uty | ubiquitously transcribed tetratricopeptide repeat gene, Y chromosome | 2.2 | 2.7 | 2.5 | 2.2 | 1.5 | 1.6 | 1.2 | 1.7 | NM_009484 |
| Vcam1 | vascular cell adhesion molecule 1 | 0.9 | 4.3 | 1.4 | 11.3 | 3.6 | 29.8 | 8.3 | 8.2 | L08431 |
| Vim | vimentin | 0.9 | 2.0 | 1.5 | 5.6 | 8.1 | 12.5 | 7.2 | 9.5 | AV147875 |
| Ywhag | 3-monooxgenase/tryptophan 5-monooxgenase activation protein, gamma polypeptide | 2.4 | 2.1 | 0.3 | 2.0 | 2.2 | 2.7 | 1.9 | 2.2 | NM_018871 |

TABLE 8

Functional annotation of injury-induced RIT

| Gene Symbol | Gene Title Affymetrix | ISO D7 vs NCBA | ISO D5 vs NCBA | WT D5 vs NCBA | IFN-γ regulated | Tgf-β1 regulated |
|---|---|---|---|---|---|---|
| Timp1 | tissue inhibitor of metalloproteinase 1 | 8.3 | 1.9 | 15.5 | yes | yes |
| Socs3 | suppressor of cytokine signaling 3 | 6.8 | 2.5 | 16.9 | yes | yes |
| Col3a1 | procollagen, type III, alpha 1 | 4.8 | 2.6 | 5.4 | *yes* | *yes* |

TABLE 8-continued

Functional annotation of injury-induced RIT

| Gene Symbol | Gene Title Affymetrix | ISO D7 vs NCBA | ISO D5 vs NCBA | WT D5 vs NCBA | IFN-γ regulated | Tgf-β1 regulated |
|---|---|---|---|---|---|---|
| Il1b | interleukin 1 beta | 3.7 | 1.1 | 2.1 | yes | |
| Cd14 | CD14 antigen | 3.6 | 1.3 | 7.3 | yes | yes |
| Adamts4 | a disintegrin-like and metalloprotease motif, 4 | 3.3 | 1.1 | 3.2 | | yes |
| Fcgr3 | Fc receptor, IgG, low affinity III | 3.0 | 2.1 | 5.2 | yes | |
| Ccl2 | chemokine (C—C motif) ligand 2 | 2.9 | 1.2 | 7.4 | yes | |
| Plek | pleckstrin | 2.6 | 2.3 | 8.3 | yes | |
| Cp | ceruloplasmin | 2.6 | 1.6 | 2.8 | yes | |
| Smpdl3b | sphingomyelin phosphodiesterase, acid-like 3B | 2.5 | 1.6 | 4.9 | yes | |
| Lox | lysyl oxidase | 2.5 | 1.3 | 4.1 | *yes* | *yes* |
| Tgfbi | transforming growth factor, beta induced, 68 kDa | 2.5 | 2.1 | 4.6 | yes | yes |
| Col1a2 | procollagen, type I, alpha 2 | 2.4 | 1.5 | 4.3 | *yes* | *yes* |
| Fbn1 | fibrillin 1 | 2.3 | 2.0 | 2.5 | | yes |
| Fn1 | fibronectin 1 | 2.3 | 1.6 | 2.1 | *yes* | *yes* |
| Fcgr1 | Fc receptor, IgG, high affinity I | 2.2 | 2.0 | 7.0 | yes | |
| Cspg2 | chondroitin sulfate proteoglycan 2 (Versican) | 2.2 | 1.3 | 4.0 | *yes* | *yes* |
| Arrb2 | similar to Beta-arrestin 2 (Arrestin, beta 2) | 2.1 | 1.0 | 5.2 | yes | |
| Fos | FBJ osteosarcoma oncogene | 2.1 | 1.2 | 5.3 | yes | |
| Ncf2 | neutrophil cytosolic factor 2 | 2.1 | 2.0 | 4.6 | yes | |
| Col1a1 | procollagen, type I, alpha 1 | 2.0 | 1.3 | 5.0 | *yes* | *yes* |
| Vim | vimentin | 2.0 | 1.5 | 5.6 | yes | yes |
| Casp12 | caspase 12 | 1.5 | 2.3 | 3.0 | yes | |
| Postn | periostin, osteoblast specific factor | 2.8 | 2.5 | 2.7 | | yes |

Bold letters indicate similar effects of cytokines, whereas italics indicate opposite effects.

Example 2

RITs and GRITs Identified Using a Second Algorithm

A second, more refined algorithm was used to identify RITs and GRITs. This method involved RMA (robust multi-chip analysis).

Revised GRITs Algorithm

Statistical analysis: Raw microarray data was pre-processed using an RMA method (Bioconductor 1.7; R version 2.2). Microarrays for control and treatment groups were pre-processed separately for each mouse strain combination. After preprocessing, data sets were subjected to variance-based filtering, i.e., all probe sets that had an inter-quartile range of less than 0.5 (log2 units), across all chips, were removed. Filtered data were then used for transcript selection. To be selected, a transcript was required to have a corrected p-value of 0.01 or lower, and had to be increased at least two-fold vs. appropriate controls. Corrected p-values (q-values) were calculated using the "limma" package (fdr adjustment method), which was uses an empirical Bayes method for assigning significance. The mean normalized value for replicate samples was used for further analysis. Finally, the data were imported into the GeneSpring™ 7.2 (Agilent, Palo Alto, Calif.) for further analyses and creation of transcript lists.

Selection and removal of transcripts associated with cytotoxic T cells: The previously defined CTL associated transcripts (CAT) selection was refined, using the transcriptome of CD8+ cells isolated from allo.CBA D5 into B6 allografts, and the CTL cell line transcriptome. Microarray data were normalized (GCOS/GeneSpring) to normal B6 kidneys. Transcripts expressed in the CTL line and in CD8 cells isolated from day 5 allografts (P flags in both samples) were selected based on their ≧5-fold expression vs. normal NCBA kidney. This selection yielded 1849 probe sets. These CTL and CD8-associated transcripts (expanded CATs) were removed from all transcript lists prior to any analysis. An exception was made for Psmb8, Psmb9 and Cc15 transcripts. Although prominently expressed in CTL, they also were expressed in rIFNg treated kidneys and/or a macrophage cell line.

Selection and removal of transcripts related to strain differences, somatically rearranged genes, and NK receptors: All probe sets showing differences in the basal signal (either 5-fold increased or decreased) between normal CBA, B6 and BALB/c kidneys were selected by the RMA-based method. These probe sets then were removed from the final transcript lists to reduce the influence of strain differences. Transcripts expressed by somatically rearranged genes, i.e., immunoglobulin genes, also were removed. In addition, transcripts for NK receptors of the Klr family were removed.

Development of the unique transcript lists: The term "transcript" refers to an mRNA identified by one or more numbered Affymetrix probe sets, while a "unique transcript" refers to an mRNA identified by only one probe set; these show the highest fold change of expression in the allografts at day 5 post-transplant. Certain probe sets representing the same transcript could appear in more than one list. These were arbitrarily kept only in the first list in which they appeared (e.g., tGRITs), and were eliminated from other lists (e.g., oGRITs, see below). All transcript name abbreviations use Entrez Gene nomenclature, which is available on the World Wide Web at ncbi.nlm.nih.gov/entrez).

IFN-γ-Dependent Rejection Induced Transcripts (GRITs)

Figure 8A:
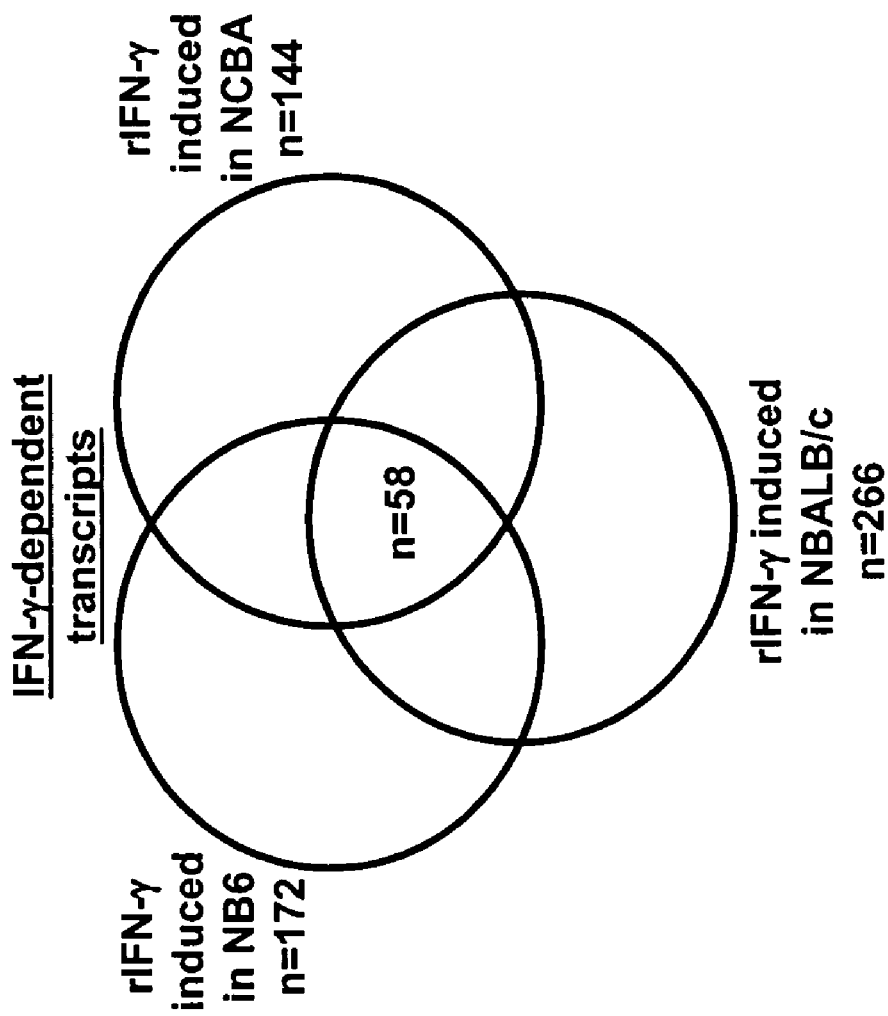
FIG. 8A is a diagram of an algorithm for identifying GRITs.
Figure 8B:
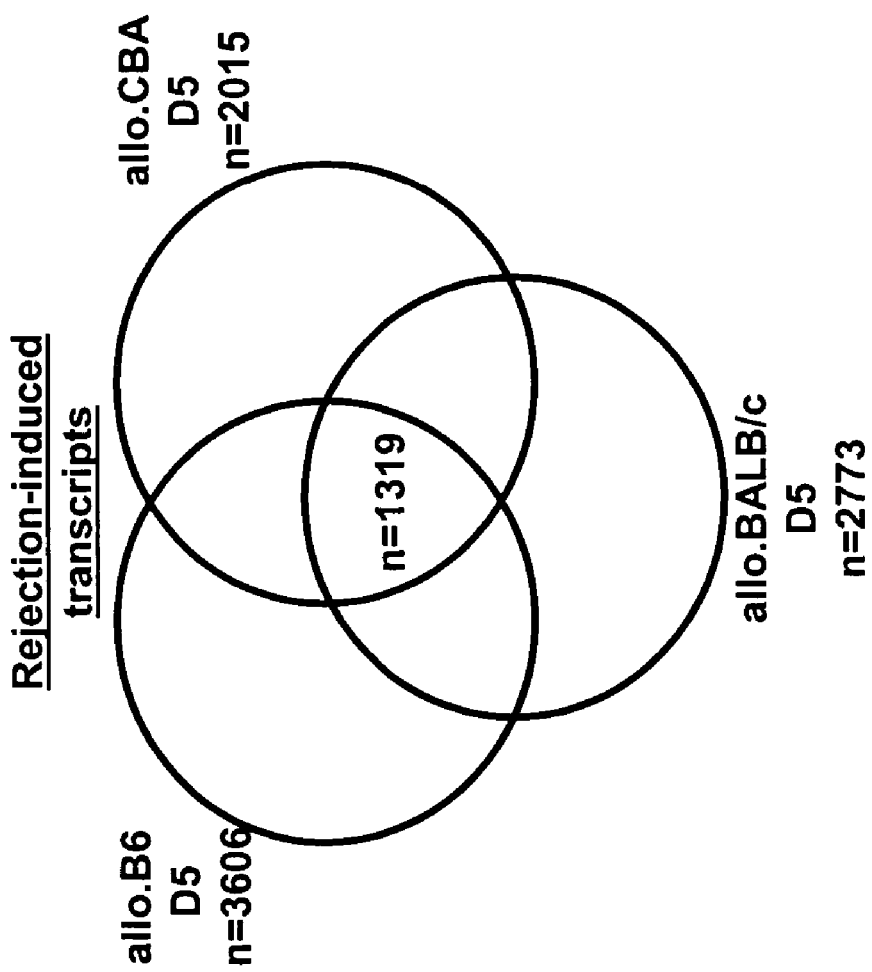
FIG. 8B is a diagram of an algorithm for identifying RITs.
Figure 8C:
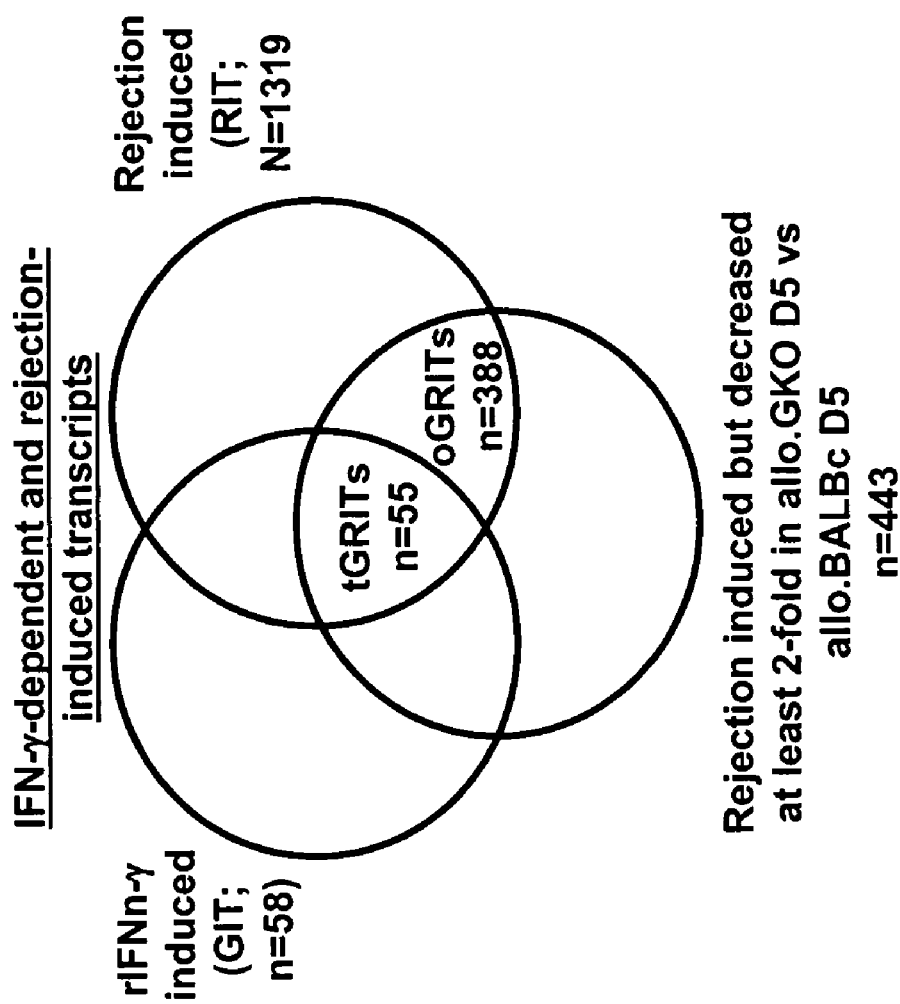
FIG. 8C is a diagram of an algorithm for identifying tGRITs and oGRITs.

The algorithms for transcript selection (applied after removing CATs and strain-differing transcripts) are shown in FIGS. 8A, 8B, and 8C. Fifty-eight transcripts were identified that were rIFN-γ-dependent in normal kidneys of CBA, B6 and BALB/c mice.

Transcripts increased at least 2-fold in day 5 allografts were termed "rejection-induced." The inflammatory changes at day 5 did not fulfill the histologic criteria for rejection (tubulitis), but the patterns established at day 5 were highly conserved as rejection lesions evolved. 1319 unique rejection-induced transcripts were identified in D5 kidney allografts of B6, CBA, and BALB/c strains (FIG. 8B).

Rejection-induced transcripts that were IFN-γ-dependent in rejection were identified by studying allografts in IFN-γ-deficient (GKO) hosts. Kidney allografts from wild-type BALB/c into B6 (allo.BALB/c) were compared to BALB/c.GKO donors (H-2d) transplanted into B6.GKO (H-2b) recipients (allo.GKO D5). 443 rejection-induced transcripts were identified that were at least 2-fold (signal ratio) greater when IFN-γ was present than when it was absent. Of these, 55 transcripts (47 of which were unique transcripts) also were increased by rIFN-γ (FIG. 8C, Table 9), and thus were labeled true interferon gamma dependent rejection-induced transcripts (tGRITs). The remaining transcripts, 270 of which were unique transcripts, were not 2-fold induced by rIFN-γ in normal kidneys, but nevertheless were IFN-γ dependent in rejecting kidneys (FIG. 8C). To reflect their lower inducibility by rIFN-7, these transcripts were termed "occult" GRITs (oGRITs; Table 10).

The "tGRIT" and "oGRIT" terms used in this example are equivalent to the "GRIT" term used in Example 1, i.e., the GRIT category includes tGRITs and oGRITs. On average, there was 70% overlap between the GRITs identified by the RMA method with the (GCOS/GeneSpring) method described in Example 1.

Injury and Repair Induced Transcripts (IRITs) Algorithm

Figure 9:
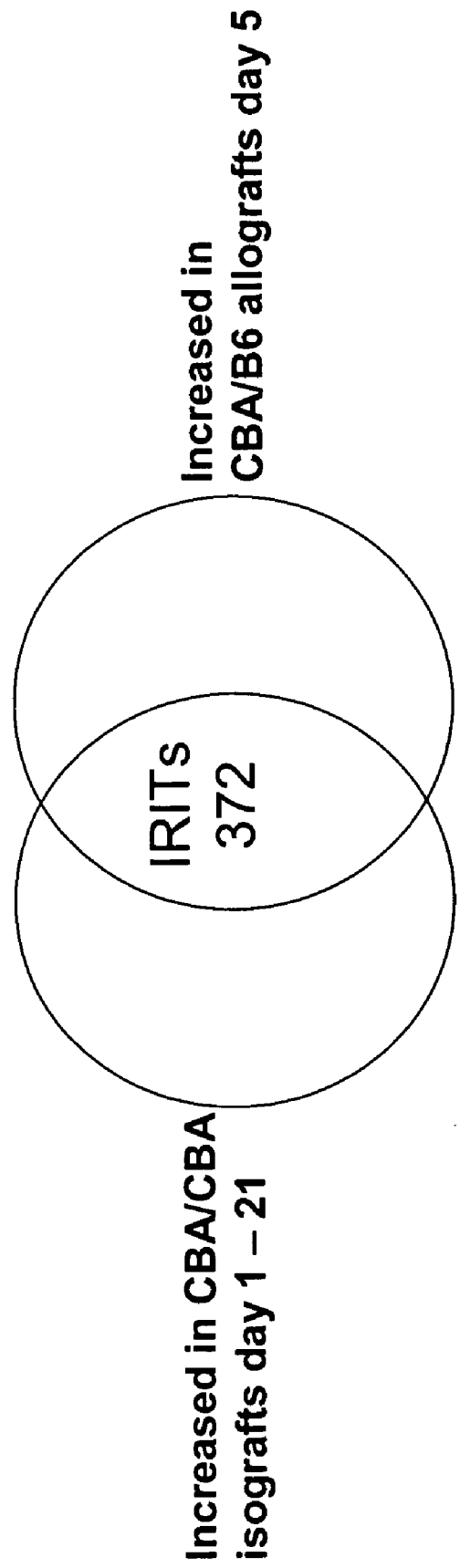
FIG. 9 is a diagram of an algorithm for identifying IRITs.

Transcript selection: Samples preprocessing, normalization and data filtering was done using the RMA-based method. Data also were corrected for the tGRITs, oGRITs and new CTL associated transcripts before transcript selection. The following algorithm was used (FIG. 9): transcripts were required to be increased in at least one of the isografts day 1-day 21 ($\geq$2-fold, p(fdr)=0.01, where "fdr" is the false discovery rate), and also in allo.CBA D5 ($\geq$2-fold, p(fdr)= 0.01). Transcripts satisfying these criteria were selected, and the overlapping 372 transcripts were termed injury and repair-induced transcripts (IRITs). The final list, corrected for polymorphisms, contained 303 unique (highest expression in allo.CBA D5 vs NCBA) IRITs (Table 11).

The IRITs listed in Table 11 show a substantial overlap with the RITs, the injury-induced RITs and the GRIT-like lists of transcripts established as described in Example 1. In addition, the IRITs recapitulate the Tgfb1 effect on the transcriptome of rejecting mouse kidneys, similarly to GRIT-like and injury-induced RITs.

TABLE 9

Refined true gamma interferon-dependent rejection-induced transcripts (tGRIT)

| Gene symbol | Gene title | NCBA raw | allo.CBA D5 vs NCBA | GenBank |
|---|---|---|---|---|
| — | — | 144 | 25.0 | BB734586 |
| AI451557 | expressed sequence AI451557 | 23 | 35.1 | AV277444 |
| AW112010 | expressed sequence AW112010 | 144 | 46.8 | BE688358 |
| B2m | beta-2 microglobulin | 3304 | 4.8 | AI099111 |
| Bst2 | bone marrow stromal cell antigen 2 | 134 | 12.9 | BC008532 |
| C1r | complement component 1, r subcomponent | 86 | 13.3 | NM_023143 |
| C2 | Complement component 2 (within H-2S), mRNA (cDNA clone MGC: 18582 IMAGE: 3992881) | 315 | 4.4 | AV227574 |
| Cxcl9 | chemokine (C—X—C motif) ligand 9 | 81 | 129.5 | NM_008599 |
| D12Ertd647e | DNA segment, Chr 12, ERATO Doi 647, expressed | 652 | 4.8 | AW554405 |
| Gbp2 | guanylate nucleotide binding protein 2 | 95 | 133.2 | NM_010260 |
| Gbp4 | guanylate nucleotide binding protein 4 | 68 | 54.4 | NM_018734 |
| H2-Aa /// H2-Ea | histocompatibility 2, class II antigen A, alpha /// histocompatibility 2, class II antigen E alpha | 926 | 10.2 | AF119253 |
| H2-Ab1 | histocompatibility 2, class II antigen A, beta 1 | 351 | 18.8 | M15848 |
| H2-D1 /// H2-K1 /// H2-L /// LOC56628 | histocompatibility 2, D region locus 1 /// histocompatibility 2, K1, K region /// histocompatibility 2, D region /// MHC (A.CA/J(H-2K-f) class I antigen | 230 | 17.2 | L23495 |
| H2-DMa | histocompatibility 2, class II, locus DMa | 100 | 21.2 | NM_010386 |
| H2-DMb1 | histocompatibility 2, class II, locus Mb1 | 58 | 19.2 | NM_010387 |
| H2-DMb1 /// H2-DMb2 | histocompatibility 2, class II, locus Mb1 /// histocompatibility 2, class II, locus Mb2 | 179 | 17.7 | NM_010388 |
| H2-DMb2 | histocompatibility 2, class II, locus Mb2 | 81 | 25.3 | NM_010388 |
| H2-Eb1 | histocompatibility 2, class II antigen E beta | 679 | 9.7 | NM_010382 |
| H2-K1 | histocompatibility 2, K1, K region | 373 | 15.8 | S70184 |
| H2-T10 /// H2-T22 /// H2-T9 | histocompatibility 2, T region locus 10 /// histocompatibility 2, T region locus 22 /// histocompatibility 2, T region locus 9 | 784 | 5.4 | NM_010395 |
| H2-T23 | histocompatibility 2, T region locus 23 | 862 | 9.5 | NM_010398 |
| Herc5 | hect domain and RLD 5 | 55 | 32.3 | AW208668 |
| Igtp | interferon gamma induced GTPase | 342 | 34.4 | NM_018738 |
| Ii | Ia-associated invariant chain | 1240 | 8.8 | BC003476 |
| Iigp1 | interferon inducible GTPase 1 | 99 | 69.1 | BM239828 |
| Iigp2 | interferon inducible GTPase 2 | 127 | 34.1 | NM_019440 |
| Il18bp | interleukin 18 binding protein | 116 | 19.6 | AF110803 |
| Irgm | immunity-related GTPase family, M | 485 | 14.5 | NM_008326 |

TABLE 9-continued

Refined true gamma interferon-dependent rejection-induced transcripts (tGRIT)

| Gene symbol | Gene title | NCBA raw | allo.CBA D5 vs NCBA | GenBank |
|---|---|---|---|---|
| Lgals3bp | lectin, galactoside-binding, soluble, 3 binding protein | 360 | 5.3 | NM_011150 |
| LOC56628 | MHC (A.CA/J(H-2K-f) class I antigen | 63 | 3.8 | M58156 |
| Mpa2l | macrophage activation 2 like | 50 | 174.1 | BM241485 |
| Mpeg1 | macrophage expressed gene 1 | 217 | 18.8 | L20315 |
| Oasl2 | 2'-5' oligoadenylate synthetase-like 2 | 56 | 22.8 | BQ033138 |
| Parp14 | poly (ADP-ribose) polymerase family, member 14 | 95 | 19.1 | BC021340 |
| Psmb10 | proteasome (prosome, macropain) subunit, beta type 10 | 251 | 16.2 | NM_013640 |
| Psmb8 | proteasome (prosome, macropain) subunit, beta type 8 (large multifunctional peptidase 7) | 205 | 29.6 | NM_010724 |
| Psmb9 | proteasome (prosome, macropain) subunit, beta type 9 (large multifunctional peptidase 2) | 142 | 25.3 | NM_013585 |
| Psme1 | proteasome (prosome, macropain) 28 subunit, alpha | 1008 | 4.5 | NM_011189 |
| Serpina10 | serine (or cysteine) peptidase inhibitor, clade A (alpha-1 antiproteinase, antitrypsin), member 10 | 95 | 44.9 | BC018416 |
| Serping1 | serine (or cysteine) peptidase inhibitor, clade G, member 1 | 721 | 7.0 | NM_009776 |
| Stat1 | signal transducer and activator of transcription 1 | 350 | 23.9 | AW214029 |
| Tap1 | transporter 1, ATP-binding cassette, sub-family B (MDR/TAP) | 60 | 24.0 | AW048052 |
| Tapbp | TAP binding protein | 962 | 6.1 | AF043943 |
| Tgtp | T-cell specific GTPase | 481 | 32.6 | NM_011579 |
| Ubd | ubiquitin D | 47 | 255.8 | NM_023137 |
| Xdh | xanthine dehydrogenase | 53 | 16.7 | AV286265 |

TABLE 10

Refined occult gamma interferon-dependent rejection-induced transcripts (oGRIT)

| Gene Symbol | Gene Title | NCBA Raw | allo.CBA D5 vs NCBA | Gen Bank |
|---|---|---|---|---|
| 1-Mar | membrane-associated ring finger (C3HC4) 1 | 21 | 7.4 | BB134696 |
| 6-Sep | septin 6 | 81 | 4.0 | BC010489 |
| — | — | 307 | 2.7 | AV340322 |
| — | — | 261 | 3.4 | AV340322 |
| — | — | 50 | 2.9 | BG695418 |
| — | — | 51 | 15.6 | BB668084 |
| — | Transcribed locus | 28 | 3.2 | BB376947 |
| — | Transcribed locus | 52 | 60.2 | AW111920 |
| — | Transcribed locus | 12 | 3.1 | BG144448 |
| — | — | 15 | 2.9 | BQ266693 |
| — | Transcribed locus, weakly similar to NP_795929.1 hypothetical protein LOC319587 [Mus musculus] | 17 | 5.4 | BB740904 |
| — | 16 days neonate thymus cDNA, RIKEN full-length enriched library, clone: A130050C20 product: hypothetical Butyrophylin-like/SPla/RYanodine receptor SPRY/B302, (SPRY)-like containing protein, full insert sequence | 113 | 5.8 | BI653857 |
| — | — | 15 | 4.9 | BG072508 |
| — | — | 32 | 11.8 | BB558917 |
| 0610025L06Rik | RIKEN cDNA 0610025L06 gene | 183 | 3.9 | AK012581 |
| 0610033I05Rik | RIKEN cDNA 0610033I05 gene | 137 | 3.5 | BC003333 |
| 1110007F12Rik | RIKEN cDNA 1110007F12 gene | 422 | 3.7 | BC020080 |
| 1110038F14Rik | RIKEN cDNA 1110038F14 gene | 187 | 2.0 | NM_054099 |
| 1500004A08Rik | RIKEN cDNA 1500004A08 gene | 109 | 2.5 | BB030508 |
| 1810009K13Rik | RIKEN cDNA 1810009K13 gene | 136 | 2.1 | AK007407 |
| 1810054D07Rik | RIKEN cDNA 1810054D07 gene | 15 | 4.1 | BB397062 |
| 2310016F22Rik /// | RIKEN cDNA 2310016F22 gene /// | 39 | 11.0 | BC020489 |

TABLE 10-continued

Refined occult gamma interferon-dependent rejection-induced transcripts (oGRIT)

| Gene Symbol | Gene Title | NCBA Raw | allo.CBA D5 vs NCBA | Gen Bank |
|---|---|---|---|---|
| LOC223672 | hypothetical protein LOC223672 | | | |
| 2700019D07Rik | RIKEN cDNA 2700019D07 gene | 160 | 2.7 | BM937429 |
| 2810417H13Rik | RIKEN cDNA 2810417H13 gene | 14 | 16.9 | AK017673 |
| 4933430F08Rik | RIKEN cDNA 4933430F08 gene | 128 | 6.4 | AK016990 |
| 5133401N09Rik | RIKEN cDNA 5133401N09 gene | 464 | 2.5 | BC026742 |
| 5830443L24Rik | RIKEN cDNA 5830443L24 gene | 49 | 115.5 | NM_029509 |
| 5830458K16Rik | RIKEN cDNA 5830458K16 gene | 149 | 13.3 | BC024872 |
| 9130017N09Rik | RIKEN cDNA 9130017N09 gene | 163 | 2.6 | BQ030875 |
| 9330175E14Rik | RIKEN cDNA 9330175E14 gene | 27 | 2.7 | BB082472 |
| 9530028C05 | hypothetical protein 9530028C05 | 80 | 5.0 | BQ175154 |
| 9830147J24Rik | RIKEN cDNA 9830147J24 gene | 46 | 56.7 | BM241271 |
| A430107D22Rik | RIKEN cDNA A430107D22 gene | 60 | 3.4 | AV312663 |
| A630077B13Rik | RIKEN cDNA A630077B13 gene | 17 | 92.0 | BB239429 |
| AB124611 | cDNA sequence AB124611 | 33 | 10.5 | BM246462 |
| Adar | RNA adenosine deaminase 1 (Adar) mRNA, complete cds, alternatively spliced | 30 | 3.3 | BB308291 |
| AI447904 | expressed sequence AI447904 | 12 | 44.0 | BM241008 |
| AI447904 /// BC094916 | expressed sequence AI447904 /// cDNA sequence BC094916 | 32 | 29.7 | BM241008 |
| AI451617 | expressed sequence AI451617 | 19 | 11.2 | BM241342 |
| AI480535 | expressed sequence AI480535 | 517 | 2.5 | BQ176847 |
| AI607873 | expressed sequence AI607873 | 10 | 11.6 | AI607873 |
| AI661384 | expressed sequence AI661384 | 11 | 5.3 | BB034038 |
| Aif1 | allograft inflammatory factor 1 | 47 | 23.0 | NM_019467 |
| Ak7 | adenylate kinase 7 | 231 | 3.0 | AV256298 |
| Akt3 | thymoma viral proto-oncogene 3 | 74 | 3.5 | BB521695 |
| Arid5a | AT rich interactive domain 5A (Mrf1 like) | 74 | 3.0 | BC027152 |
| Asah1 | N-acylsphingosine amidohydrolase (acid ceramidase)-like | 140 | 6.8 | BI106821 |
| Atp8a1 | ATPase, aminophospholipid transporter (APLT), class I, type 8A, member 1 | 67 | 6.0 | AW610650 |
| AU020206 | expressed sequence AU020206 | 69 | 12.1 | BI151331 |
| B230217C12Rik | RIKEN cDNA B230217C12 gene | 30 | 3.3 | BB376573 |
| BC006779 | cDNA sequence BC006779 | 95 | 4.9 | BE853170 |
| BC010462 | cDNA sequence BC010462 | 84 | 4.1 | BC010462 |
| BC013672 | cDNA sequence BC013672 | 12 | 3.8 | BC013672 |
| BC013712 | cDNA sequence BC013712 | 97 | 9.6 | BB262491 |
| BC023105 | cDNA sequence BC023105 | 20 | 42.8 | BC023105 |
| BC027057 | cDNA sequence BC027057 | 24 | 3.9 | BB040051 |
| Btla | B and T lymphocyte associated | 29 | 8.8 | BM240873 |
| C1s | complement component 1, s subcomponent | 156 | 13.0 | BC022123 |
| C2ta | class II transactivator | 29 | 9.5 | AF042158 |
| C2ta | class II transactivator | 40 | 6.7 | AF042158 |
| C4 | complement component 4 (within H-2S) | 367 | 6.9 | NM_009780 |
| Card4 | caspase recruitment domain 4 | 132 | 3.0 | BB138330 |
| Casp1 | caspase 1 | 44 | 9.6 | BC008152 |
| Casp11 | caspase 11, apoptosis-related cysteine peptidase | 39 | 13.6 | NM_007609 |
| Casp12 | caspase 12 | 33 | 9.5 | NM_009808 |
| Casp7 | caspase 7 | 140 | 4.0 | NM_007611 |
| Ccl19 | chemokine (C—C motif) ligand 19 | 305 | 2.1 | NM_011888 |
| Ccl5 | chemokine (C—C motif) ligand 5 | 75 | 36.7 | NM_013653 |
| Ccl8 | chemokine (C—C motif) ligand 8 | 36 | 22.0 | NM_021443 |
| Ccr5 | chemokine (C—C motif) receptor 5 | 24 | 11.5 | X94151 |
| Ccr9 | chemokine (C—C motif) receptor 9 | 16 | 2.4 | AJ131357 |
| Ccrl2 | chemokine (C—C motif) receptor-like 2 | 73 | 2.7 | AJ318863 |
| Cd2 | CD2 antigen | 26 | 8.4 | NM_013486 |
| Cd274 | CD274 antigen | 50 | 27.3 | NM_021893 |
| Cd28 | CD28 antigen | 13 | 21.6 | NM_007642 |
| Cd40 | CD40 antigen | 70 | 7.1 | BB220422 |
| Cd48 | CD48 antigen | 29 | 25.5 | BE634960 |
| Cd5 | CD5 antigen | 21 | 10.0 | NM_007650 |
| Cd6 | CD6 antigen | 57 | 3.0 | U12434 |
| Cd69 | CD69 antigen | 12 | 6.4 | AK017979 |
| Cd72 | CD72 antigen | 40 | 5.7 | BC003824 |
| Cd86 | CD86 antigen | 27 | 8.8 | NM_019388 |
| Cerkl | ceramide kinase-like | 34 | 13.8 | BB205589 |
| Clec2d | C-type lectin domain family 2, member d | 211 | 3.1 | NM_053109 |
| Csprs | component of Sp100-rs | 84 | 2.8 | BB148221 |
| Ctsc | cathepsin C | 13 | 9.7 | BM237633 |
| Ctsw | cathepsin W | 49 | 11.9 | NM_009985 |

TABLE 10-continued

Refined occult gamma interferon-dependent rejection-induced transcripts (oGRIT)

| Gene Symbol | Gene Title | NCBA Raw | allo.CBA D5 vs NCBA | Gen Bank |
|---|---|---|---|---|
| Cxcl10 | chemokine (C—X—C motif) ligand 10 | 69 | 95.2 | NM_021274 |
| Cxcl11 | chemokine (C—X—C motif) ligand 11 | 37 | 169.3 | NM_019494 |
| Cxcl16 | chemokine (C—X—C motif) ligand 16 | 652 | 3.3 | BC019961 |
| Cxcl16 /// LOC574428 | chemokine (C—X—C motif) ligand 16 /// zinc finger, MYND domain containing 15 | 99 | 2.9 | AI662455 |
| Cxcr3 | chemokine (C—X—C motif) receptor 3 | 60 | 8.2 | NM_009910 |
| Cxcr6 | chemokine (C—X—C motif) receptor 6 | 28 | 15.4 | AF301018 |
| Cybb | cytochrome b-245, beta polypeptide | 52 | 21.8 | NM_007807 |
| Cyp4v3 | cytochrome P450, family 4, subfamily v, polypeptide 3 | 49 | 3.5 | NM_133969 |
| D11Ertd759e | DNA segment, Chr 11, ERATO Doi 759, expressed | 363 | 5.0 | AW556558 |
| D11Lgp2e | DNA segment, Chr 11, Lothar Hennighausen 2, expressed | 42 | 6.8 | AF316999 |
| D14Ertd668e | DNA segment, Chr 14, ERATO Doi 668, expressed | 115 | 6.5 | AV280841 |
| Dck | deoxycytidine kinase | 13 | 7.8 | NM_007832 |
| Dnase1l3 | deoxyribonuclease 1-like 3 | 28 | 6.3 | BC012671 |
| Dtx3l | deltex 3-like (Drosophila) | 136 | 12.0 | AV327407 |
| Eif2ak2 | eukaryotic translation initiation factor 2-alpha kinase 2 | 81 | 3.2 | BE911144 |
| Eif4e3 | eukaryotic translation initiation factor 4E member 3 | 162 | 5.2 | BC027014 |
| Enc1 | ectodermal-neural cortex 1 | 77 | 4.4 | BM120053 |
| Epsti1 | epithelial stromal interaction 1 (breast) | 37 | 20.0 | BF020640 |
| Evl | Ena-vasodilator stimulated phosphoprotein | 45 | 8.3 | AW553781 |
| Fabp7 | fatty acid binding protein 7, brain | 259 | 6.6 | NM_021272 |
| Fas | Fas (TNF receptor superfamily member) | 85 | 3.2 | NM_007987 |
| Fbxo39 | F-box protein 39 | 168 | 11.3 | BB645745 |
| Fbxo6b | F-box only protein 6b | 301 | 2.8 | NM_015797 |
| Fbxw17 | F-box and WD-40 domain protein 17 | 181 | 3.3 | AV016303 |
| Fcgr1 | Fc receptor, IgG, high affinity I | 35 | 20.5 | AF143181 |
| Fcgr1 | Fc receptor, IgG, high affinity I | 80 | 2.6 | BB075261 |
| Fcgr3a | Fc fragment of IgG, low affinity IIIa, receptor | 47 | 22.5 | BC027310 |
| Fgd2 | FYVE, RhoGEF and PH domain containing 2 | 66 | 2.2 | NM_013710 |
| Fgf13 | fibroblast growth factor 13 | 18 | 2.0 | AF020737 |
| Fgl2 | fibrinogen-like protein 2 | 31 | 45.9 | BF136544 |
| Fyb | FYN binding protein (Fyb), mRNA | 31 | 4.2 | BE853428 |
| G1p2 | interferon, alpha-inducible protein | 40 | 17.2 | AK019325 |
| Gbp1 | guanylate nucleotide binding protein 1 | 22 | 23.9 | NM_010259 |
| Gdap10 | ganglioside-induced differentiation-associated-protein 10 | 99 | 4.8 | NM_010268 |
| Gimap3 | GTPase, IMAP family member 3 | 91 | 6.2 | NM_031247 |
| Gimap4 | GTPase, IMAP family member 4 | 677 | 3.6 | BC005577 |
| Gimap7 | GTPase, IMAP family member 7 | 28 | 12.3 | BC026200 |
| Gja4 | gap junction membrane channel protein alpha 4 | 86 | 2.0 | AF216832 |
| Gm376 | PREDICTED: similar to putative purinergic receptor FKSG79 [Mus musculus], mRNA sequence | 9 | 3.7 | BB241847 |
| Gpr18 | G protein-coupled receptor 18 | 32 | 10.8 | BG145550 |
| Gsdmdc1 | gasdermin domain containing 1 | 119 | 4.1 | AK007710 |
| Gvin1 | GTPase, very large interferon inducible 1 | 98 | 43.2 | BM243571 |
| Gzmk | granzyme K | 23 | 6.2 | AB032200 |
| H28 | histocompatibility 28 | 106 | 10.0 | BC024930 |
| H2-D1 | histocompatibility 2, D region locus 1 | 43 | 10.0 | M33151 |
| H2-M3 | histocompatibility 2, M region locus 3 | 106 | 6.5 | NM_013819 |
| H2-Oa | histocompatibility 2, O region alpha locus | 43 | 4.6 | NM_008206 |
| H2-Q5 | histocompatibility 2, Q region locus 5 | 40 | 5.5 | NM_010393 |
| H2-Q8 | histocompatibility 2, Q region locus 8 | 23 | 2.2 | AK013097 |
| H2-T24 | histocompatibility 2, T region locus 24 | 46 | 3.6 | L22338 |
| Hck | hemopoietic cell kinase | 41 | 18.7 | NM_010407 |
| Hk3 | hexokinase 3 | 84 | 2.9 | BB324660 |
| Hpse | Heparanase (Hpse), mRNA | 42 | 5.6 | BG094050 |
| Hrasls3 | HRAS like suppressor 3 | 166 | 20.1 | BB404920 |
| Ibrdc3 | IBR domain containing 3 | 133 | 8.4 | AK015966 |
| Icos | inducible T-cell co-stimulator | 21 | 5.4 | AB023132 |
| Ifi202b | interferon activated gene 202B | 27 | 64.8 | AV229143 |

TABLE 10-continued

Refined occult gamma interferon-dependent rejection-induced transcripts (oGRIT)

| Gene Symbol | Gene Title | NCBA Raw | allo.CBA D5 vs NCBA | Gen Bank |
|---|---|---|---|---|
| Ifi203 /// Ifi204 /// Ifi205 /// Mnda /// LOC545386 | interferon activated gene 203 /// interferon activated gene 204 /// interferon activated gene 205 /// myeloid cell nuclear differentiation antigen /// similar to Interferon-activatable protein 205 (IFI-205) (D3 protein) | 11 | 82.9 | AI481797 |
| Ifi203 /// LOC547362 | interferon activated gene 203 /// similar to interferon-inducible protein 203 | 64 | 10.1 | BC008167 |
| Ifi204 /// Mnda | interferon activated gene 204 /// myeloid cell nuclear differentiation antigen | 13 | 13.7 | NM_008329 |
| Ifi205 /// Mnda | interferon activated gene 205 /// myeloid cell nuclear differentiation antigen | 29 | 92.9 | AI481797 |
| Ifi27 | interferon, alpha-inducible protein 27 | 119 | 7.4 | AY090098 |
| Ifi35 | interferon-induced protein 35 | 406 | 6.6 | AW986054 |
| Ifi44 | interferon-induced protein 44 | 121 | 8.0 | BB329808 |
| Ifi47 | interferon gamma inducible protein 47 | 196 | 40.5 | NM_008330 |
| Ifih1 | interferon induced with helicase C domain 1 | 181 | 5.5 | AY075132 |
| Ifit1 | interferon-induced protein with tetratricopeptide repeats 1 | 29 | 23.3 | NM_008331 |
| Ifit2 | interferon-induced protein with tetratricopeptide repeats 2 | 125 | 32.5 | NM_008332 |
| Ifit3 | interferon-induced protein with tetratricopeptide repeats 3 | 317 | 6.6 | NM_010501 |
| IFNg | interferon gamma | 25 | 22.9 | K00083 |
| Il10ra | interleukin 10 receptor, alpha | 29 | 4.8 | NM_008348 |
| Il12rb1 | interleukin 12 receptor, beta 1 | 32 | 2.4 | NM_008353 |
| Il16 | interleukin 16 | 88 | 2.6 | BC026894 |
| Il18 | interleukin 18 | 141 | 2.6 | NM_008360 |
| Il2rb | interleukin 2 receptor, beta chain | 55 | 4.7 | M28052 |
| Il2rb | interleukin 2 receptor, beta chain | 27 | 8.6 | M28052 |
| Il2rg | interleukin 2 receptor, gamma chain | 121 | 18.6 | L20048 |
| Indo | indoleamine-pyrrole 2,3 dioxygenase | 21 | 2.6 | NM_008324 |
| Inpp1 | inositol polyphosphate-1-phosphatase | 63 | 3.0 | NM_008384 |
| Irf1 | interferon regulatory factor 1 | 312 | 14.9 | NM_008390 |
| Irf7 | interferon regulatory factor 7 | 118 | 6.4 | NM_016850 |
| Irf8 | interferon regulatory factor 8 | 157 | 12.0 | BG069095 |
| Irg1 | immunoresponsive gene 1 | 31 | 17.9 | L38281 |
| Isg20 | interferon-stimulated protein | 51 | 5.4 | BC022751 |
| Itgal | integrin alpha L | 41 | 2.9 | AF065902 |
| Itgal | integrin alpha L | 41 | 20.3 | BI554446 |
| Lair1 | leukocyte-associated Ig-like receptor 1 | 29 | 7.8 | AK017222 |
| Lck | lymphocyte protein tyrosine kinase | 40 | 25.5 | BC011474 |
| LOC432460 | similar to RIKEN cDNA 6330442E10 gene | 23 | 2.7 | BB302103 |
| LOC544986 /// LOC544991 /// LOC544997 /// B930046C15Rik /// LOC545001 /// LOC545005 /// LOC545007 /// LOC545008 /// 2610042L04Rik /// LOC545017 | similar to hypothetical protein LOC67055 /// similar to hypothetical protein LOC67055 /// similar to hypothetical protein LOC67055 /// RIKEN cDNA B930046C15 gene /// hypothetical protein LOC545001 /// hypothetical protein LOC545005 /// hypothetical protein LOC545007 /// similar to hypothetical protein LOC67055 /// RIKEN cDNA 2610042L04 gene /// similar to hypothetical protein LOC67055 | 47 | 7.3 | BM195235 |
| LOC547214 | similar to G protein coupled receptor | 14 | 3.8 | AF140709 |
| Lst1 | leukocyte specific transcript 1 | 125 | 8.9 | U72644 |
| Ly6c | lymphocyte antigen 6 complex, locus C | 1041 | 3.9 | NM_010741 |
| Ly6i | lymphocyte antigen 6 complex, locus I | 125 | 11.2 | AF232024 |
| Ly75 | lymphocyte antigen 75 | 12 | 3.7 | NM_013825 |
| MGI: 1933403 | type 1 tumor necrosis factor receptor shedding aminopeptidase regulator | 154 | 4.7 | NM_030711 |
| Mlkl | mixed lineage kinase domain-like | 37 | 14.3 | AK018636 |
| Ms4a4b | membrane-spanning 4-domains, subfamily A, member 4B | 18 | 92.0 | BB199001 |
| Ms4a4c | membrane-spanning 4-domains, subfamily A, member 4C | 11 | 48.3 | NM_022429 |
| Ms4a4d | membrane-spanning 4-domains, subfamily A, member 4D | 31 | 15.2 | NM_025658 |

TABLE 10-continued

Refined occult gamma interferon-dependent rejection-induced transcripts (oGRIT)

| Gene Symbol | Gene Title | NCBA Raw | allo.CBA D5 vs NCBA | Gen Bank |
|---|---|---|---|---|
| Ms4a6b | membrane-spanning 4-domains, subfamily A, member 6B | 30 | 70.6 | NM_027209 |
| Ms4a6c | membrane-spanning 4-domains, subfamily A, member 6C | 106 | 14.0 | AF237910 |
| Mx1 | myxovirus (influenza virus) resistance 1 | 22 | 3.8 | M21039 |
| Myb | myeloblastosis oncogene | 10 | 2.9 | BC011513 |
| Nkg7 | natural killer cell group 7 sequence | 57 | 23.5 | NM_024253 |
| Nmi | N-myc (and STAT) interactor | 267 | 7.2 | BC002019 |
| Oas1a | 2'-5' oligoadenylate synthetase 1A | 119 | 8.7 | BC018470 |
| Oasl1 | 2'-5' oligoadenylate synthetase-like 1 | 48 | 8.4 | AB067533 |
| P2ry13 | purinergic receptor P2Y, G-protein coupled 13 | 35 | 3.4 | AK008013 |
| P2ry14 | purinergic receptor P2Y, G-protein coupled, 14 | 57 | 3.1 | AF177211 |
| Parp11 | poly (ADP-ribose) polymerase family, member 11 | 155 | 2.7 | BB026163 |
| Parp12 | poly (ADP-ribose) polymerase family, member 12 | 161 | 8.6 | BM227980 |
| Parp3 | poly (ADP-ribose) polymerase family, member 3 | 141 | 4.4 | BC014870 |
| Parp9 | poly (ADP-ribose) polymerase family, member 9 | 179 | 12.0 | NM_030253 |
| Parvg | parvin, gamma | 41 | 2.5 | NM_022321 |
| Pbef1 | pre-B-cell colony-enhancing factor 1 | 823 | 3.1 | AW989410 |
| Pigr | polymeric immunoglobulin receptor | 857 | 3.7 | NM_011082 |
| Plac8 | placenta-specific 8 | 208 | 21.7 | AF263458 |
| Pml | promyelocytic leukemia | 58 | 2.7 | BB667149 |
| Pnp | purine-nucleoside phosphorylase | 2805 | 2.1 | BC003788 |
| Pnp /// LOC545044 | purine-nucleoside phosphorylase /// similar to purine-nucleoside phosphorylase | 1262 | 2.7 | AK008143 |
| Ppa1 | pyrophosphatase (inorganic) 1 | 609 | 3.6 | NM_026438 |
| Ppfia4 | protein tyrosine phosphatase, receptor type, f polypeptide (PTPRF), interacting protein (liprin), alpha 4 | 35 | 2.8 | AK003571 |
| Prkcq | protein kinase C, theta | 118 | 3.0 | AB062122 |
| Procr | protein C receptor, endothelial | 101 | 4.5 | NM_011171 |
| Psme2 | proteasome (prosome, macropain) 28 subunit, beta | 709 | 6.2 | NM_011190 |
| Ptprcap | protein tyrosine phosphatase, receptor type, C polypeptide-associated protein | 141 | 3.7 | NM_016933 |
| Rasa4 | RAS p21 protein activator 4 | 32 | 2.3 | NM_133914 |
| Rbl1 | retinoblastoma-like 1 (p107) | 82 | 8.2 | U27177 |
| Rgs1 | regulator of G-protein signaling 1 | 45 | 8.0 | NM_015811 |
| Rnase6 | ribonuclease, RNase A family, 6 | 31 | 4.8 | AW825994 |
| Rsad2 | radical S-adenosyl methionine domain containing 2 | 433 | 3.0 | BB132493 |
| Samhd1 | SAM domain and HD domain, 1 | 119 | 18.7 | NM_018851 |
| Scap1 | src family associated phosphoprotein 1 | 39 | 2.9 | BG075562 |
| Sectm1 | secreted and transmembrane 1 | 1125 | 4.0 | AI481997 |
| Serpina3g | serine (or cysteine) peptidase inhibitor, clade A, member 3G | 44 | 98.9 | BC002065 |
| Serpinb9 | serine (or cysteine) peptidase inhibitor, clade B, member 9 | 390 | 6.5 | NM_009256 |
| Sh2d1a | SH2 domain protein 1A | 12 | 3.5 | NM_011364 |
| Slamf6 | SLAM family member 6 | 19 | 12.8 | AF248636 |
| Slamf7 | SLAM family member 7 | 23 | 4.2 | AK016183 |
| Slamf8 | SLAM family member 8 | 18 | 45.2 | BC024587 |
| Slc28a2 /// LOC381417 | solute carrier family 28 (sodium-coupled nucleoside transporter), member 2 /// similar to solute carrier family 28 (sodium-coupled nucleoside transporter), member 2 | 14 | 8.5 | NM_021520 |
| Slc2a6 | solute carrier family 2 (facilitated glucose transporter), member 6 | 33 | 3.0 | BB196807 |
| Slfn1 | schlafen 1 | 24 | 17.5 | NM_011407 |
| Slfn8 | schlafen 8 | 55 | 4.3 | BC024709 |
| Snx10 | sorting nexin 10 | 103 | 17.3 | AK010399 |
| Socs1 | suppressor of cytokine signaling 1 | 45 | 5.3 | AB000710 |
| Sp100 | nuclear antigen Sp100 | 81 | 2.7 | U83636 |
| Stat2 | signal transducer and activator of transcription 2 | 50 | 5.0 | AF088862 |
| Tap2 | transporter 2, ATP-binding cassette, sub-family B (MDR/TAP) | 171 | 11.3 | BE691515 |

TABLE 10-continued

Refined occult gamma interferon-dependent rejection-induced transcripts (oGRIT)

| Gene Symbol | Gene Title | NCBA Raw | allo.CBA D5 vs NCBA | Gen Bank |
|---|---|---|---|---|
| Tapbpl | TAP binding protein-like | 21 | 3.6 | BC017613 |
| Tapbpl | TAP binding protein-like | 131 | 5.7 | BC017613 |
| Tbc1d10c | TBC1 domain family, member 10c | 58 | 6.8 | AV060417 |
| Tbx21 | T-box 21 | 18 | 5.5 | NM_019507 |
| Tcf7 | transcription factor 7, T-cell specific | 32 | 9.3 | AI323642 |
| Tinagl | tubulointerstitial nephritis antigen-like | 500 | 2.4 | BC005738 |
| Tlr3 | toll-like receptor 3 | 43 | 2.6 | NM_126166 |
| Tmprss4 | transmembrane protease, serine 4 | 65 | 3.2 | BC021368 |
| Tnfrsf14 | tumor necrosis factor receptor superfamily, member 14 (herpesvirus entry mediator) | 43 | 3.2 | BC022125 |
| Tnfrsf7 | tumor necrosis factor receptor superfamily, member 7 | 23 | 5.5 | L24495 |
| Tnfsf10 | tumor necrosis factor (ligand) superfamily, member 10 | 118 | 5.9 | NM_009425 |
| Tor3a | torsin family 3, member A | 63 | 4.8 | AK009693 |
| Tox | thymocyte selection-associated HMG box gene | 22 | 5.3 | BB547854 |
| Tpst1 | protein-tyrosine sulfotransferase 1 | 132 | 2.9 | NM_013837 |
| Trafd1 | TRAF type zinc finger domain containing 1 | 237 | 4.3 | AK003586 |
| Treml4 | triggering receptor expressed on myeloid cells-like 4 | 13 | 6.2 | BB740529 |
| Trex1 | three prime repair exonuclease 1 | 157 | 3.8 | NM_011637 |
| Trim21 | tripartite motif protein 21 | 125 | 5.1 | BC010580 |
| Trim30 | tripartite motif protein 30 | 48 | 11.5 | AF220015 |
| Trim34 /// LOC434218 | tripartite motif protein 34 /// similar to tripartite motif protein TRIM34 alpha | 29 | 9.7 | AF220142 |
| Tuba8 | tubulin, alpha 8 | 37 | 3.0 | NM_017379 |
| Tyki | thymidylate kinase family LPS-inducible member | 131 | 3.1 | AK004595 |
| Ube1l | ubiquitin-activating enzyme E1-like | 61 | 6.2 | AK004894 |
| Ube2l6 | ubiquitin-conjugating enzyme E2L 6 | 50 | 7.8 | BC008238 |
| Unc93b1 | unc-93 homolog B1 (*C. elegans*) | 368 | 1.9 | BC018388 |
| Upp1 | uridine phosphorylase 1 | 135 | 10.3 | NM_009477 |
| Usp18 | ubiquitin specific peptidase 18 | 50 | 29.5 | NM_011909 |
| Vcam1 | vascular cell adhesion molecule 1 | 112 | 45.1 | BB250384 |
| Wars | tryptophanyl-tRNA synthetase | 322 | 3.3 | AI528863 |
| Zap70 | zeta-chain (TCR) associated protein kinase | 43 | 6.4 | NM_009539 |
| Zbp1 | Z-DNA binding protein 1 | 75 | 23.3 | AK008179 |
| Zc3h12d | zinc finger CCCH-type containing 12D | 19 | 6.7 | BB508669 |
| Zfpn1a3 | zinc finger protein, subfamily 1A, 3 (Aiolos) | 16 | 14.6 | BB151746 |

TABLE 11

Refined injury and repair-induced transcripts (IRIT)

| Gene Symbol | Gene Title | allo.CBA D5 vs NCBA | Genbank |
|---|---|---|---|
| — | Transcribed locus | 2.8 | AA266723 |
| 1110006O17Rik | RIKEN cDNA 1110006O17 gene | 4.6 | BB736636 |
| 1200008O12Rik | RIKEN cDNA 1200008O12 gene | 12.5 | AK004655 |
| 1200016E24Rik | RIKEN cDNA 1200016E24 gene | 4.5 | BF719154 |
| 1300002K09Rik | RIKEN cDNA 1300002K09 gene | 4.7 | AV222559 |
| 2200002D01Rik | RIKEN cDNA 2200002D01 gene | 2.2 | AK008617 |
| 2310014H01Rik | RIKEN cDNA 2310014H01 gene | 5.2 | AK009340 |
| 2410006H16Rik | RIKEN cDNA 2410006H16 gene | 2.3 | AA939619 |
| 2410129E14Rik | RIKEN cDNA 2410129E14 gene | 3.9 | AA986082 |
| 2610510J17Rik | RIKEN cDNA 2610510J17 gene | 2.3 | BM230253 |
| 2810052M02Rik | RIKEN cDNA 2810052M02 gene | 3.8 | NM_023320 |
| 2810406C15Rik | RIKEN cDNA 2810406C15 gene | 4.8 | BC025460 |
| 4833427B12Rik | RIKEN cDNA 4833427B12 gene | 3.1 | AW488914 |
| 4930579G24Rik | RIKEN cDNA 4930579G24 gene | 2.8 | BB821990 |
| 9030408N13Rik | RIKEN cDNA 9030408N13 gene | 10.9 | NM_025779 |
| 9030623C06Rik | RIKEN cDNA 9030623C06 gene | 3.6 | AF473907 |
| 9230117N10Rik | RIKEN cDNA 9230117N10 gene | 13.0 | NM_133775 |
| Abca1 | ATP-binding cassette, sub-family A (ABC1), member 1 | 2.3 | BB144704 |

TABLE 11-continued

Refined injury and repair-induced transcripts (IRIT)

| Gene Symbol | Gene Title | allo.CBA D5 vs NCBA | Genbank |
|---|---|---|---|
| Abp1 | amiloride binding protein 1 (amine oxidase, copper-containing) | 6.3 | BC021880 |
| Acta2 | actin, alpha 2, smooth muscle, aorta | 2.0 | NM_007392 |
| Actn1 | actinin, alpha 1 | 3.9 | BE853286 |
| Adam12 | a disintegrin and metallopeptidase domain 12 (meltrin alpha) | 2.0 | NM_007400 |
| Adam8 | a disintegrin and metallopeptidase domain 8 | 4.2 | NM_007403 |
| Adamts1 | a disintegrin-like and metallopeptidse (reprolysin type) with thrombospondin type 1 motif, 1 | 6.0 | D67076 |
| Adamts4 | a disintegrin-like and metallopeptidase (reprolysin type) with thrombospondin type 1 motif, 4 | 2.2 | BB443585 |
| Adfp | adipose differentiation related protein | 3.6 | NM_007408 |
| Adn | adipsin | 3.5 | NM_013459 |
| Aldh1a2 | aldehyde dehydrogenase family 1, subfamily A2 | 11.2 | NM_009022 |
| Alox5ap | arachidonate 5-lipoxygenase activating protein | 16.8 | BC026209 |
| Anln | anillin, actin binding protein (scraps homolog, Drosophila) | 4.6 | BI690018 |
| Anxa1 | annexin A1 | 3.2 | NM_010730 |
| Anxa2 | annexin A2 | 3.4 | NM_007585 |
| Anxa3 | annexin A3 | 4.0 | AW702161 |
| Apobec1 | apolipoprotein B editing complex 1 | 3.5 | BC003792 |
| Arg2 | arginase type II | 7.9 | NM_009705 |
| Arhgap11a | Rho GTPase activating protein 11A | 3.1 | AV349116 |
| Arpc1b | actin related protein 2/3 complex, subunit 1B | 7.8 | BE979985 |
| Asf1b | ASF1 anti-silencing function 1 homolog B (S. cerevisiae) | 4.4 | BC003428 |
| Asns | asparagine synthetase | 6.1 | AV212753 |
| Atad2 | ATPase family, AAA domain containing 2 | 6.0 | BM206009 |
| Aurka | aurora kinase A | 4.5 | U80932 |
| Aurkb | aurora kinase B | 4.6 | BC003261 |
| AW492955 | expressed sequence AW492955 | 3.3 | AW492955 |
| Bak1 | BCL2-antagonist/killer 1 | 3.4 | NM_007523 |
| Basp1 | brain abundant, membrane attached signal protein 1 | 8.6 | AK011545 |
| Bcl3 | B-cell leukemia/lymphoma 3 | 3.8 | NM_033601 |
| Bgn | biglycan | 2.6 | BC019502 |
| Birc3 | baculoviral IAP repeat-containing 3 | 6.6 | NM_007464 |
| Brrn1 | barren homolog (Drosophila) | 4.4 | BB725358 |
| Bub1 | budding uninhibited by benzimidazoles 1 homolog (S. cerevisiae) | 7.4 | AF002823 |
| C1qa | complement component 1, q subcomponent, alpha polypeptide | 12.6 | NM_007572 |
| C1qb | complement component 1, q subcomponent, beta polypeptide | 40.7 | BB111335 |
| C1qg | complement component 1, q subcomponent, gamma polypeptide | 15.2 | NM_007574 |
| C3 | complement component 3 | 40.6 | K02782 |
| C330027C09Rik | RIKEN cDNA C330027C09 gene | 4.3 | AU018569 |
| C3ar1 | complement component 3a receptor 1 | 5.9 | NM_009779 |
| C79407 | expressed sequence C79407 | 3.5 | BE951628 |
| Capg | capping protein (actin filament), gelsolin-like | 7.4 | NM_007599 |
| Ccl12 | chemokine (C—C motif) ligand 12 | 14.5 | U50712 |
| Ccl2 | chemokine (C—C motif) ligand 2 | 11.0 | AF065933 |
| Ccl6 | chemokine (C—C motif) ligand 6 | 10.6 | BC002073 |
| Ccl9 | chemokine (C—C motif) ligand 9 | 9.3 | AF128196 |
| Ccna2 | cyclin A2 | 7.3 | X75483 |
| Ccnb1 | cyclin B1 | 6.4 | AU015121 |
| Ccnb1-rs1 /// Ccnb1 | cyclin B1, related sequence 1 /// cyclin B1 | 5.3 | NM_007629 |
| Ccnb2 | cyclin B2 | 7.8 | AK013312 |
| Ccnf | cyclin F | 2.4 | NM_007634 |
| Ccr1 | chemokine (C—C motif) receptor 1 | 9.8 | AV231648 |
| Ccr2 | chemokine (C—C motif) receptor 2 | 21.3 | BB148128 |
| Ccr2 | chemokine (C—C motif) receptor 2 | 18.1 | BB148128 |
| Cd14 | CD14 antigen | 20.8 | NM_009841 |
| Cd52 | CD52 antigen | 31.9 | NM_013706 |
| Cd68 | CD68 antigen | 11.9 | BC021637 |
| Cdc20 | cell division cycle 20 homolog (S. cerevisiae) | 5.8 | BB041150 |
| Cdca1 | cell division cycle associated 1 | 5.7 | AK010351 |

TABLE 11-continued

Refined injury and repair-induced transcripts (IRIT)

| Gene Symbol | Gene Title | allo.CBA D5 vs NCBA | Genbank |
|---|---|---|---|
| Cdca3 | cell division cycle associated 3 | 3.7 | BI081061 |
| Cdca5 | cell division cycle associated 5 | 3.2 | NM_026410 |
| Cdca8 | cell division cycle associated 8 | 3.7 | AV307110 |
| Cdh11 | cadherin 11 | 3.8 | NM_009866 |
| Cdkn1a | cyclin-dependent kinase inhibitor 1A (P21) | 3.9 | AK007630 |
| Cebpb | CCAAT/enhancer binding protein (C/EBP), beta | 3.8 | NM_009883 |
| Cebpd | CCAAT/enhancer binding protein (C/EBP), delta | 8.0 | BB831146 |
| Cenpf | centromere autoantigen F | 3.3 | BE848253 |
| Cfh | complement component factor h | 2.3 | AI987976 |
| Cfi | complement component factor i | 3.0 | NM_007686 |
| Chrnb1 | cholinergic receptor, nicotinic, beta polypeptide 1 (muscle) | 2.3 | M14537 |
| Ckap2 | cytoskeleton associated protein 2 | 2.9 | BM208103 |
| Ckap4 | cytoskeleton-associated protein 4 | 2.1 | BB818012 |
| Cklfsf3 | chemokine-like factor super family 3 | 3.4 | NM_024217 |
| Clca1 /// Clca2 | chloride channel calcium activated 1 /// chloride channel calcium activated 2 | 3.7 | AF108501 |
| Clec4a2 | C-type lectin domain family 4, member a2 | 3.0 | NM_011999 |
| Clec4a2 /// Clec4b | C-type lectin domain family 4, member a2 /// C-type lectin domain family 4, member b | 2.7 | BC006623 |
| Clec4a3 | C-type lectin domain family 4, member a3 | 23.8 | AK014135 |
| Clec4n | C-type lectin domain family 4, member n | 6.6 | NM_020001 |
| Clec7a | C-type lectin domain family 7, member a | 13.0 | NM_020008 |
| Clu | clusterin | 3.6 | AV152288 |
| Cnn2 | calponin 2 | 3.9 | BI663014 |
| Col15a1 | procollagen, type XV | 2.1 | AF011450 |
| Col1a1 | procollagen, type I, alpha 1 | 8.5 | BI794771 |
| Col1a2 | procollagen, type I, alpha 2 | 9.6 | BF227507 |
| Col1a2 | procollagen, type I, alpha 2 | 5.4 | BF227507 |
| Col3a1 | procollagen, type III, alpha 1 | 13.4 | AW550625 |
| Col5a1 | procollagen, type V, alpha 1 | 3.6 | AW744319 |
| Col5a2 | procollagen, type V, alpha 2 | 7.2 | AV229424 |
| Col6a1 | procollagen, type VI, alpha 1 | 2.1 | NM_009933 |
| Col6a2 | procollagen, type VI, alpha 2 | 2.4 | BI455189 |
| Col6a3 | procollagen, type VI, alpha 3 | 2.7 | AF064749 |
| Col8a1 | procollagen, type VIII, alpha 1 | 3.1 | AV292255 |
| Colec12 | collectin sub-family member 12 | 2.4 | NM_130449 |
| Cp | ceruloplasmin | 6.8 | BB332449 |
| Cp | ceruloplasmin | 6.0 | BB009037 |
| Crlf1 | cytokine receptor-like factor 1 | 3.9 | NM_018827 |
| Cry1 | cryptochrome 1 (photolyase-like) | 2.3 | BG069864 |
| Csrp1 | cysteine and glycine-rich protein 1 | 2.4 | BF124540 |
| Cstb | cystatin B | 3.8 | NM_007793 |
| Ctsc | cathepsin C | 10.5 | NM_009982 |
| Ctss | cathepsin S | 19.4 | NM_021281 |
| Cx3cl1 | chemokine (C—X3—C motif) ligand 1 | 2.3 | AF010586 |
| Cxcl1 | chemokine (C—X—C motif) ligand 1 | 10.9 | NM_008176 |
| Cxcl14 | chemokine (C—X—C motif) ligand 14 | 10.6 | AF252873 |
| Cybb | cytochrome b-245, beta polypeptide | 21.0 | AV373944 |
| D17H6S56E-5 | DNA segment, Chr 17, human D6S56E 5 | 9.6 | NM_033075 |
| Dcamkl1 | Double cortin and calcium/calmodulin-dependent protein kinase-like 1, mRNA (cDNA clone IMAGE: 5006471) | 9.2 | BB757120 |
| Dck | deoxycytidine kinase | 11.8 | BB030204 |
| Dpt | dermatopontin | 3.2 | NM_019759 |
| Dpysl3 | dihydropyrimidinase-like 3 | 2.5 | AV162270 |
| Ect2 | ect2 oncogene | 3.3 | NM_007900 |
| Efemp2 | epidermal growth factor-containing fibulin-like extracellular matrix protein 2 | 2.0 | NM_021474 |
| Efhd2 | EF hand domain containing 2 | 5.6 | AK007560 |
| Emilin1 | elastin microfibril interfacer 1 | 2.1 | NM_133918 |
| Emr1 | EGF-like module containing, mucin-like, hormone receptor-like sequence 1 | 4.9 | U66888 |
| Entpd1 | ectonucleoside triphosphate diphosphohydrolase 1 | 4.0 | BI151440 |
| Ercc6l | excision repair cross-complementing rodent repair deficiency complementation group 6 - like | 2.9 | BC004701 |
| Esco2 | establishment of cohesion 1 homolog 2 (S. cerevisiae) | 3.7 | AK010391 |
| F13a1 | coagulation factor XIII, A1 subunit | 6.2 | NM_028784 |
| F2r | coagulation factor II (thrombin) receptor | 3.3 | AV024285 |
| Fbn1 | fibrillin 1 | 4.0 | NM_007993 |

TABLE 11-continued

Refined injury and repair-induced transcripts (IRIT)

| Gene Symbol | Gene Title | allo.CBA D5 vs NCBA | Genbank |
|---|---|---|---|
| Fcer1g | Fc receptor, IgE, high affinity I, gamma polypeptide | 16.5 | NM_010185 |
| Fcgr3 | Fc receptor, IgG, low affinity III | 14.4 | NM_010188 |
| Fga | fibrinogen, alpha polypeptide | 8.6 | BC005467 |
| Fgg | fibrinogen, gamma polypeptide | 3.1 | NM_133862 |
| Fignl1 | fidgetin-like 1 | 6.4 | NM_021891 |
| Flna | filamin, alpha | 2.9 | BM233746 |
| Fn1 | fibronectin 1 | 2.8 | BC004724 |
| Fshprh1 | FSH primary response 1 | 2.1 | BB258991 |
| Fstl1 | follistatin-like 1 | 4.5 | BI452727 |
| Fxyd5 | FXYD domain-containing ion transport regulator 5 | 8.7 | NM_008761 |
| Gch1 | GTP cyclohydrolase 1 | 2.4 | NM_008102 |
| Gda | guanine deaminase | 16.3 | AW911807 |
| Golph2 | golgi phosphoprotein 2 | 2.4 | BC011152 |
| H2afx | H2A histone family, member X | 2.0 | NM_010436 |
| Havcr1 | hepatitis A virus cellular receptor 1 | 7.8 | NM_134248 |
| Hells | helicase, lymphoid specific | 10.2 | NM_008234 |
| Hesx1 | homeo box gene expressed in ES cells | 2.7 | NM_010420 |
| Hmga1 | high mobility group AT-hook 1 | 2.8 | NM_016660 |
| Hmmr | hyaluronan mediated motility receptor (RHAMM) | 3.3 | X64550 |
| Hp | haptoglobin | 5.9 | NM_017370 |
| Icam1 | intercellular adhesion molecule | 10.5 | BC008626 |
| Ifitm1 | interferon induced transmembrane protein 1 | 5.2 | BC027285 |
| Ifitm3 | interferon induced transmembrane protein 3 | 5.0 | BC010291 |
| Il1b | interleukin 1 beta | 3.3 | BC011437 |
| Il6 | interleukin 6 | 10.3 | NM_031168 |
| Inhbb | inhibin beta-B | 4.7 | BB253137 |
| Isgf3g | interferon dependent positive acting transcription factor 3 gamma | 3.6 | NM_008394 |
| Itgam | integrin alpha M | 6.5 | NM_008401 |
| Kdelr3 | KDEL (Lys-Asp-Glu-Leu) endoplasmic reticulum protein retention receptor 3 | 2.4 | NM_134090 |
| Kif11 | kinesin family member 11 | 4.7 | BM234447 |
| Kif20a | kinesin family member 20A | 2.4 | NM_009004 |
| Kif22 | kinesin family member 22 | 8.2 | BB251322 |
| Kif2c | kinesin family member 2C | 4.0 | BB104669 |
| Klf4 | Kruppel-like factor 4 (gut) | 2.7 | BG069413 |
| Lbp | lipopolysaccharide binding protein | 4.6 | NM_008489 |
| Lcn2 | lipocalin 2 | 57.7 | X14607 |
| Lcp1 | lymphocyte cytosolic protein 1 | 16.8 | NM_008879 |
| Lepr | leptin receptor | 2.4 | BM124366 |
| Lgals1 | lectin, galactose binding, soluble 1 | 3.5 | AI642438 |
| Lgals3 | lectin, galactose binding, soluble 3 | 3.9 | X16834 |
| Lhfp | lipoma HMGIC fusion partner | 2.0 | AV149705 |
| Lig1 | ligase I, DNA, ATP-dependent | 3.4 | NM_010715 |
| Lilrb3 | leukocyte immunoglobulin-like receptor, subfamily B (with TM and ITIM domains), member 3 | 7.3 | U96693 |
| Litaf | LPS-induced TN factor | 4.5 | AV360881 |
| Lmna | lamin A | 2.4 | AV238225 |
| Lox | lysyl oxidase | 7.5 | M65143 |
| Lrg1 | leucine-rich alpha-2-glycoprotein 1 | 4.5 | NM_029796 |
| Lum | lumican | 2.8 | AK014312 |
| Ly86 | lymphocyte antigen 86 | 21.0 | NM_010745 |
| Lyzs | lysozyme | 26.8 | AW208566 |
| Lzp-s | P lysozyme structural | 22.0 | AV066625 |
| Mad2l1 | MAD2 (mitotic arrest deficient, homolog)-like 1 (yeast) | 3.6 | NM_019499 |
| Marcks | myristoylated alanine rich protein kinase C substrate | 2.8 | AW546141 |
| Marcksl1 | MARCKS-like 1 | 4.7 | AV110584 |
| Mcm2 | minichromosome maintenance deficient 2 mitotin (S. cerevisiae) | 3.5 | NM_008564 |
| Mcm3 | minichromosome maintenance deficient 3 (S. cerevisiae) | 4.9 | C80350 |
| Mcm4 | minichromosome maintenance deficient 4 homolog (S. cerevisiae) | 5.1 | BC013094 |
| Mcm7 | minichromosome maintenance deficient 7 (S. cerevisiae) | 2.7 | BB464359 |
| Melk | maternal embryonic leucine zipper kinase | 4.4 | NM_010790 |
| Mfap5 | microfibrillar associated protein 5 | 8.0 | NM_015776 |
| Mgp | matrix Gla protein | 3.0 | NM_008597 |

TABLE 11-continued

Refined injury and repair-induced transcripts (IRIT)

| Gene Symbol | Gene Title | allo.CBA D5 vs NCBA | Genbank |
|---|---|---|---|
| Mgst1 | microsomal glutathione S-transferase 1 | 2.1 | BI150149 |
| Mmd | monocyte to macrophage differentiation-associated | 2.0 | BC021914 |
| Mmp14 | matrix metallopeptidase 14 (membrane-inserted) | 4.5 | NM_008608 |
| Mmp7 | matrix metallopeptidase 7 | 4.1 | NM_010810 |
| Ms4a7 | membrane-spanning 4-domains, subfamily A, member 7 | 5.5 | BC024402 |
| Mt2 | metallothionein 2 | 5.3 | AA796766 |
| Mvp | major vault protein | 3.5 | NM_080638 |
| Myadm | myeloid-associated differentiation marker | 2.5 | BB500055 |
| Myc | myelocytomatosis oncogene | 3.5 | BC006728 |
| Myh9 | myosin, heavy polypeptide 9, non-muscle | 2.4 | C80049 |
| Ncf1 | neutrophil cytosolic factor 1 | 6.8 | BE370703 |
| Nek2 | NIMA (never in mitosis gene a)-related expressed kinase 2 | 2.2 | C77054 |
| Nek6 | NIMA (never in mitosis gene a)-related expressed kinase 6 | 2.6 | BB528391 |
| Nfkbia | nuclear factor of kappa light chain gene enhancer in B-cells inhibitor, alpha | 4.8 | AI462015 |
| Nfkbiz | nuclear factor of kappa light polypeptide gene enhancer in B-cells inhibitor, zeta | 18.1 | AB026551 |
| Nrm | nurim (nuclear envelope membrane protein) | 2.0 | NM_134122 |
| Nuak2 | NUAK family, SNF1-like kinase, 2 | 2.1 | AK004737 |
| Nusap1 | nucleolar and spindle associated protein 1 | 7.4 | BC009096 |
| Olfml3 | olfactomedin-like 3 | 2.0 | NM_133859 |
| Osmr | oncostatin M receptor | 7.9 | AB015978 |
| P2ry6 | pyrimidinergic receptor P2Y, G-protein coupled, 6 | 5.9 | BC027331 |
| Pbk | PDZ binding kinase | 3.5 | NM_023209 |
| Pdgfrb | platelet derived growth factor receptor, beta polypeptide | 2.0 | AA499047 |
| Pdlim7 | PDZ and LIM domain 7 | 2.8 | AK010339 |
| Pdxk | pyridoxal (pyridoxine, vitamin B6) kinase | 2.0 | BG063905 |
| Pea15 | phosphoprotein enriched in astrocytes 15 | 2.3 | AI323543 |
| Pfc | properdin factor, complement | 5.0 | BB800282 |
| Pik3ap1 | phosphoinositide-3-kinase adaptor protein 1 | 5.3 | BI684288 |
| Pld4 | phospholipase D family, member 4 | 13.0 | BB210623 |
| Plk4 | polo-like kinase 4 (Drosophila) | 6.0 | AI385771 |
| Plp2 | proteolipid protein 2 | 2.5 | AK012816 |
| Pltp | phospholipid transfer protein | 2.7 | NM_011125 |
| Pola1 | polymerase (DNA directed), alpha 1 | 2.9 | NM_008892 |
| Pole | polymerase (DNA directed), epsilon | 3.3 | NM_011132 |
| Prc1 | protein regulator of cytokinesis 1 | 2.6 | BC005475 |
| Ptger4 | prostaglandin E receptor 4 (subtype EP4) | 6.3 | BC011193 |
| Ptgfrn | prostaglandin F2 receptor negative regulator | 2.2 | AV253087 |
| Ptgs2 | prostaglandin-endoperoxide synthase 2 | 5.3 | M94967 |
| Ptprc | protein tyrosine phosphatase, receptor type, C | 27.0 | NM_011210 |
| Pycard | PYD and CARD domain containing | 7.6 | BG084230 |
| Racgap1 | Rac GTPase-activating protein 1 | 4.7 | NM_012025 |
| Rad51 | RAD51 homolog (S. cerevisiae) | 8.4 | NM_011234 |
| Rcn1 | reticulocalbin 1 | 5.4 | NM_009037 |
| Relb | avian reticuloendotheliosis viral (v-rel) oncogene related B | 3.7 | NM_009046 |
| Rhob | ras homolog gene family, member B | 3.8 | BC018275 |
| Ris2 | retroviral integration site 2 | 2.4 | AF477481 |
| Rprc1 | arginine/proline rich coiled-coil 1 | 2.2 | BC019977 |
| Rras | Harvey rat sarcoma oncogene, subgroup R | 2.6 | NM_009101 |
| Rrm2 | ribonucleotide reductase M2 | 9.1 | NM_009104 |
| S100a10 | S100 calcium binding protein A10 (calpactin) | 2.4 | AV295650 |
| S100a11 | S100 calcium binding protein A11 (calizzarin) | 2.6 | BC021916 |
| S100a6 | S100 calcium binding protein A6 (calcyclin) | 4.6 | NM_011313 |
| S100a8 | S100 calcium binding protein A8 (calgranulin A) | 7.6 | NM_013650 |
| S100a9 | S100 calcium binding protein A9 (calgranulin B) | 7.1 | NM_009114 |
| Saa1 | serum amyloid A 1 | 9.6 | NM_009117 |
| Sart2 | squamous cell carcinoma antigen recognized by T cells 2 | 6.8 | BM207218 |

TABLE 11-continued

Refined injury and repair-induced transcripts (IRIT)

| Gene Symbol | Gene Title | allo.CBA D5 vs NCBA | Genbank |
|---|---|---|---|
| Scarb2 | scavenger receptor class B, member 2 | 2.2 | NM_007644 |
| Sdc1 | syndecan 1 | 3.3 | BB533095 |
| Serpina3n | serine (or cysteine) peptidase inhibitor, clade A, member 3N | 5.6 | NM_009252 |
| Serpinb6b | serine (or cysteine) peptidase inhibitor, clade B, member 6b | 5.6 | NM_011454 |
| Serpine1 | serine (or cysteine) peptidase inhibitor, clade E, member 1 | 5.4 | NM_008871 |
| Sertad4 | SERTA domain containing 4 | 7.2 | BQ174721 |
| Sh3bgrl3 | SH3 domain binding glutamic acid-rich protein-like 3 | 5.8 | NM_080559 |
| Shcbp1 | Shc SH2-domain binding protein 1 | 5.4 | NM_011369 |
| Sirpb1 | signal-regulatory protein beta 1 | 26.9 | AI662854 |
| Slamf9 | SLAM family member 9 | 4.0 | NM_029612 |
| Slc15a3 | solute carrier family 15, member 3 | 13.3 | NM_023044 |
| Slc25a24 | solute carrier family 25 (mitochondrial carrier, phosphate carrier), member 24 | 5.9 | BM230959 |
| Slc34a2 | solute carrier family 34 (sodium phosphate), member 2 | 6.7 | NM_011402 |
| Slc7a12 | solute carrier family 7 (cationic amino acid transporter, y+ system), member 12 | 3.6 | NM_080852 |
| Smc2l1 | SMC2 structural maintenance of chromosomes 2-like 1 (yeast) | 6.1 | NM_008017 |
| Smpdl3b | sphingomyelin phosphodiesterase, acid-like 3B | 7.6 | NM_133888 |
| Socs3 | suppressor of cytokine signaling 3 | 29.6 | BB831725 |
| Sp100 | nuclear antigen Sp100 | 2.6 | AV284523 |
| Sparc | secreted acidic cysteine rich glycoprotein | 2.1 | NM_009242 |
| Spbc24 | spindle pole body component 24 homolog (*S. cerevisiae*) | 2.3 | BF577722 |
| Stat3 | signal transducer and activator of transcription 3 | 3.1 | AK004083 |
| Tacc3 | transforming, acidic coiled-coil containing protein 3 | 4.0 | NM_011524 |
| Tagln2 | transgelin 2 | 2.2 | C76322 |
| Tcf19 | transcription factor 19 | 2.5 | BC004617 |
| Tgfb1 | transforming growth factor, beta 1 | 3.2 | NM_011577 |
| Tgfbi | transforming growth factor, beta induced | 31.0 | BB533460 |
| Tgm2 | transglutaminase 2, C polypeptide | 2.2 | BC016492 |
| Timp1 | tissue inhibitor of metalloproteinase 1 | 40.8 | BC008107 |
| Tlr2 | toll-like receptor 2 | 9.8 | NM_011905 |
| Tmcc2 | transmembrane and coiled-coil domains 2 | 2.1 | AK004359 |
| Tmepai | transmembrane, prostate androgen induced RNA | 2.4 | AV370981 |
| Tmsb10 | thymosin, beta 10 | 12.3 | NM_025284 |
| Tnfrsf12a | tumor necrosis factor receptor superfamily, member 12a | 2.7 | NM_013749 |
| Tpm2 | tropomyosin 2, beta | 2.3 | BC024358 |
| Tpm4 | tropomyosin 4 | 3.5 | AV122663 |
| Tpx2 | TPX2, microtubule-associated protein homolog (*Xenopus laevis*) | 3.9 | AK011311 |
| Tpx2 | TPX2, microtubule-associated protein homolog (*Xenopus laevis*) | 2.0 | AK011311 |
| Trip13 | thyroid hormone receptor interactor 13 | 8.2 | AK010336 |
| Tuba1 | tubulin, alpha 1 | 3.8 | NM_011653 |
| Tubb2 /// 2410129E14Rik /// LOC544939 | tubulin, beta 2 /// RIKEN cDNA 2410129E14 gene /// similar to TUBULIN BETA CHAIN (T BETA-15) | 3.9 | BC003475 |
| Tubb5 | tubulin, beta 5 | 3.7 | NM_011655 |
| Tubb6 | tubulin, beta 6 | 4.0 | NM_026473 |
| Tyrobp | TYRO protein tyrosine kinase binding protein | 17.4 | NM_011662 |
| Uhrf1 | ubiquitin-like, containing PHD and RING finger domains, 1 | 9.5 | BB702754 |
| Vasp | vasodilator-stimulated phosphoprotein | 3.1 | BC015289 |
| Vim | vimentin | 17.3 | AV147875 |
| Wisp1 | WNT1 inducible signaling pathway protein 1 | 2.9 | NM_018865 |
| Zwilch | Zwilch, kinetochore associated, homolog (*Drosophila*) | 3.2 | BC027435 |
| Zyx | zyxin | 2.2 | NM_011777 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for assessing transplanted tissue for an increased or decreased likelihood of rejection, wherein said method comprises:
   detecting, from human kidney tissue transplanted into a human, the presence or absence of cells that express guanylate nucleotide binding protein 1 (Gbp1) mRNA or tryptophanyl-tRNA synthetase (Wars) mRNA at an elevated level, wherein said elevated level is at least two times greater than the average level of mRNA expressed in cells from control kidney tissue from a population of humans not rejecting transplanted human kidney tissue,
   wherein the presence of said cells that express Gbp1 mRNA or Wars mRNA at said elevated level indicates that said human kidney tissue transplanted into a human has an increased likelihood of rejection, and
   wherein the absence of cells that express Gbp 1 mRNA or Wars mRNA at said elevated level indicates that said human kidney tissue transplanted into a human has a decreased likelihood of rejection.

2. The method of claim 1, wherein said human kidney tissue transplanted into a human is a kidney.

3. The method of claim 1, wherein the presence of said cells that express Gbp 1 mRNA or Wars mRNA at said elevated level is detected, and wherein said method comprises classifying said human kidney tissue transplanted into a human as having an increased likelihood of rejection.

4. A method for assessing transplanted tissue for an increased or decreased likelihood of rejection, wherein said method comprises:
   detecting, from a sample of human kidney tissue transplanted into a human, the presence or absence of cells that express guanylate nucleotide binding protein 1 (Gbp1) mRNA or tryptophanyl-tRNA synthetase (Wars) mRNA at an elevated level, wherein said elevated level is at least two times greater than the average level of mRNA expressed in cells from control kidney tissue from a population of humans not rejecting transplanted human kidney tissue, wherein said sample of human kidney tissue transplanted into a human was obtained within fifteen days of being transplanted
   wherein the presence of said cells that express Gbp1 mRNA or Wars mRNA at said elevated level indicates that said human kidney tissue transplanted into a human has an increased likelihood of rejection, and
   wherein the absence of cells that express Gbp1 mRNA or Wars mRNA at said elevated level indicates that said human kidney tissue transplanted into a human has a decreased likelihood of rejection.

5. The method of claim 4, wherein said human kidney tissue transplanted into a human is a kidney.

6. The method of claim 4, wherein said sample was obtained within ten days of being transplanted.

7. The method of claim 4, wherein said sample was obtained within five days of being transplanted.

8. The method of claim 4, wherein the presence of said cells that express Gbp 1 mRNA or Wars mRNA at said elevated level is detected, and wherein said method comprises classifying said human kidney tissue transplanted into a human as having an increased likelihood of rejection.

9. The method of claim 1, wherein the absence of said cells that express Gbp 1 mRNA or Wars mRNA at said elevated level is detected, and wherein said method comprises classifying said human kidney tissue transplanted into a human as having a decreased likelihood of rejection.

10. The method of claim 4, wherein the absence of said cells that express Gbp 1 mRNA or Wars mRNA at said elevated level is detected, and wherein said method comprises classifying said human kidney tissue transplanted into a human as having a decreased likelihood of rejection.

* * * * *

UNITED STATES PATENT AND TRADEMARK OFFICE
CERTIFICATE OF CORRECTION

PATENT NO. : 7,666,596 B2  
APPLICATION NO. : 11/434711  
DATED : February 23, 2010  
INVENTOR(S) : Philip F. Halloran It is certified that error appears in the above-identified patent and that said Letters Patent is hereby corrected as shown below:

Column 191, line 21 (Claim 1), after "of" please delete "said";

Column 192, line 10 (Claim 4), after "of" please delete "said".

Signed and Sealed this

Eleventh Day of May, 2010

David J. Kappos  
*Director of the United States Patent and Trademark Office*

UNITED STATES PATENT AND TRADEMARK OFFICE
CERTIFICATE OF CORRECTION

| | |
|---|---|
| PATENT NO. | : 7,666,596 B2 |
| APPLICATION NO. | : 11/434711 |
| DATED | : February 23, 2010 |
| INVENTOR(S) | : Halloran |

It is certified that error appears in the above-identified patent and that said Letters Patent is hereby corrected as shown below:

On the cover page, (*) Notice: Subject to any disclaimer, the term of this patent is extended or adjusted under 35 U.S.C. 154(b) by 260 days.

Delete the phrase "by 260 days" and insert -- by 284 days --

Signed and Sealed this

Tenth Day of August, 2010

David J. Kappos
*Director of the United States Patent and Trademark Office*